United States Patent
Deng et al.

(10) Patent No.: US 12,152,048 B2
(45) Date of Patent: Nov. 26, 2024

(54) NITROXOLINE PRODRUG AND USE THEREOF

(71) Applicant: Jiangsu Yahong Meditech Co., Ltd., Jiangsu (CN)

(72) Inventors: Yijun Deng, Shanghai (CN); Liang Wu, Shanghai (CN); Ke Pan, Shanghai (CN)

(73) Assignee: Jiangsu Yahong Meditech Co., Ltd., Jiangsu (CN)

( * ) Notice: Subject to any disclaimer, the term of this patent is extended or adjusted under 35 U.S.C. 154(b) by 799 days.

(21) Appl. No.: 17/280,999

(22) PCT Filed: Sep. 27, 2019

(86) PCT No.: PCT/CN2019/108419
§ 371 (c)(1),
(2) Date: Mar. 29, 2021

(87) PCT Pub. No.: WO2020/063824
PCT Pub. Date: Apr. 2, 2020

(65) Prior Publication Data
US 2021/0363165 A1    Nov. 25, 2021

(30) Foreign Application Priority Data
Sep. 29, 2018  (CN) .......................... 201811148314.0

(51) Int. Cl.
| C07F 9/60 | (2006.01) |
| C07D 215/26 | (2006.01) |
| C07D 401/12 | (2006.01) |
| C07D 401/14 | (2006.01) |
| C07D 405/12 | (2006.01) |

(52) U.S. Cl.
CPC .............. *C07F 9/60* (2013.01); *C07D 215/26* (2013.01); *C07D 401/12* (2013.01); *C07D 401/14* (2013.01); *C07D 405/12* (2013.01)

(58) Field of Classification Search
CPC . A61P 35/00; A61P 31/00; C07F 9/60; C07D 215/26; C07D 401/12; C07D 401/14; C07D 405/12
See application file for complete search history.

(56) References Cited

U.S. PATENT DOCUMENTS

| 3,828,056 A | 8/1974 | Kreider |
| 4,472,404 A | 9/1984 | Paxton et al. |
| 4,749,406 A | 6/1988 | Martin |
| 4,829,072 A | 5/1989 | Hamprecht et al. |
| 6,794,372 B2 | 9/2004 | Del Soldato |
| 8,729,097 B2 | 5/2014 | Liu et al. |
| 9,975,883 B2 | 5/2018 | Lee et al. |
| 2009/0105202 A1 | 4/2009 | Yang |
| 2023/0119296 A1* | 4/2023 | Wu ..................... C07D 401/12 514/314 |

FOREIGN PATENT DOCUMENTS

| CA | 883837 A | 10/1971 |
| CN | 1419450 A | 5/2003 |
| CN | 101951914 A | 1/2011 |
| CN | 102239149 A | 11/2011 |
| CN | 102464631 A | 5/2012 |
| CN | 105992759 A | 10/2016 |
| DE | 2728248 A1 | 1/1978 |
| DE | 3225169 A1 | 1/1984 |
| FR | 1510067 A | 1/1968 |
| GB | 1382571 A | 2/1975 |

(Continued)

OTHER PUBLICATIONS

Chardon. DE 2728248. English translation. (Year: 1978).*
Shim, J. S., et al., J Natl Cancer Inst. Dec. 15, 2010; 102(24): 1855-1873. (Year: 2010).*
Mitrovic, A., Kos, J., Acta. Biochim. Pol. 2019. 6(4): 521-531. (Year: 2019).*
Chang, W., et al. Oncotarget. 2015; 6(37):39806-20. (Year: 2015).*
Zhang, Q., et al. Oncology Letters. 2016. 11: 3265-3272. (Year: 2016).*
International Search Report dated Jan. 2, 2020 in corresponding PCT/CN2019/108419.
Written Opinion dated Jan. 2, 2020 in corresponding PCT/CN2019/108419.

(Continued)

*Primary Examiner* — Eric Olson
*Assistant Examiner* — Samuel L Galster
(74) *Attorney, Agent, or Firm* — Ice Miller LLP

(57) ABSTRACT

Provided are a nitroxoline prodrug and a use thereof. Specifically, provided are a compound represented by formula (I) or a pharmaceutically acceptable salt thereof, a preparation method therefor, a composition containing the compound, and a use thereof in the preparation of anti-infective and antitumor drugs, and definitions of groups in formula (I) are as stated in the specification. The compound represented by formula (I) has better pharmacokinetic parameters such as solubility, blood medicine concentration, or half-life period than nitroxoline. The compound represented by formula (I) can reduce the frequency of drug administration, and has potential for application in other fields other than the field of urinary tracts.

12 Claims, No Drawings

(56) References Cited

FOREIGN PATENT DOCUMENTS

WO        9320094 A1    10/1993
WO    2011121366 A1    10/2011

OTHER PUBLICATIONS

Madoery, O.D., et al., "Alkaline Hydrolysis of Quinolyl N,N-Dimethylthiocarbamates," J. Agric. Food Chem., vol. 33, No. 6, Dec. 31, 1985.

Grassmann, S., et al., "Imidazole Derivatives as a Novel Class of Hybrid Compounds with Inhibitory Histamine N-Methyltransferase Potencies and Histamine hH3 Receptor Affinities," Bioorganic & Medicinal Chemistry, vol. 11, No. 10, May 15, 2003.

Bano, H., et al., "Synthesis, Single Crystal X-Ray Diffraction, Hirshfeld Surface and Biological Activity of Quinolone Derivatives," European journal of Chemistry, vol. 8, No. 4, Dec. 31, 2017.

STN. "2375195-46-1", Registry, Sep. 13, 2019, 1 page.

STN. "4903-68-8 et al.", Registry, Apr. 16, 2018, pp. 1-40.

\* cited by examiner

NITROXOLINE PRODRUG AND USE THEREOF

CROSS-REFERENCE TO RELATED APPLICATION

This application is a Section 371 of International Application No. PCT/CN2019/108419 filed Sep. 27, 2019, which was published in the Chinese language Apr. 2, 2020, under International Publication No. WO 2020/063824 A1, which claims priority to Chinese Application No. 201811148314.0 filed Sep. 29, 2018, the disclosures of which are incorporated herein by reference in their entireties.

FIELD OF THE INVENTION

The invention relates to the field of drug. Specifically, the present invention relates to a nitroxoline prodrug and a use thereof.

BACKGROUND OF THE INVENTION

Nitroxoline, as a commercially available antibacterial drug, has long been used to treat urinary tract infections. Recent findings show that nitroxoline is also very effective in inhibiting angiogenesis and inhibiting the growth and invasion of cancer cells. Currently, nitroxoline is being developed for anti-tumor. Human pharmacokinetic studies show that nitroxoline can be rapidly absorbed into the blood circulation. However, due to the strong first-pass effect of the liver on the drug, the biological half-life of nitroxoline is very short (according to a single-arm, open, multi-center clinical phase II trial conducted by JIANGSU YAHONG MEDITECH CO., LTD. in China, the half-life of nitroxoline is 1.22 to 1.44 hours), and frequent administration is thus required. In order to maintain continuous drug exposure, nitroxoline is generally prescribed to be administered three times a day (TID) or four times a day (QID). This not only brings economic losses and reduces patient compliance, but also increases the sustained damage of the drug to the normal body. Moreover, due to the low water solubility of nitroxoline, it is often prepared into an immediate-release formulation to improve the solubility, which virtually increases the production cost.

A prodrug is a compound obtained by chemical modification of an active drug, which is transformed into the original drug by the action of enzymes in the body to exert its efficacy. Prodrugs have a wide range of applications in drug development, and they have been successfully researched in various drugs and good application effects have been obtained. The prodrug strategy can solve some defects of an active agent resulting from its own physical and chemical properties, such as: 1) eliminating the bad smell of the drug; 2) increasing the blood drug concentrations; 3) improving the fat solubility or water solubility of the drug; 4) prolonging the action period of the drug; 5) changing the administration route of the drug.

So far, there are no reports on the use of prodrug strategy to improve the biological half-life, exposure and water solubility of nitroxoline so as to reduce the administration frequency.

Regarding to the above deficiencies, the inventor designs a nitroxoline prodrug. This prodrug is metabolized into nitroxoline after entering the body to exert its effect, while enabling a prolonged half-life of nitroxoline in the body to achieve reduced administration frequency.

SUMMARY OF THE INVENTION

The metabolism of nitroxoline is characterized by low water solubility and short biological half-life. Therefore, nitroxoline is generally prescribed to be administered three times a day or four times a day in antibacterial and anticancer applications. Moreover, nitroxoline is mainly metabolized by the kidneys and excreted through the urinary tract. This metabolic pathway limits the application of nitroxoline in areas other than urinary tract infections and bladder cancer.

The present invention provides a compound that can be used as a nitroxoline prodrug. Through the screening and optimization of the structure of the compound, it is found that in animals, the compound has better pharmacokinetic parameters such as water solubility, blood concentration and biological half-life compared with nitroxoline. The compound of the present invention can reduce the administration frequency, while increase the possibility of application in areas other than urinary tract area.

Therefore, the objective of the present invention is to provide a compound of formula (I)

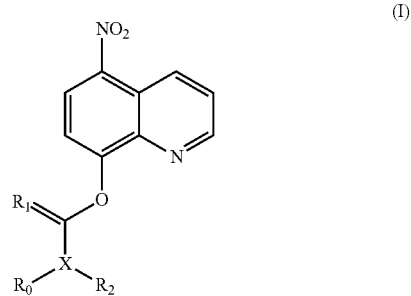

(I)

or a mesomer, racemate, enantiomer, diastereomer thereof, or a mixture thereof, or a pharmaceutically acceptable salt thereof, wherein:

⩘ represents a single bond or a double bond;

$R_1$ is selected from the group consisting of hydrogen, $C_{1-6}$ alkyl, S and O;

X is selected from the group consisting of O, N, S, —$(CH_2)_n$—, aryl and heterocyclyl;

wherein:

when X is N, $R_0$ and $R_2$ are each independently selected from the group consisting of hydrogen, $C_{1-6}$ alkyl, aryl and heterocyclyl;

when X is selected from the group consisting of aryl and heterocyclyl, $R_0$ and $R_2$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

when X is selected from the group consisting of O, S and —$(CH_2)_n$—, $R_2$ is absent, and $R_0$ is selected from the group consisting of $C_{1-6}$ alkyl, cycloalkyl, heterocyclyl, —$COR_{11}$, —$C(O)OR_{12}$,

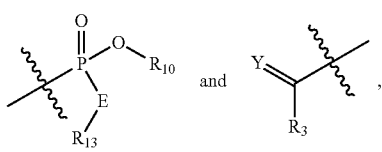 and wherein the $C_{1-6}$ alkyl, cycloalkyl and heterocyclyl are optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

wherein:

when $R_0$ is selected from

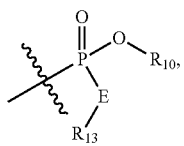

E is selected from the group consisting of O and $NR_{14}$, $R_{10}$, $R_{13}$ and $R_{14}$ are each independently selected from the group consisting of hydrogen, $C_{1-6}$ alkyl and aryl, wherein the $C_{1-6}$ alkyl and aryl are optionally further substituted by one or more substituent(s) selected from the group consisting of halogen, hydroxy, thiol, carboxy, alkoxycarbonyl, alkyl, alkoxy, cycloalkyl, heterocyclyl, aryl, arylalkyl, heteroaryl, heteroarylalkyl, $-OR_{12}$, $-COR_{11}$, $-C(O)OR_{12}$, $-OC(O)R_{11}$ and $-OC(O)OR_{12}$; when $R_0$ is selected from

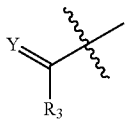

Y is selected from the group consisting of O, N and S, $R_3$ is selected from the group consisting of

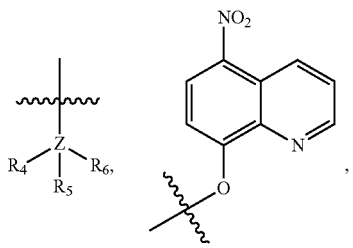

cycloalkyl, heterocyclyl, aryl and heteroaryl, wherein the cycloalkyl, heterocyclyl, aryl and heteroaryl are optionally further substituted by one or more substituent(s) selected from the group consisting of halogen, hydroxy, thiol, carboxy, alkoxycarbonyl, alkyl, alkoxy, cycloalkyl, heterocyclyl, aryl, heteroaryl and $-OC(O)R_{11}$, and Z is selected from the group consisting of C, N and O;

wherein:

when Z is C, $R_4$, $R_5$ and $R_6$ are each independently selected from the group consisting of hydrogen, halogen, alkyl, cycloalkyl, heterocyclyl, aryl, heteroaryl, $-OR_{12}$, $-SR_{12}$, $-C(O)R_{11}$, $-C(O)OR_{12}$, $-C(O)-(CH)_m-C(O)R_{11}$, $-OC(O)R_{11}$, $-NR^aR^b$, $-N(R^c)C(O)R^d$, $-C(O)N(R^a)(R^b)$, $-N(R^c)S(O)_pR^d$, $-S(O)_pN(R^a)(R^b)$, $-O(CH_2)_mO(CH_2)_qR_{12}$ and $-N(R^c)C(O)-(CH)_m-N(R^c)C(O)R^d$, wherein the alkyl, cycloalkyl, heterocyclyl, aryl and heteroaryl are optionally further substituted by one or more substituent(s) selected from the group consisting of halogen, amino, nitro, cyano, hydroxy, thiol, alkyl, alkoxy, alkenyl, alkynyl, $OR_{12}$, $SR_{12}$, $NR^aR^b$, $-COR_{11}$, $-C(O)OR_{12}$, $-OC(O)R_{11}$, $-N(R^c)C(O)R^d$, $-O(CH_2)_mO(CH_2)_qR_{12}$, cycloalkyl, heterocyclyl, aryl, arylalkyl, heteroaryl and heteroarylalkyl, wherein the aryl, arylalkyl, heteroaryl and heteroarylalkyl are optionally further substituted by one or more substituent(s) selected from the group consisting of halogen, amino, nitro, cyano, hydroxy, thiol, carboxy, alkoxycarbonyl, oxo, alkyl and alkoxy; or any one of $R_4$, $R_5$ and $R_6$ is hydrogen, and the remaining two together with Z form a cycloalkyl or heterocyclyl, wherein the cycloalkyl or heterocyclyl is optionally further substituted by one or more substituent(s) selected from the group consisting of halogen, amino, nitro, cyano, hydroxy, thiol, alkyl, alkoxy, alkenyl, alkynyl, $-C(O)R_{11}$, $-C(O)OR_{12}$, $-OC(O)R_{11}$, cycloalkyl, heterocyclyl, aryl and heteroaryl;

when Z is N, $R_6$ is absent, $R_4$ and $R_5$ are each independently selected from the group consisting of hydrogen, halogen, alkyl, cycloalkyl, heterocyclyl, aryl, heteroaryl, $-OR_{12}$, $-SR_{12}$, $-C(O)R_{11}$, $-C(O)OR_{12}$, $-OC(O)R_{11}$, $-NR^aR^b$, $-N(R^c)C(O)R^d$, $-C(O)N(R^a)(R^b)$, $-N(R^c)S(O)_pR^d$, $-S(O)_pN(R^a)(R^b)$, $-O(CH_2)_mO(CH_2)_qR_{12}$ and $-N(R^c)C(O)-(CH)_m-N(R^c)C(O)R^d$, wherein the alkyl, cycloalkyl, heterocyclyl, aryl and heteroaryl are optionally further substituted by one or more substituent(s) selected from the group consisting of halogen, amino, nitro, cyano, hydroxy, thiol, alkyl, alkoxy, alkenyl, alkynyl, $OR_{12}$, $SR_{12}$, $NR^aR^b$, $-C(O)R_{11}$, $-C(O)OR_{12}$, $-OC(O)R_{11}$, $-(CH)_m-OC(O)R_{11}$, cycloalkyl, heterocyclyl, aryl, arylalkyl, heteroaryl and heteroarylalkyl; or $R_4$, $R_5$ and Z together form a cycloalkyl or heterocyclyl, wherein the cycloalkyl or heterocyclyl is optionally further substituted by one or more substituent(s) selected from the group consisting of halogen, amino, nitro, cyano, hydroxy, thiol, alkyl, alkoxy, alkenyl, alkynyl, $-C(O)R_{11}$, $-C(O)OR_{12}$, $-OC(O)R_{11}$, cycloalkyl, heterocyclyl, aryl and heteroaryl;

when Z represents O, $R_5$ and $R_6$ are absent, $R_4$ is selected from the group consisting of $C_{1-6}$ alkyl, aryl and heterocyclyl, wherein the $C_{1-6}$ alkyl, aryl and heterocyclyl are optionally further substituted by one or more $-OH$; or when X is selected from the group consisting of O, N, S and $-(CH_2)_n-$, $R_2$ is absent, $R_1$, X and $R_0$ together form a cycloalkyl or heterocyclyl, wherein the cycloalkyl or heterocyclyl is optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

$R_{11}$ and $R_{12}$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, —NR$^a$R$^b$, —OR$^d$, —N(R$^c$)C(O)R$^d$, —C(O)N(R$^a$)(R$^b$), —N(R$^c$)S(O)$_p$R$^d$, —S(O)$_p$N(R$^a$)(R$^b$), alkenyl, alkynyl, cycloalkyl, heterocyclyl, aryl and heteroaryl;

R$^a$ and R$^b$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

or, R$^a$ and R$^b$ together with the atoms to which they are attached form a heterocyclyl, wherein the heterocyclyl is optionally further substituted by one or more substituent(s) selected from the group consisting of halogen, amino, nitro, cyano, oxo, hydroxy, thiol, carboxy, alkoxycarbonyl, alkyl, alkoxy, alkenyl, alkynyl, cycloalkyl, heterocyclyl, aryl and heteroaryl;

R$^c$ and R$^d$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

n is selected from an integer from 1 to 8;
m is selected from an integer from 0 to 6;
p is selected from the group consisting of 0, 1 and 2;
q is selected from an integer from 0 to 6.

In a preferred embodiment, the compound of formula (I) according to the present invention is a compound of formula (II),

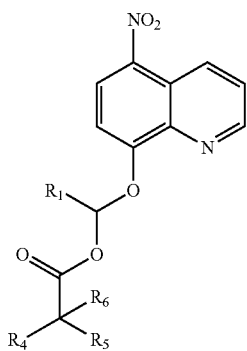

(II)

wherein,
R$_1$ is selected from the group consisting of hydrogen and C$_{1-6}$ alkyl;
R$_4$, R$_5$ and R$_6$ are each independently selected from the group consisting of hydrogen, halogen, alkyl, cycloalkyl, heterocyclyl, aryl, heteroaryl, —OR$_{12}$, —SR$_{12}$, —C(O)R$_{11}$, —C(O)OR$_{12}$, —C(O)—(CH$_2$)$_m$—C(O)R$_{11}$, —OC(O)R$_{11}$, —NR$^a$R$^b$, —N(R$^c$)C(O)R$^d$, —C(O)N(R$^a$)(R$^b$), —N(R$^c$)S(O)$_p$R$^d$, —S(O)$_p$N(R$^a$)(R$^b$), —O(CH$_2$)$_m$O(CH$_2$)$_q$R$_{12}$ and —N(R$^c$)C(O)—(CH$_2$)$_m$—N(R$^c$)C(O)R$^d$, wherein the alkyl, cycloalkyl, heterocyclyl, aryl and heteroaryl are optionally further substituted by one or more substituent(s) selected from the group consisting of halogen, amino, nitro, cyano, hydroxy, thiol, alkyl, alkoxy, alkenyl, alkynyl, OR$_{12}$, SR$_{12}$, NR$^a$R$^b$, —COR$_{11}$, —C(O)OR$_{12}$, —OC(O)R$_{11}$, —N(R$^c$)C(O)R$^d$, —O(CH$_2$)$_m$O(CH$_2$)$_q$R$_{12}$, cycloalkyl, heterocyclyl, aryl, arylalkyl, heteroaryl and heteroarylalkyl, wherein the aryl, arylalkyl, heteroaryl and heteroarylalkyl are optionally further substituted by one or more substituent(s) selected from the group consisting of halogen, amino, nitro, cyano, hydroxy, thiol, carboxy, alkoxycarbonyl, oxo, alkyl and alkoxy; or any one of R$_4$, R$_5$ and R$_6$ is hydrogen, and the remaining two together with Z form a cycloalkyl or heterocyclyl, wherein the cycloalkyl or heterocyclyl is optionally further substituted by one or more substituent(s) selected from the group consisting of halogen, amino, nitro, cyano, hydroxy, thiol, alkyl, alkoxy, alkenyl, alkynyl, —C(O)R$_{11}$, —C(O)OR$_{12}$, —OC(O)R$_{11}$, cycloalkyl, heterocyclyl, aryl and heteroaryl;

R$_{11}$ and R$_{12}$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, —NR$^a$R$^b$, —OR$^d$, —N(R$^c$)C(O)R$^d$, —C(O)N(R$^a$)(R$^b$), —N(R$^c$)S(O)$_p$R$^d$, —S(O)$_p$N(R$^a$)(R$^b$), alkenyl, alkynyl, cycloalkyl, heterocyclyl, aryl and heteroaryl;

R$^a$ and R$^b$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

or, R$^a$ and R$^b$ together with the atoms to which they are attached form a heterocyclyl, wherein the heterocyclyl is optionally further substituted by one or more substituent(s) selected from the group consisting of halogen, amino, nitro, cyano, oxo, hydroxy, thiol, carboxy, alkoxycarbonyl, alkyl, alkoxy, alkenyl, alkynyl, cycloalkyl, heterocyclyl, aryl and heteroaryl;

R$^c$ and R$^d$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

m is selected from an integer from 0 to 6;
p is selected from the group consisting of 0, 1 and 2;
q is selected from an integer from 0 to 6.

In a further preferred embodiment of the present invention, in the compound of formula (II) according to the present invention, $R_4$, $R_5$ and $R_6$ are each independently selected from the group consisting of hydrogen, alkyl, aryl, heteroaryl, —$OR_{12}$, —$SR_{12}$, —$C(O)R_{11}$, —$C(O)OR_{12}$, —C(O)—$(CH)_m$—$C(O)R_{11}$, —$OC(O)R_{11}$, —$(CH)_m$—$N(R^c)$C(O)$R_{11}$, —$NR^aR^b$, —$N(R^c)C(O)R^d$, —$C(O)N(R^a)(R^b)$, —$N(R^c)S(O)_pR^d$, —$S(O)_pN(R^a)(R^b)$, —$O(CH_2)_mO(CH_2)_qR_{12}$ and —$N(R^c)C(O)$—$(CH)_m$—$N(R^c)C(O)R^d$, wherein the alkyl, aryl and heteroaryl are optionally further substituted by one or more substituent(s) selected from the group consisting of halogen, hydroxy, alkyl, $OR_{12}$, $SR_{12}$, $NR^aR^b$, —$COR_{11}$, —$C(O)OR_{12}$, —$O(O)CR_{11}$, —$N(R^c)C(O)R^d$, —$O(CH_2)_mO(CH_2)_qR_{12}$, cycloalkyl, heterocyclyl, aryl, arylalkyl, heteroaryl and heteroarylalkyl, wherein the aryl, arylalkyl, heteroaryl and heteroarylalkyl are optionally further substituted by one or more substituent(s) selected from the group consisting of halogen, hydroxy, thiol, alkyl and alkoxy;

$R_{11}$ and $R_{12}$ are each independently selected from the group consisting of hydrogen, halogen, hydroxy, alkyl, alkoxy, cycloalkyl, heterocyclyl, aryl and heteroaryl, wherein the alkyl, alkoxy, cycloalkyl, heterocyclyl, aryl and heteroaryl are optionally further substituted by one or more substituent(s) selected from the group consisting of halogen, amino, hydroxy, alkyl, alkoxy, —$NR^aR^b$, —$OR^d$, —$N(R^c)C(O)R^d$, —$C(O)N(R^a)(R^b)$, —$N(R^c)S(O)_pR^d$, —$S(O)_pN(R^a)(R^b)$, cycloalkyl, heterocyclyl, aryl and heteroaryl;

$R^a$ and $R^b$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

or, $R^a$ and $R^b$ together with the atoms to which they are attached form a heterocyclyl, wherein the heterocyclyl is optionally further substituted by one or more substituent(s) selected from the group consisting of halogen, amino, nitro, cyano, oxo, hydroxy, thiol, carboxy, alkoxycarbonyl, alkyl, alkoxy, alkenyl, alkynyl, cycloalkyl, heterocyclyl, aryl and heteroaryl;

$R^c$ and $R^d$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

m is selected from an integer from 0 to 6;
p is selected from the group consisting of 0, 1 and 2;
q is selected from an integer from 0 to 6.

In a further preferred embodiment of the present invention, in the compound of formula (II) according to the present invention, $R_4$, $R_5$ and $R_6$ are each independently selected from the group consisting of hydrogen, alkyl, aryl, heteroaryl, —$OR_{12}$, —$SR_{12}$, —$C(O)R_{11}$, —$C(O)OR_{12}$, —C(O)—$(CH)_m$—$C(O)R_{11}$, —$OC(O)R_{11}$ and —$(CH)_m$—$N(R^c)C(O)R_{11}$, wherein the alkyl, aryl and heteroaryl are optionally further substituted by one or more substituent(s) selected from the group consisting of halogen, hydroxy, alkyl, $OR_{12}$, $SR_{12}$, $NR^aR^b$, —$COR_{11}$, —$C(O)OR_{12}$, —$O(O)CR_{11}$, —$N(R^c)C(O)R^d$, —$O(CH_2)_mO(CH_2)_qR_{12}$, cycloalkyl, heterocyclyl, aryl and heteroaryl, wherein the aryl, arylalkyl, heteroaryl and heteroarylalkyl are optionally further substituted by one or more substituent(s) selected from the group consisting of halogen and hydroxy;

$R_{11}$ and $R_{12}$ are each independently selected from the group consisting of hydrogen, halogen, hydroxy, alkyl, alkoxy, cycloalkyl, heterocyclyl, aryl and heteroaryl, wherein the alkyl, alkoxy, cycloalkyl, heterocyclyl, aryl and heteroaryl are optionally further substituted by one or more substituent(s) selected from the group consisting of halogen, amino, hydroxy, alkyl, —$OR^d$, —$N(R^c)C(O)R^d$, cycloalkyl, heterocyclyl, aryl and heteroaryl;

$R^a$ and $R^b$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

or, $R^a$ and $R^b$ together with the atoms to which they are attached form a heterocyclyl, wherein the heterocyclyl is optionally further substituted by one or more substituent(s) selected from the group consisting of halogen, amino, nitro, cyano, oxo, hydroxy, thiol, carboxy, alkoxycarbonyl, alkyl, alkoxy, alkenyl, alkynyl, cycloalkyl, heterocyclyl, aryl and heteroaryl;

$R^c$ and $R^d$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

m is selected from an integer from 0 to 6;
q is selected from an integer from 0 to 6.

In a further preferred embodiment of the present invention, in the compound of formula (II) according to the present invention, any one of $R_4$, $R_5$ and $R_6$ is hydrogen, and the remaining two together with the carbon atom to which they are attached form a cycloalkyl or heterocyclyl, wherein the cycloalkyl or heterocyclyl is optionally further substituted by one or more substituent(s) selected from the group consisting of halogen, amino, nitro, cyano, hydroxy, thiol, alkyl, alkoxy, alkenyl, alkynyl, —C(O)R$_{11}$, —C(O)OR$_{12}$, —OC(O)R$_{11}$, cycloalkyl, heterocyclyl, aryl and heteroaryl;

R$_{11}$ and R$_{12}$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, —NR$^a$R$^b$, —OR$^d$, —N(R$^c$)C(O)R$^d$, —C(O)N(R$^a$)(R$^b$), —N(R$^c$)S(O)$_p$R$^d$, —S(O)$_p$N(R$^a$)(R$^b$), alkenyl, alkynyl, cycloalkyl, heterocyclyl, aryl, hydroxyaryl and heteroaryl;

R$^a$ and R$^b$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

or, R$^a$ and R$^b$ together with the atoms to which they are attached form a heterocyclyl, wherein the heterocyclyl is optionally further substituted by one or more substituent(s) selected from the group consisting of halogen, amino, nitro, cyano, oxo, hydroxy, thiol, carboxy, alkoxycarbonyl, alkyl, alkoxy, alkenyl, alkynyl, cycloalkyl, heterocyclyl, aryl and heteroaryl;

R$^c$ and R$^d$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

p is selected from the group consisting of 0, 1 and 2.

In a further preferred embodiment of the present invention, in the compound of formula (II) according to the present invention, any one of R$_4$, R$_5$ and R$_6$ is hydrogen, and the remaining two together with the carbon atom to which they are attached form a cycloalkyl or heterocyclyl, wherein the cycloalkyl or heterocyclyl is optionally further substituted by one or more substituent(s) selected from the group consisting of —C(O)R$_{11}$ and —C(O)OR$_{12}$;

R$_{11}$ and R$_{12}$ are each independently selected from the group consisting of hydrogen, halogen, hydroxy, alkyl, alkoxy, cycloalkyl, heterocyclyl, aryl and heteroaryl, wherein the alkyl, alkoxy, cycloalkyl, heterocyclyl, aryl and heteroaryl are optionally further substituted by one or more substituent(s) selected from the group consisting of halogen, hydroxy, alkyl, —OR$^d$, —N(R$^c$)C(O)R$^d$, aryl, hydroxyaryl and heteroaryl;

R$^c$ and R$^d$ are each independently selected from the group consisting of hydrogen, alkyl, alkoxy, aryl and heteroaryl, wherein the alkyl, alkoxy, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl.

In another preferred embodiment of the present invention, the compound of formula (I) according to the present invention is a compound of formula (III),

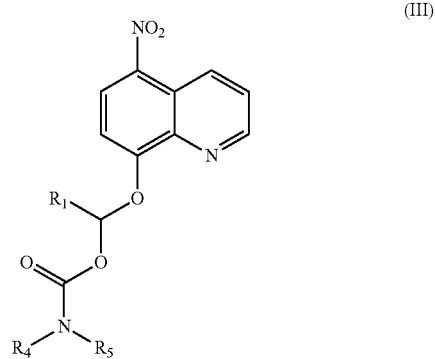

(III)

wherein,

R$_1$ is selected from the group consisting of hydrogen and C$_{1-6}$ alkyl;

R$_4$ and R$_5$ are each independently selected from the group consisting of hydrogen, halogen, alkyl, cycloalkyl, heterocyclyl, aryl, heteroaryl, —OR$_{12}$, —SR$_{12}$, —C(O)R$_{11}$, —C(O)OR$_{12}$, —OC(O)R$_{11}$, —NR$^a$R$^b$, —N(R$^c$)C(O)R$^d$, —C(O)N(R$^a$)(R$^b$), —N(R$^c$)S(O)$_p$R$^d$, —S(O)$_p$N(R$^a$)(R$^b$), —O(CH$_2$)$_m$O(CH$_2$)$_q$R$_{12}$ and —N(R$^c$)C(O)—(CH)$_m$—N(R$^c$)C(O)R$^d$, wherein the alkyl, cycloalkyl, heterocyclyl, aryl and heteroaryl are optionally further substituted by one or more substituent(s) selected from the group consisting of halogen, amino, nitro, cyano, hydroxy, thiol, alkyl, alkoxy, alkenyl, alkynyl, OR$_{12}$, SR$_{12}$, NR$^a$R$^b$, —C(O)R$_{11}$, —C(O)OR$_{12}$, —O(O)CR$_{11}$, —(CH)$_m$—OC(O)R$_{11}$, cycloalkyl, heterocyclyl, aryl, arylalkyl, heteroaryl and heteroarylalkyl; or R$_4$, R$_5$ and N atom together form a heterocyclyl, wherein the heterocyclyl is optionally further substituted by one or more substituent(s) selected from the group consisting of halogen, amino, nitro, cyano, hydroxy, thiol, alkyl, alkoxy, alkenyl, alkynyl, —C(O)R$_1$, —C(O)OR$_{12}$, —O(O)CR$_{11}$, cycloalkyl, heterocyclyl, aryl and heteroaryl;

R$_{11}$ and R$_{12}$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, —NR$^a$R$^b$, —OR$^d$, —N(R$^c$)C(O)R$^d$, —C(O)N(R$^a$)(R$^b$), —N(R$^c$)S(O)$_p$R$^d$, —S(O)$_p$N(R$^a$)(R$^b$), alkenyl, alkynyl, cycloalkyl, heterocyclyl, aryl and heteroaryl;

R$^a$ and R$^b$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

or, R$^a$ and R$^b$ together with the atoms to which they are attached form a heterocyclyl, wherein the heterocyclyl is optionally further substituted by one or more substituent(s) selected from the group consisting of halogen, amino, nitro, cyano, oxo, hydroxy, thiol, carboxy, alkoxycarbonyl, alkyl, alkoxy, alkenyl, alkynyl, cycloalkyl, heterocyclyl, aryl and heteroaryl;

R$^c$ and R$^d$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

m is selected from an integer from 0 to 6;

p is selected from the group consisting of 0, 1 and 2;

q is selected from an integer from 0 to 6.

In a further preferred embodiment of the present invention, in the compound of formula (III) according to the present invention, R$_4$ and R$_5$ are each independently selected from the group consisting of hydrogen, alkyl, aryl and heteroaryl, wherein the alkyl, aryl and heteroaryl are optionally further substituted by one or more substituent(s) selected from the group consisting of halogen, hydroxy, thiol, alkyl, —C(O)R$_{11}$, —C(O)OR$_{12}$, —O(O)CR$_{11}$, —(CH)$_m$—OC(O)R$_{11}$, aryl and heteroaryl;

R$_{11}$ and R$_{12}$ are each independently selected from the group consisting of hydrogen and alkyl, wherein the alkyl is optionally further substituted by one or more substituent(s) selected from the group consisting of halogen, —OR$^d$ and —N(R$^c$)C(O)R$^d$;

R$^c$ and R$^d$ are each independently selected from the group consisting of hydrogen, alkyl, aryl and heteroaryl, wherein the alkyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

m is selected from an integer from 0 to 6;

p is selected from the group consisting of 0, 1 and 2.

In another preferred embodiment of the present invention, the compound of formula (I) according to the present invention is a compound of formula (IV),

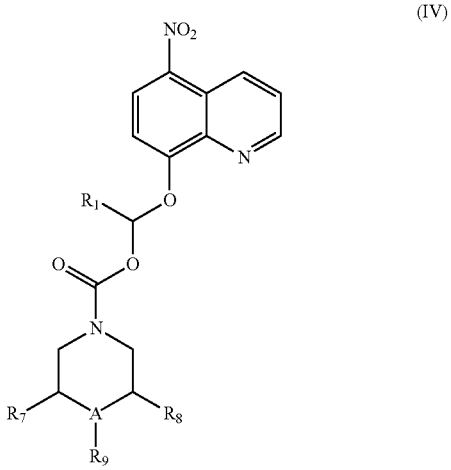

(IV)

wherein,

R$_1$ is selected from the group consisting of hydrogen and C$_{1-6}$ alkyl;

A is selected from the group consisting of C, O and N;

R$_7$ and R$_8$ are each independently selected from the group consisting of hydrogen, halogen, hydroxy, alkyl, alkoxy, haloalkyl and haloalkoxy;

R$_9$ is selected from the group consisting of hydrogen, halogen, amino, hydroxy, thiol, alkyl, alkoxy, —C(O)R$_{11}$, —C(O)OR$_{12}$, —OC(O)R$_{11}$, cycloalkyl and heterocyclyl;

R$_{11}$ and R$_{12}$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, —NR$^a$R$^b$, —OR$^d$, —N(R$^c$)C(O)R$^d$, —C(O)N(R$^a$)(R$^b$), —N(R$^c$)S(O)$_p$R$^d$, —S(O)$_p$N(R$^a$)(R$^b$), alkenyl, alkynyl, cycloalkyl, heterocyclyl, aryl and heteroaryl;

R$^a$ and R$^b$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

or, $R^a$ and $R^b$ together with the atoms to which they are attached form a heterocyclyl, wherein the heterocyclyl is optionally further substituted by one or more substituent(s) selected from the group consisting of halogen, amino, nitro, cyano, oxo, hydroxy, thiol, carboxy, alkoxycarbonyl, alkyl, alkoxy, alkenyl, alkynyl, cycloalkyl, heterocyclyl, aryl and heteroaryl;

$R^c$ and $R^d$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

p is selected from the group consisting of 0, 1 and 2.

In another preferred embodiment of the present invention, the compound of formula (I) according to the present invention is a compound of formula (V),

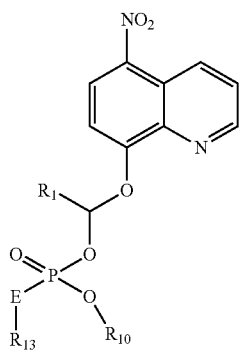

(V)

wherein,

E is selected from the group consisting of O and $NR_{14}$;

$R_{10}$, $R_{13}$ and $R_{14}$ are each independently selected from the group consisting of hydrogen, $C_{1-6}$ alkyl and aryl, wherein the $C_{1-6}$ alkyl and aryl are optionally further substituted by one or more substituent(s) selected from the group consisting of halogen, hydroxy, thiol, carboxy, alkoxycarbonyl, alkyl, alkoxy, cycloalkyl, heterocyclyl, aryl, arylalkyl, heteroaryl, heteroarylalkyl, —$OR_{12}$, —$COR_{11}$, —$C(O)OR_{12}$, —$OC(O)R_{11}$ and —$OC(O)OR_{12}$;

$R_{11}$ and $R_{12}$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, —$NR^aR^b$, —$OR^d$, —$N(R^c)C(O)R^d$, —$C(O)N(R^a)(R^b)$, —$N(R^c)S(O)_pR^d$, —$S(O)_pN(R^a)(R^b)$, alkenyl, alkynyl, cycloalkyl, heterocyclyl, aryl and heteroaryl;

$R^a$ and $R^b$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

or, $R^a$ and $R^b$ together with the atoms to which they are attached form a heterocyclyl, wherein the heterocyclyl is optionally further substituted by one or more substituent(s) selected from the group consisting of halogen, amino, nitro, cyano, oxo, hydroxy, thiol, carboxy, alkoxycarbonyl, alkyl, alkoxy, alkenyl, alkynyl, cycloalkyl, heterocyclyl, aryl and heteroaryl;

$R^c$ and $R^d$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

p is selected from the group consisting of 0, 1 and 2.

In a further preferred embodiment of the present invention, in the compound of formula (V) according to the present invention, $R_{10}$, $R_{13}$ and $R_{14}$ are each independently selected from the group consisting of hydrogen and $C_{1-6}$ alkyl, wherein the $C_{1-6}$ alkyl is optionally further substituted by one or more substituent(s) selected from the group consisting of halogen, hydroxy, thiol, alkyl, alkoxy, aryl, heteroaryl, —$OR_{12}$, —$COR_{11}$, —$C(O)OR_{12}$ and —$OC(O)OR_{11}$;

$R_{11}$ and $R_{12}$ are each independently selected from the group consisting of alkyl, aryl and heteroaryl, wherein the alkyl, aryl and heteroaryl are optionally further substituted by one or more substituent(s) selected from the group consisting of halogen, amino, nitro, cyano, hydroxy, thiol, carboxy, alkoxycarbonyl, oxo, alkyl, alkoxy, cycloalkyl, heterocyclyl, aryl and heteroaryl.

Typical compounds of the present invention include, but are not limited to the following compounds:

| Example No. | Structure and name |
|---|---|
| 1 | 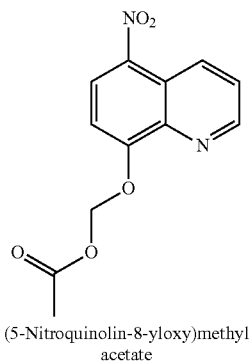<br>(5-Nitroquinolin-8-yloxy)methyl acetate |
| 2 | 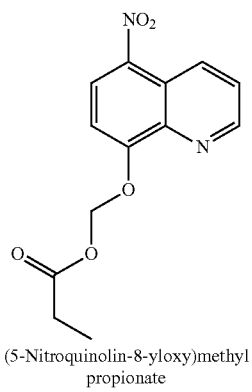<br>(5-Nitroquinolin-8-yloxy)methyl propionate |
| 3 | 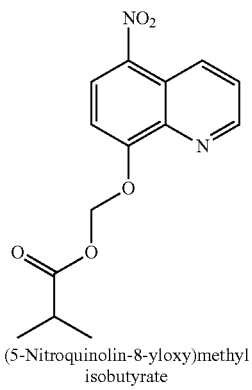<br>(5-Nitroquinolin-8-yloxy)methyl isobutyrate |
| 4 | 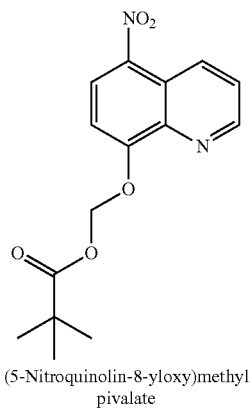<br>(5-Nitroquinolin-8-yloxy)methyl pivalate |

-continued
| Example No. | Structure and name |
|---|---|
| 5 | 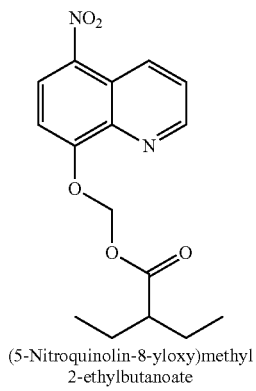(5-Nitroquinolin-8-yloxy)methyl 2-ethylbutanoate |
| 6 | 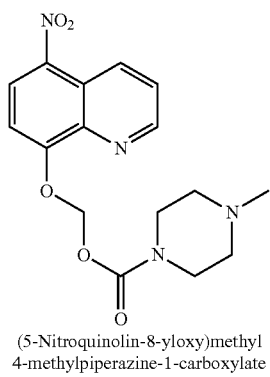(5-Nitroquinolin-8-yloxy)methyl 4-methylpiperazine-1-carboxylate |
| 7 | 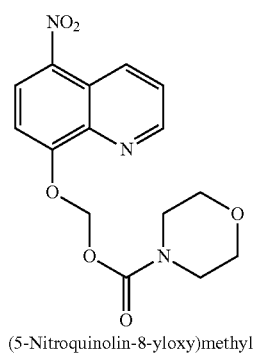(5-Nitroquinolin-8-yloxy)methyl morpholine-4-carboxylate |
| 8 | 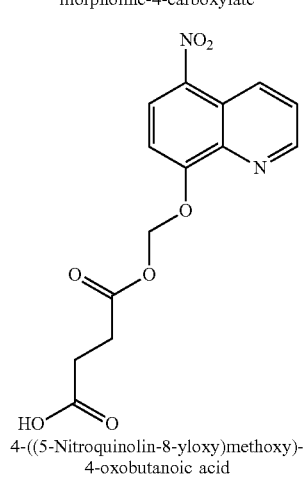4-((5-Nitroquinolin-8-yloxy)methoxy)-4-oxobutanoic acid |

| Example No. | Structure and name |
|---|---|
| 9 | 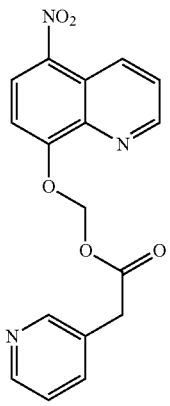<br>((5-Nitroquinolin-8-yl)oxy)methyl 2-(pyridin-3-yl)acetate |
| 10 | 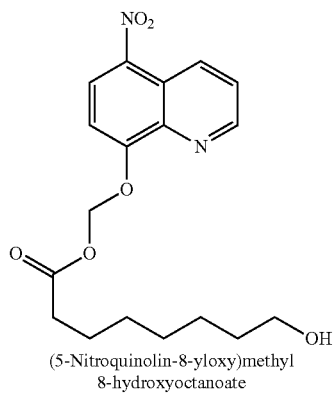<br>(5-Nitroquinolin-8-yloxy)methyl 8-hydroxyoctanoate |
| 11 | 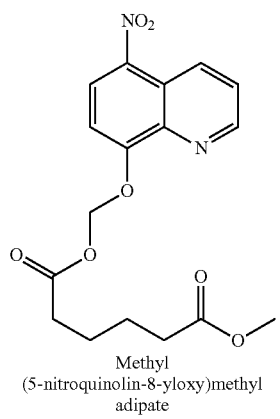<br>Methyl (5-nitroquinolin-8-yloxy)methyl adipate |

| Example No. | Structure and name |
|---|---|
| 12 | 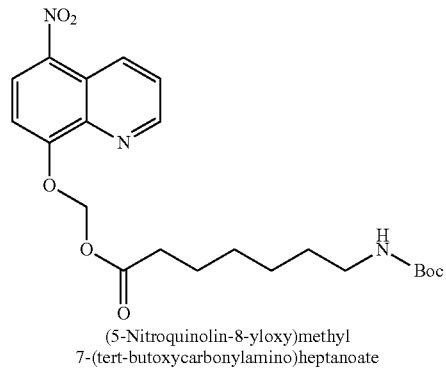<br>(5-Nitroquinolin-8-yloxy)methyl 7-(tert-butoxycarbonylamino)heptanoate |
| 13 | 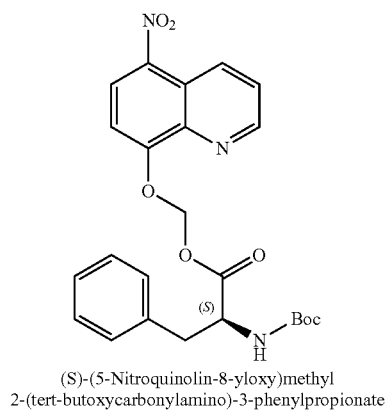<br>(S)-(5-Nitroquinolin-8-yloxy)methyl 2-(tert-butoxycarbonylamino)-3-phenylpropionate |
| 14 | 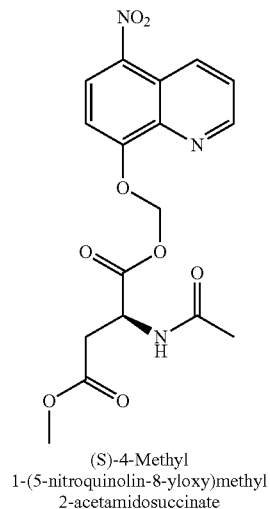<br>(S)-4-Methyl 1-(5-nitroquinolin-8-yloxy)methyl 2-acetamidosuccinate |

-continued
| Example No. | Structure and name |
|---|---|
| 15 | 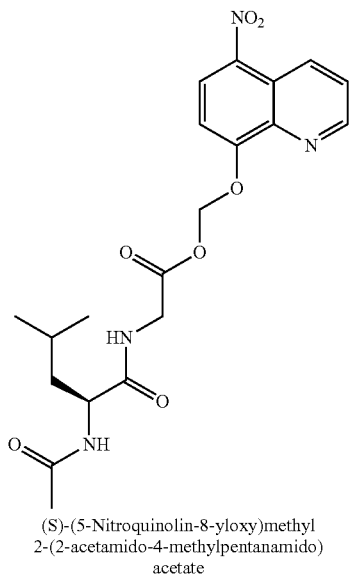<br>(S)-(5-Nitroquinolin-8-yloxy)methyl 2-(2-acetamido-4-methylpentanamido)acetate |
| 16 | 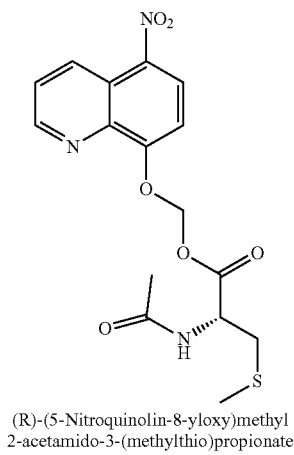<br>(R)-(5-Nitroquinolin-8-yloxy)methyl 2-acetamido-3-(methylthio)propionate |
| 17 | 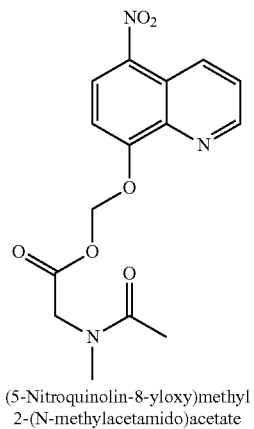<br>(5-Nitroquinolin-8-yloxy)methyl 2-(N-methylacetamido)acetate |

| Example No. | Structure and name |
|---|---|
| 18 | 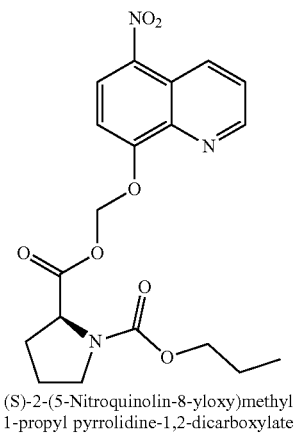<br>(S)-2-(5-Nitroquinolin-8-yloxy)methyl 1-propyl pyrrolidine-1,2-dicarboxylate |
| 19 | 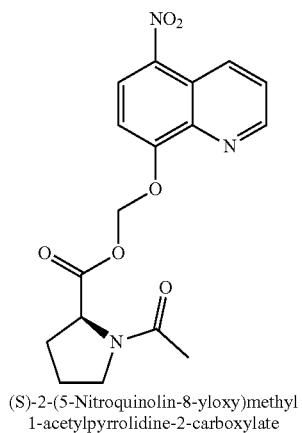<br>(S)-2-(5-Nitroquinolin-8-yloxy)methyl 1-acetylpyrrolidine-2-carboxylate |
| 20 | 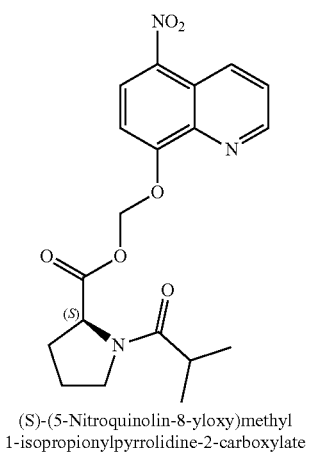<br>(S)-(5-Nitroquinolin-8-yloxy)methyl 1-isopropionylpyrrolidine-2-carboxylate |

| Example No. | Structure and name |
|---|---|
| 21 | 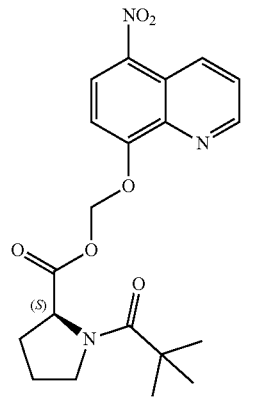<br>(S)-(5-Nitroquinolin-8-yloxy)methyl 1-pivaloylpyrrolidine-2-carboxylate |
| 22 | 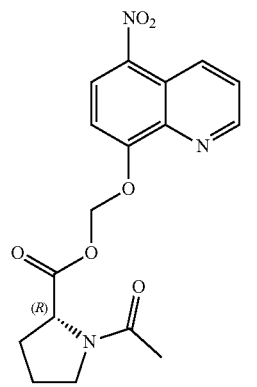<br>(R)-2-(5-Nitroquinolin-8-yloxy)methyl 1-acetylpyrrolidine-2-carboxylate |
| 23 | 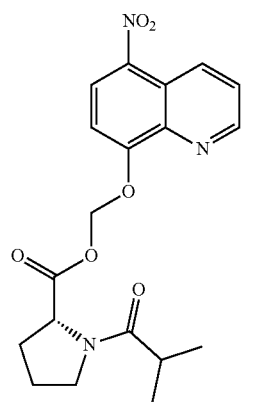<br>(R)-(5-Nitroquinolin-8-yloxy)methyl 1-isopropionylpyrrolidine-2-carboxylate |

| Example No. | Structure and name |
|---|---|
| 24 | 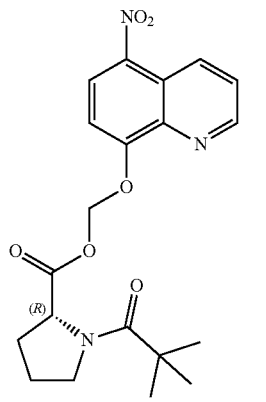<br>(R)-(5-Nitroquinolin-8-yloxy)methyl 1-pivaloylpyrrolidine-2-carboxylate |
| 25 | 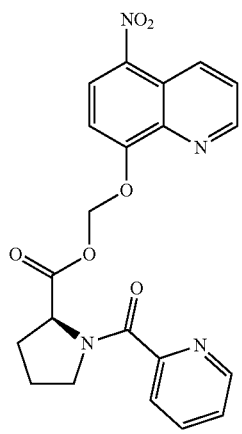<br>(S)-(5-Nitroquinolin-8-yloxy)methyl 1-pyridineformylpyrrolidine-2-carboxylate |
| 26 | 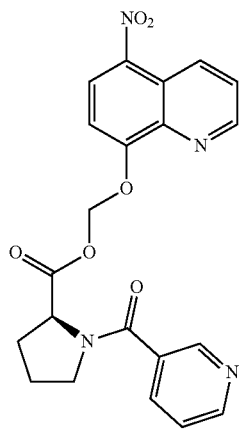<br>(S)-(5-Nitroquinolin-8-yloxy)methyl 1-nicotinoylpyrrolidine-2-carboxylate |

-continued
| Example No. | Structure and name |
|---|---|
| 27 | 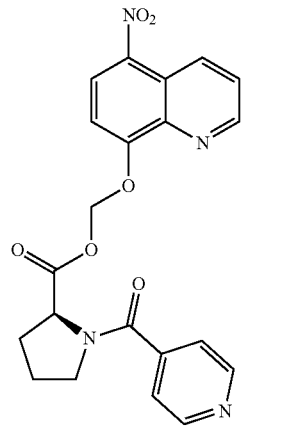<br>(S)-(5-Nitroquinolin-8-yloxy)methyl 1-isonicotinoylpyrrolidine-2-carboxylate |
| 28 | 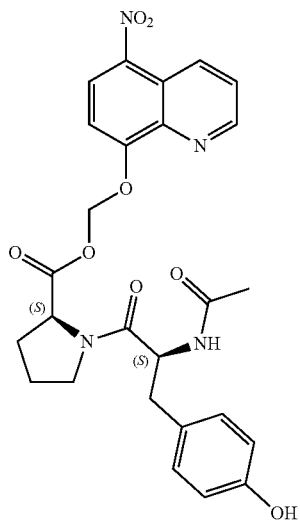<br>(S)-(5-Nitroquinolin-8-yloxy)methyl 1-((S)-2-acetamido-3-(4-hydroxyphenyl) propionyl)pyrrolidine-2-carboxylate |
| 29 | 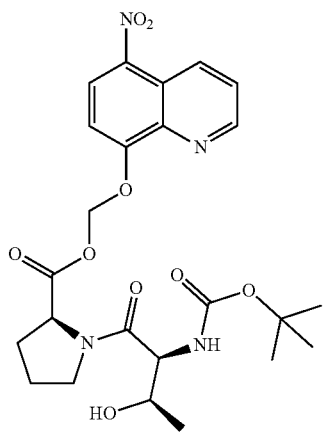<br>(S)-(5-Nitroquinolin-8-yloxy)methyl 1-((2S,3R)-2-(tert-butoxycarbonylamino)-3-hydroxybutyryl)pyrrolidine-2-carboxylate |

-continued
| Example No. | Structure and name |
|---|---|
| 30 | 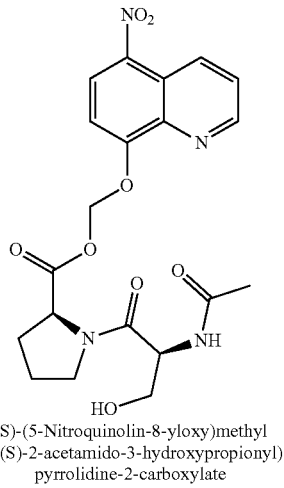
(S)-(5-Nitroquinolin-8-yloxy)methyl 1-((S)-2-acetamido-3-hydroxypropionyl) pyrrolidine-2-carboxylate |
| 31 | 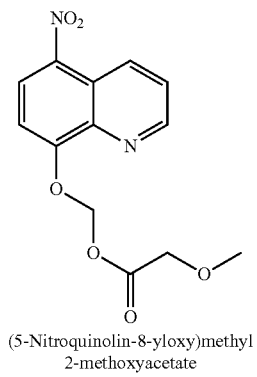
(5-Nitroquinolin-8-yloxy)methyl 2-methoxyacetate |
| 32 | 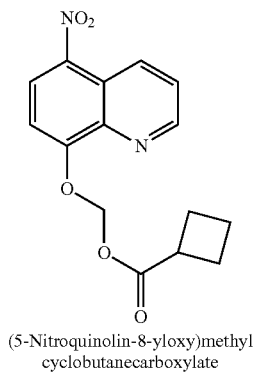
(5-Nitroquinolin-8-yloxy)methyl cyclobutanecarboxylate |
| 33 | 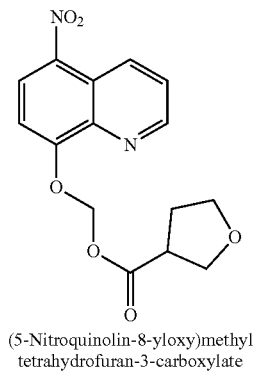
(5-Nitroquinolin-8-yloxy)methyl tetrahydrofuran-3-carboxylate |

| Example No. | Structure and name |
|---|---|
| 34 | 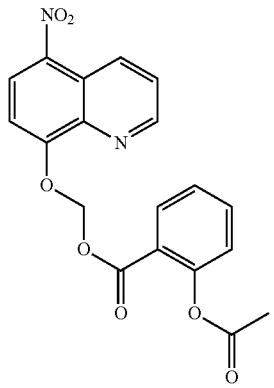<br>(5-Nitroquinolin-8-yloxy)methyl 2-acetoxybenzoate |
| 35 | 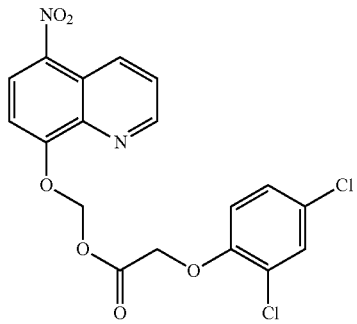<br>(5-Nitroquinolin-8-yloxy)methyl 2-(2,4-dichlorophenoxy)acetate |
| 36 | 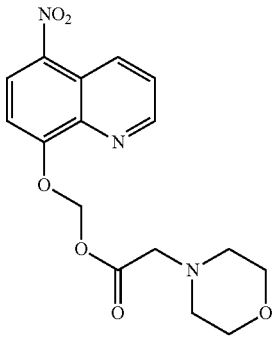<br>(5-Nitroquinolin-8-yloxy)methyl 2-morpholinoacetate |
| 37 | 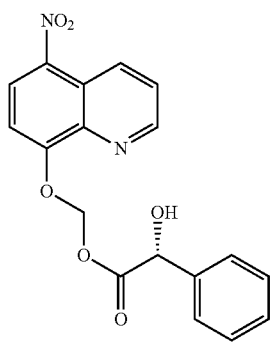<br>(R)-(5-Nitroquinolin-8-yloxy)methyl 2-hydroxy-2-phenylacetate |

| Example No. | Structure and name |
|---|---|
| 38 | 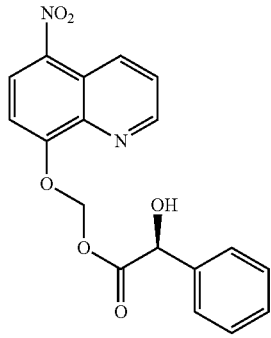<br>(S)-(5-Nitroquinolin-8-yloxy)methyl 2-hydroxy-2-phenylacetate |
| 39 | 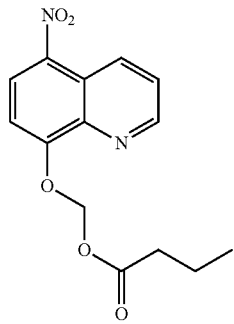<br>(5-Nitroquinolin-8-yloxy)methyl butyrate |
| 40 | 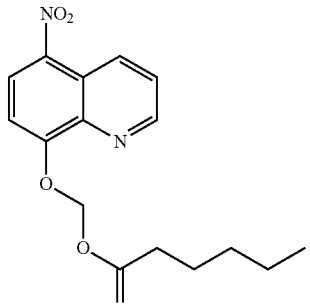<br>(5-Nitroquinolin-8-yloxy)methyl hexanoate |
| 41 | 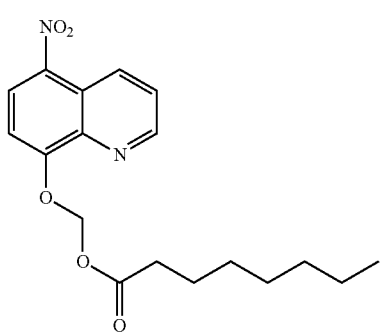<br>(5-Nitroquinolin-8-yloxy)methyl octanoate |

-continued
| Example No. | Structure and name |
|---|---|
| 42 | 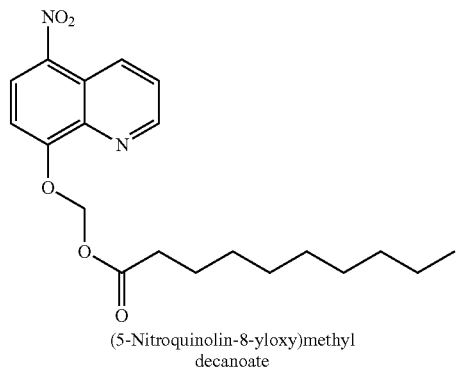<br>(5-Nitroquinolin-8-yloxy)methyl decanoate |
| 43 | 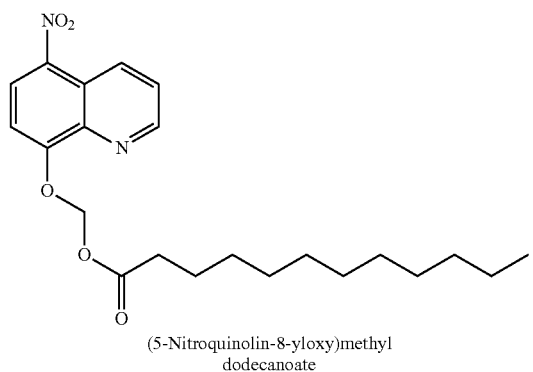<br>(5-Nitroquinolin-8-yloxy)methyl dodecanoate |
| 44 | 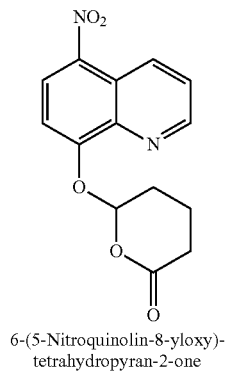<br>6-(5-Nitroquinolin-8-yloxy)-tetrahydropyran-2-one |
| 45 | 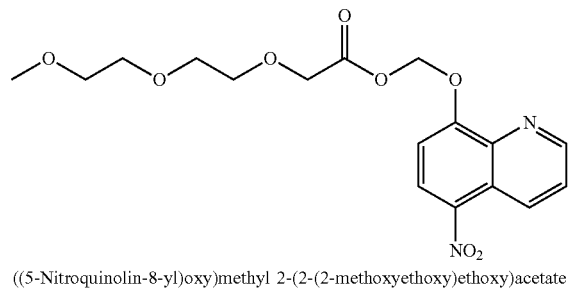<br>((5-Nitroquinolin-8-yl)oxy)methyl 2-(2-(2-methoxyethoxy)ethoxy)acetate |

-continued
| Example No. | Structure and name |
|---|---|
| 46 | 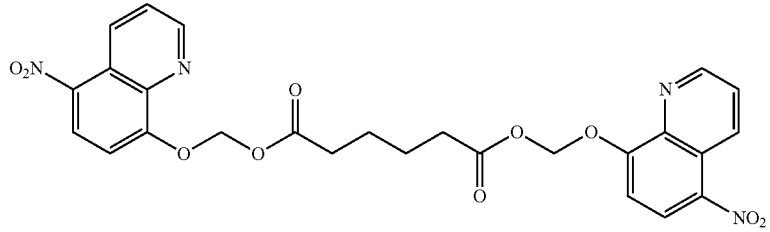
Bis(5-nitroquinolin-8-yloxy)-methyl adipate |
| 47 | 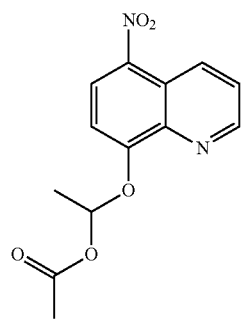
1-(5-Nitroquinolin-8-yloxy)ethyl acetate |
| 48 | 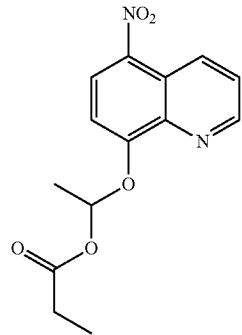
1-(5-Nitroquinolin-8-yloxy)ethyl propionate |
| 49 | 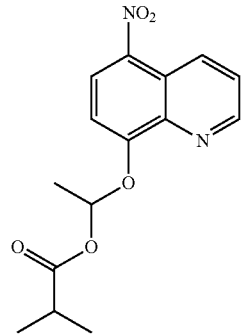
2-(5-Nitroquinolin-8-yloxy)ethyl isobutyrate |

| Example No. | Structure and name |
|---|---|
| 50 | 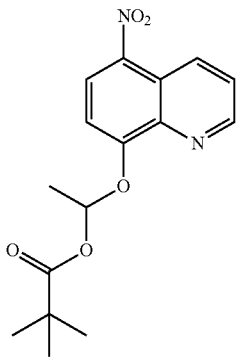<br>1-(5-Nitroquinolin-8-yloxy)ethyl pivalate |
| 51 | 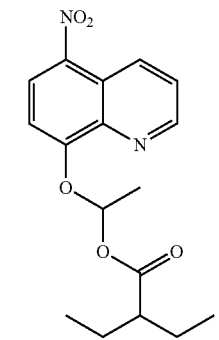<br>1-(5-Nitroquinolin-8-yloxy)ethyl 2-ethylbutanoate |
| 52 | 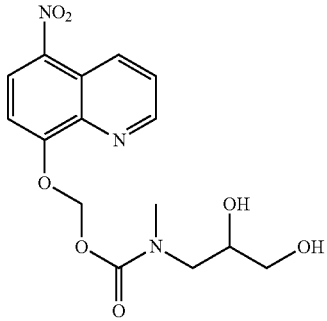<br>(5-Nitroquinolin-8-yloxy)methyl 2,3-dihydroxypropyl(methyl)carbamate |
| 53 | 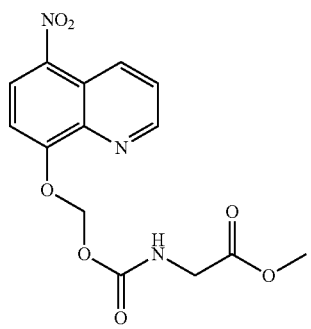<br>Methyl 2-(((5-nitroquinolin-8-yloxy)methoxy) formamido)acetate |

| Example No. | Structure and name |
|---|---|
| 54 | 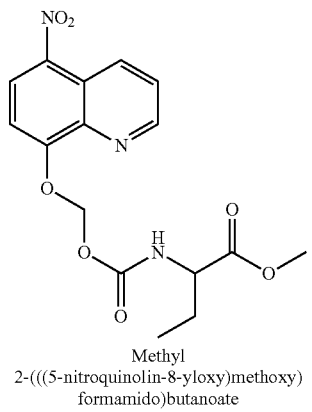<br>Methyl 2-(((5-nitroquinolin-8-yloxy)methoxy)formamido)butanoate |
| 55 | 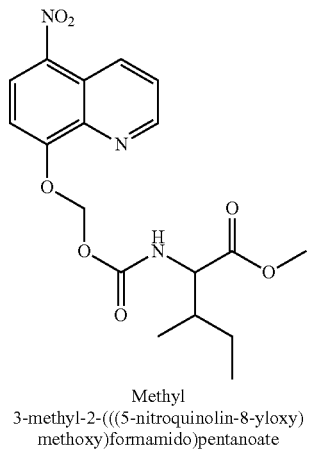<br>Methyl 3-methyl-2-(((5-nitroquinolin-8-yloxy)methoxy)formamido)pentanoate |
| 56 | 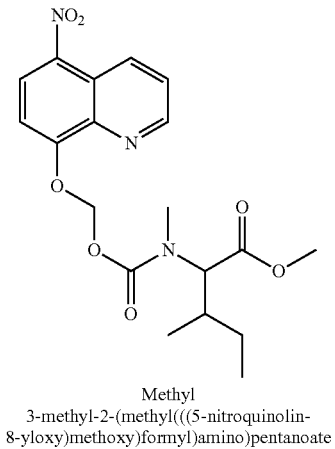<br>Methyl 3-methyl-2-(methyl(((5-nitroquinolin-8-yloxy)methoxy)formyl)amino)pentanoate |

| Example No. | Structure and name |
|---|---|
| 57 | 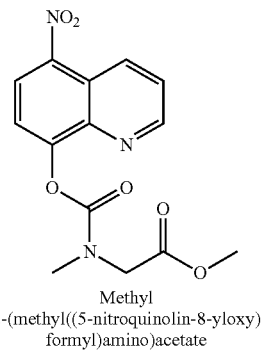
Methyl 2-(methyl((5-nitroquinolin-8-yloxy)formyl)amino)acetate |
| 58 | 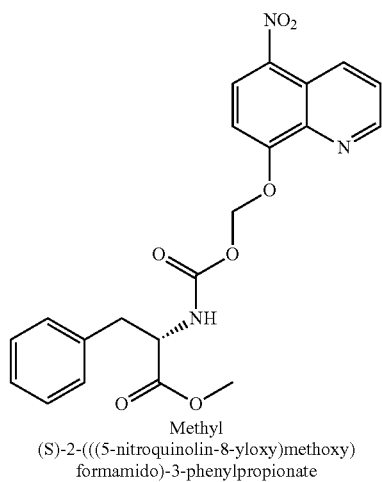
Methyl (S)-2-(((5-nitroquinolin-8-yloxy)methoxy)formamido)-3-phenylpropionate |
| 59 | 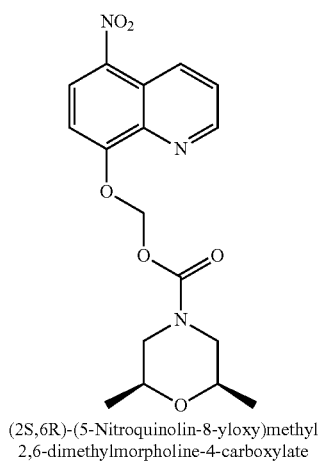
(2S,6R)-(5-Nitroquinolin-8-yloxy)methyl 2,6-dimethylmorpholine-4-carboxylate |

| Example No. | Structure and name |
|---|---|
| 60 | 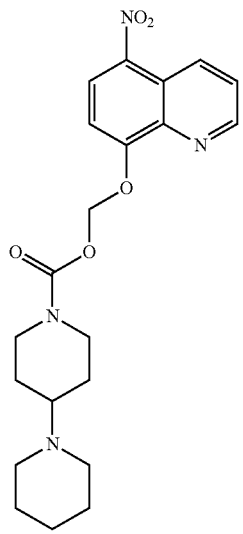<br>(5-Nitroquinoin-8-yloxy)methyl 1,4'-bipiperidine-1'-carboxylate |
| 61 | 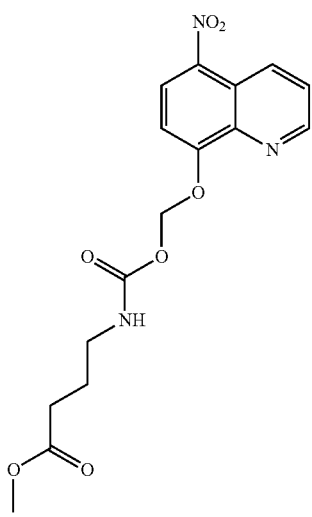<br>Methyl 4-(((5-nitroquinolin-8-yloxy)methoxy) formamido)butanoate |
| 62 | 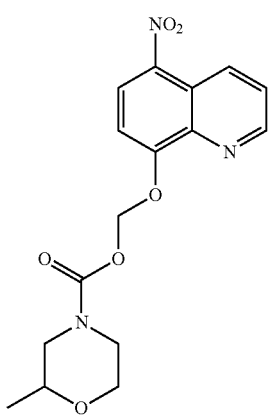<br>(5-Nitroquinolin-8-yloxy)methyl 2-methylmorpholine-4-carboxylate |

| Example No. | Structure and name |
|---|---|
| 63 | 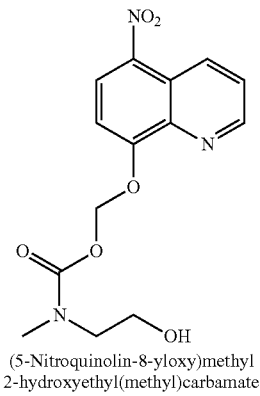<br>(5-Nitroquinolin-8-yloxy)methyl 2-hydroxyethyl(methyl)carbamate |
| 64 | 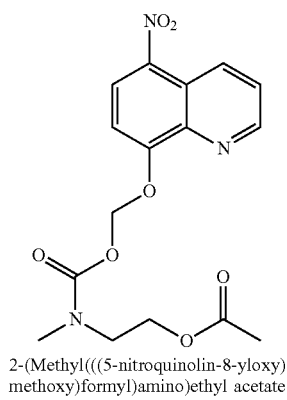<br>2-(Methyl(((5-nitroquinolin-8-yloxy)methoxy)formyl)amino)ethyl acetate |
| 65 | 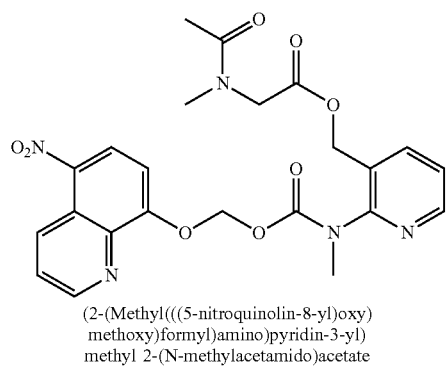<br>(2-(Methyl(((5-nitroquinolin-8-yl)oxy)methoxy)formyl)amino)pyridin-3-yl)methyl 2-(N-methylacetamido)acetate |
| 66 | 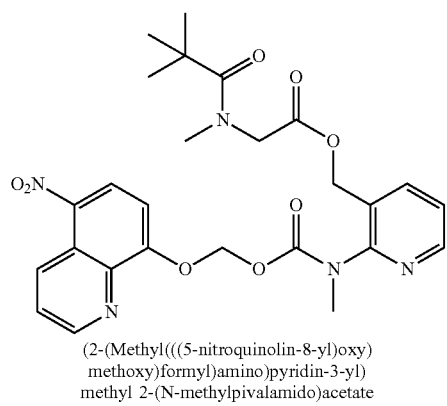<br>(2-(Methyl(((5-nitroquinolin-8-yl)oxy)methoxy)formyl)amino)pyridin-3-yl)methyl 2-(N-methylpivalamido)acetate |

| Example No. | Structure and name |
|---|---|
| 67 | 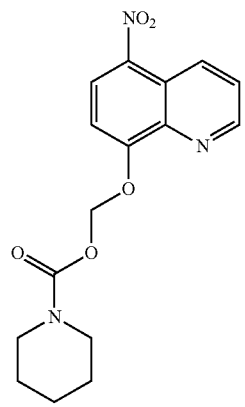<br>(5-Nitroquinolin-8-yloxy)methyl piperidine-1-carboxylate |
| 68 | 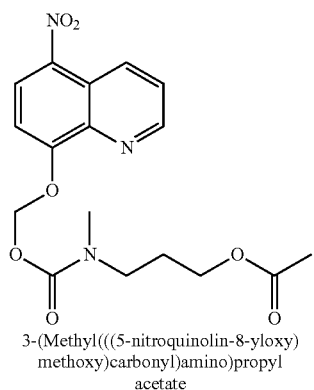<br>3-(Methyl(((5-nitroquinolin-8-yloxy)methoxy)carbonyl)amino)propyl acetate |
| 69 | 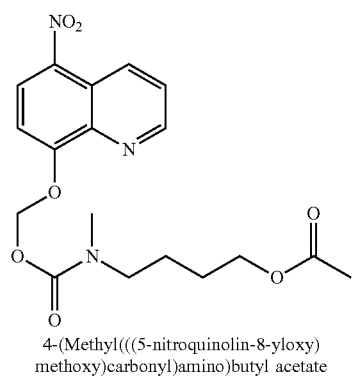<br>4-(Methyl(((5-nitroquinolin-8-yloxy)methoxy)carbonyl)amino)butyl acetate |

| Example No. | Structure and name |
|---|---|
| 70 | 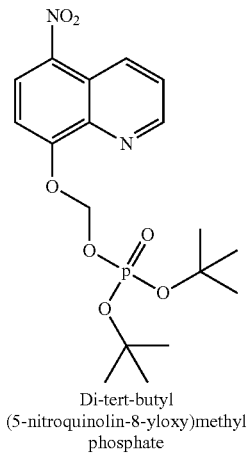<br>Di-tert-butyl (5-nitroquinolin-8-yloxy)methyl phosphate |
| 71 | 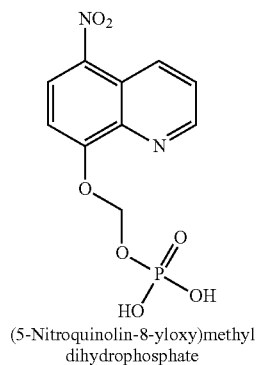<br>(5-Nitroquinolin-8-yloxy)methyl dihydrophosphate |
| 72 | 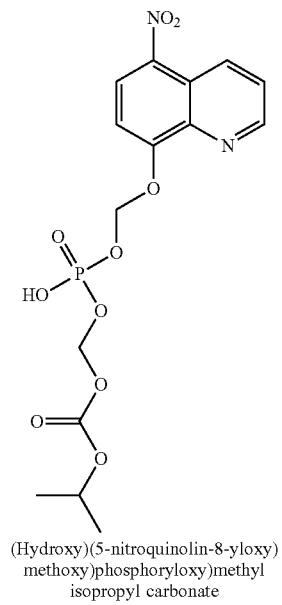<br>(Hydroxy)(5-nitroquinolin-8-yloxy) methoxy)phosphoryloxy)methyl isopropyl carbonate |

-continued
| Example No. | Structure and name |
|---|---|
| 73 | 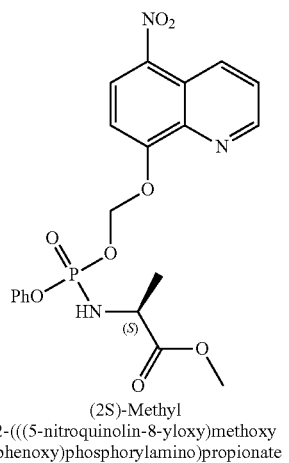<br>(2S)-Methyl 2-(((5-nitroquinolin-8-yloxy)methoxy (phenoxy)phosphorylamino)propionate |
| 74 | 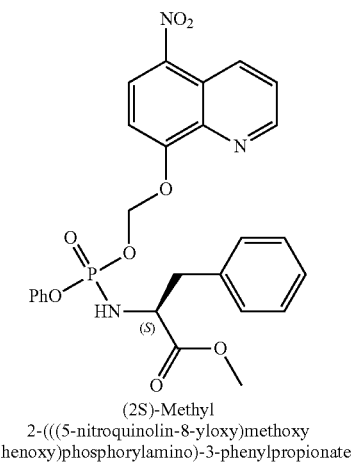<br>(2S)-Methyl 2-(((5-nitroquinolin-8-yloxy)methoxy (phenoxy)phosphorylamino)-3-phenylpropionate |
| 75 | 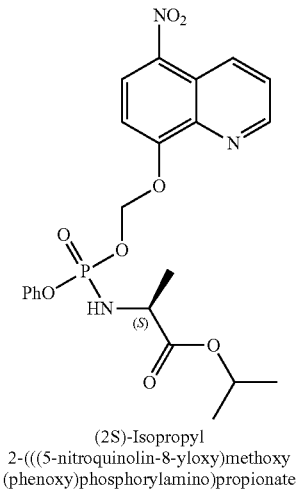<br>(2S)-Isopropyl 2-(((5-nitroquinolin-8-yloxy)methoxy (phenoxy)phosphorylamino)propionate |

-continued
| Example No. | Structure and name |
|---|---|
| 76 | 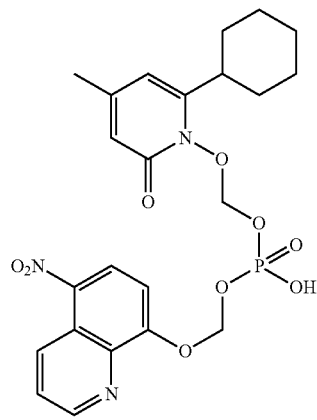
(6-Cyclohexyl-4-methyl-2-oxopyridin-1(2H)-yloxy)methyl (5-nitroquinolin-8-yloxy)methyl monohydrogenphosphate |
| 77 | 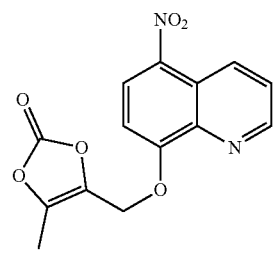
4-Methyl-5-((5-nitroquinolin-8-yloxy)methyl)-1,3-dioxol-2-one |
| 78 | 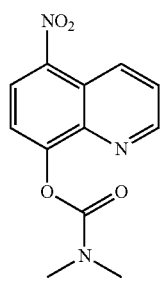
5-Nitroquinolin-8-yl dimethylcarbamate |
| 79 | 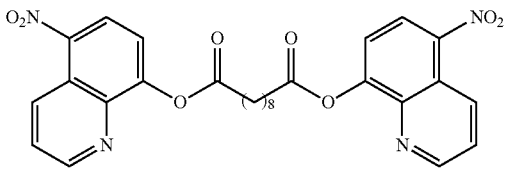
Bis(5-nitroquinolin-8-yl) sebate | or a mesomer, racemate, enantiomer, diastereomer thereof, or a mixture thereof, or a pharmaceutically acceptable salt thereof.

The present invention further relates to a method for preparing the compound of formula (II) or a mesomer, racemate, enantiomer, diastereomer thereof, or a mixture thereof, or a pharmaceutically acceptable salt thereof according to the present invention, comprising a step of:

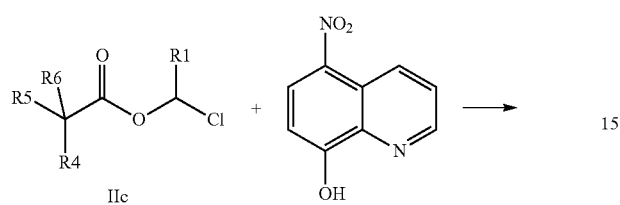

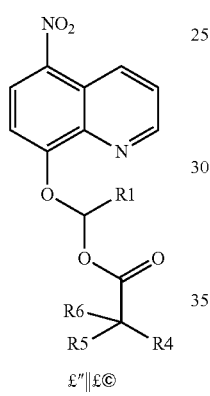

subjecting compound IIc and nitroxoline to a nucleophilic reaction in a solvent in the presence of an alkali to obtain the compound of formula (II);
wherein the alkali is preferably selected from the group consisting of potassium carbonate, sodium carbonate, potassium bicarbonate, sodium bicarbonate, triethylamine and pyridine; the solvent is preferably selected from the group consisting of dichloromethane, N,N-dimethylformamide, tetrahydrofuran and tert-butyl methyl ether;
$R_1$, $R_4$, $R_5$ and $R_6$ are as defined in formula (II).

The present invention further relates to a method for preparing the compound of formula (III) or a mesomer, racemate, enantiomer, diastereomer thereof, or a mixture thereof, or a pharmaceutically acceptable salt thereof according to the present invention, comprising a step of:

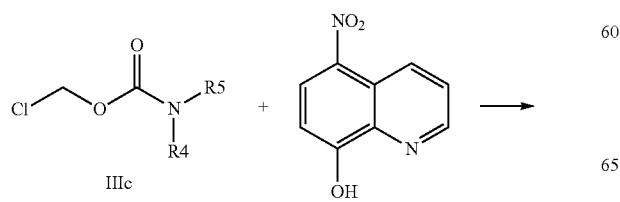

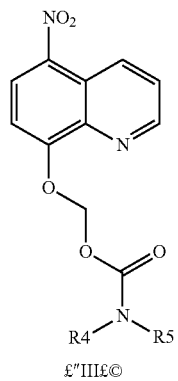

subjecting compound IIIc and nitroxoline to a nucleophilic reaction in a solvent in the presence of an alkali to obtain the compound of formula (III);
wherein the alkali is preferably selected from the group consisting of potassium carbonate, sodium carbonate, potassium bicarbonate, sodium bicarbonate, triethylamine and pyridine; the solvent is preferably selected from the group consisting of dichloromethane, N,N-dimethylformamide, tetrahydrofuran and tert-butyl methyl ether;
$R_4$ and $R_5$ are as defined in formula (III).

The present invention further relates to a method for preparing a compound of formula (II') or a mesomer, racemate, enantiomer, diastereomer thereof, or a mixture thereof, or a pharmaceutically acceptable salt thereof,

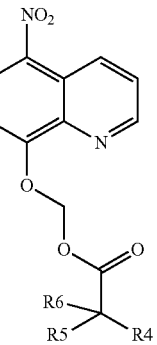

(II')

comprising a step of:

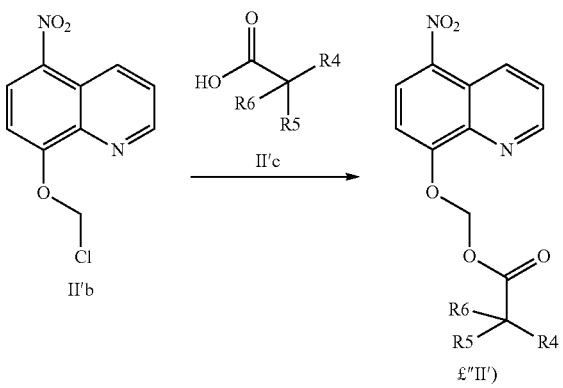

subjecting compound II'b and compound II'c to a nucleophilic reaction in a solvent in the presence of an alkali to obtain the compound of formula (II');

wherein the alkali is preferably selected from the group consisting of potassium carbonate, sodium carbonate, potassium bicarbonate, sodium bicarbonate, triethylamine and pyridine; the solvent is preferably selected from the group consisting of dichloromethane, N,N-dimethylformamide, tetrahydrofuran and tert-butyl methyl ether;

$R_4$, $R_5$ and $R_6$ are as defined in formula (II).

The present invention further relates to a method for preparing a compound of formula (V') or a mesomer, racemate, enantiomer, diastereomer thereof, or a mixture thereof, or a pharmaceutically acceptable salt thereof,

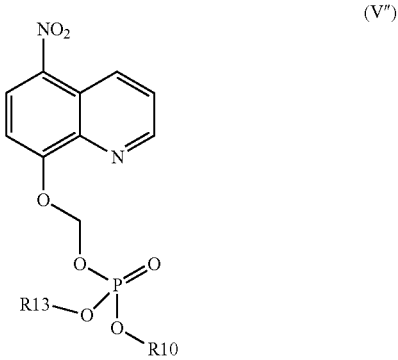

comprising a step of:

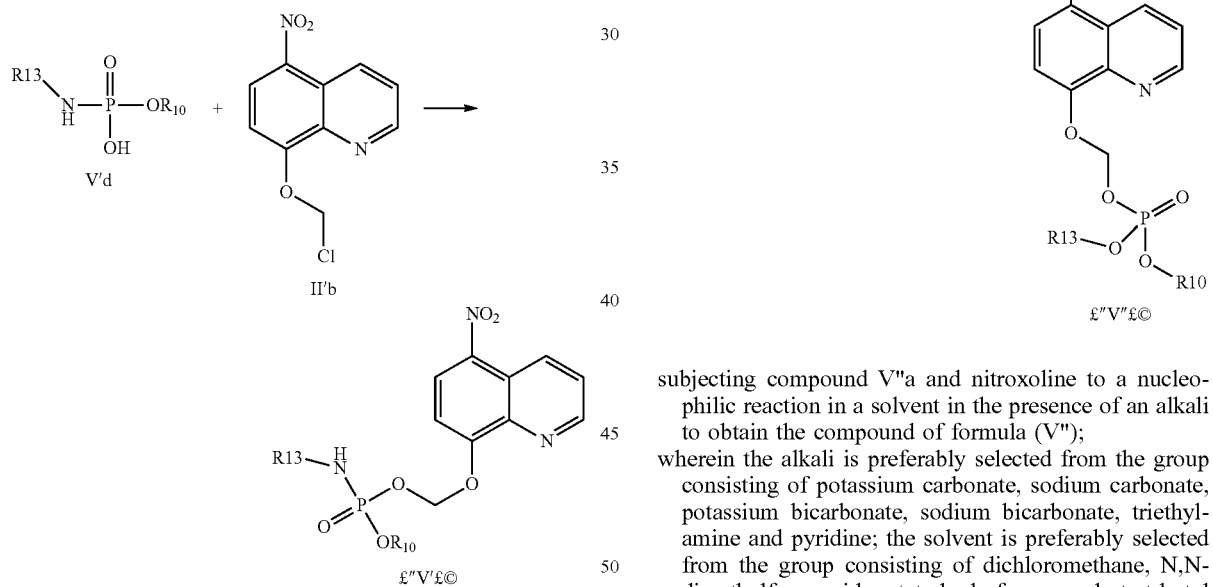

subjecting compound V'd and compound II'b to a nucleophilic reaction in a solvent in the presence of an alkali to obtain the compound of formula (V');
wherein the alkali is preferably selected from the group consisting of potassium carbonate, sodium carbonate, potassium bicarbonate, sodium bicarbonate, triethylamine and pyridine; the solvent is preferably selected from the group consisting of dichloromethane, N,N-dimethylformamide, tetrahydrofuran and tert-butyl methyl ether;

$R_{10}$ and $R_{13}$ are as defined in formula (V).

The present invention further relates to a method for preparing a compound of formula (V") or a mesomer, racemate, enantiomer, diastereomer thereof, or a mixture thereof, or a pharmaceutically acceptable salt thereof, comprising a step of:

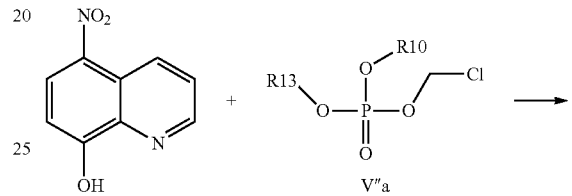

subjecting compound V"a and nitroxoline to a nucleophilic reaction in a solvent in the presence of an alkali to obtain the compound of formula (V");
wherein the alkali is preferably selected from the group consisting of potassium carbonate, sodium carbonate, potassium bicarbonate, sodium bicarbonate, triethylamine and pyridine; the solvent is preferably selected from the group consisting of dichloromethane, N,N-dimethylformamide, tetrahydrofuran and tert-butyl methyl ether;

$R_{10}$ and $R_{13}$ are as defined in formula (V).

The present invention further relates to a pharmaceutical composition comprising the compound of formula (I) or a mesomer, racemate, enantiomer, diastereomer thereof, or a mixture thereof, or a pharmaceutically acceptable salt thereof according to the present invention as the active ingredient, and a pharmaceutically acceptable carrier.

The present invention further relates to a use of the compound of formula (I) or a mesomer, racemate, enantiomer, diastereomer thereof, or a mixture thereof, or a pharmaceutically acceptable salt thereof, or the pharmaceutical composition comprising the same according to the present invention in the preparation of an anti-infective medicament or anti-tumor medicament, wherein the tumor can be a bladder cancer, prostate cancer or kidney cancer.

The pharmaceutically acceptable salt of the compound of formula (I) of the present invention can be an acid addition salt or a base addition salt. The acid can be an inorganic acid, including but not limited to hydrochloric acid, sulfuric acid, phosphoric acid, hydrobromic acid; or can be an organic acid, including but not limited to citric acid, maleic acid, oxalic acid, formic acid, acetic acid, propionic acid, valeric acid, glycolic acid, benzoic acid, fumaric acid, trifluoroacetic acid, succinic acid, tartaric acid, lactic acid, glutamic acid, aspartic acid, salicylic acid, pyruvic acid, methanesulfonic acid, benzenesulfonic acid, p-toluenesulfonic acid. The base can be an inorganic base, including but not limited to sodium hydroxide, potassium hydroxide, magnesium hydroxide, calcium hydroxide; or can be an organic base, including but not limited to ammonium hydroxide, triethylamine, N,N-dibenzyl ethylenediamine, chloroprocaine, choline, ammonia, diethanolamine and other hydroxyalkyl amines, ethylene diamine, N-methyl glucosamine, procaine, N-benzyl phenylethylamine, arginine or lysine; or can be an alkaline metal salt, including but not limited to lithium, potassium or sodium salts; or can be an alkaline earth metal salt, including but not limited to barium, calcium or magnesium salts; or can be a transition metal salt, including but not limited to zinc salt; or can be other metal salts, including but not limited to sodium hydrogen phosphate or disodium hydrogen phosphate.

In another aspect of the present invention, the compound of formula (I) or a pharmaceutically acceptable salt thereof is prepared into a clinically acceptable pharmaceutical composition. According to clinical indications, administration route and mode, such pharmaceutical composition includes, but is not limited to, oral formulations such as tablets, gels, soft/hard capsules, emulsions, dispersible powders, granules, aqueous/oily suspoemulsions; injections including intravenous injections, intramuscular injections, intraperitoneal injections, rectal administration suppositories, intracranial injections, which can be aqueous solutions or oil solutions; topical formulations including creams, ointments, gels, aqueous/oily solutions and inclusion formulations; inhalation dosage forms including fine powders, liquid aerosols, and various dosage forms suitable for implanting in body.

The pharmaceutical composition containing the active ingredient can be in a form suitable for oral administration, for example, a tablet, troche, lozenge, aqueous or oily suspension, dispersible powder or granule, emulsion, hard or soft capsule, syrup or elixir. An oral composition can be prepared according to any known method in the art for the preparation of pharmaceutical composition. Such composition can contain one or more ingredients selected from the group consisting of sweeteners, flavoring agents, colorants and preservatives, in order to provide a pleasing and palatable pharmaceutical formulation. The tablet contains the active ingredient in ada mixture with nontoxic, pharmaceutically acceptable excipients suitable for the preparation of tablets. These excipients can be inert excipients, such as calcium carbonate, sodium carbonate, lactose, calcium phosphate or sodium phosphate; granulating and disintegrating agents, such as microcrystalline cellulose, cross-linked sodium carboxymethyl cellulose, corn starch or alginic acid; binders, such as starch, gelatin, polyvinylpyrrolidone or acacia; and lubricants, such as magnesium stearate, stearic acid or talc. The tablet can be uncoated or coated by means of known techniques, which can mask drug taste or delay the disintegration and absorption of the active ingredient in the gastrointestinal tract, thereby providing sustained release over an extended period. For example, a water-soluble taste masking material can be used, such as hydroxypropyl methylcellulose or hydroxypropyl cellulose, or an extended release material can be used, such as ethyl cellulose, cellulose acetate butyrate.

An oral formulation can also be provided as hard gelatin capsules in which the active ingredient is mixed with an inert solid diluent, such as calcium carbonate, calcium phosphate or kaolin, or as soft gelatin capsules in which the active ingredient is mixed with a water-soluble carrier such as polyethylene glycol or an oil medium such as peanut oil, liquid paraffin or olive oil.

An aqueous suspension contains the active ingredient in admixture with an excipient suitable for the preparation of aqueous suspension. Such excipient is a suspending agent, such as sodium carboxymethylcellulose, methylcellulose, hydroxypropylmethylcellulose, sodium alginate, polyvinylpyrrolidone and acacia; a dispersant or humectant, which can be a naturally occurring phosphatide such as lecithin, or a condensation product of an alkylene oxide with fatty acid such as polyoxyethylene stearate, or a condensation product of ethylene oxide with a long chain aliphatic alcohol such as heptadecaethyleneoxy cetanol, or a condensation product of ethylene oxide with part esters derived from fatty acids and hexitols such as polyoxyethylene sorbitol monooleate, or a condensation product of ethylene oxide with partial esters derived from fatty acids and hexitol anhydrides such as polyoxyethylene sorbitan monooleate. The aqueous suspension can also contain one or more preservatives, such as ethylparaben or n-propylparaben, one or more colorants, one or more flavoring agents, and one or more sweeteners such as sucrose, saccharin or aspartame.

An oil suspension can be formulated by suspending the active ingredient in a vegetable oil such as peanut oil, olive oil, sesame oil or coconut oil, or in a mineral oil such as liquid paraffin. The oil suspension can contain a thickener, such as beeswax, hard paraffin or cetyl alcohol. The above sweetener and flavoring agent can be added to provide a palatable formulation. These compositions can be preserved by adding an antioxidant, such as butylated hydroxyanisole or α-tocopherol.

The active ingredient in admixture with the dispersants or wetting agents, suspending agent or one or more preservatives can be prepared as a dispersible powder or granule suitable for the preparation of an aqueous suspension by adding water. Suitable dispersants or wetting agents and suspending agents are as described above. Additional excipients, such as sweetening agents, flavoring agents and coloring agents, can also be added. These compositions are preserved by adding an antioxidant such as ascorbic acid.

The pharmaceutical composition of the present invention can also be in the form of an oil-in-water emulsion. The oil phase can be a vegetable oil such as olive oil or peanut oil, or a mineral oil such as liquid paraffin or a mixture thereof. Suitable emulsifying agent can be naturally occurring phosphatides, such as soy bean lecithin, and esters or partial esters derived from fatty acids and hexitol anhydrides such as sorbitan monooleate, and condensation products of said partial esters with ethylene oxide such as polyoxyethylene sorbitol monooleate. The emulsion can also contain a sweetener, flavoring agent, preservative and antioxidant. Syrup and elixir can be formulated with a sweetener, such as glycerol, propylene glycol, sorbitol or sucrose. Such formulations can also contain a moderator, a preservative, a colorant and an antioxidant.

The pharmaceutical composition of the present invention can be in the form of a sterile injectable aqueous solution. The acceptable vehicles and solvents that can be employed include water, Ringer's solution and isotonic sodium chloride solution. The sterile injectable formulation can be a sterile injectable oil-in-water microemulsion in which the active ingredient is dissolved in the oil phase. For example, the active ingredient can be firstly dissolved in a mixture of soybean oil and lecithin, the oil solution is then introduced into a mixture of water and glycerol and processed to form a microemulsion. The injectable solution or microemulsion can be introduced into a patient's bloodstream by local bolus injection. Alternatively, it can be advantageous to administrate the solution or microemulsion in such a way as to maintain a constant circulating concentration of the compound of the present invention. In order to maintain such a constant concentration, a continuous intravenous delivery device can be utilized.

The pharmaceutical composition of the present invention can be in the form of a sterile injectable aqueous or oily suspension for intramuscular and subcutaneous administration. Such a suspension can be formulated with suitable dispersants or wetting agents and suspending agents as described above according to known techniques. The sterile injectable formulation can also be a sterile injectable solution or suspension prepared in a nontoxic parenterally acceptable diluent or solvent, such as a solution prepared in 1,3-butanediol. Moreover, sterile fixed oils can easily be used as a solvent or suspending medium. For this purpose, any blending fixed oils including synthetic mono- or di-glyceride can be employed. Moreover, fatty acids such as oleic acid can also be employed in the preparation of an injection.

The compound of the present invention can be administrated in the form of a suppository for rectal administration. These pharmaceutical compositions can be prepared by mixing the drug with a suitable non-irritating excipient that is solid at ordinary temperatures, but liquid in the rectum, thereby melting in the rectum to release the drug. Such materials include cocoa butter, glycerin gelatin, hydrogenated vegetable oils, mixtures of polyethylene glycols with various molecular weights and fatty acid esters of polyethylene glycols.

It is well known to those skilled in the art that the dosage of a drug depends on a variety of factors including, but not limited to the following factors: activity of a specific compound, age of the patient, weight of the patient, general health of the patient, behavior of the patient, diet of the patient, administration time, administration route, excretion rate, drug combination and the like. In addition, the optimal treatment, such as treatment mode, daily dose of the compound of the present invention or the type of pharmaceutically acceptable salt thereof can be verified according to the traditional therapeutic regimens.

The present invention can contain a composition comprising the compound of formula (I) or the pharmaceutically acceptable salt, hydrate or solvate as an active ingredient, and a pharmaceutically acceptable carrier or excipient, which is formulated into a clinically acceptable formulation. The derivatives of the present invention can be used in combination with other active ingredients as long as they do not cause other adverse effects such as allergic reactions and the like. The compound of the present invention can be used as the sole active ingredient, and can also be used in combination with other therapies and other drugs. A combination therapy is achieved by administrating the individual therapeutic components simultaneously, separately or sequentially.

DETAILED DESCRIPTION OF THE INVENTION

Unless otherwise stated, the terms used in the specification and claims have the meanings described below.

The term "alkyl" refers to a saturated aliphatic hydrocarbon group, which is a straight or branched chain group comprising 1 to 20 carbon atoms, preferably an alkyl having 1 to 12 carbon atoms, and more preferably an alkyl having 1 to 6 carbon atoms.

Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. More preferably, the alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl group can be substituted or unsubstituted. When substituted, the substituent group(s) can be substituted at any available connection point. The substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl.

The term "alkenyl" refers to an alkyl group as defined above consisting of at least two carbon atoms and at least one carbon-carbon double bond, such as ethenyl, 1-propenyl, 2-propenyl, 1-, 2- or 3-butenyl and the like. The alkenyl group can be substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio and heterocyclylthio.

The term "alkynyl" refers to an alkyl group as defined above consisting of at least two carbon atoms and at least one carbon-carbon triple bond, such as ethynyl, propynyl, butynyl and the like. The alkynyl group can be substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio and heterocyclylthio.

The term "cycloalkyl" refers to a saturated or partially unsaturated monocyclic or polycyclic hydrocarbon substituent group having 3 to 20 carbon atoms, preferably 3 to 12 carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl having a spiro ring, fused ring or bridged ring.

The term "spiro cycloalkyl" refers to a 5 to 20 membered polycyclic group with individual rings connected through one common carbon atom (called a spiro atom), wherein one or more rings can contain one or more double bonds, but none of the rings has a completely conjugated π-electron system. The spiro cycloalkyl is preferably a 6 to 14 membered spiro cycloalkyl, and more preferably a 7 to 10 membered spiro cycloalkyl. According to the number of the spiro atoms shared between the rings, the spiro cycloalkyl can be divided into a mono-spiro cycloalkyl, a di-spiro cycloalkyl, or a poly-spiro cycloalkyl, and the spiro cycloalkyl is preferably a mono-spiro cycloalkyl or di-spiro cycloalkyl, and more preferably a 4-membered/4-membered, 4-membered/5-membered, 4-membered/6-membered, 5-membered/5-membered, or 5-membered/6-membered mono-spiro cycloalkyl. Non-limiting examples of spiro cycloalkyl include:

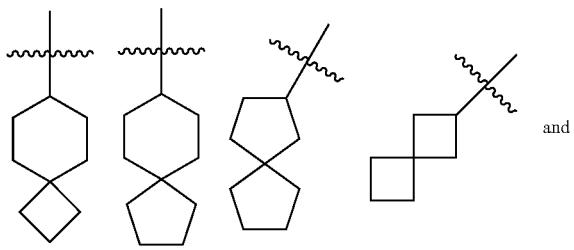

and

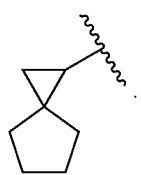

The term "fused cycloalkyl" refers to a 5 to 20 membered all-carbon polycyclic group, wherein each ring in the system shares an adjacent pair of carbon atoms with another ring, one or more rings can contain one or more double bonds, but none of the rings has a completely conjugated π-electron system. The fused cycloalkyl is preferably a 6 to 14 membered fused cycloalkyl, and more preferably a 7 to 10 membered fused cycloalkyl. According to the number of membered rings, the fused cycloalkyl can be divided into a bicyclic, tricyclic, tetracyclic or polycyclic fused cycloalkyl, and the fused cycloalkyl is preferably a bicyclic or tricyclic fused cycloalkyl, and more preferably a 5-membered/5-membered, or 5-membered/6-membered bicyclic fused cycloalkyl. Non-limiting examples of fused cycloalkyl include:

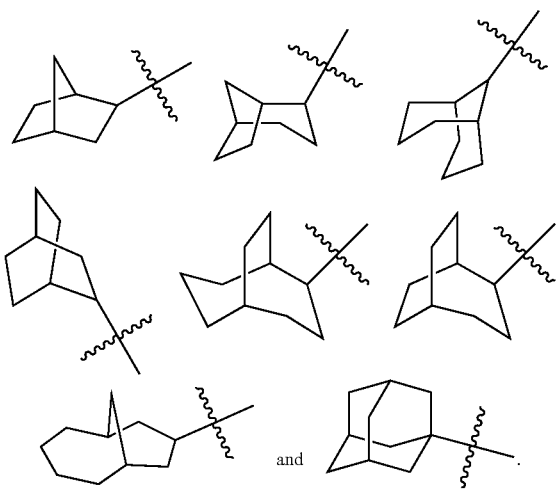

The term "bridged cycloalkyl" refers to a 5 to 20 membered all-carbon polycyclic group, wherein any two rings in the system share two disconnected carbon atoms, one or more rings can have one or more double bonds, but none of the rings has a completely conjugated π-electron system. The bridged cycloalkyl is preferably a 6 to 14 membered bridged cycloalkyl, and more preferably a 7 to 10 membered bridged cycloalkyl. According to the number of membered rings, the bridged cycloalkyl can be divided into a bicyclic, tricyclic, tetracyclic or polycyclic bridged cycloalkyl, and the bridged cycloalkyl is preferably a bicyclic, tricyclic or tetracyclic bridged cycloalkyl, and more preferably a bicyclic or tricyclic bridged cycloalkyl. Non-limiting examples of bridged cycloalkyl include:

The cycloalkyl ring can be fused to the ring of aryl, heteroaryl or heterocyclyl, wherein the ring linking to the parent structure is cycloalkyl. Non-limiting examples include indanyl, tetrahydronaphthyl, benzocycloheptyl and the like. The cycloalkyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl.

The term "heterocyclyl" refers to a 3 to 20 membered saturated or partially unsaturated monocyclic or polycyclic hydrocarbon group, wherein one or more ring atoms are heteroatoms selected from the group consisting of N, O and S(O)$_m$ (wherein m is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms; more preferably, 4 to 10 ring atoms wherein 1 to 3 atoms are heteroatoms; and most preferably 5 to 7 ring atoms wherein 1 to 2 or 1 to 3 atoms are heteroatoms. Non-limiting examples of monocyclic heterocyclyl include pyrrolidinyl, imidazolyl, tetrahydrofuranyl, tetrahydrothienyl, dihydroimidazolyl, dihydrofuranyl, dihydropyrazolyl, dihydropyrrolyl, piperidinyl, piperazinyl, morpholinyl, thiomorpholinyl, homopiperazinyl, pyranyl and the like, and preferably, 1,2,5-oxadiazolyl, pyranyl or morpholinyl. Polycyclic heterocyclyl includes a heterocyclyl having a spiro ring, fused ring or bridged ring.

The term "spiro heterocyclyl" refers to a 5 to 20 membered polycyclic heterocyclyl group with individual rings connected through one common atom (called a spiro atom), wherein one or more ring atoms are heteroatoms selected from the group consisting of N, O and S(O)$_m$ (wherein m is an integer of 0 to 2), with the remaining ring atoms being carbon atoms, and the rings can contain one or more double bonds, but none of the rings has a completely conjugated π-electron system. The spiro heterocyclyl is preferably a 6 to 14 membered spiro heterocyclyl, and more preferably a 7 to 10 membered spiro heterocyclyl. According to the number of the spiro atoms shared between the rings, the spiro heterocyclyl can be divided into a mono-spiro heterocyclyl, di-spiro heterocyclyl, or poly-spiro heterocyclyl, and the spiro heterocyclyl is preferably a mono-spiro heterocyclyl or di-spiro heterocyclyl, and more preferably a 4-membered/4-membered, 4-membered/5-membered, 4-membered/6-membered, 5-membered/5-membered, or 5-membered/6-membered mono-spiro heterocyclyl. Non-limiting examples of spiro heterocyclyl include:

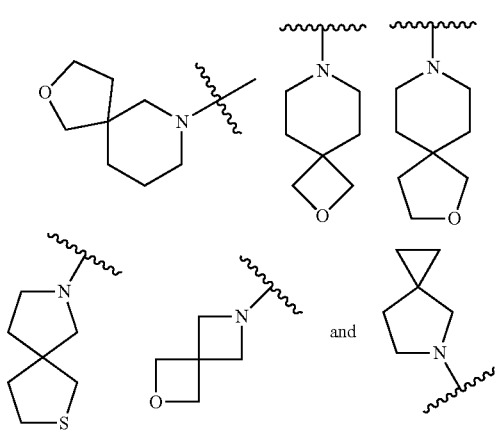

The term "fused heterocyclyl" refers to a 5 to 20 membered polycyclic heterocyclyl group, wherein each ring in the system shares an adjacent pair of atoms with another ring, one or more rings can contain one or more double bonds, but none of the rings has a completely conjugated π-electron system, and one or more ring atoms are heteroatoms selected from the group consisting of N, O and S(O)$_m$ (wherein m is an integer of 0 to 2), with the remaining ring atoms being carbon atoms. The fused heterocyclyl is preferably a 6 to 14 membered fused heterocyclyl, and more preferably a 7 to 10 membered fused heterocyclyl. According to the number of membered rings, the fused heterocyclyl can be divided into a bicyclic, tricyclic, tetracyclic or polycyclic fused heterocyclyl, and preferably a bicyclic or tricyclic fused heterocyclyl, and more preferably a 5-membered/5-membered or 5-membered/6-membered bicyclic fused heterocyclyl, Non-limiting examples of fused heterocyclyl include:

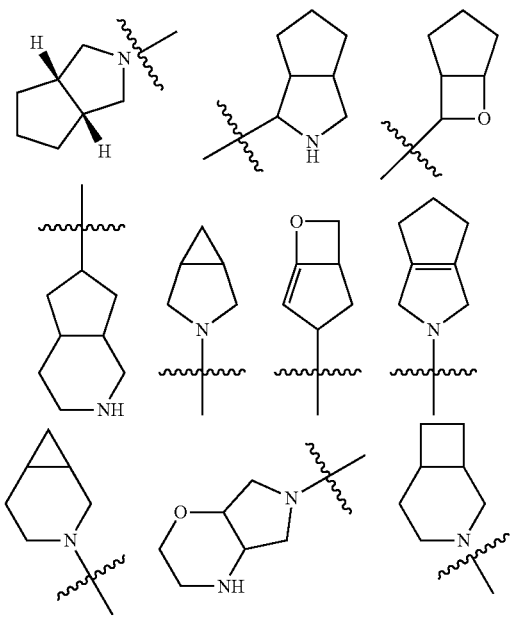

The term "bridged heterocyclyl" refers to a 5 to 14 membered polycyclic heterocyclyl group, wherein any two rings in the system share two disconnected atoms, wherein one or more rings can have one or more double bond(s), but none of the rings has a completely conjugated π-electron system, and one or more ring atoms are heteroatoms selected from the group consisting of N, O and S(O)$_m$ (wherein m is an integer of 0 to 2), with the remaining ring atoms being carbon atoms. The bridged heterocyclyl is preferably a 6 to 14 membered bridged heterocyclyl, and more preferably a 7 to 10 membered bridged heterocyclyl. According to the number of membered rings, the bridged heterocyclyl can be divided into a bicyclic, tricyclic, tetracyclic or polycyclic bridged heterocyclyl, and the bridged heterocyclyl is preferably a bicyclic, tricyclic or tetracyclic bridged heterocyclyl, and more preferably a bicyclic or tricyclic bridged heterocyclyl. Non-limiting examples of bridged heterocyclyl include:

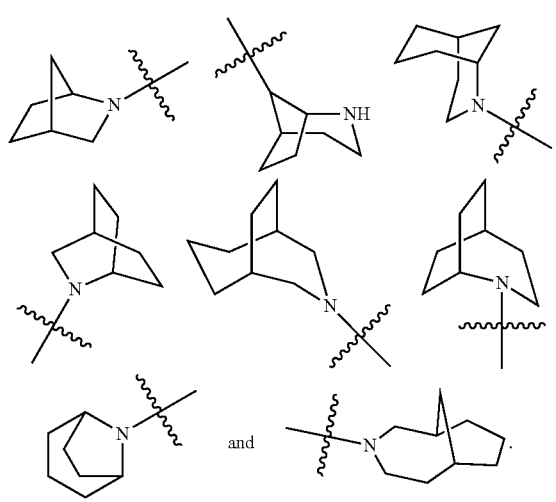

The heterocyclyl ring can be fused to the ring of aryl, heteroaryl or cycloalkyl, wherein the ring bound to the parent structure is heterocyclyl. Non-limiting examples thereof include:

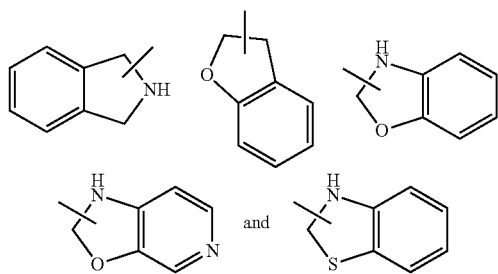

and the like.

The heterocyclyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl.

The term "aryl" refers to a 6 to 14 membered all-carbon monocyclic ring or polycyclic fused ring (i.e. each ring in the system shares an adjacent pair of carbon atoms with another ring in the system) having a conjugated 2-electron system, preferably a 6 to 10 membered aryl, for example, phenyl and naphthyl. The aryl is more preferably phenyl.

The aryl ring can be fused to the ring of heteroaryl, heterocyclyl or cycloalkyl, wherein the ring bound to the parent structure is aryl ring. Non-limiting examples thereof include:

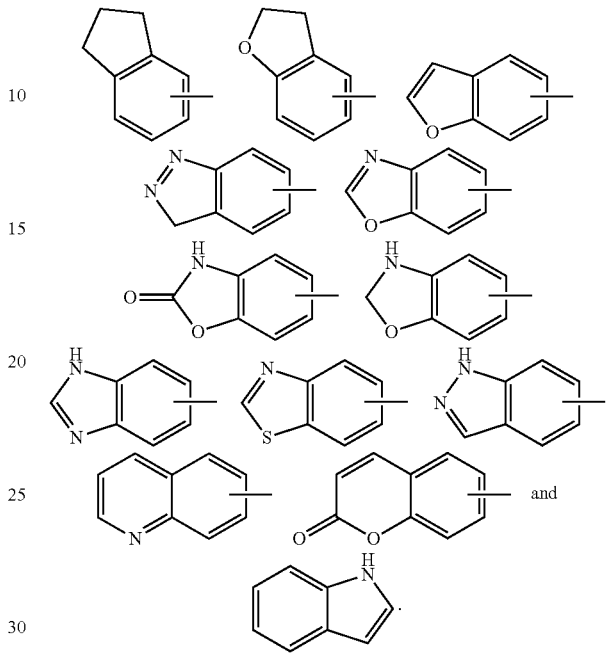

The aryl can be substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term "heteroaryl" refers to a 5 to 14 membered heteroaromatic system having 1 to 4 heteroatoms selected from the group consisting of O, S and N. The heteroaryl is preferably a 5 to 10 membered heteroaryl having 1 to 3 heteroatom(s), and more preferably a 5 or 6 membered heteroaryl having 1 to 2 heteroatom(s), for example imidazolyl, furyl, thienyl, thiazolyl, pyrazolyl, oxazolyl, pyrrolyl, tetrazolyl, pyridyl, pyrimidinyl, thiadiazolyl, pyrazinyl and the like, preferably imidazolyl, thiazolyl, pyrazolyl, pyrimidinyl or thiazolyl, and more preferably pyrazolyl or thiazolyl. The heteroaryl ring can be fused to the ring of aryl, heterocyclyl or cycloalkyl, wherein the ring bound to the parent structure is heteroaryl ring. Non-limiting examples thereof include:

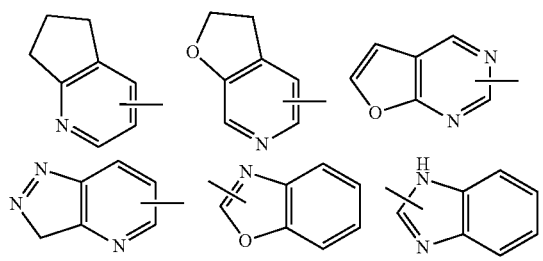

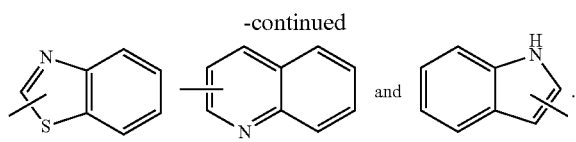

The heteroaryl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term "alkoxy" refers to an —O-(alkyl) or an —O-(unsubstituted cycloalkyl) group, wherein the alkyl is as defined above. Non-limiting examples of alkoxy include methoxy, ethoxy, propoxy, butoxy, cyclopropyloxy, cyclobutyloxy, cyclopentyloxy, cyclohexyloxy. The alkoxy can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term "haloalkyl" refers to an alkyl group substituted by one or more halogen(s), wherein the alkyl is as defined above.

The term "haloalkoxy" refers to an alkoxy group substituted by one or more halogen(s), wherein the alkoxy is as defined above.

The term "hydroxy" refers to an —OH group.

The term "halogen" refers to fluorine, chlorine, bromine or iodine.

The term "amino" refers to a —NH$_2$ group.

The term "cyano" refers to a —CN group.

The term "nitro" refers to a —NO$_2$ group.

The term "oxo" refers to a =O group.

The term "carboxy" refers to a —C(O)OH group.

The term "thiol" refers to a —SH group.

The term "alkoxycarbonyl" refers to a —C(O)O(alkyl) or a —C(O)O(cycloalkyl) group, wherein the alkyl and cycloalkyl are as defined above.

The term "acyl" refers to a compound comprising a —C(O)R group, where R is an alkyl, cycloalkyl, heterocyclyl, aryl or heteroaryl.

"Optional" or "optionally" means that the event or circumstance described subsequently can, but need not, occur, and such a description includes the situation in which the event or circumstance does or does not occur. For example, "the heterocyclyl optionally substituted by an alkyl" means that an alkyl group can be, but need not be, present, and such a description includes the situation of the heterocyclyl being substituted by an alkyl and the situation of the heterocyclyl being not substituted by an alkyl.

"Substituted" refers to one or more hydrogen atoms in a group, preferably up to 5, and more preferably 1 to 3 hydrogen atoms in a group, are independently substituted by a corresponding number of substituents. It goes without saying that the substituents only exist in their possible chemical position. The person skilled in the art is able to determine whether the substitution is possible or impossible by experiments or theory without excessive efforts. For example, the combination of amino or hydroxy having free hydrogen and carbon atoms having unsaturated bonds (such as olefinic) may be unstable.

A "pharmaceutical composition" refers to a mixture of one or more of the compounds according to the present invention or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to exert biological activity.

A "pharmaceutically acceptable salt" refers to a salt of the compound of the present invention, which is safe and effective in mammals and has the desired biological activity.

Synthesis Method of the Present Compound

In order to achieve the purpose of the present invention, the present invention applies the following synthetic schemes to prepare the compound of formula (I) of the present invention.

When the compound of formula (I) is a compound of formula (II), the compound of formula (II) is synthesized by the following Scheme 1:

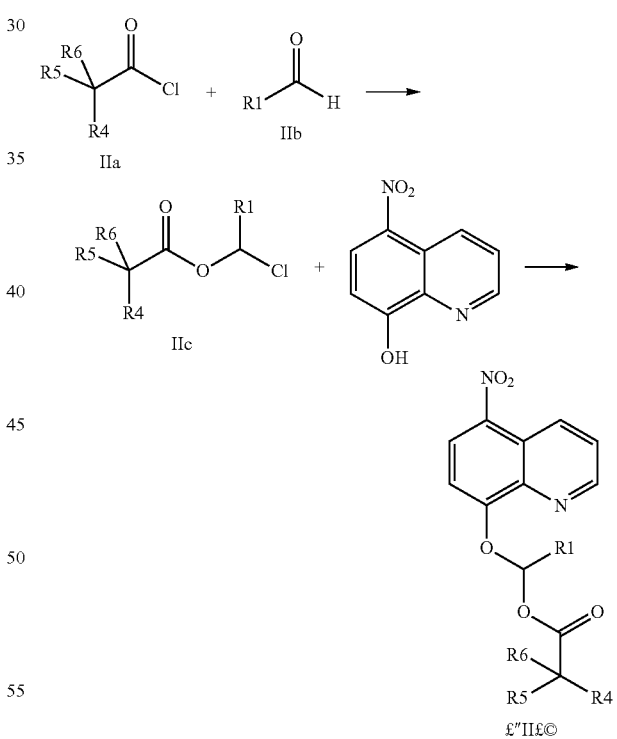

Step 1: acyl chloride compound IIa and aldehyde compound IIb are subjected to an insertion reaction in a solvent in the presence of an alkali and zinc chloride to obtain compound IIc; wherein the alkali is an inorganic alkali or an organic alkali, preferably potassium carbonate, sodium carbonate, potassium bicarbonate, sodium bicarbonate, triethylamine and pyridine; the solvent is preferably dichloromethane, N,N-dimethylformamide, tetrahydrofuran, tert-butyl methyl ether and the like.

Step 2: compound IIc and nitroxoline are subjected to a nucleophilic reaction in a solvent in the presence of an alkali to obtain the compound of formula (II); wherein the alkali is an inorganic alkali or an organic alkali, preferably potassium carbonate, sodium carbonate, potassium bicarbonate, sodium bicarbonate, triethylamine and pyridine; the solvent is preferably dichloromethane, N,N-dimethylformamide, tetrahydrofuran, tert-butyl methyl ether and the like.

When $R_1$ in the compound of formula (II) is hydrogen, the compound of formula (II') can also be synthesized by the following Scheme 2:

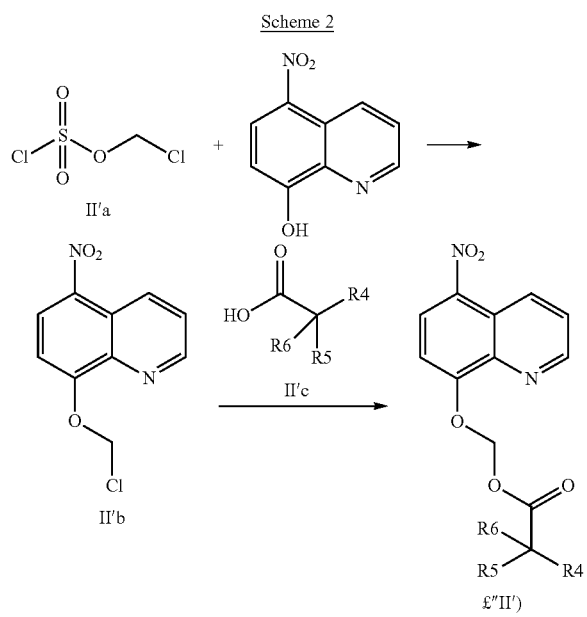

Step 1: sulfonyl chloride compound II'a and nitroxoline are subjected to a nucleophilic reaction in a solvent in the presence of an alkali to obtain compound II'b; wherein the alkali is an inorganic alkali or an organic alkali, preferably potassium carbonate, sodium carbonate, potassium bicarbonate, sodium bicarbonate, triethylamine and pyridine; the solvent is preferably dichloromethane, N,N-dimethylformamide, tetrahydrofuran, tert-butyl methyl ether and the like.

Step 2: compound II'b and compound II'c are subjected to a nucleophilic reaction in a solvent in the presence of an alkali to obtain the compound of formula (II'); wherein the alkali is an inorganic alkali or an organic alkali, preferably potassium carbonate, sodium carbonate, potassium bicarbonate, sodium bicarbonate, triethylamine and pyridine; the solvent is preferably dichloromethane, N,N-dimethylformamide, tetrahydrofuran, tert-butyl methyl ether and the like.

When the compound of formula (I) is a compound of formula (III), the compound of formula (III) is synthesized by the following Scheme 3:

Scheme 3

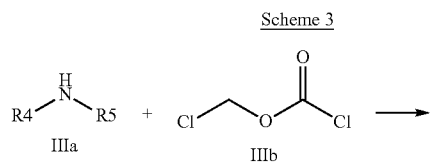

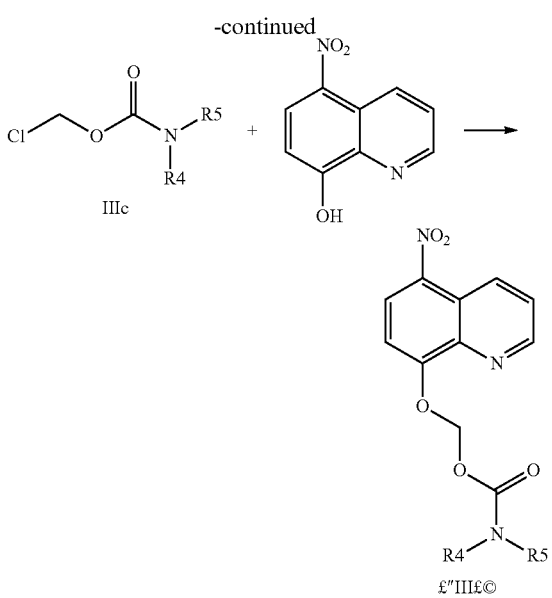

Step 1: amino compound IIIa and chloromethoxy acyl chloride compound IIb are subjected to an amide condensation reaction in a solvent in the presence of an alkali to obtain compound IIc; wherein the alkali is an inorganic alkali or an organic alkali, preferably potassium carbonate, sodium carbonate, potassium bicarbonate, sodium bicarbonate, triethylamine and pyridine; the solvent is preferably dichloromethane, N,N-dimethylformamide, tetrahydrofuran, tert-butyl methyl ether and the like.

Step 2: compound IIc and nitroxoline are subjected to a nucleophilic reaction in a solvent in the presence of an alkali to obtain the compound of formula (III); wherein the alkali is an inorganic alkali or an organic alkali, preferably potassium carbonate, sodium carbonate, potassium bicarbonate, sodium bicarbonate, triethylamine and pyridine; the solvent is preferably dichloromethane, N,N-dimethylformamide, tetrahydrofuran, tert-butyl methyl ether and the like.

When the compound of formula (I) is a compound of formula (V') or formula (V"), the compounds of formula (V') and formula (V") are synthesized by the following Scheme 4 and Scheme 5:

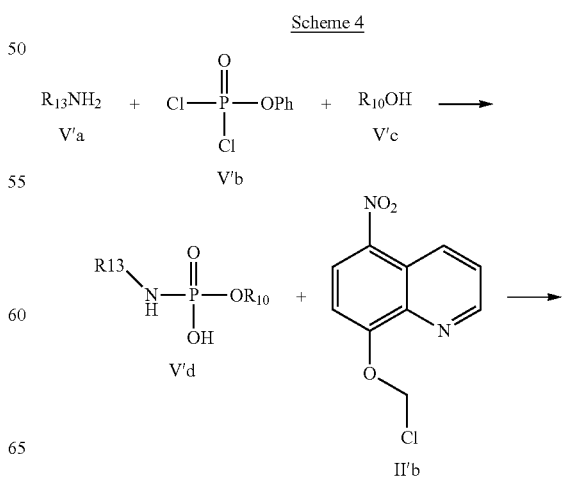

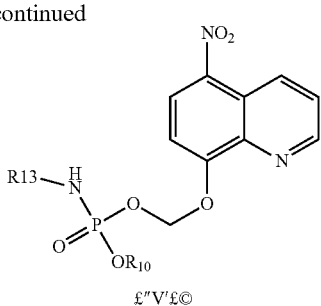

Step 1: amino compound V'a, phenoxy phosphoryl chloride compound V'b and hydroxy compound V'c are subjected to a condensation reaction in a solvent in the presence of an alkali to obtain compound V'd; wherein the alkali is an inorganic alkali or an organic alkali, preferably potassium carbonate, sodium carbonate, potassium bicarbonate, sodium bicarbonate, triethylamine and pyridine; the solvent is preferably dichloromethane, N,N-dimethylformamide, tetrahydrofuran, tert-butyl methyl ether and the like.

Step 2: compound V'd and compound II'b are subjected to a nucleophilic reaction in a solvent in the presence of an alkali to obtain the compound of formula (V'); wherein the alkali is an inorganic alkali or an organic alkali, preferably potassium carbonate, sodium carbonate, potassium bicarbonate, sodium bicarbonate, triethylamine and pyridine; the solvent is preferably dichloromethane, N,N-dimethylformamide, tetrahydrofuran, tert-butyl methyl ether and the like.

Scheme 5

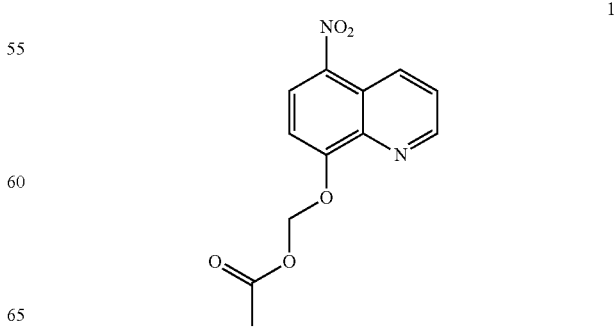

Compound V"a and nitroxoline are subjected to a nucleophilic reaction in a solvent in the presence of an alkali to obtain the compound of formula (V"); wherein the alkali is an inorganic alkali or an organic alkali, preferably potassium carbonate, sodium carbonate, potassium bicarbonate, sodium bicarbonate, triethylamine and pyridine; the solvent is preferably dichloromethane, N,N-dimethylformamide, tetrahydrofuran, tert-butyl methyl ether and the like.

Wherein, $R_1$, $R_4$, $R_5$, $R_6$, $R_{10}$ and $R_{13}$ are as defined in formula (I).

EXAMPLES

The present invention will be further described with reference to the following examples, but the examples should not be considered as limiting the scope of the present invention.

The structures of the compounds are identified by nuclear magnetic resonance (NMR) and/or mass spectrometry (MS). NMR shifts (δ) are given in $10^{-6}$ (ppm). NMR is determined by a Bruker AVANCE-400 machine. The solvents for determination are deuterated-dimethyl sulfoxide (DMSO-$d_6$), deuterated-chloroform (CDCl$_3$) and deuterated-methanol (CD$_3$OD), and the internal standard is tetramethylsilane (TMS).

MS is determined by a liquid chromatography-mass spectrometer (Thermo, Ultimate3000/MSQ).

HPLC is determined by a high pressure liquid chromatograph (Agilent 1260 Infinity, Gemini C18 250×4.6 mm, 5 u column).

Yantai Huanghai HSGF254 silica gel plate is used for the thin-layer silica gel chromatography (TLC). The dimension of the silica gel plate used in TLC is 0.15 mm to 0.2 mm, and the dimension of the silica gel plate used in product purification is 0.9 mm to 1.0 mm.

Yantai Huanghai 200 to 300 mesh silica gel is generally used as a carrier for silica gel column chromatography.

The known starting materials of the present invention can be prepared by the known methods in the art, or can be purchased from Shanghai Dari chemical Co. Ltd., Shanghai Titan Scientific Co. Ltd., Shanghai Rich Joint chemical Co. Ltd., TCI, Aldrich Chemical Company and the like. In the examples, the experiment methods that do not specify the specific conditions are generally conducted in accordance with conventional conditions, or in accordance with conditions recommended by the material or product manufacturers. The reagents without specific source are commercially available conventional reagents.

Unless otherwise stated, the reactions are carried out under argon atmosphere or nitrogen atmosphere. "Argon atmosphere" or "nitrogen atmosphere" means that a reaction flask is equipped with an argon or nitrogen balloon (about 1 L).

Unless otherwise stated, the solution refers to an aqueous solution.

Unless otherwise stated, the reaction temperature is room temperature from 20° C. to 30° C.

Example 1: Synthesis of (5-nitroquinolin-8-yloxy)methyl acetate (1)

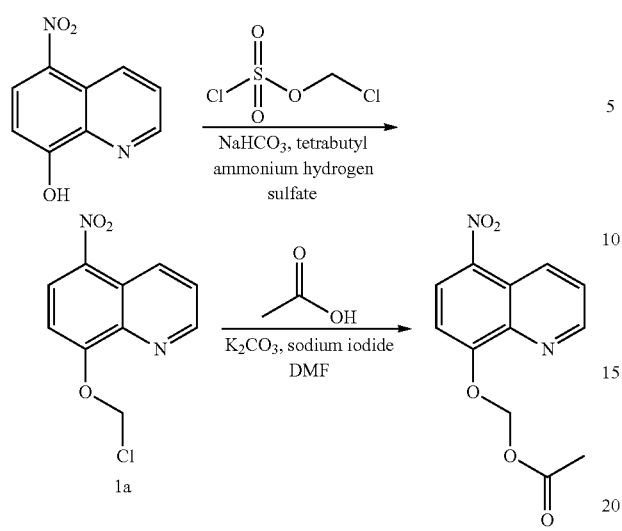

Step 1: Preparation of 5-nitro-8-chloromethoxyquinoline (1a)

Sodium bicarbonate aqueous solution (60 mL, 3.5 mol/L) and tetrabutyl ammonium hydrogen sulfate (TBAHS) (1.78 g, 5.24 mmol) were added to a solution of nitroxoline (10.00 g, 52.59 mmol) in dichloromethane (DCM) (100 mL) at room temperature, and the reaction solution was stirred for 20 minutes. Chloromethyl sulfurochloridate (10.42 g, 63.15 mmol) was added dropwise to the reaction system, followed by stirring at room temperature for 16 hours. The reaction solution was filtered. The organic phase was washed with potassium carbonate solution and saturated brine respectively, dried over anhydrous sodium sulfate, filtered and concentrated under reduced pressure. The residues were purified by silica gel column chromatography (eluent: dichloromethane) to obtain 5-nitro-8-chloromethoxyquinoline (2.5 g, yield: 20%).

Step 2: Preparation of (5-nitroquinolin-8-yloxy)methyl acetate (1)

Acetic acid (38 mg, 0.63 mmol), potassium carbonate (104 mg, 0.75 mmol) and sodium iodide (9 mg, 0.06 mmol) were added to N,N-dimethylformamide (3 mL) at room temperature and stirred well. The reaction system was warmed up to 60° C. and stirred for 10 minutes. 5-Nitro-8-chloromethoxyquinoline (150 mg, 0.63 mmol) was added, and the reaction solution was stirred for 1 hour. The reaction was quenched by water, and the solution was extracted with ethyl acetate. The organic phase was washed with saturated brine, dried over anhydrous sodium sulfate, filtered and concentrated under reduced pressure. The residues were purified by silica gel thin layer chromatography (eluent: 5% methanol/95% dichloromethane) to obtain (5-nitroquinolin-8-yloxy)methyl acetate (145 mg, yield: 88%).

$^1$H NMR (400 MHz, CDCl$_3$) δ 9.19 (dd, J=8.9, 1.6 Hz, 1H), 9.07 (dd, J=4.1, 1.6 Hz, 1H), 8.51 (d, J=8.8 Hz, 1H), 7.72 (dd, J=8.9, 4.1 Hz, 1H), 7.36 (d, J=8.8 Hz, 1H), 6.17 (s, 2H), 2.16 (s, 3H).

MS calculated: 262.2; MS observed: 263.1 [M+H]$^+$.

Example 2: Synthesis of (5-nitroquinolin-8-yloxy)methyl propionate (2)

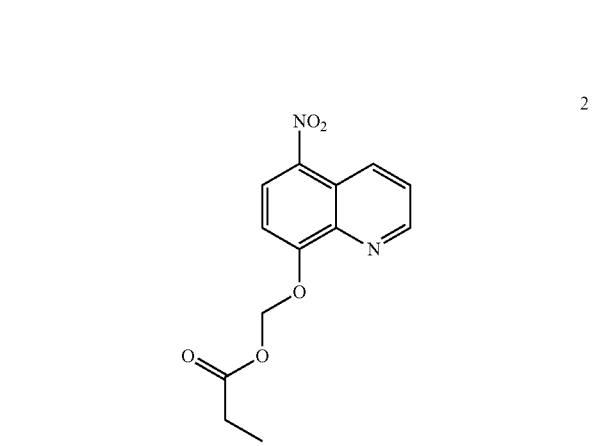

(5-Nitroquinolin-8-yloxy)methyl propionate (2) was obtained in accordance with the same preparation method of Example 1 except for replacing the acetic acid in Step 2 with propionic acid.

$^1$H NMR (400 MHz, CDCl$_3$) δ 9.19 (dd, J=8.9, 1.6 Hz, 1H), 9.07 (dd, J=4.1, 1.6 Hz, 1H), 8.50 (d, J=8.8 Hz, 1H), 7.72 (dd, J=8.9, 4.1 Hz, 1H), 7.37 (d, J=8.8 Hz, 1H), 6.19 (s, 2H), 2.44 (q, J=7.5 Hz, 2H), 1.17 (t, J=7.5 Hz, 3H).

MS calculated: 276.2; MS observed: 277.1 [M+H]$^+$.

Example 3: Synthesis of (5-nitroquinolin-8-yloxy)methyl isobutyrate (3)

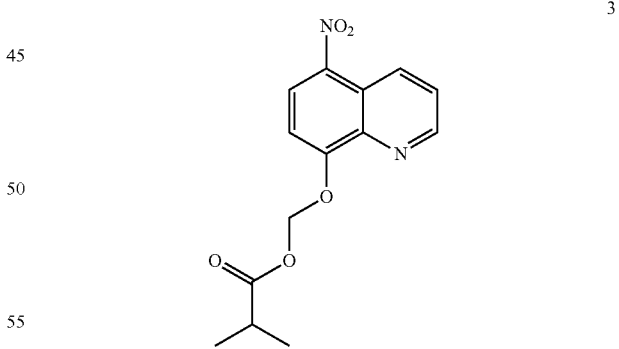

(5-Nitroquinolin-8-yloxy)methyl isobutyrate (3) was obtained in accordance with the same preparation method of Example 1 except for replacing the acetic acid in Step 2 with isobutyric acid.

$^1$H NMR (400 MHz, CDCl$_3$) δ 9.20 (dd, J=8.9, 1.6 Hz, 1H), 9.07 (dd, J=4.1, 1.6 Hz, 1H), 8.51 (d, J=8.8 Hz, 1H), 7.72 (dd, J=8.9, 4.1 Hz, 1H), 7.37 (d, J=8.8 Hz, 1H), 6.19 (s, 2H), 2.64 (hept, J=7.0 Hz, 1H), 1.19 (d, J=7.0 Hz, 6H).

MS calculated: 290.3; MS observed: 291.1 [M+H]$^+$.

Example 4: Synthesis of (5-nitroquinolin-8-yloxy)methyl pivalate (4)

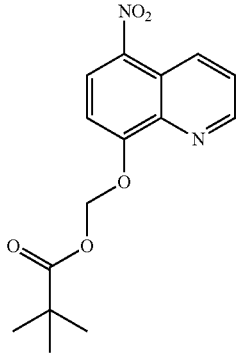 [SMILES: CC(C)(C)C(=O)OCOc1ccc([N+](=O)[O-])c2cccnc12]

4

(5-Nitroquinolin-8-yloxy)methyl pivalate (3) was obtained in accordance with the same preparation method of Example 1 except for replacing the acetic acid in Step 2 with pivalic acid.

$^1$H NMR (400 MHz, CDCl$_3$) δ 9.20 (dd, J=8.9, 1.6 Hz, 1H), 9.08 (dd, J=4.1, 1.6 Hz, 1H), 8.51 (d, J=8.8 Hz, 1H), 7.72 (dd, J=8.9, 4.1 Hz, 1H), 7.37 (d, J=8.8 Hz, 1H), 6.19 (s, 2H), 1.22 (s, 9H).

MS calculated: 304.3; MS observed: 305.1 [M+H]$^+$.

Example 5: Synthesis of (5-nitroquinolin-8-yloxy)methyl 2-ethylbutanoate (5)

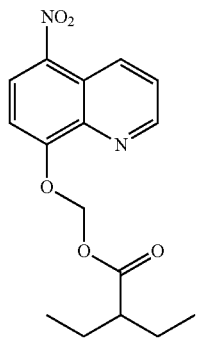 [SMILES: CCC(CC)C(=O)OCOc1ccc([N+](=O)[O-])c2cccnc12]

5

Potassium carbonate (9.59 g, 69.41 mmol) was added to a solution of nitroxoline (6.00 g, 35.55 mmol) and 1-chloromethyl 2-ethylbutanoate (10.00 g, 60.74 mmol) in N,N-dimethylformamide (100 mL) in batches at room temperature. The reaction solution was stirred at 60° C. for 16 hours. The reaction was quenched by water, and the solution was extracted with dichloromethane (100 mL×3). The organic phase was washed with 1 M hydrochloric acid, 1 M sodium bicarbonate aqueous solution and saturated brine, dried over anhydrous sodium sulfate, filtered and concentrated under reduced pressure. The residues were purified by silica gel column chromatography (eluent: 5% hexane/95% ethyl acetate) to obtain (5-nitroquinolin-8-yloxy)methyl 2-ethylbutanoate (1.4 g, yield: 14%).

$^1$H NMR (400 MHz, CD$_3$OD): δ 9.17-9.14 (m, 1H), 8.97-8.95 (m, 1H), 8.55 (d, J=8.8 Hz, 1H), 7.84-7.81 (m, 1H), 7.58 (d, J=8.8 Hz, 1H), 6.21 (s, 2H), 2.34-2.27 (m, 1H), 1.67-1.47 (m, 4H), 0.815 (t, J=7.2 Hz, 6H).

MS calculated: 318.1; MS observed: 319.1 [M+H]$^+$.

Example 6: Synthesis of (5-nitroquinolin-8-yloxy)methyl 4-methylpiperazine-1-carboxylate (6)

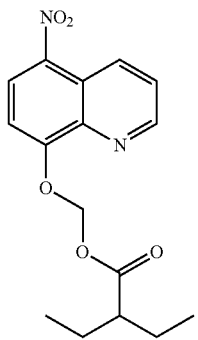

6

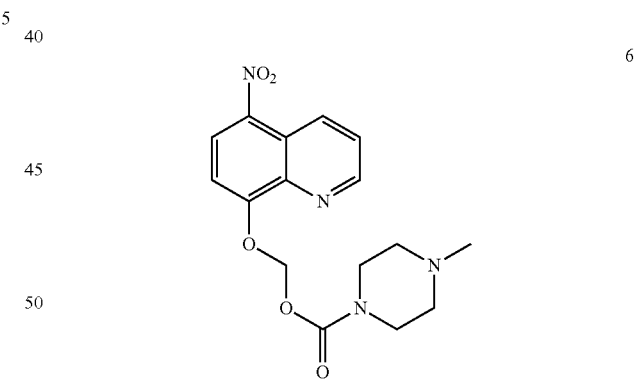

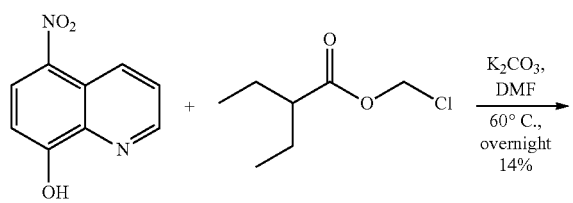

85

-continued

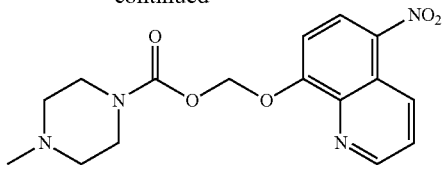

Step 1: Preparation of chloromethyl 4-methylpiperazine-1-carboxylate (6a)

1-Methylpiperazine (1 g, 10 mmol) was dissolved in dichloromethane (30 mL), and then slowly added dropwise with triethylamine (1.21 g, 12 mmol) and chloromethyl chloroformate (1.29 g, 10 mmol) successively under an ice-water bath. The reaction solution was stirred at 0° C. for 30 minutes and at 25° C. for 16 hours. Water (50 mL) was added to quench the reaction, and the solution was extracted with dichloromethane (100 mL×3). The organic phases were combined, dried over anhydrous sodium sulfate and filtered. The filtrate was concentrated under reduced pressure to obtain chloromethyl 4-methylpiperazine-1-carboxylate (1.7 g, yield: 89%).

Step 2: Preparation of (5-nitroquinolin-8-yloxy)methyl 4-methylpiperazine-1-carboxylate (6)

Nitroxoline (600 mg, 3.16 mmol) and chloromethyl 4-methylpiperazine-1-carboxylate (915 mg, 4.74 mmol) were dissolved in N,N-dimethylformamide (15 mL). Potassium carbonate (870 mg, 6.31 mmol) and sodium iodide (45 mg, 0.32 mmol) were added at 0° C. The reaction solution was stirred at 60° C. for 4 hours. The reaction solution was cooled to room temperature, quenched with water and extracted with dichloromethane (100 mL×3). The organic phases were combined, dried over anhydrous sodium sulfate and filtered. The filtrate was concentrated under reduced pressure. The residues were purified by silica gel column chromatography (eluent: 5% methanol/95% dichloromethane) to obtain the product (5-nitroquinolin-8-yloxy)methyl 4-methylpiperazine-1-carboxylate (150 mg, yield: 14%) as a yellow solid.

$^1$H NMR (400 MHz, CDCl$_3$) δ: 9.20 (dd, J=8.8, 1.6 Hz, 1H), 9.06 (dd, J=4.0, 1.2 Hz, 1H), 8.51 (d, J=8.8 Hz, 1H), 7.72 (dd, J=8.8, 4.4 Hz, 1H), 7.41 (d, J=8.4 Hz, 1H), 6.21 (s, 2H), 3.52 (dd, J=10.0, 4.8 Hz, 4H), 2.39 (t, J=4.8 Hz, 2H), 2.32 (t, J=4.8 Hz, 2H), 2.28 (s, 3H).

MS calculated: 346.13; MS observed: 347.1 [M+H]$^+$.

Example 7: Synthesis of (5-nitroquinolin-8-yloxy)methyl morpholine-4-carboxylate (7)

(5-Nitroquinolin-8-yloxy)methyl morpholine-4-carboxylate was obtained in accordance with the same preparation method of Example 6 except for replacing the 1-methylpiperazine in Step 1 with morpholine.

$^1$H NMR (400 MHz, CDCl$_3$) δ: 9.20-9.18 (s, 1H), 9.07-9.06 (s, 1H), 8.50 (d, J=8.8 Hz, 1H), 7.73-7.70 (m, 1H), 7.40 (d, J=8.8 Hz, 1H), 6.22 (s, 2H), 3.68 (s, 2H), 3.61 (s, 2H), 3.50 (s, 4H).

MS calculated: 333; MS observed: 334 [M+H]$^+$.

86

Example 8: Synthesis of 4-((5-nitroquinolin-8-yloxy)methoxy)-4-oxobutanoic acid (8)

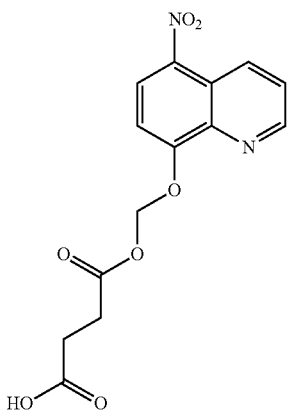 [SMILES: O=C(O)CCC(=O)OCOc1ccc([N+](=O)[O-])c2cccnc12]

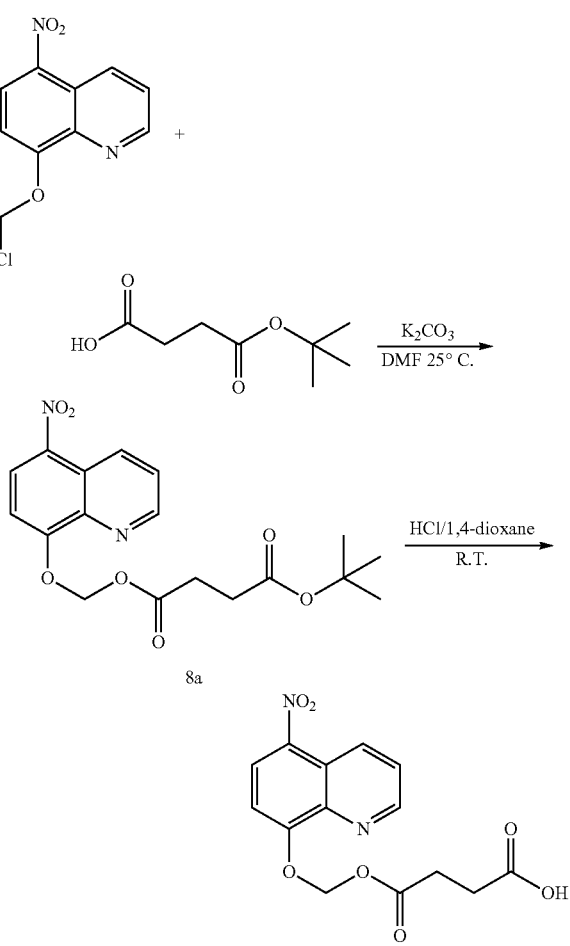

Step 1: Preparation of tert-butyl (((5-nitroquinolin-8-yl)oxy)methyl) succinate (8a)

8-(Chloromethoxy)-5-nitroquinoline (400 mg, 1.68 mmol) and 4-(tert-butoxy)-4-oxobutanoic acid (584 mg, 3.36 mmol) were dissolved in DMF (10 mL), followed by the addition of potassium carbonate (463 mg, 3.36 mmol). The reaction solution was stirred at 25° C. for 3 hours. The reaction was quenched by water (100 mL), and the solution was extracted with ethyl acetate (20 mL×2). The organic phases were combined, dried over anhydrous sodium sulfate and filtered. The filtrate was concentrated under reduced pressure. The residues were purified by silica gel column chromatography (PE:EA=1:1) to obtain 310 mg of the product tert-butyl (((5-nitroquinolin-8-yl)oxy)methyl) succinate.

Step 2: Preparation of 4-((5-nitroquinolin-8-yloxy)methoxy)-4-oxobutanoic acid (8)

Tert-butyl (((5-nitroquinolin-8-yl)oxy)methyl) succinate (230 mg, 0.718 mmol) was added to 10 mL of HCl/dioxane, and the reaction solution was stirred at room temperature for 20 minutes. The reaction solution was concentrated under reduced pressure to obtain the product 4-((5-nitroquinolin-8-yloxy)methoxy)-4-oxobutanoic acid (128 mg, yield: 65%) as a yellow solid.

$^1$H-NMR (400 MHz, DMSO-$d_6$) δ: 12.3 (br, 1H). 9.05 (d, J=2.8 Hz, 1H), 9.00 (d, J=8.8 Hz, 1H), 8.55 (d, J=8.8 Hz, 1H), 7.87 (dd, J=8.8, 4.0 Hz, 1H), 7.54 (d, J=8.8 Hz, 1H), 6.14 (s, 2H), 2.60~2.65 (m, 2 Hz, 4H), 2.50~2.55 (m, 2H).

MS calculated: 320.26; MS observed: 321.1 [M+H]$^+$.

Example 9: Synthesis of (5-nitroquinolin-8-yloxy)methyl 2-(pyridin-3-yl)acetate (9)

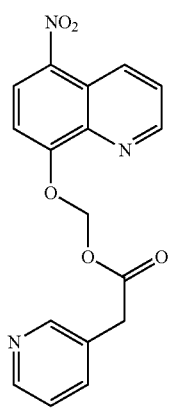

9

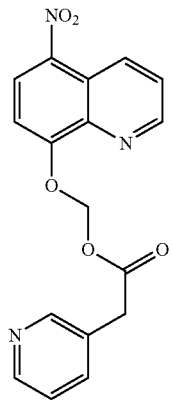

5-Nitro-8-chloromethoxyquinoline (1a) (250 mg, 1.05 mmol) was dissolved in DMF (10 mL). 3-Pyridineacetic acid (186 mg, 1.05 mmol) and triethylamine (510 mg, 5.25 mmol) were then added, and the reaction solution was stirred at room temperature for 2 hours. The reaction solution was concentrated under reduced pressure, and the residues were purified by silica gel column chromatography (PE:EA=1:1~0:1) to obtain the product ((5-nitroquinolin-8-yl)oxy)methyl 2-(pyridin-3-yl)acetate (90 mg, yield: 26%, purity: 97%) as a green solid.

$^1$H NMR (400 MHz, DMSO-$d_6$) δ: 8.95~9.10 (d, 2H), 8.47~8.54 (d, 2H), 7.33~7.89 (m, 4H), 7.54 (d, J=8.4 Hz, 1H), 6.18 (s, 2H), 3.89 (s, 2H), 4.72~4.75 (m, 2H).

MS calculated: 339.31; MS observed: 340.1[M+H]$^+$.

Example 10: Synthesis of (5-nitroquinolin-8-yloxy)methyl 8-hydroxyoctanoate

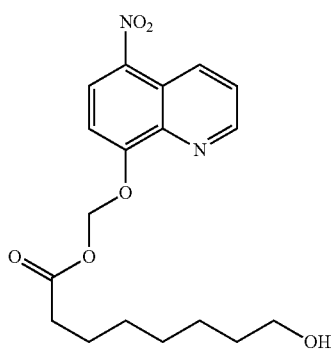 [SMILES: O=C(CCCCCCCO)OCOc1ccc([N+](=O)[O-])c2cccnc12]

10

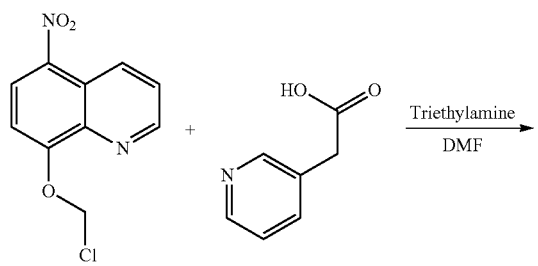

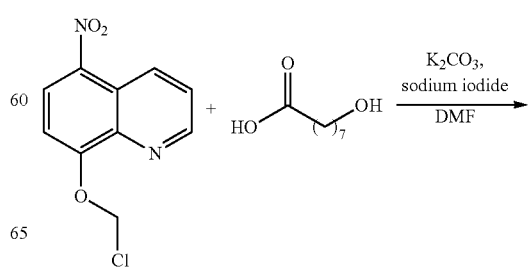

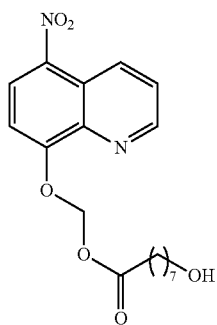

8-Hydroxyoctanoic acid (201 mg, 1.25 mmol), potassium carbonate (209 mg, 1.51 mmol) and sodium iodide (19 mg, 0.13 mmol) were added to N,N-dimethylformamide (6 mL) at room temperature and stirred well. The reaction system was warmed up to 60° C. and stirred for 10 minutes. 5-Nitro-8-chloromethoxyquinoline (1a) (300 mg, 1.26 mmol) was added, and the reaction solution was stirred for 1 hour. The reaction was quenched by water, and the solution was extracted with ethyl acetate. The organic phase was washed with saturated brine, dried over anhydrous sodium sulfate and filtered. The filtrate was concentrated under reduced pressure, and the residues were purified by silica gel column chromatography (eluted with dichloromethane) to obtain (5-nitroquinolin-8-yloxy)methyl 8-hydroxyoctanoate (200 mg, purity: 44%).

$^1$H NMR (400 MHz, DMSO-$d_6$) δ 9.04 (dd, J=4.1, 1.6 Hz, 1H), 9.00 (dd, J=8.9, 1.6 Hz, 1H), 8.56 (d, J=8.8 Hz, 1H), 7.87 (dd, J=8.9, 4.1 Hz, 1H), 7.55 (d, J=8.9 Hz, 1H), 6.14 (s, 2H), 3.30 (t, J=6.6 Hz, 2H), 2.39 (t, J=7.3 Hz, 2H), 1.56-1.45 (m, 2H), 1.35-1.24 (m, 2H), 1.15 (s, 6H).

MS calculated: 362.4; MS observed: 363.3[M+H]$^+$.

Example 11: Synthesis of methyl (5-nitroquinolin-8-yloxy)methyl adipate (11)

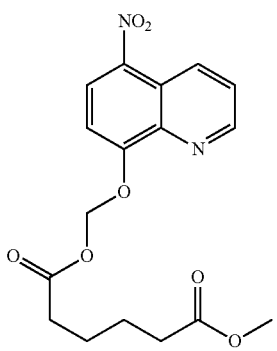 [SMILES: COC(=O)CCCCC(=O)OCOc1ccc([N+](=O)[O-])c2cccnc12]

Methyl (5-nitroquinolin-8-yloxy)methyl adipate (11) was obtained in accordance with the same preparation method of Example 10 except for replacing the 8-hydroxyoctanoic acid with monomethyl adipate.

$^1$H NMR (400 MHz, DMSO-$d_6$) δ 10.03 (dd, J=4.1, 1.6 Hz, 1H), 9.99 (dd, J=8.9, 1.5 Hz, 1H), 9.55 (d, J=8.8 Hz, 1H), 8.86 (dd, J=8.9, 4.1 Hz, 1H), 8.54 (d, J=8.9 Hz, 1H), 7.13 (s, 2H), 4.53 (s, 3H), 4.32 (s, 4H), 3.42 (t, J=7.0 Hz, 2H), 3.25 (t, J=7.1 Hz, 2H).

MS calculated: 362.3; MS observed: 363.3[M+H]$^+$.

Example 12: Synthesis of (5-nitroquinolin-8-yloxy) methyl 7-(tert-butoxycarbonylamino)heptanoate (12)

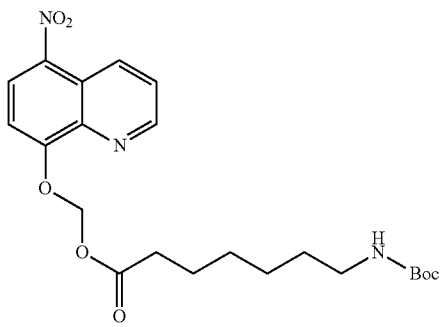 [SMILES: CC(C)(C)OC(=O)NCCCCCCC(=O)OCOc1ccc([N+](=O)[O-])c2cccnc12]

(5-Nitroquinolin-8-yloxy)methyl 7-(tert-butoxycarbonylamino)heptanoate was obtained in accordance with the same preparation method of Example 10 except for replacing the 8-hydroxyoctanoic acid with 7-(tert-butoxycarbonylamino)-heptanoic acid (purchased from Shanghai Dan chemical Co. Ltd.).

$^1$H NMR (400 MHz, CDCl$_3$) δ 9.19 (dd, J=8.9, 1.6 Hz, 1H), 9.07 (dd, J=4.1, 1.6 Hz, 1H), 8.50 (d, J=8.8 Hz, 1H), 7.72 (dd, J=8.9, 4.1 Hz, 1H), 7.36 (d, J=8.8 Hz, 1H), 6.18 (s, 2H), 4.47 (s, 1H), 3.07 (d, J=6.4 Hz, 2H), 2.40 (t, J=7.5 Hz, 2H), 1.69-1.60 (m, 2H), 1.42 (d, J=10.2 Hz, 11H), 1.35-1.25 (m, 4H).

MS calculated: 447.5; MS observed: 448.4[M+H]$^+$.

Example 13: Synthesis of (S)-(5-nitroquinolin-8-yloxy)methyl 2-(tert-butoxy carbonylamino)-3-phenylpropionate (13)

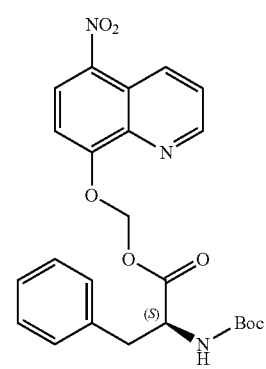

(S)-(5-Nitroquinolin-8-yloxy)methyl 2-(tert-butoxycarbonylamino)-3-phenyl propionate (13) was obtained in accordance with the same preparation method of Example 10 except for replacing the 8-hydroxyoctanoic acid with tert-butoxycarbonyl-L-phenylalanine.

$^1$H NMR (400 MHz, CDCl$_3$) δ 9.19 (dd, J=8.9, 1.5 Hz, 1H), 9.08 (dd, J=4.1, 1.5 Hz, 1H), 8.41 (d, J=8.8 Hz, 1H), 7.72 (dd, J=8.9, 4.1 Hz, 1H), 7.20-7.03 (m, 6H), 6.17 (dd, J=63.5, 6.5 Hz, 2H), 4.95 (d, J=7.7 Hz, 1H), 4.62 (dd, J=13.8, 6.8 Hz, 1H), 3.06 (d, J=6.3 Hz, 2H), 1.40 (s, 9H).

MS calculated: 467.5; MS observed: 468.3 [M+H]$^+$.

Example 14: Synthesis of (S)-4-methyl 1-(5-nitro-quinolin-8-yloxy)methyl 2-acetamidosuccinate (14)

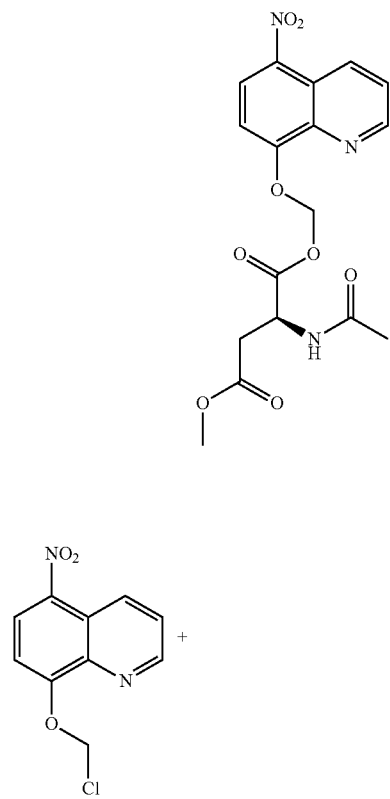

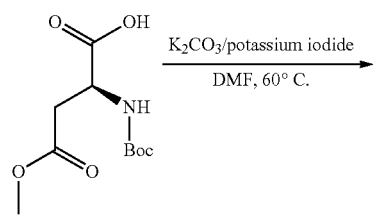

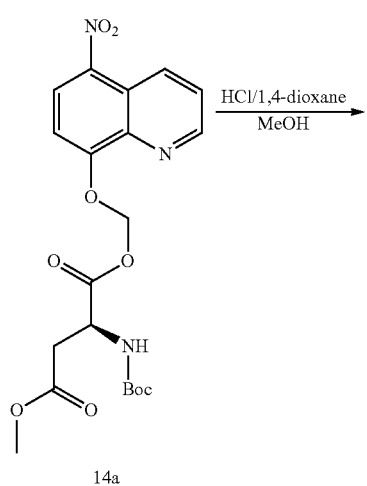

14a

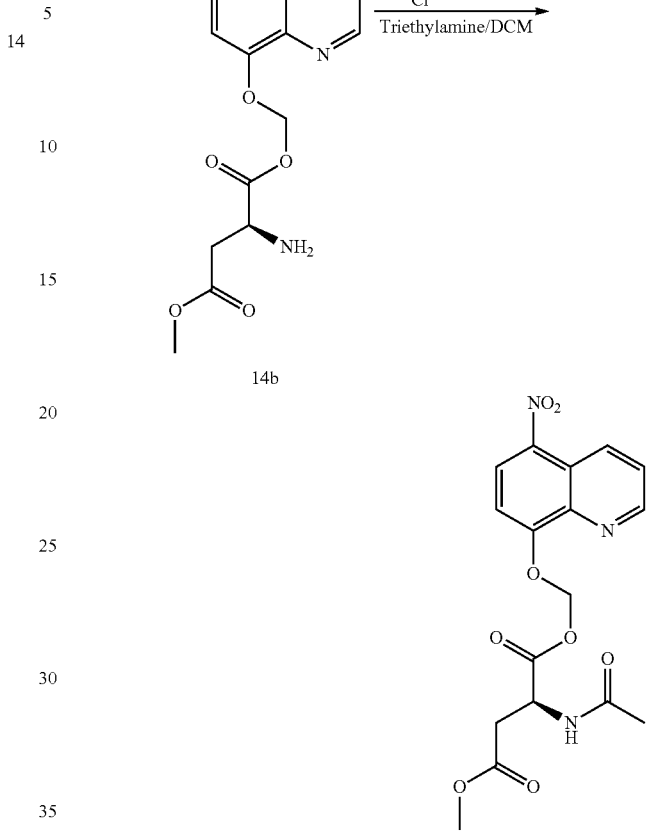

Step 1: Preparation of (S)-4-methyl 1-(5-nitroquinolin-8-yloxy)methyl 2-(tert-butoxycarbonylamino)succinate (14a)

N-(Tert-butoxycarbonyl)-S-methyl-L-cysteine (590 mg, 2.5 mmol), potassium carbonate (580 mg, 4.2 mmol) and potassium iodide (83 mg, 0.5 mmol) were added to N,N-dimethylformamide (5 mL) and stirred well. The reaction system was warmed up to 60° C. and stirred for 10 minutes. 5-Nitro-8-chloromethoxyquinoline (1a) (500 mg, 2.1 mmol) was added, and the reaction solution was stirred for 1 hour. The reaction was quenched by water, and the solution was extracted with ethyl acetate. The organic phase was washed with saturated brine, dried over anhydrous sodium sulfate, filtered and concentrated under reduced pressure. The residues were purified by silica gel thin layer chromatography (eluent: 5% methanol/95% dichloromethane) to obtain (S)-4-methyl 1-(5-nitroquinolin-8-yloxy)methyl 2-(tert-butoxycarbonylamino)succinate (200 mg, yield: 33%).

Step 2: Preparation of (S)-4-methyl 1-(5-nitroquinolin-8-yloxy)methyl 2-aminosuccinate (14b)

Trifluoroacetic acid (5 mL) was added dropwise to a solution of (S)-4-methyl 1-(5-nitroquinolin-8-yloxy)methyl 2-(tert-butoxycarbonylamino)succinate (200 mg, 0.46 mmol) in dichloromethane (5 mL) at room temperature. The reaction solution was stirred at room temperature for 2 hours, and concentrated under reduced pressure to obtain the crude product (S)-4-methyl 1-(5-nitroquinolin-8-yloxy)methyl 2-aminosuccinate (220 mg, yield: 99%).

Step 3: Preparation of (S)-4-methyl 1-(5-nitroquinolin-8-yloxy)methyl 2-acetamidosuccinate (14)

(S)-4-Methyl 1-(5-nitroquinolin-8-yloxy)methyl 2-aminosuccinate (200 mg, 0.68 mmol) and acetyl chloride (80 mg, 1.0 mmol) were dissolved in dichloromethane (10 mL), and then slowly added dropwise with triethylamine (140 mg, 2.0 mmol) under an ice-water bath, and the reaction solution was warmed up to room temperature and stirred for 1 hour. Dichloromethane (100 mL) was added to the reaction solution, and the solution was washed with water once. The organic phases were combined, dried over anhydrous sodium sulfate and filtered. The filtrate was concentrated under reduced pressure to obtain the product (178 mg, yield: 57%).

$^1$H-NMR (400 Hz, CDCl$_3$) δ: 9.20 (dd, J=8.8, 1.6 Hz, 1H), 9.10 (dd, J=4, 1.6 Hz, 1H), 8.50 (d, J=8.8 Hz, 1H), 7.77 (dd, J=8.8 Hz, 4.4 Hz, 1H), 7.35 (d, J=8.8 Hz, 1H), 6.49 (d, J=8 Hz, 1H), 6.23-6.27 (m, 2H), 4.94-4.98 (m, 1H), 3.61 (s, 3H), 3.03-3.09 (m, 1H), 3.85-2.90 (m, 1H), 2.03 (s, 3H).

Example 15: Synthesis of (S)-(5-nitroquinolin-8-yloxy)methyl 2-(2-acetamido-4-methylpentanamido)acetate (15)

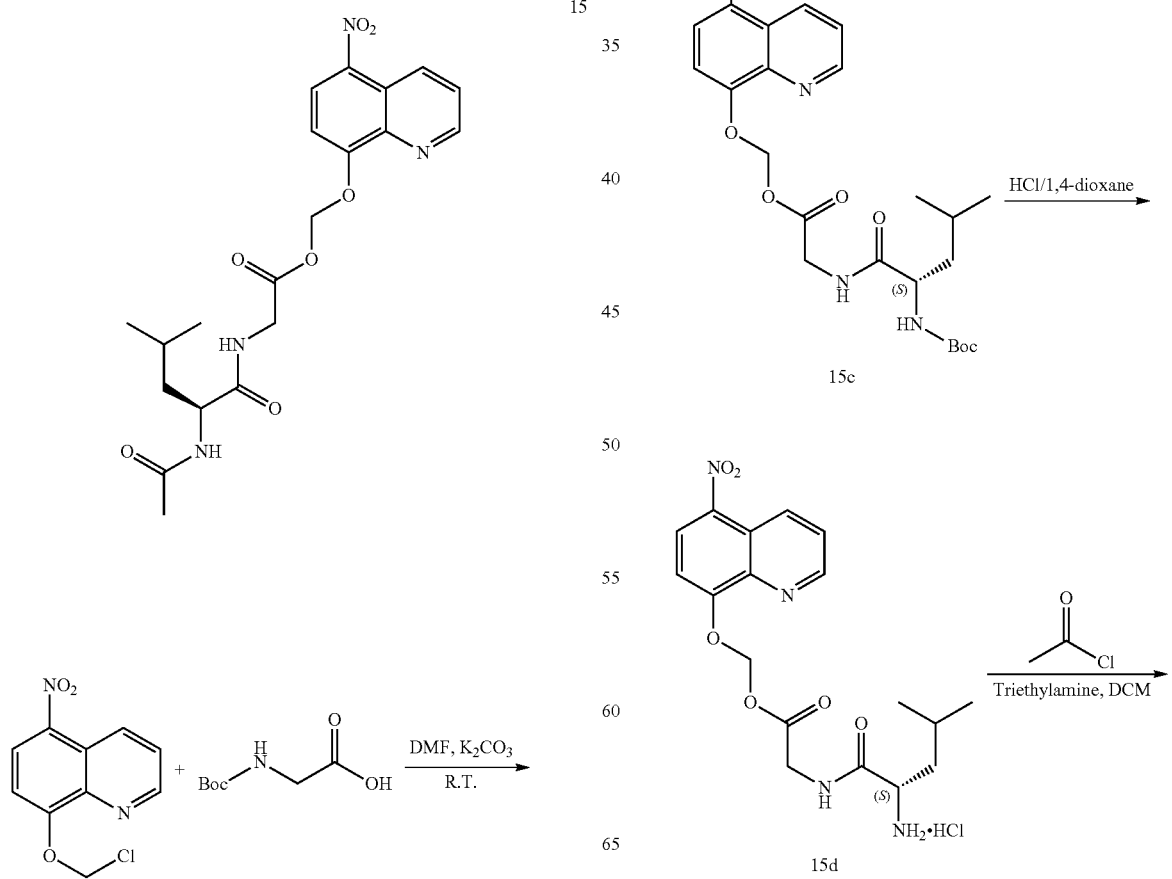

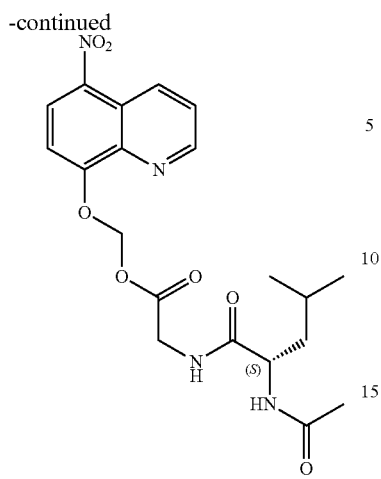

Step 1: Preparation of (5-nitroquinolin-8-yloxy) methyl 2-(tert-butoxycarbonylamino)acetate (15a)

Potassium carbonate (0.65 g, 4.2 mmol) was added to a solution of Boc-glycine (700 mg, 4.1 mmol) and 5-nitro-8-(chloromethoxy)quinoline (1a) (500 mg, 2.1 mmol) in N,N-dimethylformamide (10 mL) at room temperature. The reaction solution was reacted at room temperature for 2 hours. 30 mL of water was added, and the solution was extracted with dichloromethane (20 mL×2). The organic phase was washed with brine and concentrated under reduced pressure. The residues were purified by silica gel column chromatography (PE:EA=1:1) to obtain 600 mg of the product (yield: 75.7%, purity: 95%) as a white solid.

Step 2: Preparation of (5-nitroquinolin-8-yloxy)methyl 2-aminoacetate hydrochloride (15b)

(5-Nitroquinolin-8-yloxy)methyl 2-(tert-butoxycarbonylamino)acetate (600 mg, 1.59 mmol) was added to 10 mL of HCl/dioxane solution at room temperature, and the reaction solution was stirred at room temperature for 20 minutes. The reaction solution was concentrated under reduced pressure to obtain 600 mg of the product (purity: 97%) as a white solid.

Step 3: Preparation of ((S)-(5-nitroquinolin-8-yloxy)methyl 2-(2-(tert-butoxycarbonylamino)-4-methylpentanamido)acetate (15c)

(5-Nitroquinolin-8-yloxy)methyl 2-aminoacetate hydrochloride (500 mg, 1.6 mmol) and Boc-L-leucine (553 mg, 2.4 mmol) were added to 10 mL of DMF at room temperature, and the reaction solution was cooled to 0° C. 1-Hydroxy-benzo-triazole (HOBt) (342 mmol, 2.4 mmol), 1-ethyl-(3-dimethylaminopropyl)carbodiimide hydrochloride (EDCI) (480 mg, 2.4 mmol) and TEA (500 mg, 4.8 mmol) were added successively, and the reaction solution was stirred at room temperature for 1 hour. The reaction solution was concentrated under reduced pressure, and the residues were purified by silica gel column chromatography (dichloromethane/methanol=15:1) to obtain 80 mg of the product (purity: 97%).

Step 4: Preparation of (S)-(5-nitroquinolin-8-yloxy) methyl 2-(2-amino-4-methylpentanamido)acetate hydrochloride (15d)

((S)-(5-Nitroquinolin-8-yloxy)methyl 2-(2-(tert-butoxycarbonylamino)-4-methyl pentanamido)acetate (80 mg, 0.16 mmol) was added to 10 mL of HCl/dioxane (4M), and the reaction solution was stirred for 20 minutes. The reaction solution was concentrated under reduced pressure to obtain 70 mg of the product (purity: 95%) as a white solid.

Step 5: Preparation of (S)-(5-nitroquinolin-8-yloxy) methyl 2-(2-acetamido-4-methylpentanamido)acetate (15)

(S)-(5-Nitroquinolin-8-yloxy)methyl 2-(2-amino-4-methylpentanamido)acetate hydrochloride (70 mg, 0.16 mmol) was added to 10 mL of dichloromethane, and cooled under an ice bath. Acetyl chloride (39 mg, 0.48 mmol) was added, then TEA (80 mg, 0.8 mmol) was slowly added, and the reaction solution was stirred at 10° C. for 10 minutes. The reaction solution was concentrated under reduced pressure, and the residues were purified by silica gel column chromatography (DCM:MeOH=10:1) to obtain the product (S)-(5-nitroquinolin-8-yloxy)methyl 2-(2-acetamido-4-methylpentanamido)acetate (40 mg, yield: 57%, purity: 97%) as a light yellow solid.

$^1$H-NMR (400 MHz, DMSO-$d_6$) δ: 9.05 (dd, J=4.4 Hz, 1.4 Hz, 1H), 9.00 (dd, J=8.8 Hz, 1.6 Hz, 1H), 8.55 (d, J=8.8 Hz, 1H), 8.41 (t, J=6 Hz, 1H), 8.00 (d, J=8.8 Hz, 1H), 7.88 (dd, J=8.8 Hz, 4.0 Hz, 1H), 7.54 (d, J=8.8 Hz, 1H), 6.14-6.18 (m, 2H), 4.26-4.32 (m, 1H), 3.85-3.99 (m, 2H), 1.825 (s, 3H), 1.52-1.58 (m, 1H), 1.35-1.39 (m, 2H), 0.81 (d, J=6.8 Hz, 3H), 0.78 (d, J=6.4 Hz, 3H).

MS calculated: 432.16; MS observed: 433.2 [M+H]$^+$.

Example 16: Synthesis of (R)-(5-nitroquinolin-8-yloxy)methyl 2-acetamido-3-(methylthio)propionate (16)

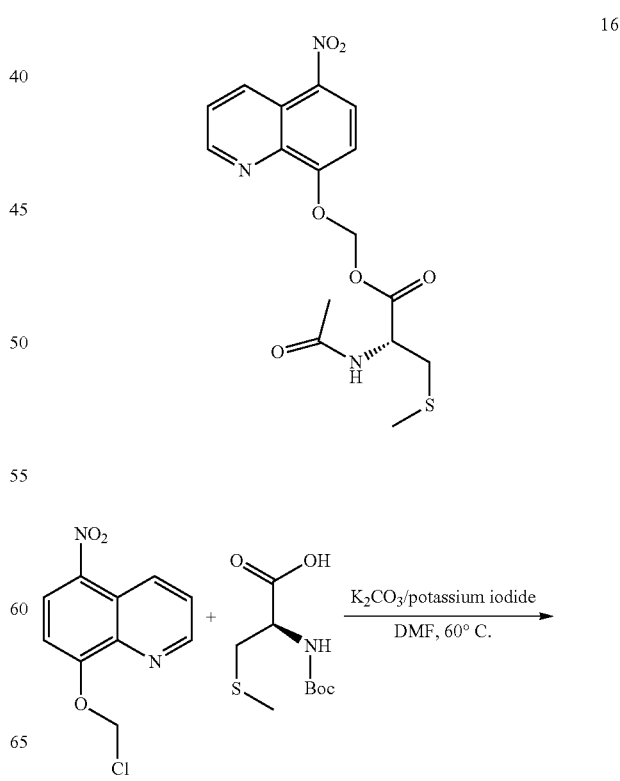

-continued

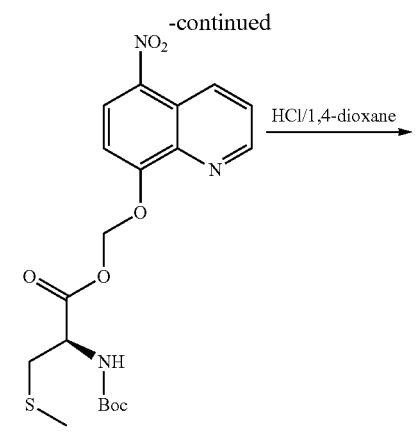

16a

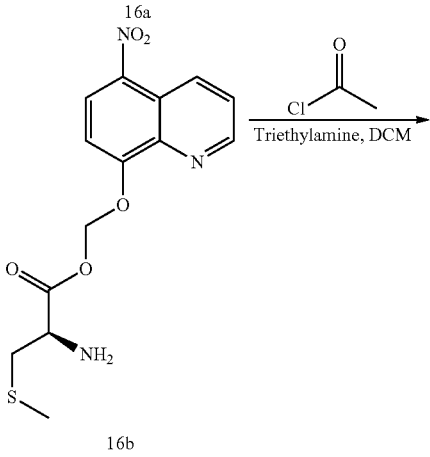

16b

Step 1: Preparation of (R)-(5-nitroquinolin-8-yloxy) methyl 2-(tert-butoxycarbonylamino)-3-(methylthio) propionate (16a)

N-(Tert-butoxycarbonyl)-S-methyl-L-cysteine (590 mg, 2.5 mmol), potassium carbonate (580 mg, 4.2 mmol) and potassium iodide (83 mg, 0.5 mmol) were added to N,N-dimethylformamide (5 mL) at room temperature and stirred well. The reaction system was warmed up to 60° C. and stirred for 10 minutes. 5-Nitro-8-chloromethoxyquinoline (1a) (500 mg, 2.1 mmol) was then added, and the reaction solution was stirred for 1 hour. The reaction was quenched by water, and the solution was extracted with ethyl acetate. The organic phase was washed with saturated brine, dried over anhydrous sodium sulfate, filtered and concentrated under reduced pressure. The residues were purified by silica gel thin layer chromatography (eluent: 5% methanol/95% dichloromethane) to obtain (R)-(5-nitroquinolin-8-yloxy) methyl 2-(tert-butoxycarbonylamino)-3-(methylthio)propionate (300 mg, yield: 33%).

Step 2: Preparation of (R)-(5-nitroquinolin-8-yloxy) methyl 2-amino-3-(methylthio)propionate (16b)

Trifluoroacetic acid (2 mL) was added dropwise to a solution of (R)-(5-nitroquinolin-8-yloxy)methyl 2-(tert-butoxycarbonylamino)-3-(methylthio) propionate (200 mg, 0.46 mmol) in dichloromethane (5 mL) at room temperature. The reaction solution was stirred at room temperature for 2 hours, and concentrated under reduced pressure to obtain (R)-(5-nitroquinolin-8-yloxy)methyl 2-amino-3-(methylthio)propionate (150 mg, yield: 99%).

Step 3: Preparation of (R)-(5-nitroquinolin-8-yloxy) methyl 2-acetamido-3-(methylthio)propionate (16)

(R)-(5-Nitroquinolin-8-yloxy)methyl 2-amino-3-(methylthio)propionate (200 mg, 0.68 mmol) and acetyl chloride (80 mg, 1.0 mmol) were dissolved in dichloromethane (10 mL) at 0° C. Triethylamine (140 mg, 2.0 mmol) was slowly added dropwise under ice-water bath, and the reaction solution was warmed up to room temperature and stirred for 1 hour. Dichloromethane (100 mL) was added to the reaction solution, and the solution was washed with water once. The organic phases were combined, dried over anhydrous sodium sulfate and filtered. The filtrate was concentrated under reduced pressure. The residues were purified by reversed-phase high performance liquid chromatography (column: Eclipse XDB-C18 (21.2 mm×250 mm, 7 μm), mobile phase: acetonitrile-0.1% formic acid, flow rate: 20.0 mL/min) to obtain the product (R)-(5-nitroquinolin-8-yloxy) methyl 2-acetamido-3-(methylthio)propionate (178 mg, yield: 57%).

$^1$H-NMR (400 Hz, CDCl$_3$) δ: 9.37-9.41 (m, 1H), 9.17-9.19 (m, 1H), 8.60 (d, J=8.8 Hz, 1H), 7.89 (dd, J=8.8, 4.4 Hz, 1H), 7.48 (d, J=8.8 Hz, 1H), 6.56 (d, J=6.8 Hz, 1H), 6.19-6.24 (m, 2H), 4.83-4.88 (m, 1H), 2.90-3.0 (m, 2H), 2.10 (s, 3H), 2.06 (s, 3H).

MS calculated: 379.39; MS observed: 380.1 [M+H]$^+$.

Example 17: Synthesis of (5-nitroquinolin-8-yloxy) methyl 2-(N-methylacetamido)acetate (17)

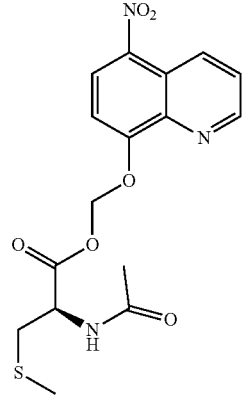

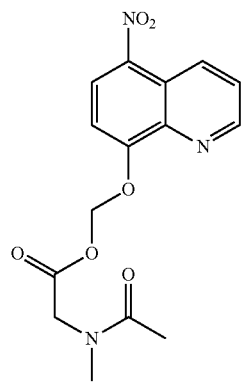 [SMILES: CC(=O)N(C)CC(=O)OCOc1ccc([N+](=O)[O-])c2cccnc12]

17

(5-Nitroquinolin-8-yloxy)methyl 2-(N-methylacetamido)acetate was obtained in accordance with the same preparation method of Example 16 except for replacing the N-(tert-butoxycarbonyl)-S-methyl-L-cysteine in Step 1 with tert-butoxycarbonyl sarcosine.

$^1$H-NMR (400 Hz, CDCl$_3$) δ: 9.23 (d, J=8.8 Hz, 1H), 9.11 (d, J=2.8 Hz, 1H), 8.53 (d, J=8.8 Hz, 1H), 7.77 (dd, J=8.8, 4.4 Hz, 1H), 7.40 (d, J=8.8 Hz, 1H), 6.21 (s, 2H), 4.20 (s, 2H), 3.11 (s, 3H), 2.16 (s, 3H).

MS calculated: 333.30; MS observed: 334.1 [M+H]$^+$.

Example 18: Synthesis of (S)-2-(5-nitroquinolin-8-yloxy)methyl 1-propyl pyrrolidine-1,2-dicarboxylate (18)

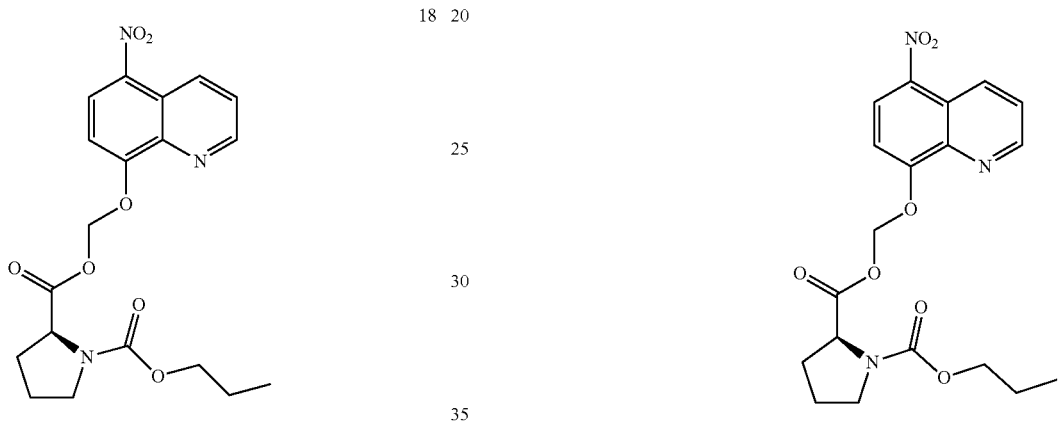

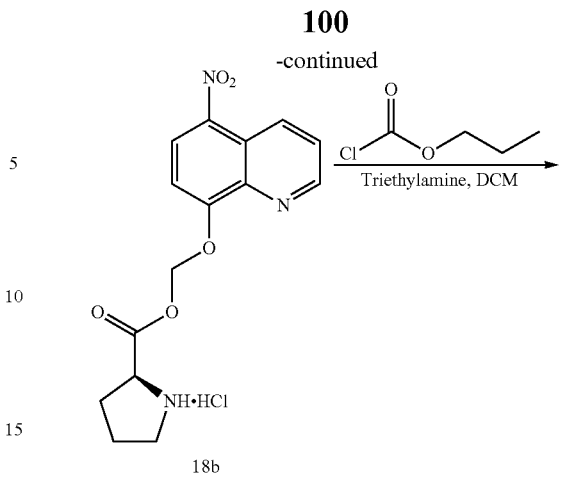

Step 1: Preparation of 1-(tert-butyl) 2-(((5-nitroquinolin-8-yl)oxy)methyl) (S)-pyrrolidine-1,2-dicarboxylate (18a)

5-Nitro-8-(chloromethoxy)quinoline (1a) (1.5 g, 6.3 mmol) and L-Boc-proline (2.02 g, 9.4 mmol) were dissolved in 15 mL of DMF at room temperature, followed by the addition of potassium carbonate (1.73 g, 12.6 mmol). The reaction solution was reacted at room temperature for 3 hours. 70 mL of water were added, and the solution was extracted with ethyl acetate (50 mL×2). The organic phase was washed with saturated brine, dried over anhydrous sodium sulfate, filtered and concentrated under reduced pressure. The residues were purified by silica gel column chromatography (PE:EA=1:1) to obtain the product 1-(tert-butyl) 2-(((5-nitroquinolin-8-yl)oxy)methyl) (S)-pyrrolidine-1,2-dicarboxylate (2.8 g, yield: 106%).

Step 2: Preparation of ((5-nitroquinolin-8-yl)oxy)methyl L-prolinate hydrochloride (18b)

1-(Tert-butyl) 2-(((5-nitroquinolin-8-yl)oxy)methyl) (S)-pyrrolidine-1,2-dicarboxylate (2.8 g, 6.71 mmol) was added to 30 mL of HCl/dioxane at 0° C., and the reaction solution was stirred at room temperature for 20 minutes. The reaction solution was concentrated under reduced pressure to obtain the product ((5-nitroquinolin-8-yl)oxy)methyl L-prolinate hydrochloride (2.3 g, yield: 97%).

Step 3: Preparation of (S)-2-(5-nitroquinolin-8-yloxy)methyl 1-propyl pyrrolidine-1,2-dicarboxylate (18)

((5-Nitroquinolin-8-yl)oxy)methyl L-prolinate hydrochloride (150 mg, 0.424 mmol) was added to 10 mL of DCM at room temperature, and cooled to 0~5° C. under an ice bath. Propyl chloroformate (104 mg, 0.85 mmol) was added, then TEA (170 mg, 1.7 mmol) was slowly added. After completion of the addition, the reaction solution was stirred at room temperature for 20 minutes. The reaction solution was concentrated under reduced pressure, and the resulting residues were purified by silica gel column chromatography (PE:EA=1:1) to obtain the product (S)-2-(5-nitroquinolin-8-yloxy)methyl 1-propyl pyrrolidine-1,2-dicarboxylate (70 mg, yield: 40%).

$^1$H-NMR (400 MHz, DMSO-$d_6$): δ 9.05~9.06 (m, 1H), 9.01 (dd, J=8.8, 1.6 Hz, 1H), 8.56 (dd, J=8.8, 4.8 Hz, 1H), 7.87 (d, J=8.8, 4.0 Hz, 1H), 7.55 (dd, J=8.8, 2.2 Hz, 1H), 6.14~6.15 (m, 2H), 4.29-4.31 (m, 1H), 3.88-3.81 (m, 1H), 3.47-3.59 (m, 1H), 3.40-3.45 (m, 2H), 1.75-1.95 (m, 3H), 1.51~1.45 (m, 1H), 0.83-0.85 (m, 2H) 0.50-0.51 (m, 2H).

MS calculated: 403.39 MS observed: 426.1 [M+Na$^+$].

Example 19: Synthesis of (S)-2-(5-nitroquinolin-8-yloxy)methyl 1-acetylpyrrolidine-2-carboxylate (19)

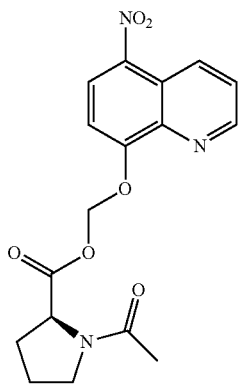 [SMILES: CC(=O)N1CCC[C@H]1C(=O)OCOc1ccc([N+](=O)[O-])c2cccnc12]

19

(S)-2-(5-Nitroquinolin-8-yloxy)methyl 1-acetylpyrrolidine-2-carboxylate was obtained in accordance with the same preparation method of Example 18 except for replacing the propyl chloroformate in Step 3 with acetyl chloride.

$^1$H-NMR (400 MHz, DMSO-$d_6$): δ: 9.05 (dd, J=4.0 Hz, 1.2 Hz, 1H), 9.00 (dd, J=8.8 Hz, 1.2 Hz, 1H), 8.55 (d, J=8.8 Hz, 1H), 7.88 (dd, J=4.0 Hz, 8.8 Hz, 1H), 7.55 (d, J=8.8 Hz, 1H), 6.11-6.24 (m, 2H), 4.34-4.31 (m, 1H), 3.55-3.35 (m, 2H), 2.34-2.27 (m, 1H), 2.19-1.79 (m, 3H), 1.94 (s, 3H).

MS calculated: 359.3; MS observed: 360.2 [M+H]$^+$.

Example 20: Synthesis of (S)-(5-nitroquinolin-8-yloxy)methyl 1-isopropionylpyrrolidine-2-carboxylate (20)

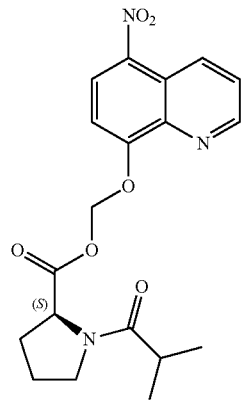

20

(S)-(5-Nitroquinolin-8-yloxy)methyl 1-isopropionylpyrrolidine-2-carboxylate was obtained in accordance with the same preparation method of Example 18 except for replacing the propyl chloroformate in Step 3 with isobutyryl chloride.

$^1$H-NMR (400 MHz, DMSO-$d_6$): δ: 9.05 (d, J=4.0 Hz, 1H), 9.00 (d, J=8.8 Hz, 1H), 8.56 (d, J=8.8 Hz, 1H), 7.89-7.86 (dd, J=4.0 Hz, 8.8 Hz, 1H), 7.55 (d, J=8.8 Hz, 1H), 6.24-6.11 (m, 2H), 4.36-4.33 (m, 1H), 3.59-3.68 (m, 2H), 2.51-2.66 (m, 1H), 2.14~2.19 (m, 1H), 1.92-1.85 (m, 2H), 1.83-1.78 (m, 1H), 0.95 (d, J=6.8 Hz 0.3H), 0.89 (d, J=6.8 Hz 0.3H).

MS calculated: 387.3; MS observed: 388.2 [M+H]$^+$.

Example 21: Synthesis of (S)-(5-nitroquinolin-8-yloxy)methyl 1-pivaloylpyrrolidine-2-carboxylate (21)

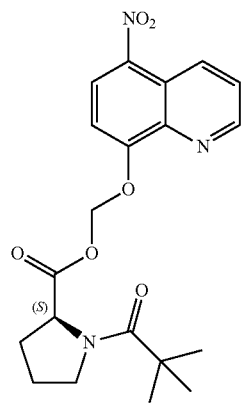

21

(S)-(5-Nitroquinolin-8-yloxy)methyl 1-pivaloylpyrrolidine-2-carboxylate was obtained in accordance with the same preparation method of Example 18 except for replacing the propyl chloroformate in Step 3 with pivaloyl chloride.

$^1$H-NMR (400 MHz, DMSO-$d_6$): δ: 9.05 (m, 1H), 9.00 (m, 1H), 8.56 (d, J=8.0 Hz, 1H), 7.88 (d, J=5.2 Hz, 1H), 7.55

(d, J=7.6 Hz, 1H), 6.24-6.11 (m, 2H), 4.35 (m, 1H), 3.66 (m, 2H), 2.08 (m, 1H), 1.88 (m, 2H), 1.70 (m, 1H), 1.09 (s, 9H).
MS calculated: 401.4; MS observed: 402.2 [M+H]+.

Example 22: Synthesis of (R)-2-(5-nitroquinolin-8-yloxy)methyl 1-acetylpyrrolidine-2-carboxylate (22)

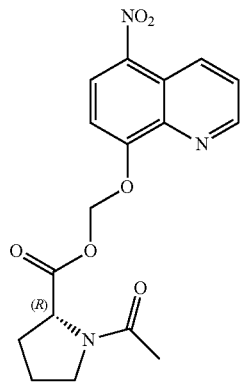

(R)-2-(5-Nitroquinolin-8-yloxy)methyl-acetylpyrrolidine-2-carboxylate was obtained in accordance with the same preparation method of Example 19 except for replacing the L-Boc-proline in Step 1 with D-Boc-proline.

1H-NMR (400 MHz, DMSO-$d_6$): δ: 9.05 (dd, J=4.0 Hz, 1.2 Hz, 1H), 9.00 (dd, J=8.8 Hz, 1.2 Hz, 1H), 8.56 (d, J=8.8 Hz, 1H), 7.88 (dd, J=4.0 Hz, 8.8 Hz, 1H), 7.55 (d, J=8.8 Hz, 1H), 6.15 (m, 2H), 4.34-4.31 (m, 1H), 3.55-3.34 (m, 2H), 2.18-2.14 (m, 1H), 1.91-1.78 (m, 3H), 1.94 (s, 3H).
MS calculated: 359.3; MS observed: 360.2 [M+H]+.

Example 23: Synthesis of (R)-(5-nitroquinolin-8-yloxy)methyl 1-isopropionylpyrrolidine-2-carboxylate (23)

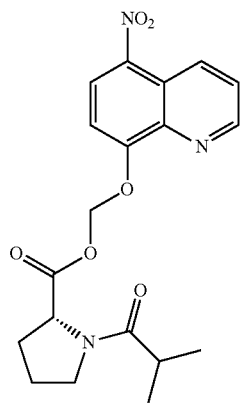

(R)-(5-Nitroquinolin-8-yloxy)methyl 1-isopropionylpyrrolidine-2-carboxylate was obtained in accordance with the same preparation method of Example 22 except for replacing the propyl chloroformate in Step 3 with isobutyryl chloride.

1H-NMR (400 MHz, DMSO-$d_6$): δ: 9.05 (d, J=2.8 Hz, 1H), 9.00 (d, J=8.4 Hz, 1H), 8.56 (d, J=8.8 Hz, 1H), 7.88 (dd, J=4.0 Hz, 8.8 Hz, 1H), 7.55 (d, J=8.8 Hz, 1H), 6.19 (d, J=6.4 Hz, 1H), 6.11 (d, J=6.4 Hz, 1H), 4.36-4.33 (m, 1H), 3.58-3.55 (m, 2H), 2.70-2.63 (m, 1H), 2.19-2.14 (m, 1H), 1.92-1.87 (m, 2H), 1.82-1.77 (m, 1H), 0.95 (d, J=6.8 Hz, 3H), 0.89 (d, J=6.8 Hz, 3H).
MS calculated: 387.3; MS observed: 388.2 [M+H]+.

Example 24: Synthesis of (R)-(5-nitroquinolin-8-yloxy)methyl 1-pivaloylpyrrolidine-2-carboxylate (24)

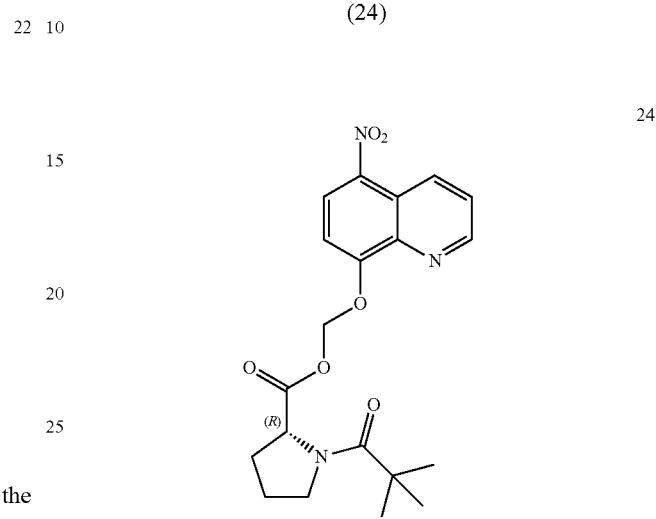

(R)-(5-Nitroquinolin-8-yloxy)methyl 1-pivaloylpyrrolidine-2-carboxylate was obtained in accordance with the same preparation method of Example 22 except for replacing the propyl chloroformate in Step 3 with pivaloyl chloride.

1H-NMR (400 MHz, DMSO-$d_6$): δ: 9.06 (dd, J=4.0 Hz, 1.2 Hz, 1H), 9.00 (dd, J=8.8 Hz, 1.2 Hz, 1H), 8.55 (d, J=8.8 Hz, 1H), 7.88 (dd, J=4.0 Hz, 8.8 Hz, 1H), 7.55 (d, J=8.8 Hz, 1H), 6.19 (d, J=6.8 Hz, 1H), 6.11 (d, J=6.8 Hz, 1H), 4.36-4.33 (m, 1H), 3.67-3.64 (m, 2H), 2.11-2.04 (m, 1H), 1.90-1.85 (m, 2H), 1.72-1.67 (m, 1H), 1.09 (s, 9H).
MS calculated: 401.2; MS observed: 402.2 [M+H]+.

Example 25: Synthesis of (S)-(5-nitroquinolin-8-yloxy)methyl 1-pyridineformylpyrrolidine-2-carboxylate (25)

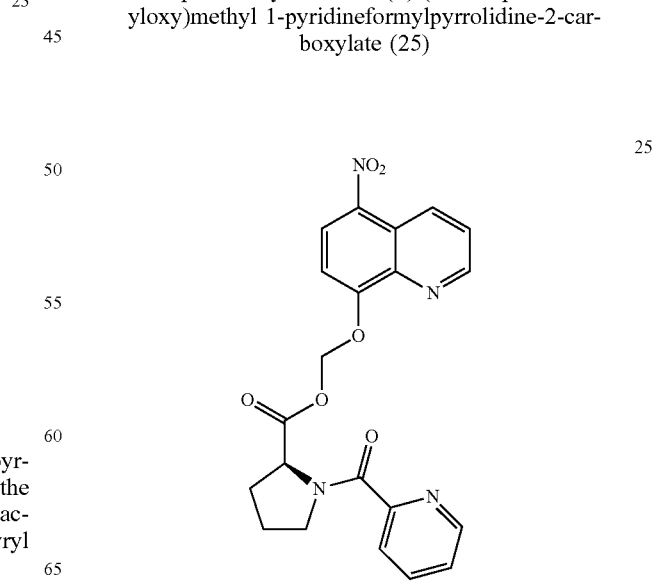

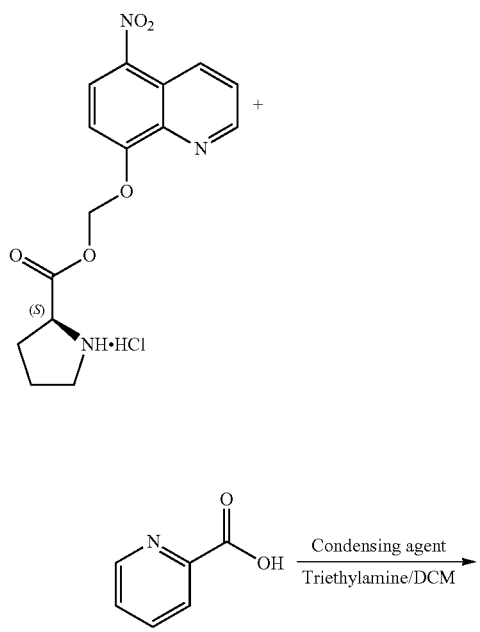

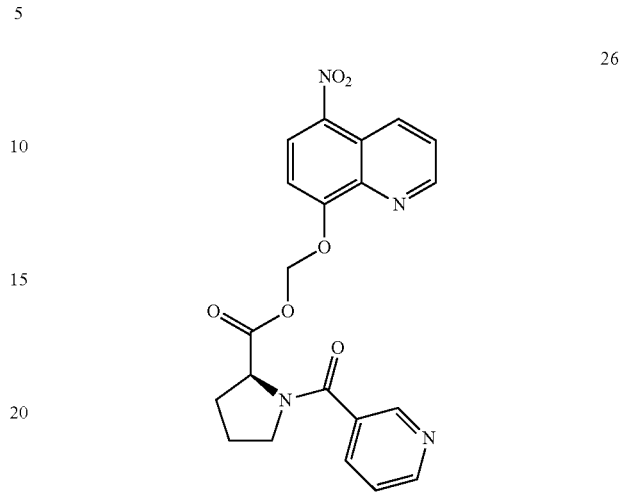

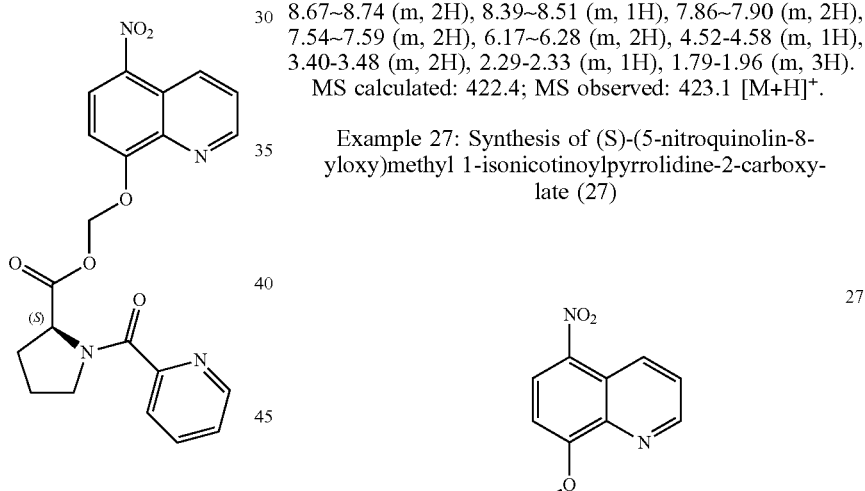

((5-Nitroquinolin-8-yl)oxy)methyl L-prolinate hydrochloride (18b) (150 mg, 0.43 mmol) was added to anhydrous dichloromethane (15 mL) at room temperature, and cooled under an ice bath. 1-Ethyl-(3-dimethylaminopropyl)carbodiimide hydrochloride (EDCI) (121.4 mg, 0.636 mmol), 1-hydroxy-benzo-triazole (HOBt) (86 mg, 0.636 mmol) and 2-picolinic acid (78.22 mg, 0.636 mmol) were added successively, and the reaction solution was stirred at 0 to 20° C. for 30 minutes. The reaction solution was concentrated under reduced pressure, and the residues were purified by silica gel column chromatography (PE:EA=1:1 to 0:1) to obtain (S)-(5-nitroquinolin-8-yloxy)methyl 1-pyridineformylpyrrolidine-2-carboxylate (30 mg, yield: 17%).

$^1$H-NMR (400 MHz, DMSO-d$_6$): δ: 9.01~9.07 (m, 2H), 8.67~8.74 (m, 2H), 8.39~8.51 (m, 1H), 7.86~7.90 (m, 1H), 7.30~7.60 (m, 3H), 6.02~6.28 (m, 2H), 4.52-4.58 (m, 1H), 3.50-3.58 (m, 2H), 2.29-2.33 (m, 1H), 1.79-1.96 (m, 3H).

MS calculated: 422.4; MS observed: 423.2 [M+H]$^+$.

Example 26: Synthesis of (S)-(5-nitroquinolin-8-yloxy)methyl 1-nicotinoylpyrrolidine-2-carboxylate (26)

(S)-(5-Nitroquinolin-8-yloxy)methyl 1-nicotinoylpyrrolidine-2-carboxylate was obtained in accordance with the same preparation method of Example 25 except for replacing the 2-picolinic acid with 3-picolinic acid.

$^1$H-NMR (400 MHz, DMSO-d$_6$): δ: 8.98~9.06 (m, 2H), 8.67~8.74 (m, 2H), 8.39~8.51 (m, 1H), 7.86~7.90 (m, 2H), 7.54~7.59 (m, 2H), 6.17~6.28 (m, 2H), 4.52-4.58 (m, 1H), 3.40-3.48 (m, 2H), 2.29-2.33 (m, 1H), 1.79-1.96 (m, 3H).

MS calculated: 422.4; MS observed: 423.1 [M+H]$^+$.

Example 27: Synthesis of (S)-(5-nitroquinolin-8-yloxy)methyl 1-isonicotinoylpyrrolidine-2-carboxylate (27)

(S)-(5-Nitroquinolin-8-yloxy)methyl 1-isonicotinoylpyrrolidine-2-carboxylate was obtained in accordance with the same preparation method of Example 25 except for replacing the 2-picolinic acid with 4-picolinic acid.

$^1$H-NMR (400 MHz, DMSO-d$_6$): δ: 8.98~9.07 (m, 2H), 8.67~8.74 (m, 2H), 8.39~8.51 (m, 1H), 7.86~7.90 (m, 1H), 7.30~7.60 (m, 3H), 6.02~6.28 (m, 2H), 4.52-4.58 (m, 1H), 3.40-3.48 (m, 2H), 2.29-2.33 (m, 1H), 1.79-1.96 (m, 3H).

MS calculated: 422.4; MS observed: 423.1 [M+H]$^+$.

Example 28: Synthesis of (S)-(5-nitroquinolin-8-yloxy)methyl 1-((S)-2-acetamido-3-(4-hydroxyphenyl)propionyl)pyrrolidine-2-carboxylate (28)

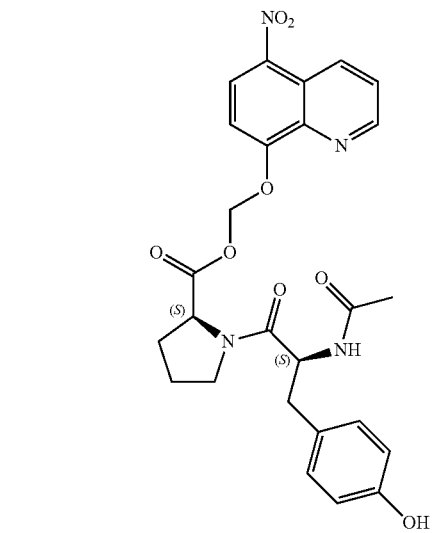

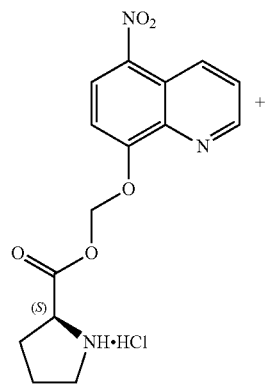

+

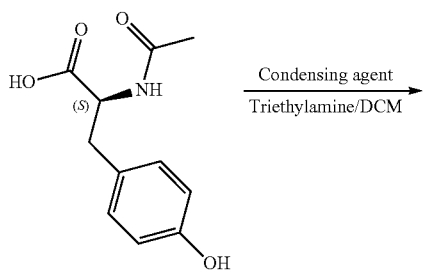

Condensing agent
Triethylamine/DCM

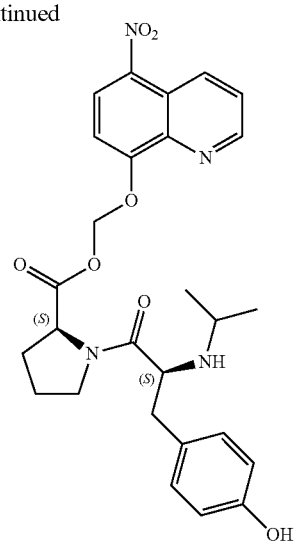

28

((5-Nitroquinolin-8-yl)oxy)methyl L-prolinate hydrochloride (18b) (300 mg, 0.85 mmol) was added to anhydrous DMF (10 mL), and cooled under an ice bath. 2-(7-oxybenzotriazol)-N,N,N',N'-tetramethyluronium hexafluorophosphate (HATU) (484 mg, 1.27 mmol), triethylamine (260 mg, 2.55 mmol) and N-acetyl-L-tyrosine (189 mg, 0.85 mmol) were added successively. The reaction solution was stirred at 0 to 20° C. for 20 minutes. The reaction solution was concentrated under reduced pressure, and the residues were purified by silica gel column chromatography (PE:EA=1:1 to 0:1) to obtain (S)-(5-nitroquinolin-8-yloxy)methyl 1-((S)-2-acetamido-3-(4-hydroxyphenyl)propionyl) pyrrolidine-2-carboxylate (100 mg, yield: 22.5%).

$^1$H-NMR (400 MHz, DMSO-d$_6$): δ: 9.19 (s, 1H), 9.04~9.05 (m, 1H), 8.98~9.07 (m, 2H), 8.48~8.55 (m, 1H), 8.19~8.24 (m, 1H), 7.86~7.90 (m, 1H), 7.52~7.56 (m, 1H), 6.95~6.97 (m, 2H), 6.61~6.65 (m, 2H), 6.02~6.28 (m, 2H), 4.53-4.57 (m, 1H), 4.37-4.40 (m, 1H), 3.65-3.70 (m, 1H), 3.41-3.47 (m, 1H), 2.61-2.67 (m, 1H) 2.41-2.47 (m, 1H), 2.11-2.18 (m, 1H), 1.80-1.81 (m, 3H), 1.72 (s, 3H).

MS calculated: 522.51; MS observed: 523.2 [M+H]$^+$.

Example 29: Synthesis of (S)-(5-nitroquinolin-8-yloxy)methyl 1-((2S,3R)-2-(tert-butoxycarbonylamino)-3-hydroxybutyryl)pyrrolidine-2-carboxylate (29)

29

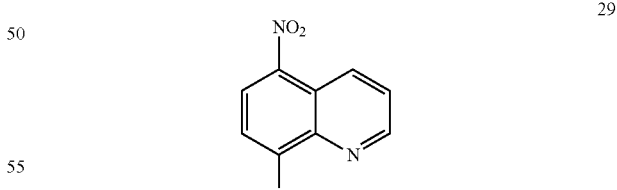

(S)-(5-Nitroquinolin-8-yloxy)methyl 1-((2S,3R)-2-(tert-butoxycarbonylamino)-3-hydroxybutyryl)pyrrolidine-2-carboxylate was obtained in accordance with the same preparation method of Example 28 except for replacing the N-acetyl-L-tyrosine with N-Boc-L-threonine.

$^1$H-NMR (400 MHz, DMSO-d$_6$): δ: 8.98~9.07 (m, 2H), 8.77 (br, 1H) 8.54~8.56 (m, 1H), 8.19~8.24 (m, 1H), 7.86~7.90 (m, 1H), 7.52~7.56 (m, 1H), 615~6.16 (m, 2H), 4.37-4.41 (m, 1H), 4.06-4.07 (m, 1H), 3.65-3.70 (m, 3H), 2.16-2.20 (m, 1H) 1.78-1.90 (m, 3H), 1.36 (s, 9H), 0.84 (d, J=8 Hz, 3H).

MS calculated: 518.52; MS observed: 519.2 [M+H]$^+$.

Example 30: Synthesis of (S)-(5-nitroquinolin-8-yloxy)methyl 1-((S)-2-acetamido-3-hydroxypropionyl)pyrrolidine-2-carboxylate (30)

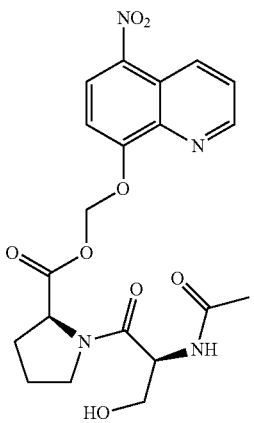

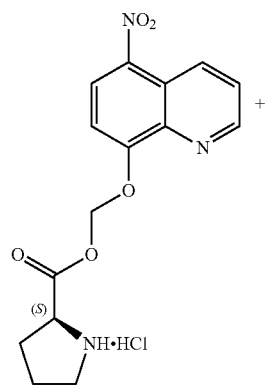

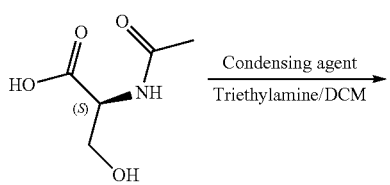

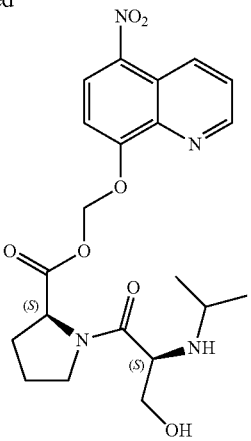

(S)-(5-Nitroquinolin-8-yloxy)methyl 1-((S)-2-acetamido-3-hydroxypropionyl) pyrrolidine-2-carboxylate was obtained in accordance with the same preparation method of Example 28 except for replacing the N-acetyl-L-tyrosine with N-acetyl-L-serine.

$^1$H-NMR (400 MHz, DMSO-d$_6$): δ: 8.98~9.07 (m, 2H), 8.48~8.55 (m, 1H), 8.19~8.24 (m, 1H), 7.86~7.90 (m, 1H), 7.52~7.56 (m, 1H), 6.02~6.28 (m, 2H), 4.85-4.95 (m, 1H), 4.40-4.60 (m, 2H), 3.65-3.70 (m, 3H), 1.80-2.01 (m, 7H).

MS calculated: 446.42; MS observed: 447.1 [M+H]$^+$.

Example 31: Synthesis of (5-nitroquinolin-8-yloxy)methyl 2-methoxyacetate (31)

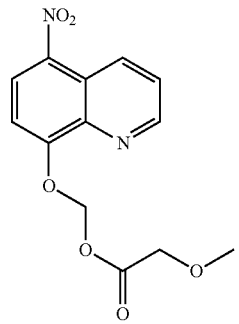 [SMILES: COCC(=O)OCOc1ccc([N+](=O)[O-])c2cccnc12]

(5-Nitroquinolin-8-yloxy)methyl 2-methoxyacetate was obtained in accordance with the same preparation method of Example 1 except for replacing the acetic acid in Step 2 with methoxyacetic acid.

$^1$H NMR (400 MHz, CDCl$_3$) δ 9.19 (dd, J=8.9, 1.6 Hz, 1H), 9.07 (dd, J=4.1, 1.6 Hz, 1H), 8.49 (d, J=8.8 Hz, 1H), 7.72 (dd, J=8.9, 4.1 Hz, 1H), 7.37 (d, J=8.8 Hz, 1H), 6.26 (s, 2H), 4.12 (s, 2H), 3.45 (s, 3H).

MS calculated: 292.2; MS observed: 293.1 [M+H]$^+$.

Example 32: Synthesis of (5-nitroquinolin-8-yloxy)methyl cyclobutanecarboxylate (32)

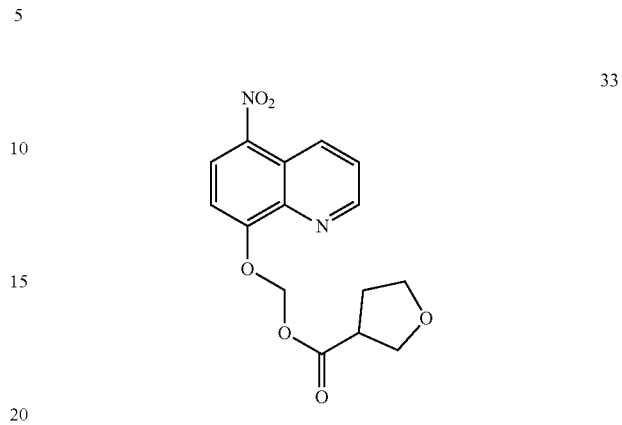

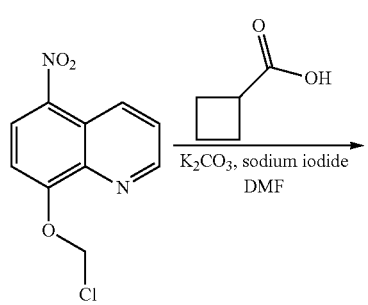

(5-Nitroquinolin-8-yloxy)methyl cyclobutanecarboxylate was obtained in accordance with the same preparation method of Example 1 except for replacing the acetic acid in Step 2 with cyclobutanecarboxylic acid.

$^1$H NMR (400 MHz, CDCl$_3$) δ 9.19 (dd, J=8.9, 1.5 Hz, 1H), 9.07 (dd, J=4.1, 1.5 Hz, 1H), 8.50 (d, J=8.8 Hz, 1H), 7.71 (dd, J=8.9, 4.1 Hz, 1H), 7.36 (d, J=8.8 Hz, 1H), 6.18 (s, 2H), 3.22 (p, J=8.3 Hz, 1H), 2.37-2.16 (m, 4H), 2.06-1.84 (m, 2H).

MS calculated: 302.3; MS observed: 303.1[M+H]$^+$.

Example 33: Synthesis of (5-nitroquinolin-8-yloxy)methyl tetrahydrofuran-3-carboxylate (33)

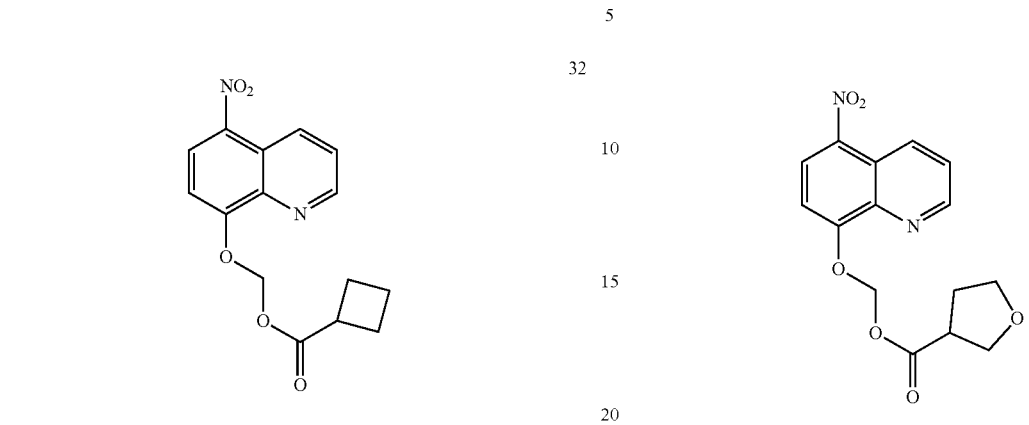

(5-Nitroquinolin-8-yloxy)methyl tetrahydrofuran-3-carboxylate was obtained in accordance with the same preparation method of Example 1 except for replacing the acetic acid in Step 2 with 3-tetrahydrofurancarboxylic acid.

$^1$H NMR (400 MHz, CDCl$_3$) δ 9.19 (dd, J=8.9, 1.6 Hz, 1H), 9.07 (dd, J=4.1, 1.5 Hz, 1H), 8.50 (d, J=8.8 Hz, 1H), 7.72 (dd, J=8.9, 4.1 Hz, 1H), 7.36 (d, J=8.8 Hz, 1H), 6.21 (q, J=6.5 Hz, 2H), 4.01-3.91 (m, 2H), 3.84 (qd, J=14.9, 8.3 Hz, 2H), 3.18 (ddt, J=8.9, 7.8, 5.9 Hz, 1H), 2.28-2.09 (m, 2H).

MS calculated: 318.3; MS observed: 319.1[M+H]$^+$.

Example 34: Synthesis of (5-nitroquinolin-8-yloxy)methyl 2-acetoxybenzoate (34)

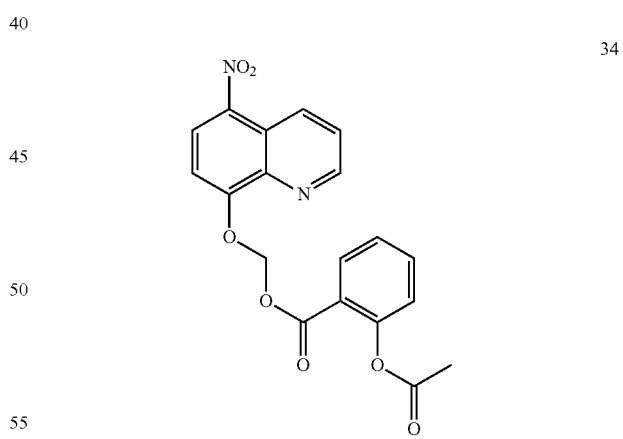

(5-Nitroquinolin-8-yloxy)methyl 2-acetoxybenzoate was obtained in accordance with the same preparation method of Example 1 except for replacing the acetic acid in Step 2 with o-acetylsalicylic acid.

$^1$H NMR (400 MHz, CDCl$_3$) δ 9.30 (s, 1H), 9.17 (s, 1H), 8.55 (s, 1H), 8.03 (s, 1H), 7.81 (s, 1H), 7.61 (t, J=7.3 Hz, 1H), 7.47 (s, 1H), 7.31 (s, 1H), 7.13 (d, J=8.0 Hz, 1H), 6.40 (s, 2H), 2.31 (s, 3H).

MS calculated: 382.3; MS observed: 383.1 [M+H]$^+$.

Example 35: Synthesis of (5-nitroquinolin-8-yloxy) methyl 2-(2,4-dichlorophenoxy)acetate (35)

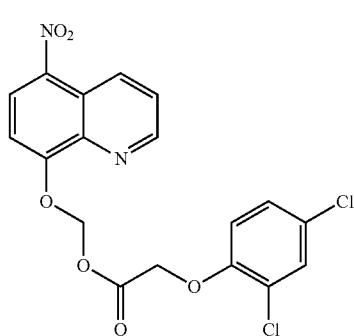 [SMILES: O=C(COc1ccc(Cl)cc1Cl)OCOc1ccc([N+](=O)[O-])c2cccnc12]

(5-Nitroquinolin-8-yloxy)methyl 2-(2,4-dichlorophenoxy)acetate was obtained in accordance with the same preparation method of Example 1 except for replacing the acetic acid in Step 2 with sodium 2,4-dichlorophenoxyacetate (purchased from Shanghai Dan chemical Co. Ltd.).

$^1$H NMR (400 MHz, CDCl$_3$) δ 9.18 (dd, J=8.9, 1.5 Hz, 1H), 9.06 (dd, J=4.1, 1.5 Hz, 1H), 8.40 (d, J=8.8 Hz, 1H), 7.72 (dd, J=8.9, 4.1 Hz, 1H), 7.29 (d, J=2.5 Hz, 1H), 7.24 (d, J=8.8 Hz, 1H), 6.91 (dd, J=8.8, 2.5 Hz, 1H), 6.68 (d, J=8.8 Hz, 1H), 6.26 (s, 2H), 4.79 (s, 2H).

MS calculated: 423.2; MS observed: 423.0[M+H]$^+$.

Example 36: Synthesis of (5-nitroquinolin-8-yloxy)methyl 2-morpholinoacetate (36)

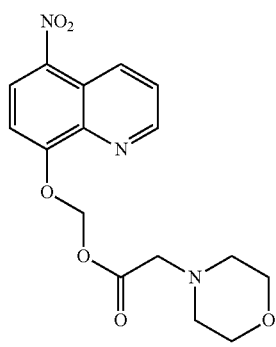 [SMILES: O=C(CN1CCOCC1)OCOc1ccc([N+](=O)[O-])c2cccnc12]

(5-Nitroquinolin-8-yloxy)methyl 2-morpholinoacetate was obtained in accordance with the same preparation method of Example 1 except for replacing the acetic acid in Step 2 with 4-morpholinoacetic acid.

$^1$H NMR (400 MHz, CDCl$_3$) δ 9.19 (dd, J=8.9, 1.6 Hz, 1H), 9.07 (dd, J=4.1, 1.6 Hz, 1H), 8.49 (d, J=8.8 Hz, 1H), 7.72 (dd, J=8.9, 4.1 Hz, 1H), 7.37 (d, J=8.8 Hz, 1H), 6.23 (s, 2H), 3.77-3.68 (m, 4H), 3.31 (s, 2H), 2.63-2.53 (m, 4H).

MS calculated: 347.3; MS observed: 348.2 [M+H]$^+$.

Example 37: Synthesis of (R)-(5-nitroquinolin-8-yloxy)methyl 2-hydroxy-2-phenylacetate (37)

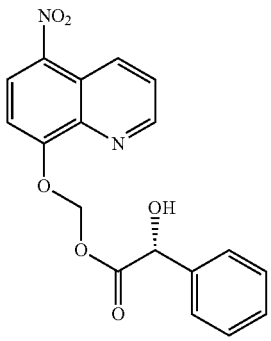 [SMILES: O=C(OCOc1ccc([N+](=O)[O-])c2cccnc12)[C@H](O)c1ccccc1]

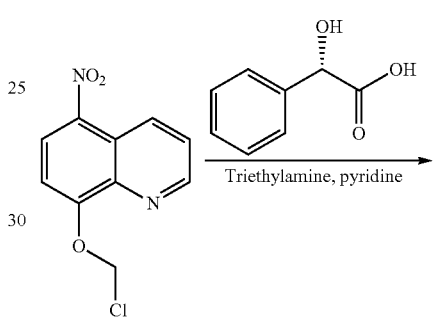

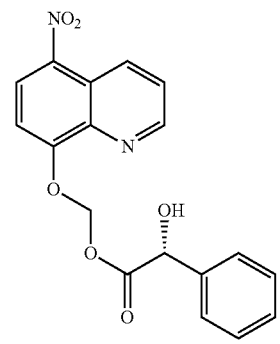

(S)-Mandelic acid (64 mg, 0.42 mmol), triethylamine (51 mg, 0.50 mmol) and pyridine (33 mg, 0.42 mmol) were added to N,N-dimethylformamide (1 mL) at room temperature and stirred well. The reaction system was warmed up to 35° C. and stirred for 10 minutes. 5-Nitro-8-chloromethoxyquinoline (1a) (100 mg, 0.42 mmol) was added, and the reaction solution was stirred for 1 hour. The reaction was quenched by water, and the solution was extracted with ethyl acetate. The organic phase was washed with saturated brine, dried over anhydrous sodium sulfate, filtered and concentrated under reduced pressure. The residues were purified by silica gel thin layer chromatography (eluent: 5% methanol/95% dichloromethane) to obtain (R)-(5-nitroquinolin-8-yloxy)methyl 2-hydroxy-2-phenylacetate (50 mg, yield: 34%).

$^1$H NMR (400 MHz, CDCl$_3$) δ 9.14 (dd, J=8.9, 1.6 Hz, 1H), 9.03 (dd, J=4.1, 1.6 Hz, 1H), 8.24 (d, J=8.8 Hz, 1H), 7.70 (dd, J=8.9, 4.1 Hz, 1H), 7.35 (dd, J=7.1, 2.4 Hz, 2H), 7.25 (dd, J=5.2, 1.9 Hz, 2H), 6.91 (d, J=8.8 Hz, 1H), 6.18 (dd, J=31.0, 6.4 Hz, 2H), 5.24 (s, 1H), 3.39 (s, 1H).

MS calculated: 354.3; MS observed: 355.1[M+H]⁺.

Example 38: Synthesis of (S)-(5-nitroquinolin-8-yloxy)methyl 2-hydroxy-2-phenylacetate (38)

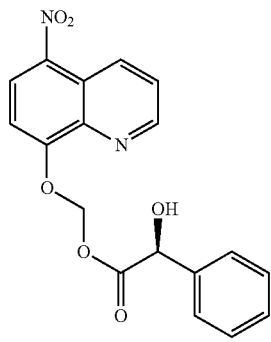 [SMILES: O=C(OCOc1ccc([N+](=O)[O-])c2cccnc12)[C@@H](O)c1ccccc1]

38

(S)-(5-Nitroquinolin-8-yloxy)methyl 2-hydroxy-2-phenylacetate was obtained in accordance with the same preparation method of Example 37 except for replacing the (S)-mandelic acid with (R)-mandelic acid.

¹H NMR (400 MHz, CDCl₃) δ 9.14 (dd, J=8.9, 1.6 Hz, 1H), 9.03 (dd, J=4.1, 1.6 Hz, 1H), 8.24 (d, J=8.8 Hz, 1H), 7.70 (dd, J=8.9, 4.1 Hz, 1H), 7.35 (dd, J=7.1, 2.4 Hz, 2H), 7.25 (dd, J=5.2, 1.9 Hz, 2H), 6.91 (d, J=8.8 Hz, 1H), 6.18 (dd, J=31.1, 6.4 Hz, 2H), 5.24 (s, 1H), 3.40 (s, 1H).

MS calculated: 354.3; MS observed: 355.1[M+H]⁺.

Example 39: Synthesis of (5-nitroquinolin-8-yloxy)methyl butyrate (39)

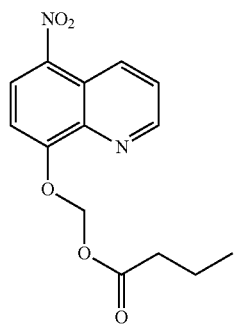 [SMILES: CCCC(=O)OCOc1ccc([N+](=O)[O-])c2cccnc12]

39

(5-Nitroquinolin-8-yloxy)methyl butyrate was obtained in accordance with the same preparation method of Example 1 except for replacing the acetic acid in Step 2 with n-butyric acid.

¹H NMR (400 MHz, CDCl₃) δ 9.19 (dd, J=8.9, 1.6 Hz, 1H), 9.07 (dd, J=4.1, 1.6 Hz, 1H), 8.50 (d, J=8.8 Hz, 1H), 7.72 (dd, J=8.9, 4.1 Hz, 1H), 7.37 (d, J=8.8 Hz, 1H), 6.18 (s, 2H), 2.39 (t, J=7.4 Hz, 2H), 1.69 (dt, J=14.8, 7.4 Hz, 2H), 0.94 (t, J=7.4 Hz, 3H).

MS calculated: 290.3; MS observed: 291.1[M+H]⁺.

Example 40: Synthesis of (5-nitroquinolin-8-yloxy)methyl hexanoate (40)

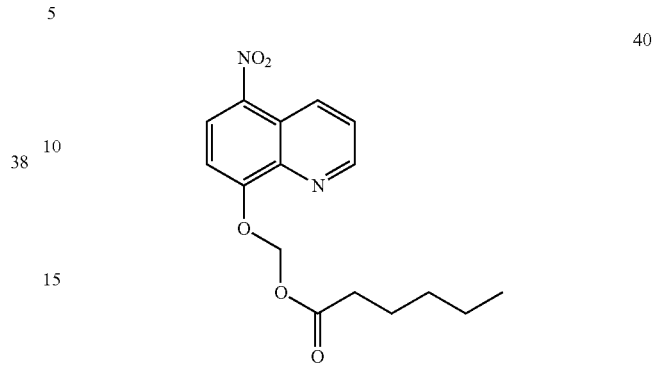

40

(5-Nitroquinolin-8-yloxy)methyl hexanoate was obtained in accordance with the same preparation method of Example 1 except for replacing the acetic acid in Step 2 with n-hexanoic acid.

¹H NMR (400 MHz, CDCl₃) δ 9.19 (dd, J=8.9, 1.6 Hz, 1H), 9.07 (dd, J=4.1, 1.6 Hz, 1H), 8.50 (d, J=8.8 Hz, 1H), 7.71 (dd, J=8.9, 4.1 Hz, 1H), 7.36 (d, J=8.8 Hz, 1H), 6.18 (s, 2H), 2.40 (t, J=7.5 Hz, 2H), 1.68-1.60 (m, 2H), 1.33-1.22 (m, 4H), 0.91-0.79 (m, 3H).

MS calculated: 318.3; MS observed: 319.2[M+H]⁺.

Example 41: Synthesis of (5-nitroquinolin-8-yloxy)methyl octanoate (41)

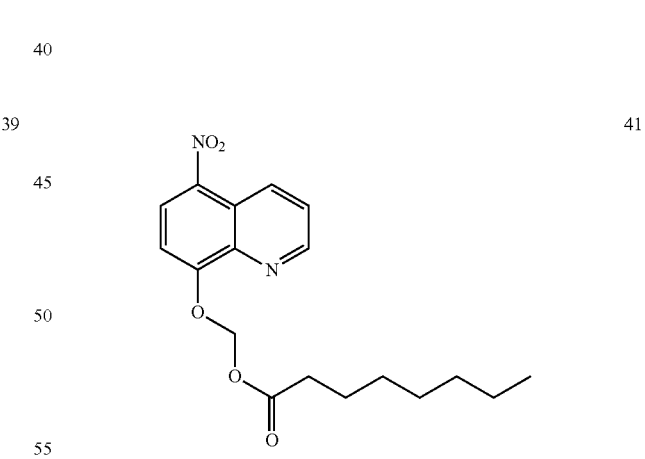

41

(5-Nitroquinolin-8-yloxy)methyl octanoate was obtained in accordance with the same preparation method of Example 1 except for replacing the acetic acid in Step 2 with n-octanoic acid.

¹H NMR (400 MHz, CDCl₃) δ 9.19 (dd, J=8.9, 1.6 Hz, 1H), 9.07 (dd, J=4.1, 1.6 Hz, 1H), 8.50 (d, J=8.8 Hz, 1H), 7.72 (dd, J=8.9, 4.1 Hz, 1H), 7.37 (d, J=8.8 Hz, 1H), 6.18 (s, 2H), 2.40 (t, J=7.5 Hz, 2H), 1.64 (dd, J=14.6, 7.4 Hz, 2H), 1.32-1.16 (m, 8H), 0.84 (t, J=7.0 Hz, 3H).

MS calculated: 346.4; MS observed: 347.2[M+H]⁺.

Example 42: Synthesis of (5-nitroquinolin-8-yloxy)methyl decanoate (42)

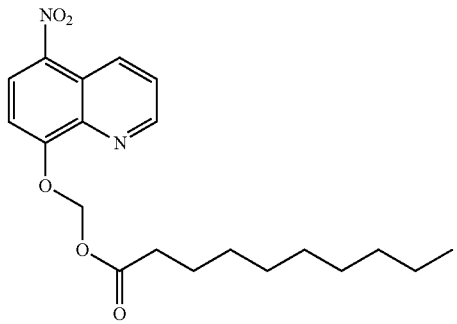 [SMILES: CCCCCCCCCC(=O)OCOc1ccc([N+](=O)[O-])c2cccnc12]

(5-Nitroquinolin-8-yloxy)methyl decanoate was obtained in accordance with the same preparation method of Example 1 except for replacing the acetic acid in Step 2 with n-decanoic acid.

$^1$H NMR (400 MHz, CDCl$_3$) δ 9.20 (dd, J=8.9, 1.6 Hz, 1H), 9.07 (dd, J=4.1, 1.6 Hz, 1H), 8.50 (d, J=8.8 Hz, 1H), 7.71 (dd, J=8.9, 4.1 Hz, 1H), 7.36 (d, J=8.8 Hz, 1H), 6.18 (s, 2H), 2.40 (t, J=7.5 Hz, 2H), 1.63 (dt, J=15.2, 7.5 Hz, 2H), 1.32-1.17 (m, 12H), 0.86 (t, J=6.9 Hz, 3H).

MS calculated: 374.4; MS observed: 375.2[M+H]$^+$.

Example 43: Synthesis of (5-nitroquinolin-8-yloxy)methyl dodecanoate (43)

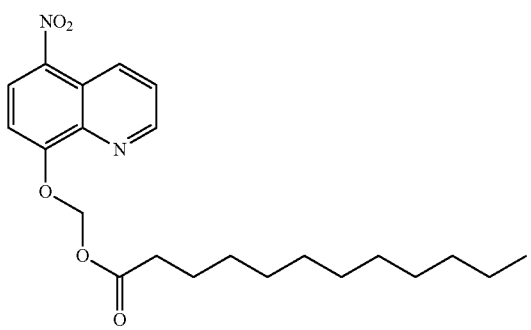 [SMILES: CCCCCCCCCCCC(=O)OCOc1ccc([N+](=O)[O-])c2cccnc12]

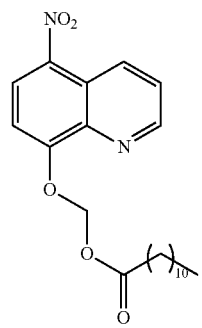

(5-Nitroquinolin-8-yloxy)methyl dodecanoate was obtained in accordance with the same preparation method of Example 1 except for replacing the acetic acid in Step 2 with lauric acid.

$^1$H-NMR (400 Hz, CDCl$_3$) δ: 9.22 (dd, J=8.8, 1.2 Hz, 1H), 9.10 (dd, J=4.0, 1.6 Hz, 1H), 8.52 (d, J=8.8 Hz, 1H), 7.77 (dd, J=8.8 Hz, 4.0 Hz, 1H), 7.35 (d, J=9.2 Hz, 1H), 6.20 (s, 2H), 2.41 (t, J=3.6 Hz, 2H), 1.61-1.68 (m, 2H), 1.23-1.25 (m, 12H), 0.87-0.91 (m, 3H), 0.05-0.09 (4H).

MS calculated: 402.49; MS observed: 403.3 [M+H]$^+$.

Example 44: Synthesis of 6-(5-nitroquinolin-8-yloxy)-tetrahydropyran-2-one (44)

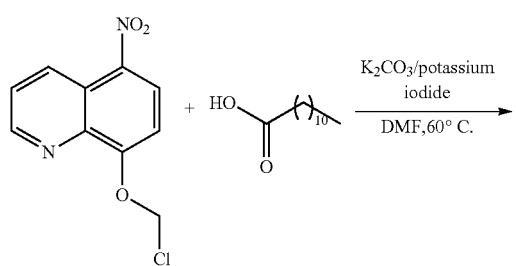

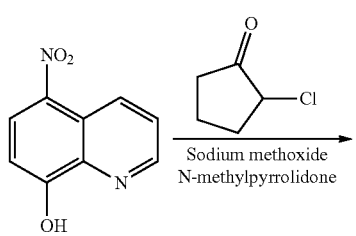

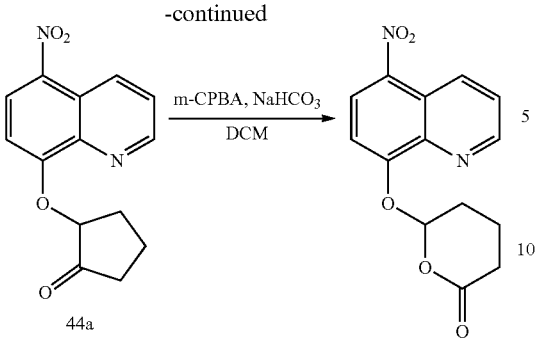

Step 1: Preparation of 2-((5-nitroquinolin-8-yl)oxy)cyclopentan-1-one (44a)

Sodium methoxide (170 mg, 3.15 mmol) and potassium iodide (87 mg, 0.52 mmol) were added to a solution of nitroxoline (500 mg, 2.63 mmol) in N-methylpyrrolidone (12.5 mL) at room temperature. The reaction system was warmed up to 60° C. and stirred for 15 minutes. 2-Chlorocyclopentanone (623 mg, 5.25 mmol) was added, and the reaction solution was stirred for 7 hours. The reaction was quenched by water, and the solution was extracted with ethyl acetate. The organic phase was washed with saturated brine, dried over anhydrous sodium sulfate, filtered and concentrated. The residues were purified by silica gel column chromatography (50% petroleum ether/50% ethyl acetate) to obtain 2-(5-nitroquinolin-8-yloxy)-cyclopentanone (240 mg, purity: 34%).

Step 2: Preparation of 6-(5-nitroquinolin-8-yloxy)-tetrahydropyran-2-one (44)

Sodium bicarbonate (56 mg, 0.67 mmol) was added to a solution of 2-(5-nitroquinolin-8-yloxy)-cyclopentanone (44a) (140 mg, 0.51 mmol) in dichloromethane (2 mL) at room temperature. The reaction system was cooled to 0° C., and m-chloroperoxybenzoic acid (m-CPBA) (purity: 85%, 136 mg, 0.67 mmol) was added. The reaction solution was naturally warmed up to room temperature and stirred for 16 hours. The reaction was quenched by water, and the solution was extracted with dichloromethane. The organic phase was washed with saturated brine, dried over anhydrous sodium sulfate, filtered and concentrated under reduced pressure. The residues were purified by silica gel thin layer chromatography (eluent: 5% methanol/95% dichloromethane) to obtain 6-(5-nitroquinolin-8-yloxy)-tetrahydropyran-2-one (94 mg, purity: 63%).

$^1$H NMR (400 MHz, CDCl$_3$) δ 9.17 (dd, J=8.9, 1.5 Hz, 1H), 9.04 (dd, J=4.1, 1.5 Hz, 1H), 8.48 (d, J=8.8 Hz, 1H), 7.70 (dd, J=8.9, 4.1 Hz, 1H), 7.51 (d, J=8.8 Hz, 1H), 6.39 (t, J=3.3 Hz, 1H), 2.89-2.63 (m, 2H), 2.56-2.44 (m, 2H), 2.37-1.97 (m, 2H).

MS calculated: 288.3; MS observed: 289.1[M+H]$^+$.

Example 45: Synthesis of ((5-nitroquinolin-8-yl)oxy)methyl 2-(2-(2-methoxyethoxy)ethoxy)acetate (45)

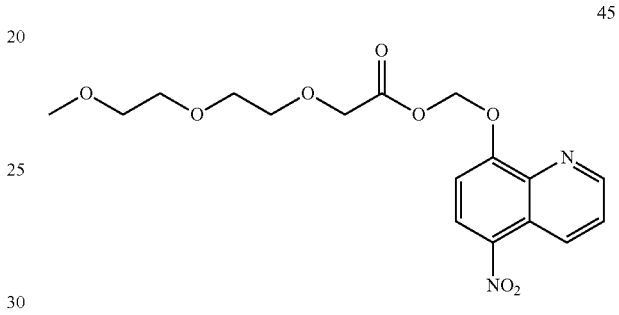

((5-Nitroquinolin-8-yl)oxy)methyl 2-(2-(2-methoxyethoxy)ethoxy)acetate was obtained in accordance with the same preparation method of Example 1 except for replacing the acetic acid in Step 2 with 2-(2-(2-methoxyethoxy)ethoxy)acetic acid (purchased from Shanghai Dan chemical Co. Ltd.).

$^1$H-NMR (400 Hz, CDCl$_3$) δ: 9.20 (dd, J=6.0 Hz, 1H), 9.08 (d, J=2.8 Hz, 1H), 8.51 (d, J=8.8 Hz, 1H), 7.77 (dd, J=8.8 Hz, 4.0 Hz, 1H), 7.40 (d, J=8.8 Hz, 1H), 6.26 (s, 2H), 4.27 (s, 2H), 3.75-3.76 (m, 2H), 3.69-3.70 (m, 2H), 3.63-3.65 (m, 2H), 3.53-3.55 (m, 2H), 3.37 (s, 3H).

MS calculated: 380.35; MS observed: 381.1 [M+H]$^+$.

Example 46: Synthesis of bis(5-nitroquinolin-8-yloxy)-methyl adipate (46)

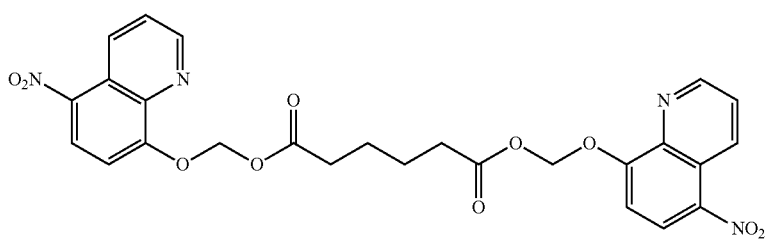 [SMILES: O=C(CCCCC(=O)OCOc1ccc([N+](=O)[O-])c2cccnc12)OCOc1ccc([N+](=O)[O-])c2cccnc12]

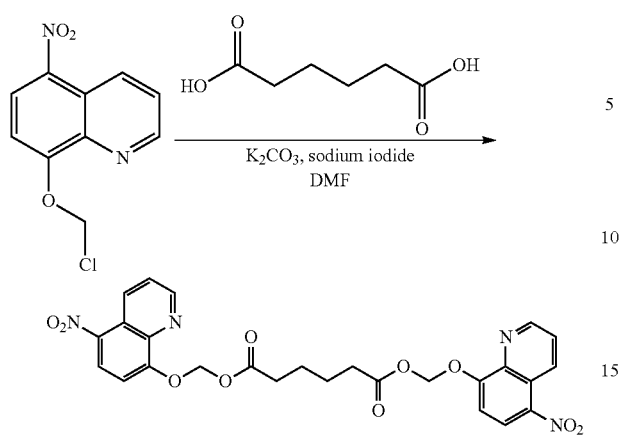

Adipic acid (300 mg, 2.05 mmol), potassium carbonate (680 mg, 4.92 mmol) and sodium iodide (62 mg, 0.41 mmol) were added to N,N-dimethylformamide (20 mL) at room temperature and stirred well. The reaction system was warmed up to 60° C. and stirred for 10 minutes. 5-Nitro-8-chloromethoxyquinoline (1a) (980 mg, 4.11 mmol) was added, and the reaction solution was stirred for 2 hours. The reaction was quenched by water, and the solution was extracted with ethyl acetate. The organic phase was washed with saturated brine, dried over anhydrous sodium sulfate, filtered and concentrated under reduced pressure. The residues were purified by silica gel thin layer chromatography (eluent: 5% methanol/95% dichloromethane) to obtain bis (5-nitroquinolin-8-yloxy)-methyl adipate (78 mg, yield: 7%).

$^1$H NMR (400 MHz, CDCl$_3$) δ 9.18 (dd, J=8.9, 1.6 Hz, 2H), 9.06 (dd, J=4.1, 1.6 Hz, 2H), 8.49 (d, J=8.8 Hz, 2H), 7.71 (dd, J=8.9, 4.1 Hz, 2H), 7.34 (d, J=8.8 Hz, 2H), 6.16 (s, 4H), 2.41 (s, 4H), 1.68 (t, J=3.2 Hz, 4H).

MS calculated: 550.5; MS observed: 551.3[M+H]$^+$.

Example 47: Synthesis of 1-(5-nitroquinolin-8-yloxy)ethyl acetate (47)

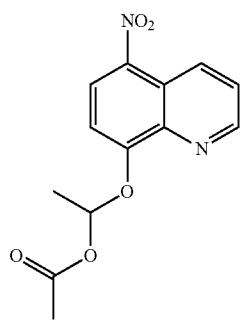 [SMILES: CC(=O)OC(C)Oc1ccc([N+](=O)[O-])c2cccnc12]

47

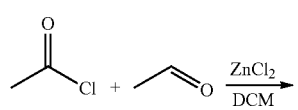

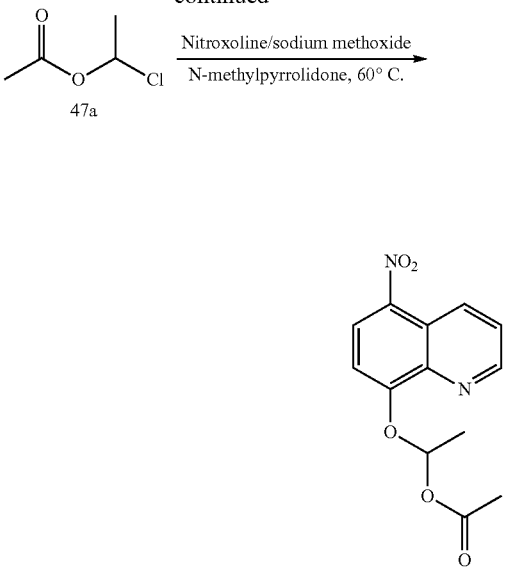

Step 1: Preparation of 1-chloroethyl acetate (47a)

Acetyl chloride (1.00 g, 12.74 mmol) was slowly added to a solution of acetaldehyde (0.56 g, 12.71 mmol) and zinc chloride (0.17 g, 1.25 mmol) in dichloromethane (20 mL) at 0° C. The reaction solution was stirred at 0° C. for 10 minutes, then warmed up to room temperature and stirred for 16 hours. The reaction was quenched by water, and the solution was extracted with dichloromethane. The organic phase was washed with saturated brine, dried over anhydrous sodium sulfate, filtered and concentrated under reduced pressure to obtain the crude product 1-chloroethyl acetate (1.39 g).

Step 2: Preparation of 1-(5-nitroquinolin-8-yloxy)ethyl acetate (47)

Sodium methoxide (68 mg, 1.26 mmol) and potassium iodide (17 mg, 0.10 mmol) were added to a solution of nitroxoline (200 mg, 1.05 mmol) in N-methylpyrrolidone (5 mL) at room temperature. The reaction system was warmed up to 60° C. and stirred for 15 minutes. 1-Chloroethyl acetate (193 mg, 1.57 mmol) was added, and the reaction solution was stirred for 16 hours. The reaction was quenched by water, and the solution was extracted with ethyl acetate. The organic phase was washed with saturated brine, dried over anhydrous sodium sulfate, filtered and concentrated under reduced pressure. The residues were purified by silica gel thin layer chromatography (eluent: 5% methanol/95% dichloromethane) to obtain 1-(5-nitroquinolin-8-yloxy)ethyl acetate (124 mg, yield: 43%).

1H NMR (400 MHz, CDCl$_3$) δ 9.18 (dd, J=8.9, 1.6 Hz, 1H), 9.08 (dd, J=4.1, 1.6 Hz, 1H), 8.47 (d, J=8.8 Hz, 1H), 7.70 (dd, J=8.9, 4.1 Hz, 1H), 7.21 (d, J=8.8 Hz, 1H), 6.97 (q, J=5.3 Hz, 1H), 2.10 (s, 3H), 1.87 (d, J=5.3 Hz, 3H).

MS calculated: 276.2; MS observed: 277.1 [M+H]$^+$.

Example 48: Synthesis of 1-(5-nitroquinolin-8-yloxy)ethyl propionate (48)

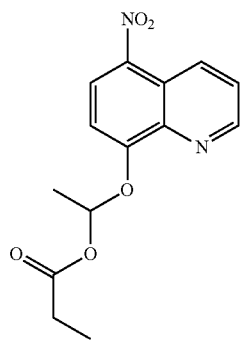 [SMILES: CCC(=O)OC(C)Oc1ccc([N+](=O)[O-])c2cccnc12]

1-(5-Nitroquinolin-8-yloxy)ethyl propionate was obtained in accordance with the same preparation method of Example 47 except for replacing the acetyl chloride in Step 1 with propionyl chloride.

$^1$H NMR (400 MHz, CDCl$_3$) δ 9.18 (dd, J=8.9, 1.5 Hz, 1H), 9.08 (dd, J=4.1, 1.5 Hz, 1H), 8.46 (d, J=8.8 Hz, 1H), 7.70 (dd, J=8.9, 4.1 Hz, 1H), 7.20 (d, J=8.8 Hz, 1H), 6.99 (q, J=5.2 Hz, 1H), 2.38 (q, J=7.5 Hz, 2H), 1.87 (d, J=5.3 Hz, 3H), 1.12 (t, J=7.5 Hz, 3H).

MS calculated: 290.3; MS observed: 291.1 [M+H]$^+$.

Example 49: Synthesis of 1-(5-nitroquinolin-8-yloxy)ethyl isobutyrate (49)

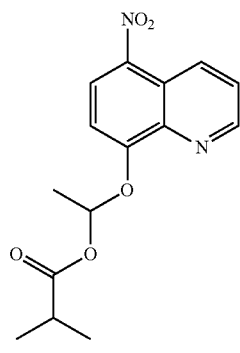 [SMILES: CC(OC(=O)C(C)C)Oc1ccc([N+](=O)[O-])c2cccnc12]

1-(5-Nitroquinolin-8-yloxy)ethyl isobutyrate was obtained in accordance with the same preparation method of Example 47 except for replacing the acetyl chloride in Step 1 with isobutyryl chloride.

$^1$H NMR (400 MHz, CDCl$_3$) δ 9.18 (dd, J=8.9, 1.2 Hz, 1H), 9.08 (dd, J=3.9, 1.1 Hz, 1H), 8.46 (d, J=8.8 Hz, 1H), 7.70 (dd, J=8.9, 4.1 Hz, 1H), 7.18 (d, J=8.8 Hz, 1H), 6.98 (q, J=5.2 Hz, 1H), 2.64-2.51 (m, 1H), 1.87 (d, J=5.2 Hz, 3H), 1.14 (dd, J=14.4, 7.0 Hz, 6H).

MS calculated: 304.3; MS observed: 305.2 [M+H]$^+$.

Example 50: Synthesis of 1-(5-nitroquinolin-8-yloxy)ethyl pivalate (50)

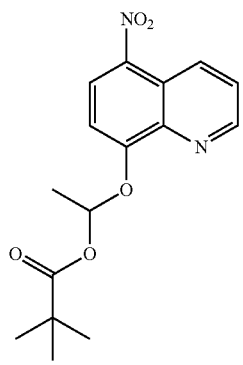 [SMILES: CC(OC(=O)C(C)(C)C)Oc1ccc([N+](=O)[O-])c2cccnc12]

1-(5-Nitroquinolin-8-yloxy)ethyl pivalate was obtained in accordance with the same preparation method of Example 47 except for replacing the acetyl chloride in Step 1 with pivaloyl chloride.

$^1$H NMR (400 MHz, CDCl$_3$) δ 9.19 (dd, J=8.9, 1.5 Hz, 1H), 9.08 (dd, J=4.1, 1.5 Hz, 1H), 8.45 (d, J=8.8 Hz, 1H), 7.70 (dd, J=8.9, 4.1 Hz, 1H), 7.15 (d, J=8.8 Hz, 1H), 6.96 (q, J=5.2 Hz, 1H), 1.88 (d, J=5.2 Hz, 3H), 1.17 (s, 9H).

MS calculated: 318.3; MS observed: 319.2 [M+H]$^+$.

Example 51: Synthesis of 1-(5-nitroquinolin-8-yloxy)ethyl 2-ethylbutanoate (51)

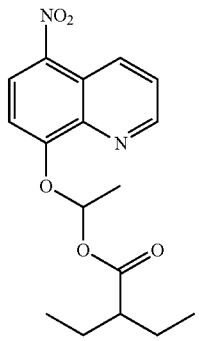 [SMILES: CCC(CC)C(=O)OC(C)Oc1ccc([N+](=O)[O-])c2cccnc12]

1-(5-Nitroquinolin-8-yloxy)ethyl 2-ethylbutanoate was obtained in accordance with the same preparation method of Example 47 except for replacing the acetyl chloride in Step 1 with 2-ethylbutyryl chloride.

$^1$H NMR (400 MHz, CDCl$_3$) δ: 9.20-9.17 (m, 1H), 9.08-9.07 (m, 1H), 8.45 (d, J=8.4 Hz, 1H), 7.72-7.68 (m, 1H), 7.21 (d, J=8.8 Hz, 1H), 7.03-7.01 (m, 1H), 2.25-2.11 (m, 1H), 1.88 (d, J=5.2 Hz, 3H), 1.60-1.49 (m, 4H), 0.88-0.81 (m, 6H).

MS calculated: 332; MS observed: 333[M+H]$^+$.

Example 52: Synthesis of (5-nitroquinolin-8-yloxy)methyl 2,3-dihydroxypropyl(methyl)carbamate (52)

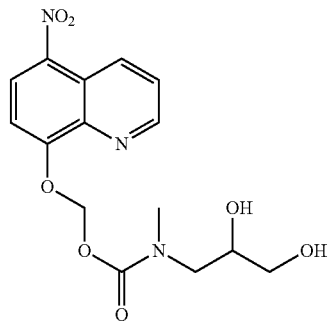 [SMILES: CN(CC(O)CO)C(=O)OCOc1ccc([N+](=O)[O-])c2cccnc12]

52

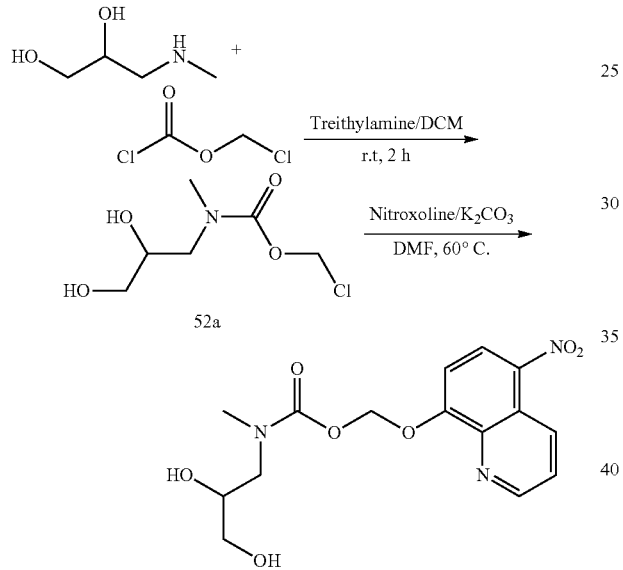

Step 1: Preparation of chloromethyl 2,3-dihydroxypropyl(methyl)carbamate (52a)

N-Methyl-2,3-dihydroxypropylamine (1 g, 10 mmol) was dissolved in a mixed solvent of acetonitrile (40 mL) and methanol (8 mL), and then slowly added dropwise with triethylamine (1.15 g, 11.4 mmol) and chloromethyl chloroformate (1.35 g, 10.48 mmol) under an ice-water bath. The reaction solution was stirred at 0° C. for 30 minutes, then warmed up to 25° C. and stirred for 16 hours. Water (50 mL) was added to quench the reaction, and the solution was extracted with dichloromethane (100 mL×3). The organic phases were combined, dried over anhydrous sodium sulfate and filtered. The filtrate was concentrated under reduced pressure to obtain the product chloromethyl 2,3-dihydroxypropyl(methyl)carbamate (1.7 g, yield: 89%).

Step 2: Preparation of (5-nitroquinolin-8-yloxy)methyl 2,3-dihydroxypropyl(methyl)carbamate (52)

Nitroxoline (600 mg, 3.16 mmol) and chloromethyl 2,3-dihydroxypropyl(methyl)carbamate (940 mg, 4.7 mmol) were dissolved in N,N-dimethylformamide (15 mL). Potassium carbonate (871 mg, 6.31 mmol) and sodium iodide (47 mg, 0.32 mmol) were added at 0° C. The reaction solution was stirred at 60° C. for 4 hours. The reaction solution was cooled to room temperature, quenched with water and extracted with dichloromethane (100 mL×3). The organic phases were combined, dried over anhydrous sodium sulfate and filtered. The filtrate was concentrated under reduced pressure. The residues were purified by silica gel column chromatography (eluent: 5% methanol/95% dichloromethane) to obtain the product (5-nitroquinolin-8-yloxy)methyl 2,3-dihydroxypropyl(methyl)carbamate (300 mg, yield: 27%).

$^1$H NMR (400 MHz, CDCl$_3$) δ: 9.20-9.18 (m, 1H), 9.06 (dd, J=4.0, 1.2 Hz, 1H), 8.51 (d, J=8.8 Hz, 1H), 7.73-7.70 (m, 1H), 7.40 (d, J=8.8 Hz, 1H), 6.21-6.13 (m, 2H), 3.88 (s, 1H), 3.67-3.40 (m, 4H), 3.04-2.95 (m, 5H).

MS calculated: 351.11; MS observed: 352.1 [M+H]$^+$.

Example 53: Synthesis of methyl 2-(((5-nitroquinolin-8-yloxy)methoxy)formamido)acetate (53)

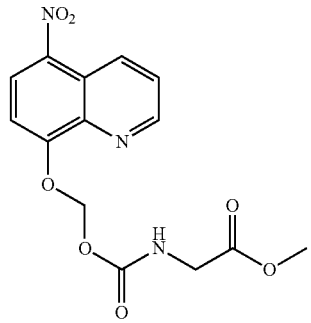 [SMILES: COC(=O)CNC(=O)OCOc1ccc([N+](=O)[O-])c2cccnc12]

53

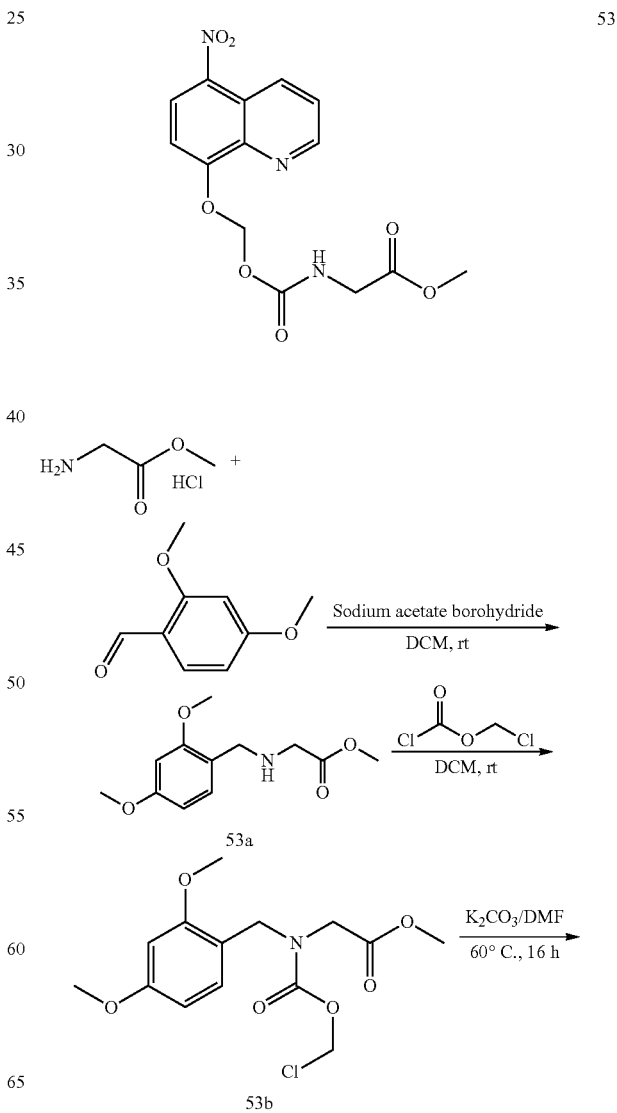

-continued

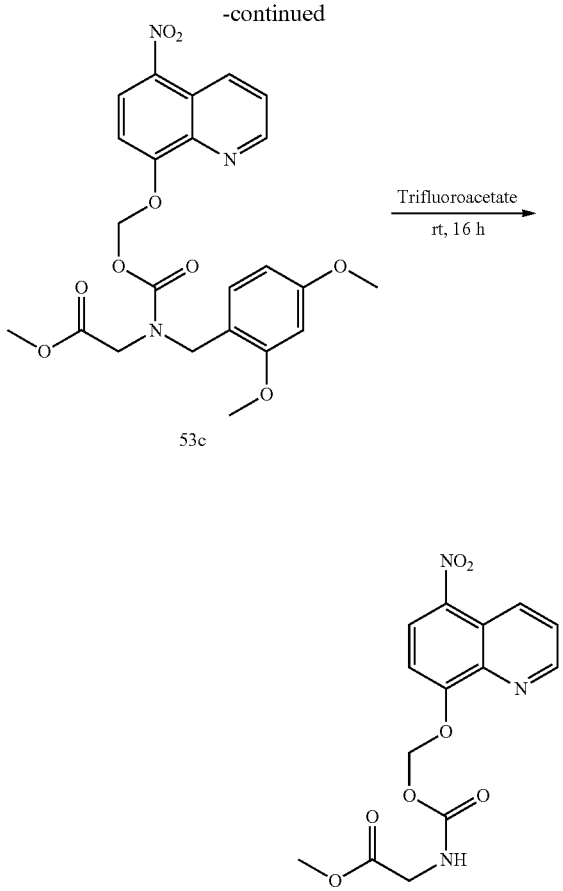

53c

Step 1: Preparation of methyl 2-(2,4-dimethoxy benzylamino)acetate (53a)

2,4-Dimethoxybenzaldehyde (720 mg, 4.34 mmol) and sodium acetate borohydride (1.38 g, 6.51 mmol) were successively slowly added to a solution of triethylamine (658 mg, 6.51 mmol) and methyl 2-amino-acetate hydrochloride (1.00 g, 6.51 mmol) in dichloromethane (40 mL) at 0° C. The reaction solution was stirred at 60° C. for 2 hours, and then cooled to room temperature. The reaction was quenched by water, and the solution was extracted with dichloromethane (100 mL×3). The organic phase was washed with 1 M hydrochloric acid, 1 M sodium bicarbonate aqueous solution and saturated brine, dried over anhydrous sodium sulfate, filtered and concentrated under reduced pressure. The residues were purified by silica gel column chromatography (eluent: 5% methanol/95% dichloromethane) to obtain methyl 2-(2,4-dimethoxybenzylamino)acetate (1.1 g, yield: 950%).

MS[M+H]$^+$: 240.0.

Step 2: Preparation of methyl 2-(((chloromethoxy) formyl)(2,4-dimethoxy benzyl)amino)acetate (53b)

Chloromethyl chloroformate (595 mg, 4.60 mmol) was slowly added dropwise to a solution of methyl 2-(2,4-dimethoxybenzylamino)acetate (1.0 g, 4.39 mmol) and triethylamine (485 mg, 4.80 mmol) in dichloromethane (20 mL) at 0° C. The reaction solution was stirred at 50° C. for 2 hours, and then cooled to room temperature. The reaction was quenched by water, and the solution was extracted with dichloromethane (100 mL×3). The organic phase was washed with 1 M hydrochloric acid, 1 M sodium bicarbonate aqueous solution and saturated brine, dried over anhydrous sodium sulfate, filtered and concentrated under reduced pressure. The residues were purified by silica gel column chromatography (eluent: 5% hexane/95% ethyl acetate) to obtain methyl 2-(((chloromethoxy)formyl)(2,4-dimethoxy benzyl)amino)acetate (1.00 g, yield: 69%).

MS[M+H]$^+$: 332.1.

Step 3: Preparation of methyl 2-((2,4-dimethoxy-benzyl)(((5-nitroquinolin-8-yloxy)methoxy)formyl) amino)acetate (53c)

Methyl 2-(((chloromethoxy)formyl)(2,4-dimethoxybenzyl)amino)acetate (1.05 g, 2.79 mmol) was added to a solution of nitroxoline (360 mg, 1.9 mmol), potassium carbonate (385 mg, 2.79 mmol) and sodium iodide (30 mg, 0.19 mmol) in N,N-dimethylformamide (15 mL) at room temperature. The reaction solution was stirred at 50° C. for 2 hours, and then cooled to room temperature. The reaction was quenched by water, and the solution was extracted with dichloromethane (100 mL×3). The organic phase was washed with 1 M hydrochloric acid, 1 M sodium bicarbonate aqueous solution and saturated brine, dried over anhydrous sodium sulfate, filtered and concentrated under reduced pressure. The residues were purified by silica gel column chromatography (eluent: 5% hexane/95% ethyl acetate) to obtain methyl 2-((2,4-dimethoxybenzyl)(((5-nitroquinolin-8-yloxy)methoxy)formyl)amino)acetate (440 mg, yield: 48%).

MS[M+H]$^+$: 486.0.

Step 4: Preparation of methyl 2-(((5-nitroquinolin-8-yloxy)methoxy)formamido)acetate (53)

Trifluoroacetic acid (8 mL) was added dropwise to a solution of methyl 2-((2,4-dimethoxybenzyl)(((5-nitroquinolin-8-yloxy)methoxy)formyl)amino)acetate (440 mg, 0.91 mmol) in dichloromethane (8 mL) at room temperature. The reaction solution was stirred at room temperature for 2 hours. The reaction was quenched by water, and the solution was extracted with dichloromethane (100 mL×3). The organic phase was washed with 1 M hydrochloric acid, 1 M sodium bicarbonate aqueous solution and saturated brine, dried over anhydrous sodium sulfate, filtered and concentrated under reduced pressure. The residues were purified by silica gel column chromatography (eluent: 50% hexane/50% ethyl acetate) to obtain methyl 2-(((5-nitroquinolin-8-yloxy)methoxy)formamido)acetate (200 mg, yield: 67%).

$^1$H NMR (400 MHz, CDCl$_3$) δ: 9.18 (dd, J=8.8, 1.6 Hz, 1H), 9.06 (dd, J=4.0, 1.6 Hz, 1H), 8.49 (d, J=8.8 Hz, 1H), 7.70 (dd, J=8.4, 4.4 Hz, 1H), 7.40 (d, J=9.2 Hz, 1H), 6.18 (s, 2H), 5.41 (s, 1H), 4.01 (d, J=5.6 Hz, 2H), 3.77 (s, 3H).

MS calculated: 335.08; MS observed: 336.1 [M+H]$^+$.

Example 54: Synthesis of methyl 2-(((5-nitroquino-lin-8-yloxy)methoxy)formamido)butanoate (54)

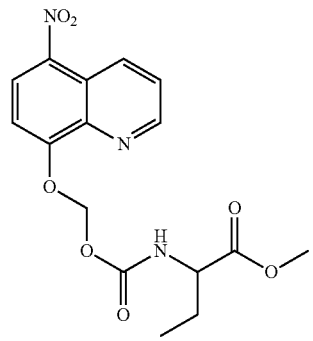 [SMILES: CCC(NC(=O)OCOc1ccc([N+](=O)[O-])c2cccnc12)C(=O)OC]

Methyl 2-(((5-nitroquinolin-8-yloxy)methoxy)forma-mido)butanoate was obtained in accordance with the same preparation method of Example 53 except for replacing the methyl 2-amino-acetate hydrochloride in Step 1 with methyl 2-amino-butanoate.

$^1$H NMR (400 MHz, CDCl$_3$): δ 9.19 (dd, J=8.8, 1.6 Hz, 1H), 9.06 (s, 1H), 8.49 (d, J=8.8 Hz, 1H), 7.70 (d, J=8.8 Hz, 1H), 7.40 (d, J=8.8 Hz, 1H), 6.17 (d, J=7.6 Hz, 2H), 5.43 (d, J=8.0 Hz, 1H), 4.36 (d, J=5.6 Hz, 1H), 3.75 (s, 3H), 1.90 (s, 1H), 1.72 (d, J=7.2 Hz, 1H), 0.90 (d, J=7.4 Hz, 3H).

MS calculated: 363; MS observed: 364.

Example 55: Synthesis of methyl 3-methyl-2-(((5-nitroquinolin-8-yloxy)methoxy)formamido)pentano-ate (55)

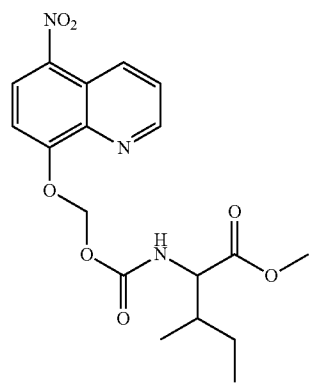 [SMILES: CCC(C)C(NC(=O)OCOc1ccc([N+](=O)[O-])c2cccnc12)C(=O)OC]

Methyl 3-methyl-2-(((5-nitroquinolin-8-yloxy)methoxy) formamido)pentanoate was obtained in accordance with the same preparation method of Example 53 except for replacing the methyl 2-amino-acetate hydrochloride in Step 1 with methyl 2-amino-3-methylpentanoate hydrochloride.

$^1$H NMR (400 MHz, CDCl$_3$) δ: 9.19 (dd, J=9.2, 1.2 Hz, 1H), 9.06 (dd, J=4.0, 1.6 Hz, 1H), 8.49 (d, J=8.8 Hz, 1H), 7.70 (dd, J=9.2, 4.4 Hz, 1H), 7.40 (dd, J=8.8, 1.2 Hz, 1H), 6.18-6.16 (m, 2H), 5.38 (m, 1H), 4.45 (dd, J=9.2, 4.0 Hz, 1H), 3.74 (s, 3H), 1.99-1.87 (m, 1H), 1.43-1.37 (m, 1H), 1.21-1.14 (m, 1H), 0.95-0.89 (m, 4H), 0.84-0.82 (d, J=8.8 Hz, 2H).

MS calculated: 391.14; MS observed: 392.1 [M+H]$^+$.

Example 56: Synthesis of methyl 3-methyl-2-(methyl(((5-nitroquinolin-8-yloxy)methoxy)formyl) amino)pentanoate (56)

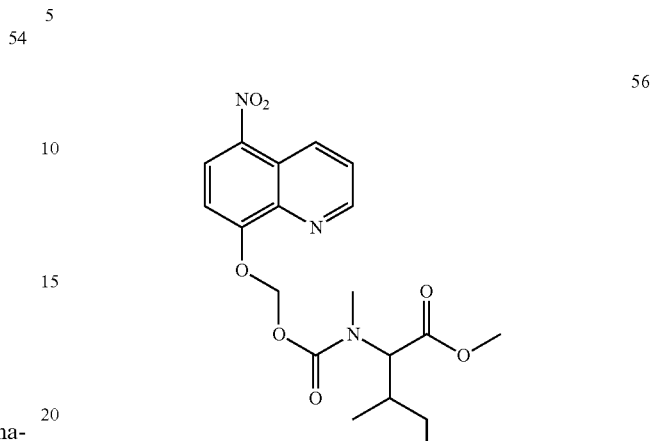

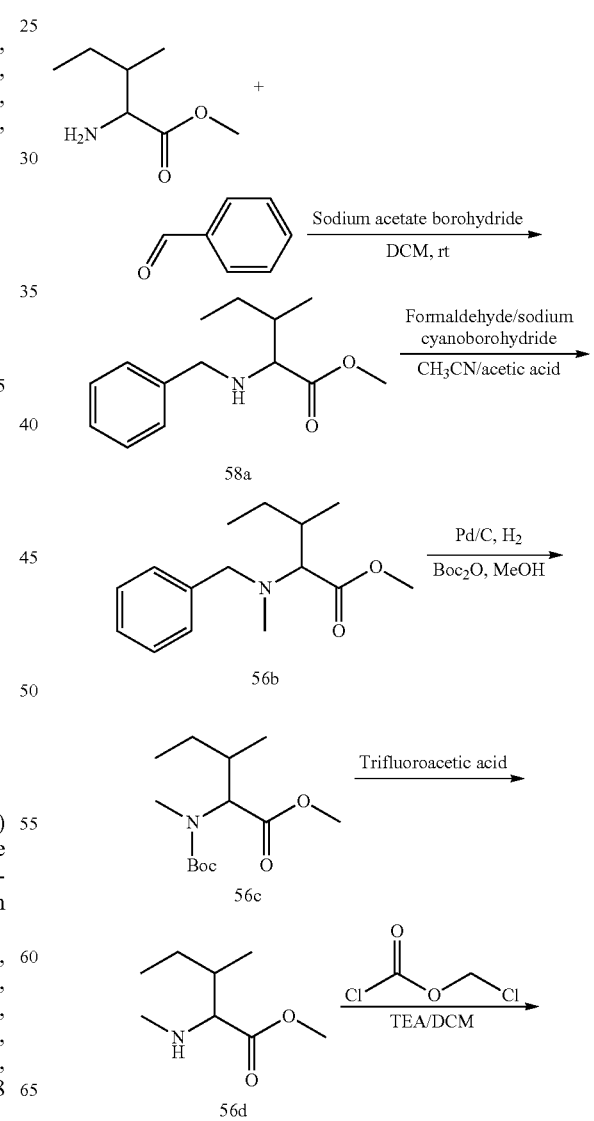

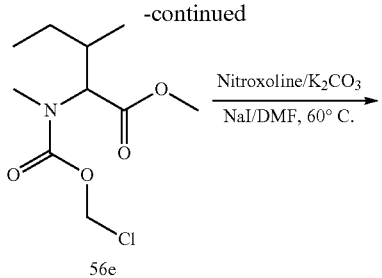

Step 1: Preparation of methyl N-benzyl-2-amino-3-methylpentanoate (56a)

Methyl 2-amino-3-methylpentanoate hydrochloride (4.0 g, 21.9 mmol) and sodium acetate borohydride (9.2 g, 43.4 mmol) were successively slowly added to a solution of benzaldehyde (1.6 g, 14.7 mmol) and triethylamine (2.2 g, 21.9 mmol) in dichloromethane (80 mL) at 0° C. The reaction solution was stirred at 0° C. for 30 minutes and at room temperature for 16 hours. Saturated aqueous sodium bicarbonate solution (20 mL) was added to quench the reaction, and the solution was extracted with dichloromethane (150 mL×3). The organic phases were combined, dried and concentrated under reduced pressure to obtain the crude product methyl N-benzyl-2-amino-3-methylpentanoate (4.2 g, yield: 100%).
MS[M+H]$^+$: 236.0.

Step 2: Preparation of methyl N-methyl-N-benzyl-2-amino-3-methylpentanoate (56b)

37% Formaldehyde (5.4 g, 179 mmol) aqueous solution, sodium cyanoborohydride (2.5 g, 39.4 mmol) and acetic acid (2 mL) were successively added to a solution of methyl N-benzyl-2-amino-3-methylpentanoate (4.2 g, 17.9 mmol) in acetonitrile (100 mL) at 0° C. The reaction solution was stirred at room temperature for 16 hours, and then saturated aqueous sodium bicarbonate solution (100 mL) was added to quench the reaction. The solution was extracted with dichloromethane (150 mL×3). The organic phase was dried over magnesium sulfate, filtered and concentrated under reduced pressure. The residues were purified by silica gel column chromatography (eluent: 5% methanol/95% dichloromethane) to obtain methyl N-methyl-N-benzyl-2-amino-3-methylpentanoate (4.2 g, yield: 93%).
MS[M+H]$^+$: 250.0.

Step 3: Preparation of methyl N-methyl-N-Boc-2-amino-3-methylpentanoate (56c)

Methyl N-methyl-N-benzyl-2-amino-3-methylpentanoate (4.2 g, 16.8 mmol), Pd/C (900 mg) and Boc$_2$O (10 mL) were added to methanol (30 mL). The reaction solution was stirred under a hydrogen atmosphere at 50° C. for 16 hours. The reaction solution was filtered to remove the solid, and concentrated under reduced pressure to obtain the crude product methyl N-methyl-N-Boc-2-amino-3-methylpentanoate (5.2 g, yield: 100%).
MS[M+H]$^+$: 260.0.

Step 4: Preparation of methyl N-methyl-2-amino-3-methylpentanoate (56d)

A solution of 5 M hydrochloric acid in 1,4-dioxane (10 mL) was added to a solution of methyl N-methyl-N-Boc-2-amino-3-methylpentanoate (5.2 g, 20 mmol) in tetrahydrofuran (50 mL) at 0° C. The reaction solution was stirred at room temperature for 2 hours, and concentrated under reduced pressure to obtain methyl N-methyl-2-amino-3-methylpentanoate (3.2 g, yield: 82%).
MS[M+H]$^+$: 160.0.

Step 5: Preparation of methyl N-methyl-N-chloromethoxyformyl-2-amino-3-methylpentanoate (56e)

Chloromethyl chloroformate (0.48 mL, 5.37 mmol) was slowly added dropwise to a solution of methyl N-methyl-2-amino-3-methylpentanoate (1 g, 5.12 mmol) and triethylamine (1.8 mL, 12.8 mmol) in dichloromethane (30 mL) at 0° C. The reaction solution was stirred at 0° C. for 30 minutes and at room temperature for 16 hours. Water (25 mL) was added to quench the reaction, and the solution was extracted with dichloromethane (100 mL×3). The organic phase was dried over magnesium sulfate and filtered. The filtrate was concentrated under reduced pressure to obtain the crude product methyl N-methyl-N-chloromethoxyformyl-2-amino-3-methylpentanoate (638 mg, yield: 49%).
MS[M+H]$^+$: 252.0.

Step 6: Preparation of methyl 3-methyl-2-(methyl (((5-nitroquinolin-8-yloxy)methoxy)formyl)amino) pentanoate (56)

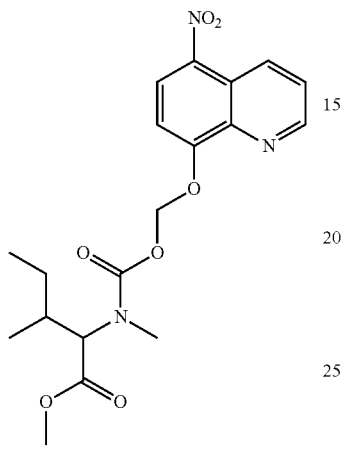

Methyl N-methyl-N-chloromethoxyformyl-2-amino-3-methylpentanoate (638 mg, 2.53 mmol) was slowly added dropwise to a solution of nitroxoline (350 mg, 2.63 mmol), potassium carbonate (464 mg, 3.36 mmol) and sodium iodide (27 mg, 0.18 mmol) in N,N-dimethylformamide (10 mL) at room temperature. The reaction solution was stirred at 60° C. for 2 hours. Water (25 mL) was added to quench the reaction, and the solution was extracted with dichloromethane (100 mL×3). The organic phase was dried over magnesium sulfate and filtered. The filtrate was concentrated under reduced pressure. The residues were purified by silica gel column chromatography (eluent: 5% methanol/ 95% dichloromethane) to obtain methyl 3-methyl-2-(methyl (((5-nitroquinolin-8-yloxy)methoxy)formyl)amino)pentanoate (70 mg, yield: 10%).
$^1$H NMR (400 MHz, CDCl$_3$) δ 9.20 (d, J=8.8 Hz, 1H), 9.07-9.06 (m, 1H), 8.50 (dd, J=8.8, 3.2 Hz, 1H), 7.72 (dd, J=8.8, 4.0 Hz, 1H), 7.42 (d, J=8.8 Hz, 1H), 6.25-6.21 (m, 2H), 4.61-4.30 (m, 1H), 3.71-3.58 (m, 3H), 2.94-2.89 (m, 3H), 1.98 (br s, 1H), 1.39-1.34 (m, 1H), 0.95-0.75 (m, 7H). MS calculated: 405.15; MS observed: 406.1 [M+H]$^+$.

Example 57: Synthesis of methyl 2-(methyl((5-nitroquinolin-8-yloxy)formyl)amino)acetate (57)

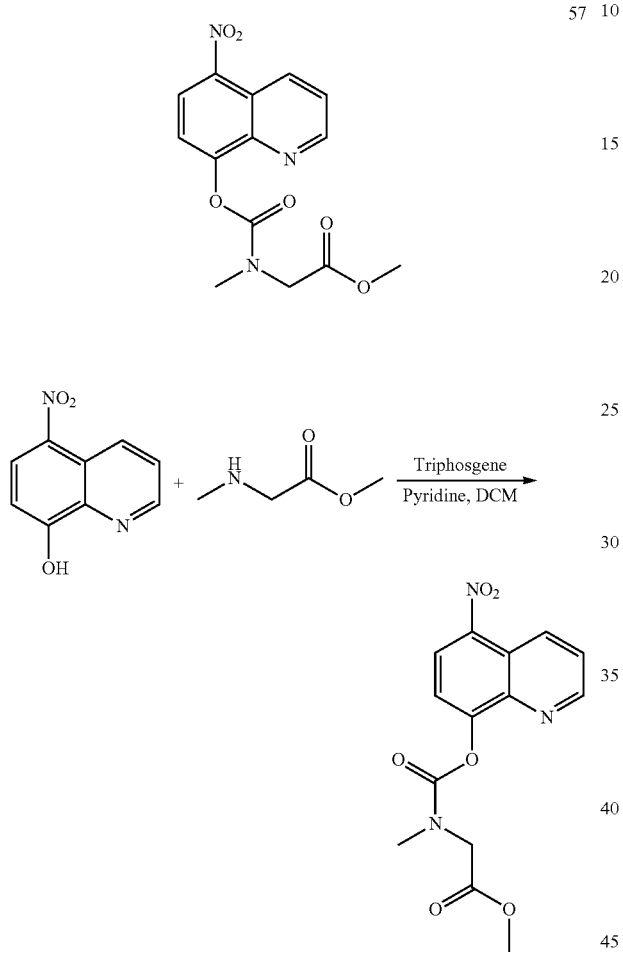

Triphosgene (296.8 mg, 1 mmol) and pyridine (790 mg, 10 mmol) were added to dichloromethane (6 mL) in batches at 0° C. The reaction solution was stirred at room temperature for 20 minutes. A solution of methyl N-methyl-2-aminoacetate (124 mg, 1.2 mmol) in acetonitrile (2 mL) was slowly added dropwise to the reaction solution, and stirred at room temperature for 1 hour. After removing the solvent under reduced pressure, pyridine (2 mL) was added, and nitroxoline (190 mg, 1 mmol) was added in batches. The reaction solution was heated to 110° C. under microwave for 2 hours. The reaction was quenched by water, and the solution was extracted with dichloromethane (100 mL×3). The organic phase was washed with 1 M hydrochloric acid, 1 M sodium bicarbonate aqueous solution and saturated brine, dried over anhydrous sodium sulfate, filtered and concentrated under reduced pressure. The residues were purified by silica gel column chromatography (eluent: 5% hexane/95% ethyl acetate) to obtain methyl 2-(methyl((5-nitroquinolin-8-yloxy)formyl)amino)acetate (100 mg, yield: 31%).

$^1$H NMR (400 MHz, CDCl$_3$) δ: 9.10-9.04 (m, 2H), 8.47-8.43 (m, 1H), 7.68-7.60 (m, 2H), 4.30 (d, J=84.8 Hz, 2H), 3.82 (d, J=13.6 Hz, 3H), 3.27 (d, J=88.0 Hz, 3H).

MS calculated: 319.08; MS observed: 320.0 [M+H]$^+$.

Example 58: Synthesis of methyl (S)-2-(((5-nitroquinolin-8-yloxy)methoxy)formamido)-3-phenylpropionate (58)

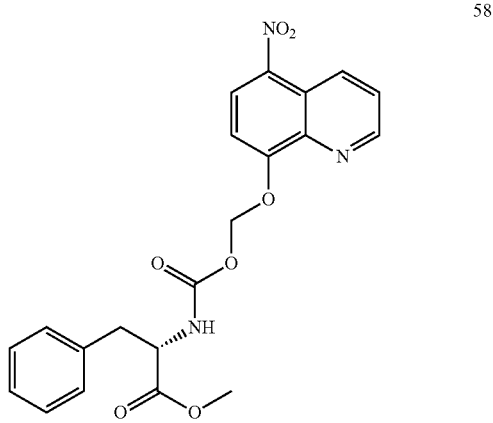

Methyl (S)-2-(((5-nitroquinolin-8-yloxy)methoxy)formamido)-3-phenylpropionate was obtained in accordance with the same preparation method of Example 53 except for replacing the methyl 2-amino-acetate hydrochloride in Step 1 with methyl L-phenylalaninate.

$^1$H-NMR (400 Hz, CDCl$_3$) δ: 9.35 (dd, J=8.8, 1.6 Hz, 1H), 9.15 (dd, J=4.4, 1.6 Hz, 1H), 8.53 (d, J=8.8 Hz, 1H), 7.83 (dd, J=8.8 Hz, 4.4 Hz, 1H), 7.56 (br, 1H), 7.40 (d, J=8.8 Hz, 1H), 7.25-7.17 (m, 3H), 7.04-7.18 (m, 2H), 6.10 (s, 2H), 4.51-4.68 (m, 1H), 3.72 (s, 3H), 2.95-3.18 (m, 2H).

MS calculated: 425.40; MS observed: 426.3 [M+H]$^+$.

Example 59: Synthesis of (2S,6R)-(5-nitroquinolin-8-yloxy)methyl 2,6-dimethylmorpholine-4-carboxylate (59)

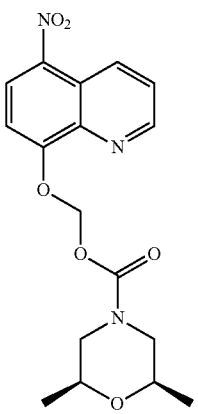 [SMILES: C[C@@H]1CN(C(=O)OCOc2ccc([N+](=O)[O-])c3cccnc23)C[C@H](C)O1]

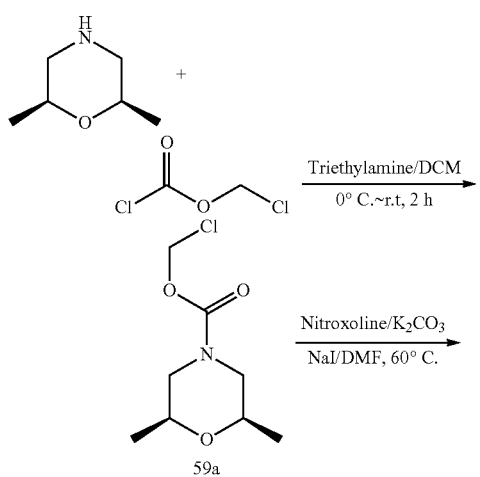

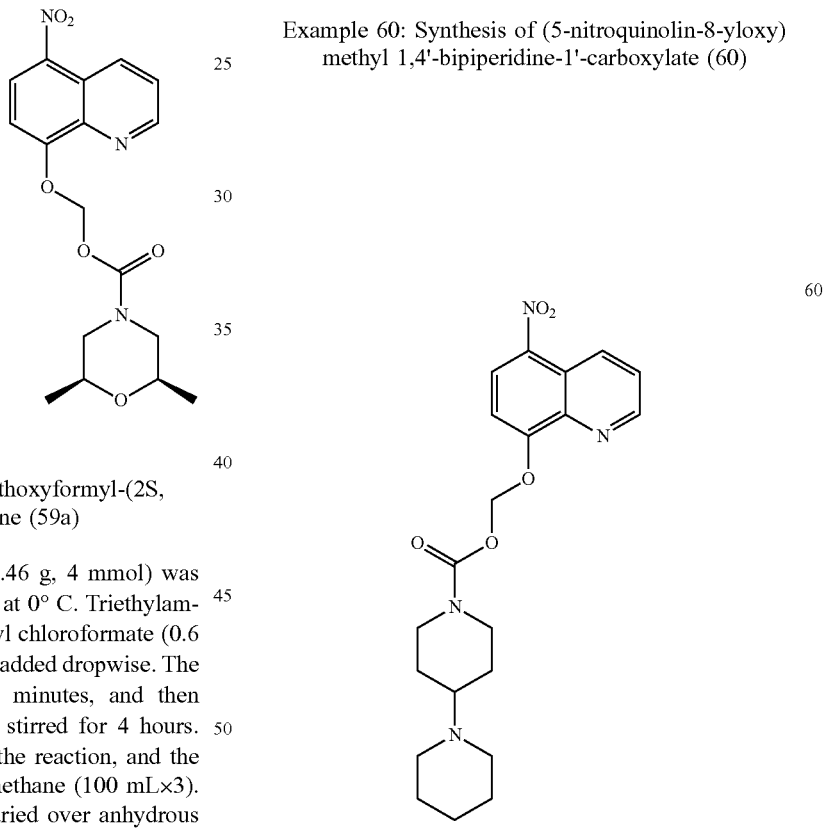

Step 1: Preparation of N-chloromethoxyformyl-(2S, 6R)-2,6-dimethylmorpholine (59a)

(2S,6R)-2,6-Dimethylmorpholine (0.46 g, 4 mmol) was dissolved in dichloromethane (10 mL) at 0° C. Triethylamine (1.1 mL, 8 mmol) and chloromethyl chloroformate (0.6 g, 4.6 mmol) were slowly successively added dropwise. The reaction solution was stirred for 30 minutes, and then warmed up to room temperature and stirred for 4 hours. Water (50 mL) was added to quench the reaction, and the solution was extracted with dichloromethane (100 mL×3). The organic phases were combined, dried over anhydrous sodium sulfate, filtered and concentrated under reduced pressure to obtain the product N-chloromethoxyformyl-(2S, 6R)-2,6-dimethylmorpholine (0.5 g, yield: 60%).

Step 2: Preparation of (2S,6R)-(5-nitroquinolin-8-yloxy)methyl 2,6-dimethylmorpholine-4-carboxylate (59)

Nitroxoline (0.6 g, 3.1 mmol) and N-chloromethoxyformyl-(2S,6R)-2,6-dimethylmorpholine (0.5 g, 2.4 mmol) were dissolved in N,N-dimethylformamide (10 mL) at room temperature. Potassium carbonate (0.7 g, 5.0 mmol) and potassium iodide (83 mg, 0.5 mmol) were added. The reaction solution was stirred at 60° C. for 4 hours. The reaction solution was cooled to room temperature, quenched with water and extracted with dichloromethane (100 mL×3). The organic phases were combined, dried over anhydrous sodium sulfate, filtered and concentrated under reduced pressure. The residues were purified by reversed-phase high performance liquid chromatography (column: Eclipse XDB-C18 (21.2 mm×250 mm, 7 μm), mobile phase: acetonitrile-0.1% formic acid, flow rate: 20.0 mL/min) to obtain (2S, 6R)-(5-nitroquinolin-8-yloxy)methyl 2,6-dimethylmorpholine-4-carboxylate (90 mg, yield: 11%).

$^1$H-NMR (400 Hz, CDCl$_3$) δ: 9.23 (dd, J=8.8, 1.2 Hz, 1H), 9.10 (d, J=3.2 Hz, 1H), 8.54 (d, J=8.8 Hz, 1H), 7.77 (dd, J=8.8 Hz, 4.0 Hz, 1H), 7.41 (d, J=8.8 Hz, 1H), 6.49 (d, J=8 Hz, 1H), 6.20-6.24 (m, 2H), 4.02 (d, J=12.8 Hz, 1H), 3.87 (d, J=12.8 Hz, 1H), 3.50-3.60 (m, 2H), 2.52-2.64 (m, 2H), 1.20 (d, J=6.4 Hz, 3H), 1.16 (d, J=6.0 Hz, 3H).

MS calculated: 361.35; MS observed: 362.3 [M+H]$^+$.

Example 60: Synthesis of (5-nitroquinolin-8-yloxy) methyl 1,4'-bipiperidine-1'-carboxylate (60)

(5-Nitroquinolin-8-yloxy)methyl 1,4'-bipiperidine-1'-carboxylate was obtained in accordance with the same preparation method of Example 59 except for replacing the (2S,6R)-2,6-dimethylmorpholine in Step 1 with 4-piperidinylpiperidine.

$^1$H-NMR (400 Hz, CDCl$_3$) δ: 9.25-9.27 (m, 1H), 9.12-9.13 (m, 1H), 8.53-8.55 (m, 1H), 7.75-7.78 (m, 1H), 7.42-7.44 (m, 1H), 6.21-6.22 (s, 2H), 3.53-4.03 (m, 8H), 2.52-2.64 (m, 2H), 1.08-1.20 (m, 9H).

MS calculated: 414.46; MS observed: 415.3 [M+H]$^+$.

Example 61: Synthesis of methyl 4-(((5-nitroquinolin-8-yloxy)methoxy)formamido)butanoate (61)

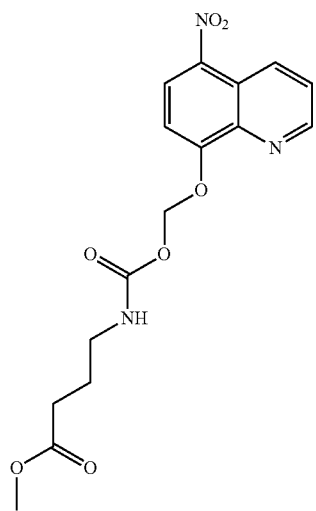 [SMILES: COC(=O)CCCNC(=O)OCOc1ccc([N+](=O)[O-])c2cccnc12]

61

Methyl 4-(((5-nitroquinolin-8-yloxy)methoxy)formamido)butanoate was obtained in accordance with the same preparation method of Example 53 except for replacing the methyl 2-amino-acetate hydrochloride in Step 1 with methyl 4-aminobutanoate hydrochloride.

¹H-NMR (400 Hz, CDCl₃) δ: 9.23 (dd, J=8.8, 0.8 Hz, 1H), 9.22 (dd, J=4.4, 3.6 Hz, 1H), 8.60 (d, J=9.2 Hz, 1H), 7.91 (dd, J=8.8, 4.4 Hz, 1H), 7.50 (d, J=8.8 Hz, 1H), 6.11 (s, 2H), 5.27 (s, 1H), 3.67 (s, 3H), 3.25-3.30 (m, 2H), 2.36-2.39 (m, 2H), 1.82-1.86 (m, 2H).

MS calculated: 363.33; MS observed: 364.3 [M+H]⁺.

Example 62: Synthesis of (5-nitroquinolin-8-yloxy)methyl 2-methylmorpholine-4-carboxylate (62)

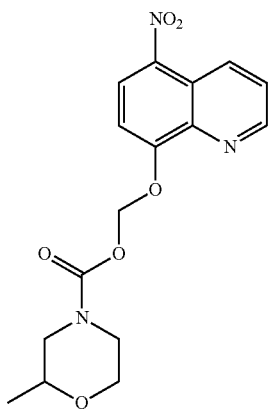 [SMILES: CC1CN(C(=O)OCOc2ccc([N+](=O)[O-])c3cccnc23)CCO1]

62

(5-Nitroquinolin-8-yloxy)methyl 2-methylmorpholine-4-carboxylate was obtained in accordance with the same preparation method of Example 59 except for replacing the (2S,6R)-2,6-dimethylmorpholine in Step 1 with 2-methylmorpholine.

¹H-NMR (400 Hz, CDCl₃) δ: 9.37-9.39 (m, 1H), 9.18-9.19 (m, 1H), 8.59 (d, J=8.4 Hz, 1H), 7.75 (dd, J=8.8 Hz, 4.4 Hz, 1H), 7.44 (d, J=8.8 Hz, 1H), 6.15-6.22 (s, 2H), 3.88-4.03 (m, 3H), 3.51-3.59 (m, 2H), 2.98-3.10 (m, 1H), 2.62-2.69 (m, 1H), 1.18-1.20 (m, 3H).

MS calculated: 347.33; MS observed: 338.3 [M+H]⁺.

Example 63: Synthesis of (5-nitroquinolin-8-yloxy)methyl 2-hydroxyethyl(methyl)carbamate (63)

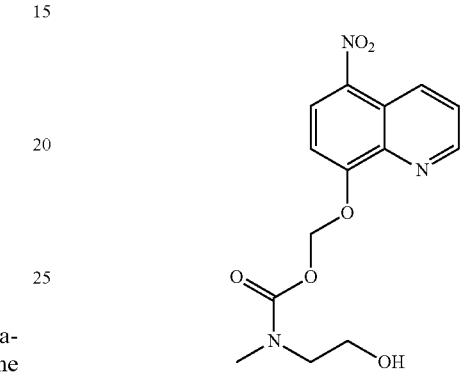

63

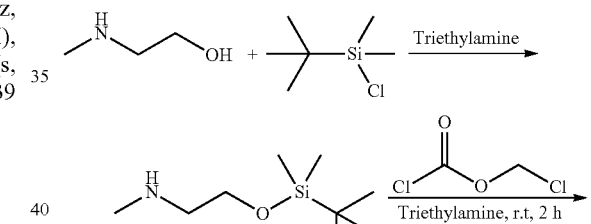

63a

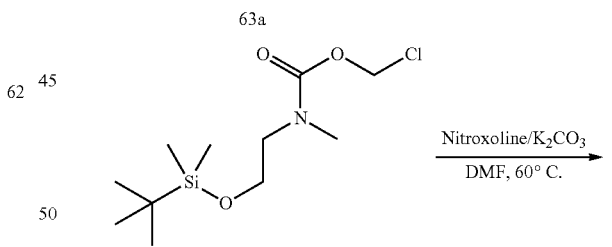

63b

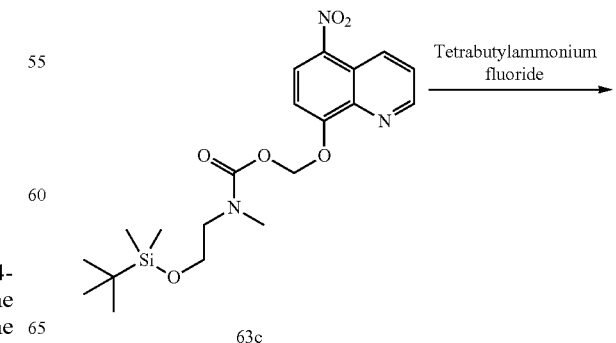

63c

-continued

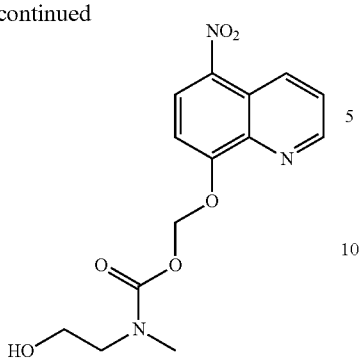

Step 1: Preparation of N-[2-(tert-butyldimethylsilyloxy)ethyl]methylamine (63a)

N-Methyl-2-hydroxyethylamine (3.5 g, 46.6 mmol) and tert-butylchlorodimethylsilane (7.7 g, 51.2 mmol) were dissolved in dichloromethane (100 mL) at 0° C., and triethylamine (13 mL, 93 mmol) was slowly added dropwise. The reaction solution was stirred at 0° C. for 30 minutes and at room temperature overnight. The reaction solution was concentrated to dryness and dissolved in methyl tert-butyl ether (200 mL). The solution was washed with 1 M sodium bicarbonate aqueous solution and saturated brine, dried over anhydrous sodium sulfate and filtered. The filtrate was concentrated under reduced pressure to obtain the product N-[2-(tert-butyldimethylsilyloxy)ethyl]methylamine (6 g, yield: 68%).

Step 2: Preparation of N-(chloromethoxycarbonyl)-N-[2-(tert-butyldimethylsilyloxy)ethyl]methylamine (63b)

N-[2-(Tert-butyldimethylsilyloxy)ethyl]methylamine (3 g, 15.8 mmol) was dissolved in dichloromethane (80 mL) at 0° C. Triethylamine (4.5 mL, 31.6 mmol) and chloromethyl chloroformate (2.6 g, 20.6 mmol) were slowly added dropwise successively. The reaction solution was stirred at 0° C. for 30 minutes and at room temperature overnight. Water (100 mL) was added to quench the reaction, and the solution was extracted with dichloromethane (200 mL×3). The organic phases were combined, dried over anhydrous sodium sulfate and filtered. The filtrate was concentrated under reduced pressure to obtain N-(chloromethoxyformyl)-N-[2-(tert-butyldimethylsilyloxy)ethyl]methylamine (2 g, yield: 29%).

Step 3: Preparation of (5-nitroquinolin-8-yloxy)methyl (2-(tert-butyldimethylsilyloxy)ethyl(methyl)carbamate (63c)

Nitroxoline (1.75 g, 9.2 mmol) and N-(chloromethoxyformyl)-N-[2-(tert-butyldimethylsilyloxy)ethyl]methylamine (2.0 g, 7.1 mmol) were dissolved in N,N-dimethylformamide (10 mL) at room temperature. Potassium carbonate (2 g, 14.2 mmol) and potassium iodide (230 mg, 1.4 mmol) were added. The reaction solution was stirred at 60° C. for 4 hours. The reaction solution was cooled to room temperature, quenched with water and extracted with dichloromethane (200 mL×3). The organic phases were combined, dried over anhydrous sodium sulfate, filtered and concentrated under reduced pressure. The residues were purified by silica gel column chromatography (eluent: 5% methanol/95% dichloromethane) to obtain (5-nitroquinolin-8-yloxy)methyl (2-(tert-butyldimethylsilyloxy)ethyl(methyl)carbamate (500 mg, yield: 16.2%).

Step 4: Preparation of (5-nitroquinolin-8-yloxy)methyl 2-hydroxyethyl(methyl)carbamate (63)

(5-Nitroquinolin-8-yloxy)methyl (2-(tert-butyldimethylsilyloxy)ethyl(methyl) carbamate (0.5 g, 1.1 mmol) and tetrabutylammonium fluoride (TBAF) (0.35 g, 1.3 mmol) were dissolved in dichloromethane (20 mL) at room temperature, and stirred for 4 hours. The reaction solution was filtered and concentrated under reduced pressure.

The residues were purified by reversed-phase high performance liquid chromatography (column: Eclipse XDB-C18 (21.2 mm×250 mm, 7 μm), mobile phase: acetonitrile-0.1% formic acid, flow rate: 20.0 mL/min) to obtain the product (5-nitroquinolin-8-yloxy)methyl 2-hydroxyethyl(methyl)carbamate (0.2 g, yield: 29%).

Example 64: Synthesis of 2-(methyl(((5-nitroquinolin-8-yloxy)methoxy)formyl)amino)ethyl acetate (64)

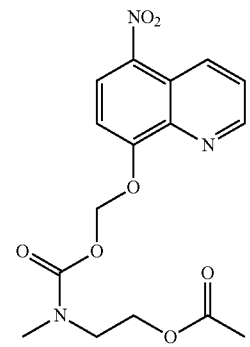 [SMILES: CC(=O)OCCN(C)C(=O)OCOc1ccc([N+](=O)[O-])c2cccnc12]

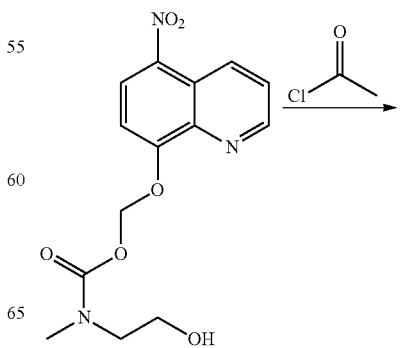

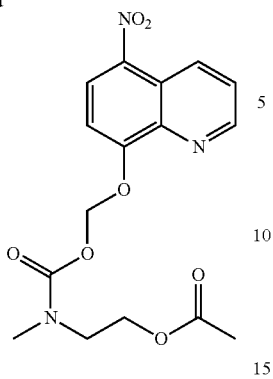

(5-Nitroquinolin-8-yloxy)methyl 2-hydroxyethyl(methyl) carbamate (320 mg, 1.0 mmol) and acetyl chloride (100 mg, 1.2 mmol) were dissolved in dichloromethane (10 mL) at 0° C., and pyridine (160 mg, 2.0 mmol) was slowly added dropwise. The reaction solution was warmed up to room temperature and stirred for 2 hours. The reaction solution was cooled to room temperature, quenched with water and extracted with dichloromethane (100 mL×3). The organic phases were combined, dried over anhydrous sodium sulfate and filtered. The filtrate was concentrated under reduced pressure. The residues were purified by reversed-phase high performance liquid chromatography (column: Eclipse XDB-C18 (21.2 mm×250 mm, 7 μm), mobile phase: acetonitrile-0.1% formic acid, flow rate: 20.0 mL/min) to obtain the product 2-(methyl(((5-nitroquinolin-8-yloxy)methoxy) formyl)amino)ethyl acetate.

$^1$H-NMR (400 Hz, CDCl$_3$) δ: 9.21 (d, J=8.0 Hz, 1H), 9.08 (d, J=4 Hz, 1H), 8.53 (d, J=8.0 Hz, 1H), 7.77 (dd, J=8.0 Hz, 4.0 Hz, 1H), 7.44 (d, J=8.8 Hz, 1H), 6.22 (s, 2H), 4.13-4.25 (m, 2H), 3.53-3.58 (m, 2H), 3.00 (s, 3H), 2.00 (s, 3H).

MS calculated: 363.33; MS observed: 364.1 [M+H]$^+$.

Example 65: Synthesis of (2-(methyl(((5-nitroquinolin-8-yl)oxy)methoxy)formyl) amino)pyridin-3-yl)methyl 2-(N-methylacetamido)acetate (65)

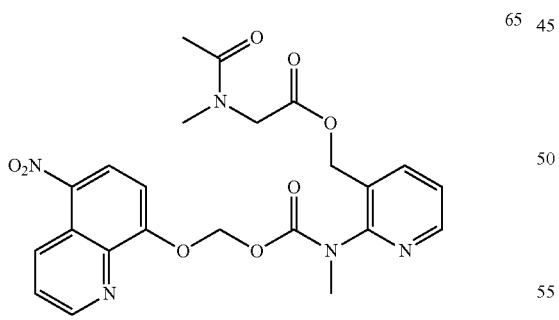

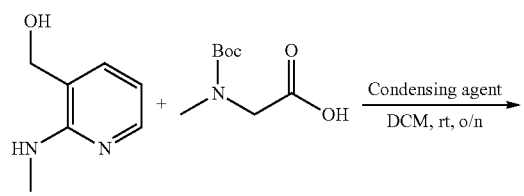

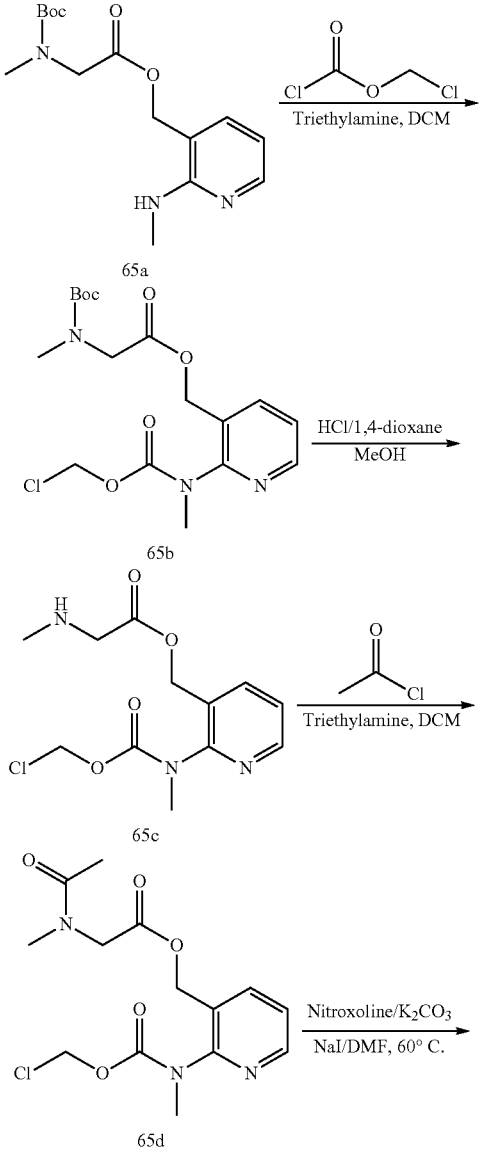

Step 1: Preparation of (2-(methylamino)pyridin-3-yl)methyl 2-(tert-butoxycarbonyl(methyl)amino) acetate (65a)

2-Methylamino-3-pyridylmethanol (2.8 g, 20.3 mmol), tert-butoxycarbonyl sarcosine (5 g, 26.4 mmol), 1-(3-dimethylaminopropyl)-3-ethylcarbodiimide hydrochloride (EDCI) (5.1 g, 26.4 mmol) and 4-dimethylaminopyridine (DMAP) (250 mg, 2 mmol) were added to dichloromethane (100 mL) at room temperature, and stirred overnight. The reaction was quenched by water, and the solution was extracted with ethyl acetate (100 mL×3). The organic phase was washed with saturated brine, dried over anhydrous sodium sulfate, filtered and concentrated under reduced pressure. The residues were purified by silica gel thin layer chromatography (developing agent: 5% methanol/95% dichloromethane) to obtain (2-(methylamino)pyridin-3-yl) methyl 2-(tert-butoxycarbonyl(methyl)amino)acetate (3 g, yield: 49%).

Step 2: Preparation of (2-(((chloromethoxy)carbonyl)(methyl)amino)pyridin-3-yl)methyl 2-(tert-butoxy carbonyl(methyl)amino)acetate (65b)

(2-(Methylamino)pyridin-3-yl)methyl 2-(tert-butoxycarbonyl(methyl)amino) acetate (3.4 g, 11 mmol) was dissolved in dichloromethane (80 mL) at 0° C. N,N-Diisopropylethylamine (2.8 g, 22 mmol) and chloromethyl chloroformate (2.1 g, 16.5 mmol) were slowly added dropwise successively. The reaction solution was stirred at 0° C. for 30 minutes and at room temperature overnight. Water (100 mL) was added to quench the reaction, and the solution was extracted with dichloromethane (200 mL×3). The organic phases were combined, dried over anhydrous sodium sulfate, filtered and concentrated under reduced pressure to obtain the product (2-(((chloromethoxy)carbonyl)(methyl)amino)pyridin-3-yl)methyl 2-(tert-butoxycarbonyl(methyl)amino)acetate (4 g, yield: 91%).

Step 3: Preparation of (2-(((chloromethoxy)carbonyl)(methyl)amino)pyridin-3-yl)methyl 2-(methylamino) acetate (65c)

(2-(((Chloromethoxy)carbonyl)(methyl)amino)pyridin-3-yl)methyl 2-(tert-butoxy carbonyl(methyl)amino)acetate (1.7 g, 5.6 mmol) was dissolved in dichloromethane (50 mL) at room temperature. Hydrochloric acid/dioxane (4.5 mL, 18 mmol) was slowly added dropwise, and the reaction solution was stirred for 4 hours. The reaction solution was concentrated under reduced pressure to obtain the product (2-(((chloromethoxy)carbonyl)(methyl)amino)pyridin-3-yl) methyl 2-(methylamino) acetate (1.27 g, yield: 99%).

Step 4: Preparation of (2-(((chloromethoxy)carbonyl)(methyl)amino)pyridin-3-yl)methyl 2-(N-methylacetamido)acetate (65d)

(2-(((Chloromethoxy)carbonyl)(methyl)amino)pyridin-3-yl)methyl 2-(methyl amino)acetate (1 g, 3.3 mmol) and acetyl chloride (390 mg, 5.0 mmol) were dissolved in dichloromethane (50 mL) at 0° C. Triethylamine (0.7 mL, 6.6 mmol) was slowly added dropwise, and the reaction solution was warmed up to room temperature and stirred for 2 hours. The reaction solution was cooled to room temperature, quenched with water and extracted with dichloromethane (100 mL×3). The organic phases were combined, dried over anhydrous sodium sulfate and filtered. The filtrate was concentrated under reduced pressure to obtain the product (2-(((chloromethoxy)carbonyl)(methyl)amino)pyridin-3-yl) methyl 2-(N-methyl acetamido)acetate (1.0 g, yield: 91%).

Step 5: Preparation of (2-(methyl(((5-nitroquinolin-8-yl)oxy)methoxy)formyl)amino)pyridin-3-yl) methyl 2-(N-methylacetamido)acetate (65)

Nitroxoline (1.5 g, 7.9 mmol) and (2-(((chloromethoxy) carbonyl)(methyl)amino)pyridin-3-yl)methyl 2-(N-methyl acetamido)acetate (2.7 g, 7.9 mmol) were dissolved in N,N-dimethylformamide (10 mL) at room temperature. Potassium carbonate (2.2 g, 16.0 mmol) and potassium iodide (270 mg, 1.6 mmol) were added. The reaction solution was stirred at 60° C. for 4 hours. The reaction solution was cooled to room temperature, quenched with water and extracted with dichloromethane (200 mL×3). The organic phases were combined, dried over anhydrous sodium sulfate and filtered. The filtrate was concentrated under reduced pressure. The residues were purified by reversed-phase high performance liquid chromatography (column: Eclipse XDB-C18 (21.2 mm×250 mm, 7 μm), mobile phase: acetonitrile-0.1% formic acid, flow rate: 20.0 mL/min) to obtain the product (2-(methyl(((5-nitroquinolin-8-yl)oxy)methoxy) formyl)amino)pyridin-3-yl)methyl 2-(N-methylacetamido) acetate (500 mg, yield: 13%).

$^1$H-NMR (400 Hz, CDCl$_3$) δ: 9.05-9.18 (m, 2H), 8.32-8.57 (m, 2H), 7.79-7.83 (m, 2H), 7.29-7.32 (m, 2H), 6.06-6.30 (m, 2H), 5.00-5.11 (m, 2H), 4.01-4.06 (m, 2H), 3.34 (s, 3H), 3.00 (s, 3H), 2.13 (s, 3H).

MS calculated: 497.46; MS observed: 498.2 [M+H]$^+$.

Example 66: Synthesis of (2-(methyl(((5-nitroquinolin-8-yl)oxy)methoxy)formyl)amino)pyridin-3-yl) methyl 2-(N-methylpivalamido)acetate (66)

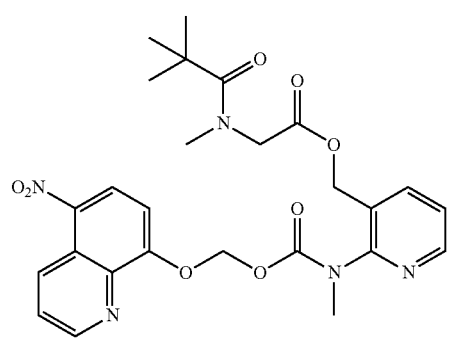 [SMILES: CN(CC(=O)OCc1cccnc1N(C)C(=O)OCOc1ccc([N+](=O)[O-])c2cccnc12)C(=O)C(C)(C)C]

(2-(Methyl(((5-nitroquinolin-8-yl)oxy)methoxy)formyl) amino)pyridin-3-yl)methyl 2-(N-methylpivalamido)acetate was obtained in accordance with the same preparation method of Example 65 except for replacing the acetyl chloride in Step 4 with pivaloyl chloride.

$^1$H-NMR (400 Hz, CDCl$_3$) δ: 9.05-9.18 (m, 2H), 8.32-8.57 (m, 2H), 7.79-7.83 (m, 2H), 7.29-7.32 (m, 2H), 6.06-6.30 (m, 2H), 5.04-5.12 (m, 2H), 4.01-4.06 (m, 2H), 3.340 (s, 3H), 3.00 (s, 3H), 1.31 (s, 9H).

MS calculated: 539.55; MS observed: 540.2 [M+H]$^+$.

Example 67: Synthesis of (5-nitroquinolin-8-yloxy)methyl piperidine-1-carboxylate (67)

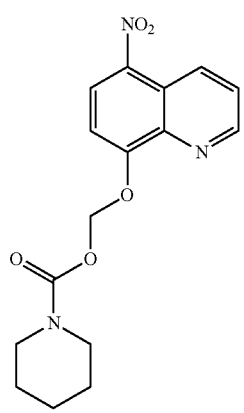 [SMILES: O=C(OCOc1ccc([N+](=O)[O-])c2cccnc12)N1CCCCC1]

(5-Nitroquinolin-8-yloxy)methyl piperidine-1-carboxylate was obtained in accordance with the same preparation method of Example 6 except for replacing the 1-methylpiperazine in Step 1 with piperidine hydrochloride.

$^1$H-NMR (400 Hz, CDCl$_3$) δ: 9.23 (dd, J=8.8, 1.6 Hz, 1H), 9.09 (dd, J=4.0, 1.6 Hz, 1H), 8.53 (d, J=8.8 Hz, 1H), 7.77 (dd, J=8.8 Hz, 4.0 Hz, 1H), 7.35 (d, J=8.8 Hz, 1H), 6.22 (s, 2H), 3.42-3.47 (m, 4H), 1.35-1.63 (m, 6H).

MS calculated: 331.33; MS observed: 332.3 [M+H]$^+$.

Example 68: Synthesis of 3-(methyl(((5-nitroquinolin-8-yloxy)methoxy)carbonyl)amino)propyl acetate (68)

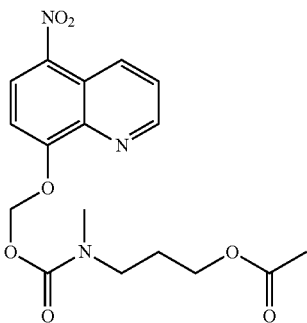 [SMILES: CC(=O)OCCCN(C)C(=O)OCOc1ccc([N+](=O)[O-])c2cccnc12]

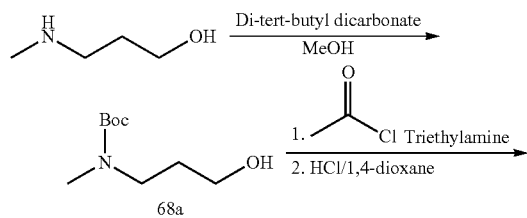

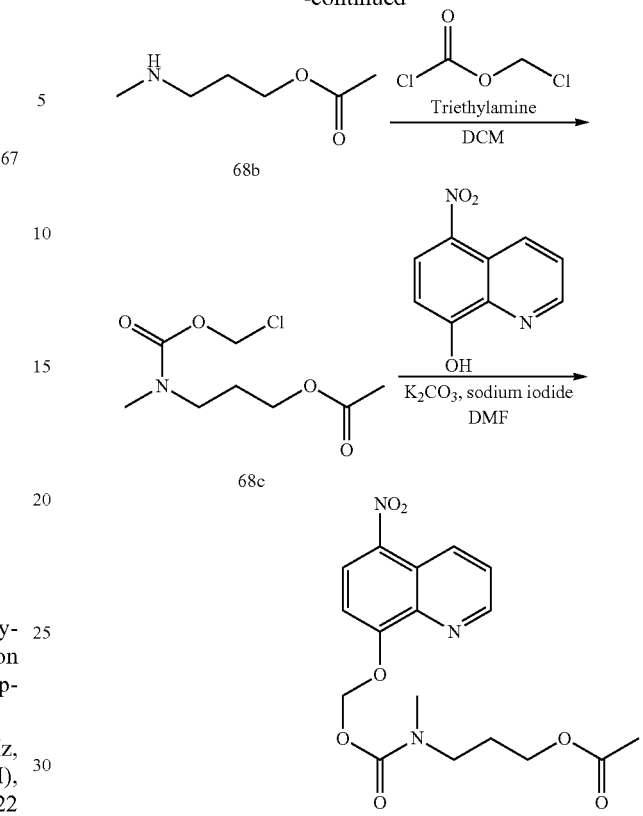

Step 1: Preparation of tert-butyl 3-hydroxypropyl-methylcarbamate (68a)

Triethylamine (1.36 g, 13.44 mmol) was added to a solution of 3-methylamino-1-propanol (1.00 g, 11.22 mmol) in methanol (10 mL) at room temperature and stirred until clear. Di-tert-butyl dicarbonate (2.94 g, 13.47 mmol) was added dropwise and stirred for 16 hours. The reaction solution was concentrated under reduced pressure and diluted with dichloromethane. The organic phase was washed with saturated brine, dried over anhydrous sodium sulfate and filtered. The filtrate was concentrated under reduced pressure to obtain the crude product tert-butyl 3-hydroxypropyl-methylcarbamate (2.20 g).

Step 2: Preparation of 3-(methylamino)propyl acetate (68b)

Triethylamine (0.64 g, 6.32 mmol) was added to a solution of tert-butyl 3-hydroxypropyl-methylcarbamate (1.00 g, 5.28 mmol) in dichloromethane (5 mL) at room temperature and stirred until clear. The reaction system was cooled to 0° C., and acetyl chloride (0.50 g, 6.37 mmol) was added dropwise. The reaction solution was naturally warmed up to room temperature and stirred for 1 hour. The reaction solution was filtered, and the solid was rinsed with dichloromethane. The filtrate was concentrated to obtain the crude solid product. A solution of hydrogen chloride in dioxane (3.3 mL, 4 M) was added dropwise to the crude product at 0° C., and the reaction solution was stirred for 16 hours. The reaction solution was concentrated to obtain the crude product 3-(methylamino)propyl acetate.

Step 3: Preparation of 3-(((chloromethoxy)carbonyl)(methyl)amino)propyl acetate (68c)

The crude 3-(methylamino)propyl acetate was dissolved completely in dichloromethane (8 mL). Triethylamine (1.07 g, 10.57 mmol) and chloromethyl chloroformate (0.68 g, 5.27 mmol) were added successively to the solution at 0° C. The reaction solution was naturally warmed up to room temperature and stirred for 1 hour. The reaction was quenched by water, and the solution was extracted with dichloromethane. The organic phase was washed with saturated brine, dried over anhydrous sodium sulfate, filtered and concentrated under reduced pressure. The residues were purified by silica gel column chromatography (eluent: 83% petroleum ether/17% ethyl acetate) to obtain 3-(((chloromethoxy)carbonyl)(methyl)amino)propyl acetate (400 mg, yield: 34%).

Step 4: Preparation of 3-(methyl(((5-nitroquinolin-8-yloxy)methoxy)carbonyl)amino)propyl acetate (68)

Nitroxoline (340 mg, 1.79 mmol), potassium carbonate (297 mg, 2.15 mmol) and sodium iodide (27 mg, 0.18 mmol) were added to N,N-dimethylformamide (8 mL) at room temperature and stirred well. The reaction system was warmed up to 60° C. and stirred for 15 minutes. 3-(((Chloromethoxy)carbonyl)(methyl)amino)propyl acetate (400 mg, 1.79 mmol) was added, and the reaction solution was stirred for 16 hours. The reaction was quenched by water, and the solution was extracted with ethyl acetate. The organic phase was washed with saturated brine, dried over anhydrous sodium sulfate, filtered and concentrated under reduced pressure. The residues were purified by silica gel thin layer chromatography (developing agent: 5% methanol/95% dichloromethane) to obtain 3-(methyl(((5-nitroquinolin-8-yloxy)methoxy)carbonyl)amino)propyl acetate (196 mg, yield: 29%).

$^1$H NMR (400 MHz, CDCl$_3$) δ 9.20 (dd, J=8.8, 2.4 Hz, 1H), 9.07 (d, J=1.4 Hz, 1H), 8.64-8.46 (m, 1H), 7.81-7.66 (m, 1H), 7.52-7.38 (m, 1H), 6.21 (s, 2H), 4.05 (dd, J=28.3, 3.6 Hz, 2H), 3.38 (dd, J=14.3, 7.2 Hz, 2H), 3.02-2.89 (m, 3H), 2.03 (dd, J=17.5, 3.7 Hz, 3H), 1.86 (d, J=24.3 Hz, 2H).

MS calculated: 377.3; MS observed: 378.2 [M+H]$^+$.

Example 69: Synthesis of 4-(methyl(((5-nitroquinolin-8-yloxy)methoxy)carbonyl)amino)butyl acetate (69)

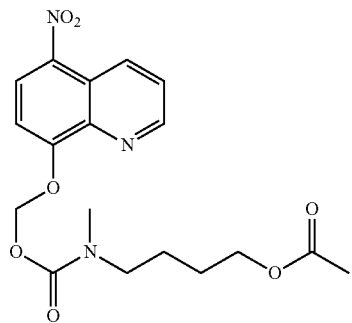 [SMILES: CC(=O)OCCCCN(C)C(=O)OCOc1ccc([N+](=O)[O-])c2cccnc12]

69

4-(Methyl(((5-nitroquinolin-8-yloxy)methoxy)carbonyl)amino)butyl acetate was obtained in accordance with the same preparation method of Example 68 except for replacing the 3-methylamino-1-propanol in Step 1 with 4-methylamino-1-butanol.

$^1$H NMR (400 MHz, CDCl$_3$) δ 9.18 (dd, J=8.9, 1.3 Hz, 1H), 9.06 (d, J=4.0 Hz, 1H), 8.50 (d, J=8.8 Hz, 1H), 7.70 (dd, J=8.9, 4.1 Hz, 1H), 7.42 (dd, J=8.8, 3.9 Hz, 1H), 6.20 (d, J=4.7 Hz, 2H), 4.04 (dd, J=27.3, 21.6 Hz, 2H), 3.36-3.22 (m, 2H), 2.96-2.86 (m, 3H), 2.01 (d, J=19.7 Hz, 3H), 1.64-1.57 (m, 2H), 1.53 (s, 2H).

MS calculated: 391.4; MS observed: 392.2 [M+H]$^+$.

Examples 70 and 71: Synthesis of di-tert-butyl (5-nitroquinolin-8-yloxy)methyl phosphate (70) and (5-nitroquinolin-8-yloxy)methyl dihydrophosphate (71)

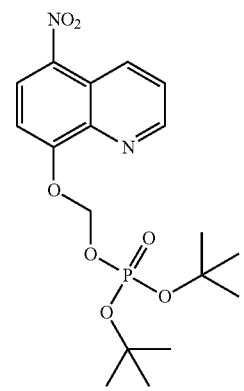

70

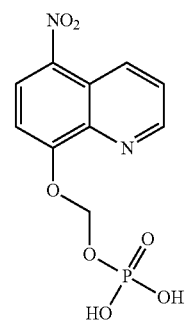 [SMILES: O=[N+]([O-])c1ccc(OCOP(=O)(O)O)c2ncccc12]

71

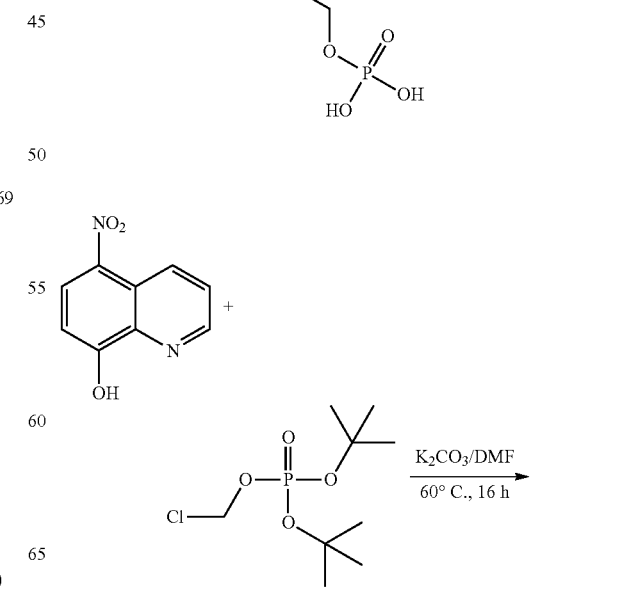

-continued

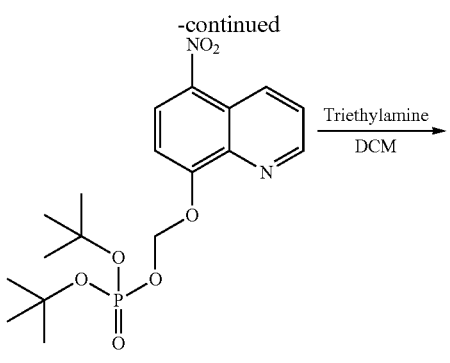

70

Step 1: Preparation of di-tert-butyl (5-nitroquinolin-8-yloxy)methyl phosphate (70)

Potassium carbonate (1.45 g, 10.52 mmol) was added to a solution of nitroxoline (1.0 g, 5.26 mmol) and di-tert-butyl chloromethyl phosphate (2.04 g, 7.89 mmol) in N,N-dimethylformamide (17 mL) at room temperature. The reaction solution was stirred at 60° C. for 2 hours. The reaction was quenched by water, and the solution was extracted with dichloromethane (100 mL×3). The organic phase was washed with 1 M hydrochloric acid, 1 M sodium bicarbonate aqueous solution and saturated brine, dried over anhydrous sodium sulfate, filtered and concentrated under reduced pressure. The residues were purified by silica gel column chromatography (eluent: 5% hexane/95% ethyl acetate) to obtain di-tert-butyl (5-nitroquinolin-8-yloxy)methyl phosphate (570 mg, yield: 26%).

MS[M+H]$^+$: 413.3.

Step 2: Preparation of (5-nitroquinolin-8-yloxy)methyl dihydrophosphate (71)

Trifluoroacetic acid (7 mL) was slowly added dropwise to a solution of di-tert-butyl (5-nitroquinolin-8-yloxy)methyl phosphate (520 mg, 1.18 mmol) in dichloromethane (7 mL) at room temperature. The reaction solution was stirred at room temperature for 2 hours, and then concentrated under reduced pressure. Saturated sodium bicarbonate solution was added until pH=7 to precipitate a solid, and the a mixture was filtered to obtain the crude product. The crude product was purified by preparative liquid chromatography (Agilent 1260 preparative liquid chromatography; a gradient of acetonitrile/water of 95/5 to 50/50) to obtain the product (5-nitroquinolin-8-yloxy)methyl dihydrophosphate (100.24 mg, yield: 24%).

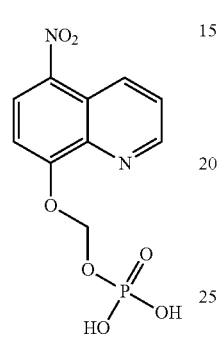

$^1$H NMR (400 MHz, D$_2$O): δ 8.97-8.94 (m, 1H), 8.76-8.75 (m, 1H), 8.42 (d, J=8.8 Hz, 1H), 7.69-7.65 (m, 1H), 7.38 (d, J=9.2 Hz, 1H), 5.76 (d, J=11.2 Hz, 1H).

MS calculated: 300.0; MS observed: 301.0 [M+H]$^+$.

Example 72: Synthesis of (hydroxy((5-nitroquinolin-8-yloxy)methoxy)phosphoryloxy)methyl isopropyl carbonate (72)

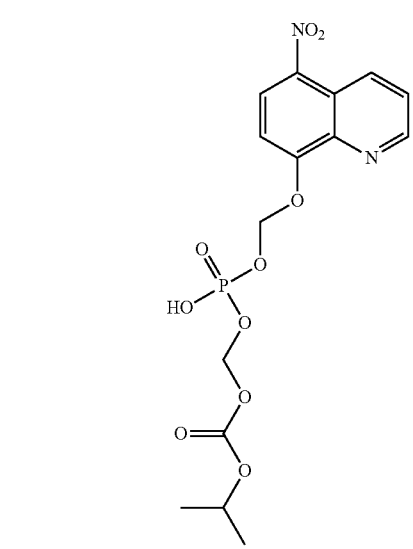 [SMILES: CC(C)OC(=O)OCOP(=O)(O)OCOc1ccc([N+](=O)[O-])c2cccnc12]

72

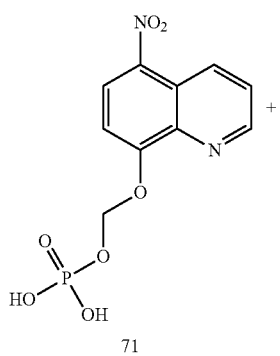

71

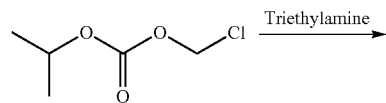

Step 1: Preparation of (hydroxy((5-nitroquinolin-8-yloxy)methoxy)phosphoryloxy)methyl isopropyl carbonate (72)

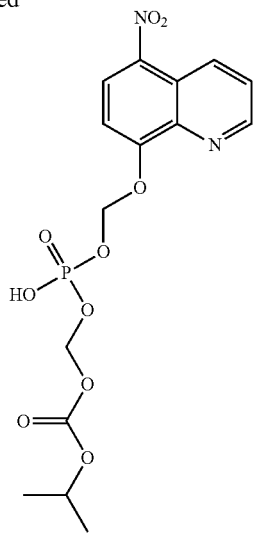

(5-Nitroquinolin-8-yloxy)methyl dihydrophosphate hydrochloride (672 mg, 2 mmol, obtained in accordance with the synthesis procedure of Example 71), chloromethyl isopropyl carbonate (1.22 g, 8 mmol) and triethylamine (1.01 g, 10 mmol) were added to 20 mL of DMF, and stirred at 50° C. for 5 hours. The reaction solution was concentrated under reduced pressure, and the residues were purified by pre-HPLC (Agilent 1260 preparative liquid chromatography; a gradient of acetonitrile/water of 95/5 to 50/50) to obtain (hydroxy((5-nitroquinolin-8-yloxy)methoxy)phosphoryloxy)methyl isopropyl carbonate (121 mg, yield: 14.5%).

$^1$H-NMR (400 MHz, DMSO-d$_6$) δ: 9.05 (d, J=2.8 Hz, 1H), 9.00 (d, J=8.4 Hz, 1H), 8.55 (d, J=8.4 Hz, 1H), 7.87 (dd, J=8.4, 4.0 Hz, 1H), 7.54 (d, J=8.4 Hz, 1H), 5.91~5.94 (m, 2H), 5.45~5.49 (m, 2H), 4.72~4.75 (m, 2H), 1.18 (d, J=6.0 Hz, 6H).

MS calculated: 416.28; MS observed: 417.1 [M+H]$^+$.

Example 73: Synthesis of (2S)-methyl 2-(((5-nitroquinolin-8-yloxy)methoxy(phenoxy)phosphorylamino)propionate (73)

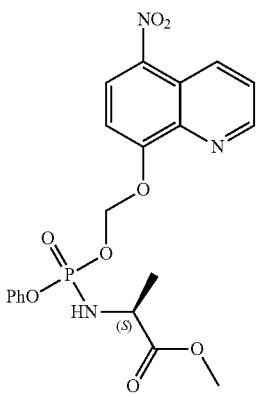

73

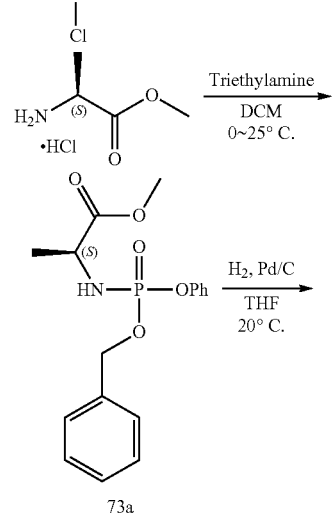

73a

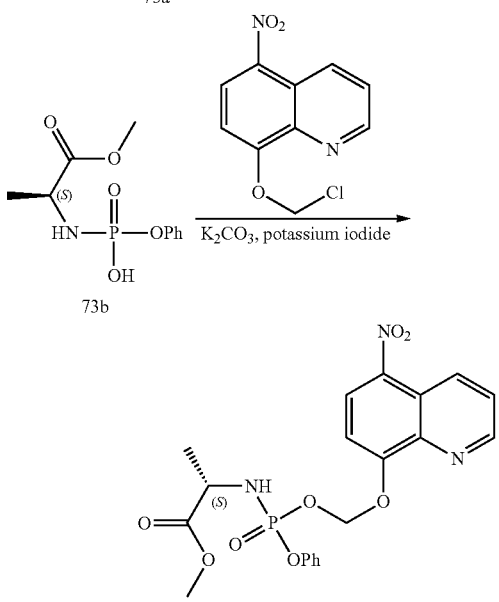

73b

Step 1: Preparation of (2S)-methyl 2-(benzyloxy(phenoxy)phosphorylamino)propionate (73a)

Benzyl alcohol (2 g, 18.49 mmol) and phenyl phosphorodichloridate (4.29 g, 20.34 mmol) were added to 40 mL of dichloromethane at room temperature. The reaction solution was cooled to 0-5° C. under an ice bath, and then slowly added with triethylamine (7.47 g, 73.96 mmol) and methyl L-alaninate hydrochloride (2.84 g, 20.34 mmol) successively, and stirred for 20 minutes followed by stirring at room temperature for 5 hours. The reaction solution was washed with water (20 mL×2), and the organic phase was concentrated under reduced pressure. The residues were purified by silica gel column chromatography (DCM: MeOH=10:1) to obtain (2S)-methyl 2-(benzyloxy(phenoxy) phosphorylamino)propionate (4.2 g, yield: 65.6%).

Step 2: Preparation of (2S)-methyl 2-(hydroxy(phenoxy)phosphorylamino)propionate (73b)

(2S)-Methyl 2-(benzyloxy(phenoxy)phosphorylamino)propionate (2.5 g, 7.16 mmol) was dissolved in 25 mL of tetrahydrofuran at room temperature, followed by the addition of 500 mg of wet Pd/C. The reaction solution was stirred under a hydrogen atmosphere at room temperature for 8 hours. The reaction solution was filtered, and the filtrate was concentrated under reduced pressure to obtain (2S)-methyl 2-(hydroxy(phenoxy)phosphorylamino)propionate (1.5 g, yield: 81%).

Step 3: Preparation of (2S)-methyl 2-(((5-nitroquinolin-8-yloxy)methoxy(phenoxy)phosphorylamino) propionate (73)

(2S)-Methyl 2-(hydroxy(phenoxy)phosphorylamino)propionate (1.5 g, 5.79 mmol) and 5-nitro-8-(chloromethoxy)quinoline (1a) (921 mg, 3.86 mmol) was dissolved in 20 mL of DMF at room temperature. Catalytic amount of KI (10 mg) and potassium carbonate (1.6 g, 11.58 mmol) were added, and the reaction solution was stirred at room temperature for 6 hours. The reaction solution was filtered, and the filtrate was concentrated under reduced pressure. The residues were purified by silica gel column chromatography (DCM:MeOH=40:1) to obtain (2S)-methyl 2-(((5-nitroquinolin-8-yloxy)methoxy(phenoxy)phosphorylamino)propionate (160 mg, yield: 8.9%).

$^1$H-NMR (400 MHz, DMSO-d$_6$): δ 9.05-9.06 (m, 1H), 8.99-9.01 (m, 1H), 8.54 (dd, J=8.4, 3.2 Hz, 1H), 7.87 (dd, J=8.8 Hz, 4.0 Hz, 1H), 7.50~7.55 (m, 1H), 7.25~7.30 (m, 2H), 7.09~7.18 (m, 3H), 6.29~6.35 (m, 1H), 6.03~6.11 (m, 2H), 5.60 (br, 1H), 3.88~3.97 (m, 1H), 3.54 (d, J=10 Hz, 3H), 1.18~1.21 (m, 3H)

MS calculated: 461.37; MS observed: 462.2 [M+H]$^+$.

Example 74: Synthesis of (2S)-methyl 2-(((5-nitroquinolin-8-yloxy)methoxy(phenoxy)phosphorylamino)-3-phenylpropionate (74)

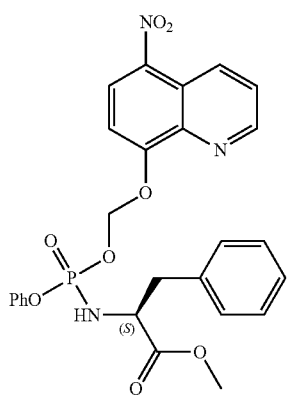

74

(2S)-Methyl 2-(((5-nitroquinolin-8-yloxy)methoxy(phenoxy)phosphorylamino)-3-phenylpropionate was obtained in accordance with the same preparation method of Example 73 except for replacing the methyl L-alaninate hydrochloride in Step 1 with methyl L-phenylalaninate hydrochloride.

$^1$H-NMR (400 MHz, DMSO-d$_6$): δ 9.03 (d, J=4 Hz, 1H), 8.99 (dd, J=8.8, 1.2 Hz, 1H), 8.52 (dd, J=8.4, 6.4 Hz, 1H), 7.87 (dd, J=6.4 Hz, 1.6 Hz, 1H), 7.50~7.55 (m, 1H), 7.10~7.29 (m, 6H), 7.00~709 (m, 2H), 6.98~6.99 (m, 2H), 6.40~6.51 (m, 1H), 5.85~5.95 (m, 2H), 3.98~4.02 (m, 1H), 3.54 (s, 3H), 2.95~3.01 (m, 1H), 2.75~2.85 (m, 1H).

MS calculated: 537.46; MS observed: 538.3 [M+H]$^+$.

Example 75: Synthesis of (2S)-isopropyl 2-(((5-nitroquinolin-8-yloxy)methoxy(phenoxy)phosphorylamino)propionate (75)

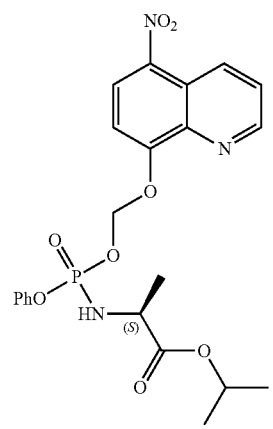

75

(2S)-Isopropyl 2-(((5-nitroquinolin-8-yloxy)methoxy(phenoxy)phosphorylamino)propionate was obtained in accordance with the same preparation method of Example 73 except for replacing the methyl L-alaninate hydrochloride in Step 1 with isopropyl L-alaninate hydrochloride.

$^1$H-NMR (400 MHz, DMSO-d$_6$): δ 9.05~9.06 (m, 1H), 8.99~9.01 (m, 1H), 8.54 (dd, J=8.4, 3.2 Hz, 1H), 7.87 (dd, J=8.8 Hz, 4.0 Hz, 1H), 7.50~7.55 (m, 1H), 7.25~7.30 (m, 2H), 7.09~7.18 (m, 3H), 6.29~6.35 (m, 1H), 6.03~6.11 (m, 2H), 4.85~4.95 (m, 1H), 3.88~3.97 (m, 1H), 1.18~1.21 (m, 9H).

MS calculated: 489.42; MS observed: 490.3 [M+H]$^+$.

Example 76: Synthesis of (6-cyclohexyl-4-methyl-2-oxopyridin-1(2H)-yloxy)methyl (5-nitroquinolin-8-yloxy) methyl monohydrogen phosphate (76)

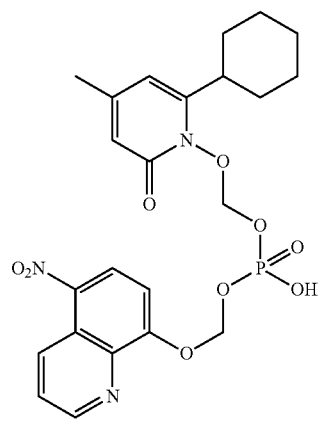 [SMILES: Cc1cc(C2CCCCC2)n(OCOP(=O)(O)OCOc2ccc([N+](=O)[O-])c3cccnc23)c(=O)c1]

76

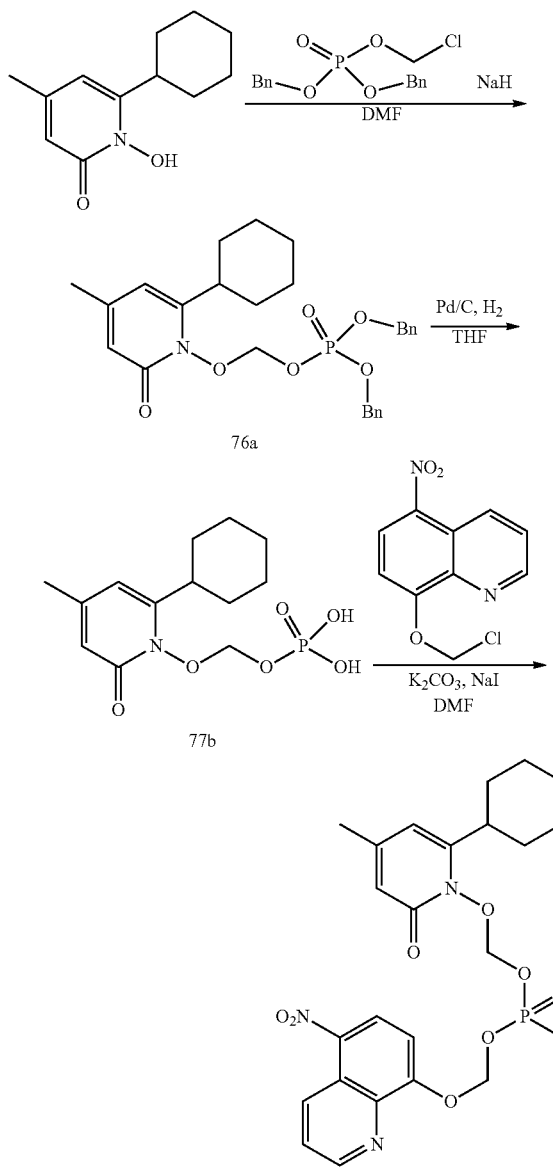

Step 1: Preparation of dibenzyl (6-cyclohexyl-4-methyl-2-oxopyridin-1(2H)-yloxy)methyl phosphate (76a)

Sodium hydride (purity: 60%, 0.42 g, 10.5 mmol) was added to a solution of 6-cyclohexyl-4-methyl-pyridin-1-hydroxy-2-one (purchased from Shanghai Dari chemical Co. Ltd.) (2.00 g, 9.65 mmol) in N,N-dimethylformamide (30 mL) at 0° C., and stirred for 30 minutes. Dibenzyl (chloromethyl) phosphate (4.10 g, 12.55 mmol) was added, and the reaction solution was naturally warmed up to room temperature and stirred for 5 hours. The reaction was quenched by ammonium chloride aqueous solution, and the solution was extracted with ethyl acetate. The organic phase was washed with saturated brine, dried over anhydrous sodium sulfate, filtered and concentrated under reduced pressure. The residues were purified by silica gel column chromatography (eluent: 75% petroleum ether/25% ethyl acetate) to obtain dibenzyl (6-cyclohexyl-4-methyl-2-oxopyridin-1(2H)-yloxy)methyl phosphate (1.58 g, yield: 33%).

Step 2: Preparation of (6-cyclohexyl-4-methyl-2-oxopyridin-1(2H)-yloxy)methyl dihydrophosphate (76b)

Palladium on carbon (content: 10%, 0.20 g) was added to a solution of dibenzyl (6-cyclohexyl-4-methyl-2-oxopyridin-1(2H)-yloxy)methyl phosphate (1.58 g, 3.18 mmol) in tetrahydrofuran (16 mL) at room temperature. The reaction solution was stirred under a hydrogen atmosphere for 3 hours. The reaction solution was filtered, and rinsed with tetrahydrofuran. The filtrate was concentrated under reduced pressure to obtain (6-cyclohexyl-4-methyl-2-oxopyridin-1(2H)-yloxy)methyl dihydrophosphate (0.35 g, yield: 35%).

Step 3: Preparation of (6-cyclohexyl-4-methyl-2-oxopyridin-1(2H)-yloxy)methyl (5-nitroquinolin-8-yloxy)methyl monohydrogen phosphate (76)

(6-Cyclohexyl-4-methyl-2-oxopyridin-1(2H)-yloxy) methyl dihydrophosphate (350 mg, 1.10 mmol), potassium carbonate (305 mg, 2.21 mmol) and sodium iodide (28 mg, 0.19 mmol) were added to N,N-dimethylformamide (7 mL) at room temperature and stirred well. The reaction system was warmed up to 40° C. and stirred for 10 minutes. 5-Nitro-8-chloromethoxyquinoline (1a) (448 mg, 1.88 mmol) was added, and the reaction solution was stirred for 4 hours. The reaction was quenched by water, and the solution was reverse-extracted with ethyl acetate to remove impurities. The aqueous phase was lyophilized, and purified by preparative liquid chromatography with a reversed phase system of 95% water/5% acetonitrile (Agilent 1260 preparative liquid chromatography; a gradient of acetonitrile/water of 95/5 to 50/50) to obtain (6-cyclohexyl-4-methyl-2-oxopyridin-1(2H)-yloxy)methyl (5-nitroquinolin-8-yloxy) methyl monohydrogen phosphate (66 mg, yield: 12%).

$^1$H NMR (400 MHz, CDCl$_3$) δ 9.65 (d, J=7.6 Hz, 1H), 9.21 (s, 1H), 8.66 (d, J=8.4 Hz, 1H), 8.06 (s, 1H), 7.65 (d, J=8.7 Hz, 1H), 6.36 (s, 1H), 6.07 (s, 1H), 6.00 (d, J=15.2 Hz, 2H), 5.73 (d, J=12.0 Hz, 2H), 2.15 (s, 3H), 1.94 (d, J=10.2 Hz, 2H), 1.79 (d, J=11.8 Hz, 2H), 1.75-1.68 (m, 1H), 1.47-1.13 (m, 6H).

MS calculated: 519.4; MS observed: 520.2 [M+H]$^+$.

Example 77: Synthesis of 4-methyl-5-((5-nitroquinolin-8-yloxy)methyl)-1,3-dioxol-2-one (77)

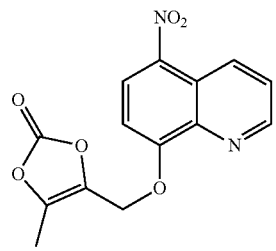 [SMILES: Cc1oc(=O)oc1COc1ccc([N+](=O)[O-])c2cccnc12]

77

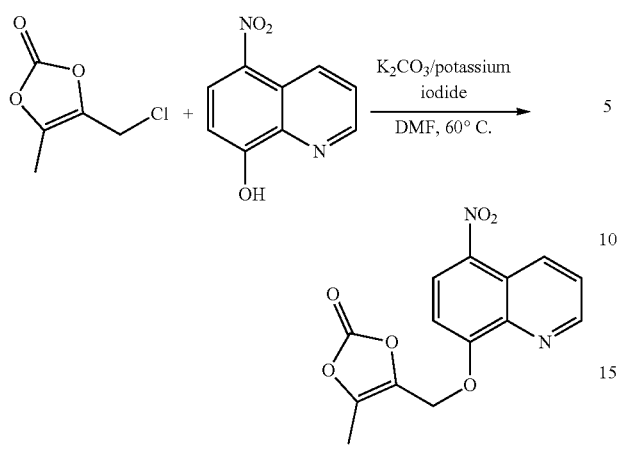

Potassium iodide (83 mg, 0.5 mmol) and 4-chloromethyl-5-methyl-1,3-dioxol-2-one (1.8 g, 12 mmol) were added to a solution of nitroxoline (1.9 g, 10 mmol) and potassium carbonate (2.7 g, 20 mmol) in N,N-dimethylformamide (10 mL) in batches at 60° C., and stirred for 2 hours. The reaction was quenched by water, and the solution was extracted with dichloromethane (100 mL×3). The organic phase was washed with 1 M hydrochloric acid, 1 M sodium bicarbonate aqueous solution and saturated brine, dried over anhydrous sodium sulfate, filtered and concentrated under reduced pressure. The residues were purified by reversed-phase high performance liquid chromatography (column: Eclipse XDB-C18 (21.2 mm×250 mm, 7 μm), mobile phase: acetonitrile-0.1% formic acid, flow rate: 20.0 mL/min) to obtain 4-methyl-5-((5-nitroquinolin-8-yloxy)methyl)-1,3-dioxol-2-one (0.6 g, yield: 20%).

$^1$H-NMR (400 Hz, CDCl$_3$) δ: 9.23 (dd, J=8.8, 1.6 Hz, 1H), 9.09 (dd, J=4.0, 1.6 Hz, 1H), 8.53 (d, J=8.8 Hz, 1H), 7.77 (dd, J=8.8, 4.0 Hz, 1H), 7.22 (d, J=8.8 Hz, 1H), 5.22 (s, 2H), 2.26 (s, 3H).

MS calculated: 302.24; MS observed: 303.1 [M+H]$^+$.

Example 78: Synthesis of 5-nitroquinolin-8-yl dimethylcarbamate (78)

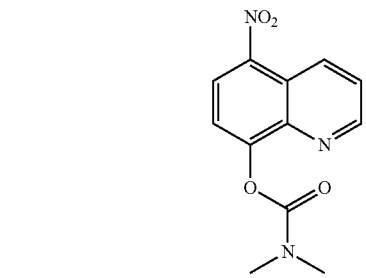

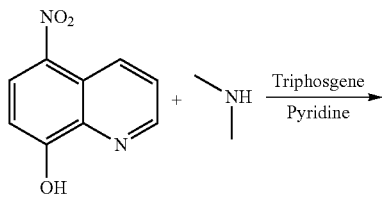

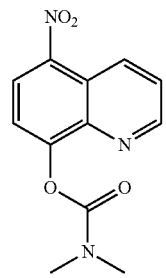

Pyridine (790 mg, 10 mmol) was slowly added to a solution of triphosgene (296.75 mg, 1 mmol) in dichloromethane (6 mL) at 0° C. The reaction solution was stirred at room temperature for 20 minutes, to which a solution of dimethylamine in tetrahydrofuran (0.53 mL, 1.07 mmol) was added. The reaction solution was stirred for 1 hour, and concentrated under reduced pressure to remove the solvent. Pyridine (1 mL) and nitroxoline (190 mg, 1 mmol) were added successively, and the reaction solution was stirred at 110° C. for 3 hours. The reaction was quenched by water, and the solution was extracted with dichloromethane (100 mL×3). The organic phase was washed with 1 M hydrochloric acid, 1 M sodium bicarbonate aqueous solution and saturated brine, dried over anhydrous sodium sulfate, filtered and concentrated under reduced pressure. The residues were purified by silica gel column chromatography (eluent: 5% hexane/95% ethyl acetate) to obtain 5-nitroquinolin-8-yl dimethylcarbamate (80 mg, yield: 31%).

$^1$H NMR (400 MHz, DMSO-d$_6$) δ: 9.09 (dd, J=4.0, 1.2 Hz, 1H), 8.93 (dd, J=9.2, 1.6 Hz, 1H), 8.52 (d, J=8.4 Hz, 1H), 7.86 (dd, J=8.8, 4.0 Hz, 1H), 7.75 (d, J=8.4 Hz, 1H), 3.21 (s, 3H), 2.96 (s, 3H).

MS calculated: 261.07; MS observed: 262.0 [M+H]$^+$.

Example 79: Synthesis of bis(5-nitroquinolin-8-yl) sebate (79)

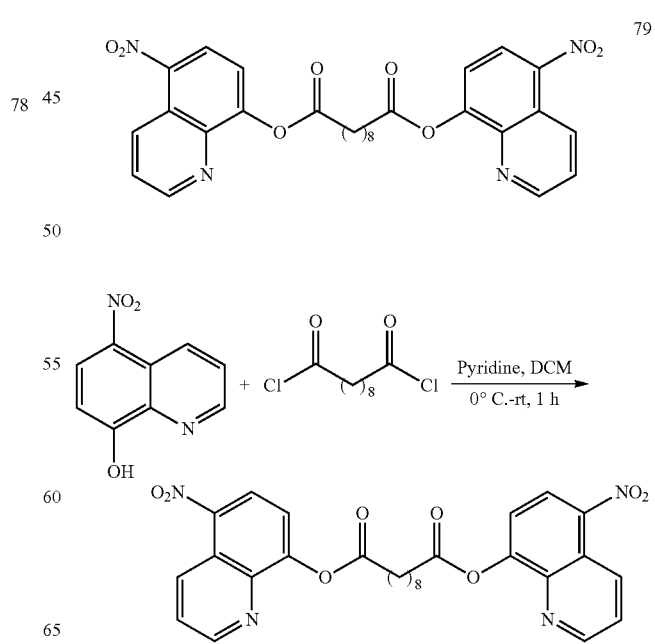

Nitroxoline (332 mg, 1.76 mmol) and pyridine (417 mg, 5.28 mmol) were added to a solution of sebacoyl dichloride (200 mg, 0.84 mmol) in dichloromethane (6 mL) in batches at 0° C. The reaction solution was stirred at room temperature for 2 hours, and then was quenched by water. The solution was extracted with dichloromethane (100 mL×3). The organic phase was washed with 1 M hydrochloric acid, 1 M sodium bicarbonate aqueous solution and saturated brine, dried over anhydrous sodium sulfate, filtered and concentrated under reduced pressure. The residues were purified by silica gel column chromatography (eluent: 5% hexane/95% ethyl acetate) to obtain bis(5-nitroquinolin-8-yl) sebate (100 mg, yield: 22%).

$^1$H NMR (400 MHz, DMSO-$d_6$) δ: 9.05 (dd, J=4.4, 1.6 Hz, 2H), 8.92 (dd, J=8.4, 1.6 Hz, 2H), 8.52 (d, J=8.8 Hz, 2H), 7.85 (dd, J=9.2, 4.4 Hz, 2H), 7.77 (d, J=8.8 Hz, 2H), 2.80 (t, J=7.2 Hz, 4H), 1.76 (d, J=7.2 Hz, 4H), 1.52-1.41 (m, 8H).

MS calculated: 546.18; MS observed: 547.2 [M+H]$^+$.

Test Example 1: Determination of the Water Solubility of the Compounds of the Present Invention The compounds of formula (I) according to the present invention can slowly release the active ingredient nitroxoline after entering the human body, and the latter can simultaneously inhibit methionine aminopeptidase MetAP2 and silent information regulator 2 related enzymes in vascular endothelial cells, and exert a synergistic effect in inhibiting tumor angiogenesis. Moreover, nitroxoline also has an inhibitory effect on the proliferation of tumor cell. In addition, the released active ingredient nitroxoline exerts a bacteriostatic effect by inhibiting the methionine aminopeptidase MetAP in bacteria.

The inventors first conducted a study on the water solubility of nitroxoline and nitroxoline prodrugs.

Experimental instruments: 96-well filter plate (MSHVN4510 or MSHVN4550, Millipore); electronic digital display vortex mixer (MS3 Digital, IKA); multi-purpose vacuum pump (circulating water type, SHB-111, Zhengzhou Greatwall Scientific Industrial and Trade Co., Ltd.); balance (XSLT05, Mettler-Toledo); comfortable mixer (Eppendorf AG 22331 Hamburg, Eppendorf); liquid chromatography (LC-3AD, Shimadzu); mass spectrometry (API4000, Applied Biosystems, USA); sample injector (Anylytics AG System, CTC). Nitroxoline was prepared according to the method disclosed in Journal of Heterocyclic Chemistry, 1971, vol. 8, p 821 by Wisdom Pharmaceutical Co., Ltd.

Experimental process: 500 μL of phosphate buffer (pH=1.2, 4.5, 6.8 or 7.4) were added to a glass flask, to which 2 mg of compound powder were added. The flask was sealed with a cap and shaked on a mixer (VORTEX-GENIE2) at room temperature for 24 hours. The solution was subjected to vacuum filtration, and the filtrate was processed to determine the compound concentration by LC/MS/MS.

The solubility results of the compounds of the present invention are shown in Table 1 below.

TABLE 1

Solubility of the compounds of the present invention

| Compound No. | pH of the buffer | Solubility (μg/mL) |
|---|---|---|
| Nitroxoline | 7.4 | 351.73 |
| Compound 1 | 7.4 | 91.09 |
| Compound 2 | 7.4 | 72.66 |
| Compound 3 | 7.4 | 59.21 |
| Compound 5 | 1.2 | 203.71 |
| Compound 5 | 4.5 | 13.07 |
| Compound 5 | 6.8 | 11.12 |
| Compound 5 | 7.4 | 13.03 |
| Compound 6 | 7.4 | 984.75 |
| Compound 7 | 7.4 | 134.26 |
| Compound 8 | 7.4 | <0.44* |
| Compound 10 | 7.4 | 39.13 |
| Compound 11 | 7.4 | 66.87 |
| Compound 12 | 7.4 | 1.85 |
| Compound 15 | 7.4 | 205.26 |
| Compound 16 | 1.2 | 443.40 |
| Compound 16 | 7.4 | 253.73 |
| Compound 18 | 7.4 | 132.20 |
| Compound 20 | 1.2 | 1012.57 |
| Compound 20 | 4.5 | 1045.45 |
| Compound 20 | 6.8 | 962.10 |
| Compound 20 | 7.4 | 978.26 |
| Compound 23 | 1.2 | 944.78 |
| Compound 23 | 7.4 | 818.18 |
| Compound 24 | 1.2 | 941.66 |
| Compound 24 | 7.4 | 73.59 |
| Compound 25 | 7.4 | 275.18 |
| Compound 28 | 1.2 | 341.92 |
| Compound 28 | 7.4 | 25.13 |
| Compound 30 | 1.2 | 940.16 |
| Compound 30 | 7.4 | <0.25 |
| Compound 31 | 7.4 | 10.84 |
| Compound 32 | 7.4 | 28.43 |
| Compound 34 | 7.4 | 6.67 |
| Compound 35 | 7.4 | 0.04 |
| Compound 36 | 7.4 | 297.85 |
| Compound 40 | 7.4 | 7.40 |
| Compound 41 | 7.4 | <0.40* |
| Compound 42 | 7.4 | <0.26* |
| Compound 43 | 7.4 | <0.25* |
| Compound 44 | 7.4 | 19.86 |
| Compound 47 | 7.4 | 284.96 |
| Compound 49 | 7.4 | 104.72 |
| Compound 51 | 1.2 | 91.42 |
| Compound 51 | 4.5 | 7.07 |
| Compound 51 | 6.8 | 5.69 |
| Compound 51 | 7.4 | 6.62 |
| Compound 52 | 7.4 | 686.89 |
| Compound 53 | 7.4 | 45.55 |
| Compound 54 | 7.4 | 24.45 |
| Compound 55 | 7.4 | 15.54 |
| Compound 56 | 7.4 | 39.83 |
| Compound 57 | 7.4 | 137.78 |
| Compound 65 | 7.4 | 965.10 |
| Compound 66 | 7.4 | 540.27 |
| Compound 70 | 1.2 | 639.16 |
| Compound 70 | 4.5 | 843.20 |
| Compound 70 | 6.8 | 940.48 |
| Compound 70 | 7.4 | 998.31 |
| Compound 72 | 7.4 | 1036.09 |
| Compound 77 | 7.4 | 21.24 |
| Compound 78 | 7.4 | 225.55 |
| Compound 79 | 7.4 | 0.002 |

Conclusion

It can be seen that the water solubility of the prodrug molecule is significantly higher than nitroxoline due to the structure optimization. For example, the water solubility of compounds 18, 20, 23, 30, 52, 65, 66, 70 and 72 are increased by several times. Moreover, the water solubility of some compounds does not vary with the pH value, which is a particularly important feature in the development of pharmaceutical preparation.

Test Example 2: Determination of the Stability of the Compounds of the Present Invention in Liver Microsome and Plasma It is expected that the compound of formula (I) of the present invention is decomposed into nitroxoline in the body, thereby exerting an anticancer effect. Liver microsomal enzymes and plasma metabolic enzymes are important ways for compound metabolism in vivo. Therefore, in vitro experiments were conducted to determine the stability of the compound of the present invention in liver microsome and plasma.

1. Determination of the Stability in Liver Microsome

Experimental instruments: thermostatic shaker (SHA-B, Guohua Electric Appliance Co., Ltd.); centrifuge (5810R, Eppendorf); mass spectrometry (API4000, Applied Biosystems, USA); liquid chromatography (LC-30AD, Shimadzu); sample injector (CTC Analytics AG System, CTC).

Experimental process: 25 µg/mL alamethicin (Aldrich), 5 mM magnesium chloride and 0.5 mg/mL microsome (XE-NOTECH) were added to 100 mM phosphate buffer to obtain a coenzyme-free reaction solution. A portion of the coenzyme-free reaction solution was added with 1 mM reductive nicotinamide adenine dinucleotide phosphate (Aldrich) and 5 mM uridine diphosphate glucuronic acid (Aldrich) to obtain a coenzyme-containing reaction solution. The working solution of the compound of the present invention was added to the two reaction solutions so that the final concentration of the compound was 2 µM. Immediately after mixing well, 50 µL of the solution were taken out as the 0 minute sample, and 50 µL of the remaining sample were taken out after incubating at 37° C. for 30 minutes. All the samples taken out were immediately processed to precipitate protein, and centrifuged to obtain a supernate for the determination of the compound concentration by LC/MS/MS.

The stability results of the compounds of the present invention in microsome are shown in Table 2 below.

TABLE 2

Stability of the compound of the present invention in microsome

| Compound No. | Percentage of the compound remaining in human liver microsome (%) | | Percentage of the compound remaining in dog liver microsome (%) | | Percentage of the compound remaining in rat liver microsome (%) | | Percentage of the compound remaining in mouse liver microsome (%) | |
|---|---|---|---|---|---|---|---|---|
| | With coenzyme | Without coenzyme | With coenzyme | Without coenzyme | With coenzyme | Without coenzyme | With coenzyme | Without coenzyme |
| Compound 1 | 0.24 | 0.76 | 0.42 | 0.73 | 0.15 | 0.27 | 0.16 | 0.27 |
| Compound 2 | 0.27 | 0.16 | 0.13 | 0.18 | 0.52 | 0.45 | 0.10 | 0.02 |
| Compound 3 | 0.05 | 0.06 | 0.16 | 0.19 | 0.08 | 0.04 | 0.01 | 0.01 |
| Compound 5 | 0.15 | 0.88 | 0.19 | 4.06 | 0.16 | 1.10 | 0.44 | 0.34 |
| Compound 6 | 109.46 | 118.37 | 38.76 | 114.53 | 75.71 | 99.73 | 51.08 | 116.52 |
| Compound 7 | 91.44 | 96.71 | 28.07 | 83.78 | 69.51 | 90.84 | 55.15 | 82.50 |
| Compound 10 | 0.01 | 0.04 | 0.01 | 0.04 | 0.02 | 0.03 | Not applicable | Not applicable |
| Compound 11 | 0.01 | 0.01 | 0.01 | 0.04 | 0.05 | 0.03 | Not applicable | Not applicable |
| Compound 12 | 0.00 | 0.03 | 0.00 | 0.02 | 0.00 | 0.02 | Not applicable | Not applicable |
| Compound 13 | 0.01 | 0.02 | 0.02 | 0.02 | 0.01 | 0.02 | Not applicable | Not applicable |
| Compound 18 | 2.65 | 5.06 | 0.14 | 1.40 | 0.06 | 4.63 | 0.26 | 0.00 |
| Compound 20 | 26.92 | 59.42 | 33.13 | 53.50 | 3.64 | 46.82 | 0.09 | 49.07 |
| Compound 46 | 0.00 | 0.06 | 0.01 | 0.03 | 0.00 | 0.05 | Not applicable | Not applicable |
| Compound 47 | 0.03 | 0.02 | 0.01 | 0.02 | 0.01 | 0.02 | 0.04 | 0.04 |
| Compound 48 | 0.08 | 0.10 | 0.03 | 0.02 | 0.06 | 0.03 | 0.03 | 0.05 |
| Compound 49 | 0.03 | 0.03 | 0.01 | 0.01 | 0.01 | 0.03 | 0.01 | 0.03 |
| Compound 51 | 0.06 | 0.25 | 0.07 | 0.28 | 0.08 | 2.92 | 0.02 | 0.09 |
| Compound 52 | 102.24 | 108.46 | 85.67 | 91.82 | 101.34 | 99.39 | 95.16 | 105.69 |
| Compound 53 | 79.98 | 84.61 | 70.38 | 82.59 | 54.58 | 54.77 | 32.13 | 55.80 |
| Compound 54 | 31.49 | 29.40 | 61.38 | 70.31 | 10.77 | 13.97 | 9.85 | 31.90 |

TABLE 2-continued

Stability of the compound of the present invention in microsome

| Compound No. | Percentage of the compound remaining in human liver microsome (%) | | Percentage of the compound remaining in dog liver microsome (%) | | Percentage of the compound remaining in rat liver microsome (%) | | Percentage of the compound remaining in mouse liver microsome (%) | |
|---|---|---|---|---|---|---|---|---|
| | With coenzyme | Without coenzyme | With coenzyme | Without coenzyme | With coenzyme | Without coenzyme | With coenzyme | Without coenzyme |
| Compound 55 | 61.24 | 81.91 | 70.73 | 84.65 | 8.58 | 52.76 | 2.01 | 90.39 |
| Compound 56 | 0.12 | 71.66 | 14.94 | 118.35 | 0.45 | 62.17 | 0.44 | 103.05 |
| Compound 57 | 0.16 | 0.15 | 0.03 | 75.50 | 23.06 | 44.33 | 5.57 | 76.69 |
| Compound 65 | 29.88 | 39.15 | 65.08 | 93.36 | 4.33 | 59.38 | 0.72 | 2.63 |
| Compound 66 | 9.77 | 74.45 | 13.05 | 67.43 | 0.06 | 12.10 | 0.02 | 4.32 |
| Compound 70 | 91.20 | 91.76 | 91.42 | 90.90 | 94.34 | 96.79 | Not applicable | Not applicable |
| Compound 75 | 1.64 | 6.45 | 12.95 | 48.90 | 0.00 | 0.02 | Not applicable | Not applicable |
| Compound 78 | 14.46 | 90.37 | 0.36 | 98.41 | 2.40 | 91.50 | 0.00 | 100.18 |
| Compound 79 | 1.71 | 2.84 | 1.18 | 4.75 | 3.02 | 3.37 | 0.98 | 1.41 |

Conclusion

Compounds with various microsome stabilities can be obtained by the structure optimization of prodrug molecule. The high stability of compounds 6, 7, 52 and 53 in microsome indicates that these compounds have the possibility of having a longer half-life in the body. The low stability of other compounds in microsome indicates that these compounds have the possibility of being rapidly converted into nitroxoline and having a reduced unnecessary biological toxicity in the body. Both types of molecules have advantages and characteristics in drug development.

2. Determination of the Stability in Plasma

Experimental instruments: thermostatic shaker (SHA-B, Guohua Electric Appliance Co., Ltd.); centrifuge (5810R, Eppendorf); mass spectrometry (AP4000, Applied Biosystems, USA); liquid chromatography (LC-30AD, Shimadzu); sample injector (CTC Analytics AG System, CTC).

Test animals: plasma of human (batch number: BRH1343165), rat (batch number: RAT336728), mouse (batch number: MSE280000), dog (batch number: BGL99137) and monkey (batch number: PH-Monkey-20180821) are purchased from Shanghai Sixin Biological Technology Co., Ltd.

Experimental process: the compound of the present invention was dissolved in an organic solvent to obtain a 1 mM working solution. 3 µL of the working solution were added to 597 µL of pre-incubated human or rat plasma and mixed well. 50 µL of the solution were immediately taken out as the 0 minute sample. The remaining sample was incubated at 37° C., and 50 µL of sample were taken out at 15, 30, 60 and 120 minutes respectively. All the samples taken out were immediately processed to precipitate protein, and centrifuged to obtain a supernate for the determination of the compound concentration by LC/MS/MS.

The stability results of the compound of the present invention in plasma are shown in Table 3 below.

TABLE 3

Stability results of the compound of the present invention in plasma

| Compound No. | Plasma type | Percentage of the compound remaining in plasma (%) | | | | |
|---|---|---|---|---|---|---|
| | | 0 minute | 15 minutes | 30 minutes | 60 minutes | 120 minutes |
| Nitroxoline | Human | 100.0 | 99.3 | 98.3 | 100.6 | 91.6 |
| | Rat | 100.0 | 93.9 | 94.1 | 95.3 | 88.4 |
| | Mouse | 100.0 | 95.8 | 97.4 | 97.4 | 93.0 |
| | Dog | 100.0 | 100.8 | 101.1 | 95.3 | 98.4 |
| | Monkey | 100.0 | 101.2 | 104.0 | 101.8 | 100.4 |
| Compound 4 | Human | 100.0 | 80.9 | 70.7 | 54.7 | 31.4 |
| | Rat | 100.0 | 0.0 | 0.0 | 0.0 | 0.0 |
| | Dog | 100.0 | 80.0 | 56.3 | 32.7 | 18.2 |
| | Monkey | 100.0 | 4.8 | 0.3 | 0.0 | 0.0 |
| Compound 5 | Human | 100.0 | 68.5 | 39.5 | 11.9 | 1.6 |
| | Rat | 100.0 | 2.2 | 0.0 | 0.0 | 0.0 |
| | Dog | 100.0 | 75.0 | 50.6 | 27.1 | 12.0 |
| | Monkey | 100.0 | 0.0 | 0.0 | 0.0 | 0.0 |
| Compound 6 | Human | 100.0 | 97.5 | 106.0 | 95.0 | 99.3 |
| | Rat | 100.0 | 95.5 | 98.8 | 90.2 | 89.4 |
| | Mouse | 100.0 | 97.7 | 95.4 | 98.9 | 92.1 |
| | Dog | 100.0 | 111.5 | 111.9 | 114.6 | 105.9 |
| | Monkey | 100.0 | 98.3 | 101.1 | 91.6 | 98.9 |
| Compound 7 | Human | 100.0 | 93.5 | 97.8 | 99.6 | 105.2 |
| | Rat | 100.0 | 94.0 | 98.6 | 95.0 | 91.6 |
| | Mouse | 100.0 | 98.5 | 98.8 | 96.1 | 89.3 |
| | Dog | 100.0 | 104.0 | 107.2 | 106.5 | 101.8 |
| | Monkey | 100.0 | 96.5 | 105.9 | 99.0 | 98.7 |
| Compound 51 | Human | 100.0 | 97.2 | 98.0 | 94.1 | 84.6 |
| | Rat | 100.0 | 70.2 | 67.8 | 48.0 | 35.3 |
| | Dog | 100.0 | 103.7 | 93.7 | 89.1 | 93.3 |
| | Monkey | 100.0 | 96.4 | 87.0 | 78.1 | 69.0 |
| Compound 52 | Human | 100.0 | 95.6 | 94.1 | 89.2 | 83.3 |
| | Rat | 100.0 | 102.5 | 90.1 | 84.6 | 71.3 |
| Compound 53 | Dog | 100.0 | 96.3 | 92.3 | 78.6 | 67.3 |
| Compound 54 | Human | 100.0 | 108.6 | 103.3 | 93.4 | 71.9 |
| | Rat | 100.0 | 0.0 | 0.0 | 0.0 | 0.0 |
| | Dog | 100.0 | 100.3 | 99.2 | 92.4 | 74.7 |
| Compound 55 | Human | 100.0 | 91.3 | 94.5 | 92.1 | 68.7 |
| | Rat | 100.0 | 48.9 | 24.7 | 5.0 | 0.3 |
| | Dog | 100.0 | 99.6 | 97.5 | 83.3 | 70.1 |

TABLE 3-continued

Stability results of the compound of the present invention in plasma

| Compound No. | Plasma type | Percentage of the compound remaining in plasma (%) | | | | |
|---|---|---|---|---|---|---|
| | | 0 minute | 15 minutes | 30 minutes | 60 minutes | 120 minutes |
| Compound 56 | Human | 100.0 | 98.9 | 98.2 | 103.6 | 93.2 |
| | Rat | 100.0 | 2.8 | 0.1 | 0.0 | 0.0 |
| Compound 57 | Human | 100.0 | 99.8 | 93.0 | 76.2 | 60.2 |
| | Rat | 100.0 | 0.1 | 0.0 | 0.0 | 0.0 |
| Compound 58 | Human | 100.0 | 95.2 | 83.6 | 60.9 | 21.6 |
| | Rat | 100.0 | 0.0 | 0.0 | 0.0 | 0.0 |
| | Dog | 100.0 | 96.3 | 90.4 | 74.4 | 49.8 |
| Compound 59 | Human | 100.0 | 102.3 | 100.9 | 103.1 | 100.3 |
| | Rat | 100.0 | 95.8 | 94.1 | 92.4 | 92.4 |
| | Dog | 100.0 | 96.7 | 95.0 | 102.8 | 99.9 |
| Compound 62 | Human | 100.0 | 95.4 | 101.8 | 99.7 | 92.7 |
| | Rat | 100.0 | 92.4 | 97.3 | 95.8 | 89.0 |
| Compound 70 | Human | 100.0 | 85.6 | 89.0 | 75.2 | 74.4 |
| | Rat | 100.0 | 93.4 | 80.7 | 84.1 | 72.9 |
| Compound 75 | Human | 100.0 | 98.5 | 94.0 | 87.2 | 65.5 |
| | Rat | 100.0 | 0.0 | 0.0 | 0.0 | 0.0 |
| | Dog | 100.0 | 98.3 | 95.6 | 80.8 | 67.8 |
| Compound 79 | Human | 100.0 | 0.0 | 0.0 | 0.0 | 0.0 |
| | Rat | 100.0 | 0.0 | 0.0 | 0.0 | 0.0 |

Conclusion

Compounds with various plasma stabilities can be obtained by the structure optimization of prodrug molecule. The high stability of compounds 6, 7, 52, 53, 54, 55, 56, 57, 58, 59, 62, 70 and 75 in plasma indicates that these compounds have the possibility of having a longer half-life in the body. The low stability of other compounds in plasma indicates that these compounds have the possibility of being rapidly converted into nitroxoline and having a reduced unnecessary biological toxicity in the body. Both types of molecules have advantages and characteristics in drug development.

Test Example 3: Pharmacokinetics Assay of the Compounds of the Present Invention in Rat Nitroxoline is mainly metabolized by the phase II metabolism in liver with a fast metabolism rate, so it has a short half-life in the body. The present invention modified its structure and 13 compounds of formula (I) were obtained through chemical synthesis. The change of nitroxoline concentration in rat plasma after a single intravenous or oral administration of nitroxoline and the compounds of formula (I) was studied to evaluate the pharmacokinetic behavior of nitroxoline and the compound of formula (I) in rat body.

1. Experimental Instruments

Tandem quadrupole mass spectrometer (AP14000, Applied Biosystems, USA); liquid chromatography (1200, Agilent); auto sample injector (CTC Analytics HTC PAL); Applied Biosystems Analyst v 1.6.2; low-temperature refrigerated centrifuge (1-15PK, Sigma); vortex shaker (VX-III, Beijing Targin Technology Co., Ltd.).

2. Pharmacokinetics Experiment

Male SD rats (Beijing Vital River Laboratory Animal Technology Co., Ltd., Certificate No.: SCXK (BJ) 2016-0006, Qualified number: 11400700325643), 3 rats per group, weight 180 to 250 g, 6 to 7 weeks old. The rats were fasted overnight before the administration with free access to water, and fed 4 hours after the administration. The test compound was added to an EP tube, to which 1.017 mL of DMSO, 2.035 mL of solutol and sterilized water for injection (the volume ratio of the three was 1:2:17, v:v:v) were added. The EP tube was subjected to ultrasound for 20 minutes to make the test compound dissolve well (compound concentration: 0.005 mmol/mL). The dose for intravenous administration was 0.01 mmol/kg, and the dose for oral administration was 0.1 mmol/kg. 0.3 ml of whole blood was collected from orbital venous plexus before the administration (0 hour) and 0.0833, 0.25, 0.5, 1, 2, 4, 6, 8, 10, 24, 28, 32 and 48 hours after the administration (sampling points can be adjusted according to the specific situation) respectively. The blood sample was placed in a centrifuge tube containing EDTA-K2 anticoagulant (Aldrich), and the centrifuge tube was left to stand in ice. The blood sample was centrifuged for 5 minutes at 5000 rpm within 0.5 hour to obtain all clean plasma. The plasma was placed in another clean centrifuge tube, to which a stabilizing solution was added in a ratio of 100:3 (plasma/stabilizing solution, v/v), and stored in a refrigerator at −20° C. for later use.

Formulation of the stabilizing solution: 200 mg of Vitamin C (Aldrich) was dissolved in 8 mL of normal saline and then added with 2 mL of formic acid and mixed well to obtain the stabilizing solution.

3. Determination of Sample Concentration

Standard curve: working solution for standard curve was formulated. 5 µL of the working solution was added to 50 µL of blank rat plasma. 150 µL of internal standard working solution (containing 2 ng/mL solution of diphenhydramine (Aldrich) in acetonitrile) was added, and the mixture was shaken by vortex for 1 minute. The mixture was centrifuged for 10 minutes at 4° C., 12000 rpm. 100 µL of the supernatant were placed in an injection tube, and 10 µL of the supernatant were injected into the liquid chromatography-mass spectrometry system for determination.

Test sample: 5 µL of diluted solution of the working solution were added to 50 µL of the test plasma. 150 µL of internal standard working solution (containing 2 ng/mL solution of diphenhydramine in acetonitrile) were added, and the mixture was shaken by vortex for 1 minute. The mixture was centrifuged for 10 minutes at 4° C., 12000 rpm. 100 µL of the supernatant was placed in an injection tube, and 10 µL of the supernatant were injected into the liquid chromatography-mass spectrometry system for determination. The pharmacokinetic parameters were calculated by the WinNonlin V 6.2 non-compartmental model.

The results are shown in Table 4 to Table 45 below.

TABLE 4

Concentration of nitroxoline in SD rat plasma after intravenous administration of nitroxoline

| Time (hours) | Concentration of nitroxoline in plasma (ng/ml) | | | | |
|---|---|---|---|---|---|
| | Rat-01 | Rat-02 | Rat-03 | Average value | Standard deviation |
| 0.00 | <5.0 | <5.0 | <5.0 | Not applicable | Not applicable |
| 0.08 | 2935 | 3098 | 6177 | 4070 | 1827 |
| 0.25 | 588 | 853 | 897 | 779 | 167 |
| 0.50 | 71.1 | 297 | 196 | 188 | 113 |
| 1.0 | 16.0 | 35.5 | 18.4 | 23.3 | 10.6 |
| 2.0 | 26.4 | 23.5 | 10.9 | 20.3 | 8.25 |
| 4.0 | 7.77 | <5.0 | 8.34 | 8.06 | Not applicable |
| 6.0 | <5.0 | <5.0 | <5.0 | Not applicable | Not applicable |
| 8.0 | <5.0 | <5.0 | <5.0 | Not applicable | Not applicable |

TABLE 4-continued

Concentration of nitroxoline in SD rat plasma after intravenous administration of nitroxoline

| Time (hours) | Concentration of nitroxoline in plasma (ng/ml) | | | | |
|---|---|---|---|---|---|
| | Rat-01 | Rat-02 | Rat-03 | Average value | Standard deviation |
| 10 | <5.0 | <5.0 | <5.0 | Not applicable | Not applicable |
| 24 | <5.0 | <5.0 | <5.0 | Not applicable | Not applicable |
| Half-life (h) | | | 0.614 | | |

TABLE 5

Concentration of nitroxoline in SD rat plasma after oral administration of nitroxoline

| Time (hours) | Concentration of nitroxoline in plasma (ng/mL) | | | | |
|---|---|---|---|---|---|
| | Rat-04 | Rat-05 | Rat-06 | Average value | Standard deviation |
| 0.00 | <5.0 | <5.0 | <5.0 | Not applicable | Not applicable |
| 0.08 | 13864 | 9616 | 9797 | 11092 | 2402 |
| 0.25 | 9102 | 3736 | 5661 | 6167 | 2718 |
| 0.50 | 2214 | 1248 | 2410 | 1957 | 622 |
| 1.0 | 1146 | 639 | 766 | 850 | 263 |
| 2.0 | 278 | 334 | 406 | 339 | 63.8 |
| 4.0 | 161 | 168 | 54.4 | 128 | 63.5 |
| 6.0 | 12.2 | 54.2 | 16.9 | 27.7 | 23.0 |
| 8.0 | 8.37 | 36.7 | 5.77 | 16.9 | 17.1 |
| 10 | 8.82 | 14.6 | <5.0 | 11.7 | Not applicable |
| 24 | <5.0 | 14.6 | <5.0 | Not applicable | Not applicable |
| Half-life (h) | | | 1.39 | | |

TABLE 6

Concentration of nitroxoline in SD rat plasma after oral administration of compound 1

| Time (hours) | Concentration of nitroxoline in plasma (ng/ml) | | | | | | | |
|---|---|---|---|---|---|---|---|---|
| | Rat-07 | Rat-08 | Rat-09 | Rat-10 | Rat-11 | Average value | Standard deviation |
| 0 | <5.0 | <5.0 | <5.0 | <5.0 | <5.0 | Not applicable | Not applicable |
| 0.083 | 3684.8 | 6577.0 | 1006.5 | 7446.2 | 7525.6 | 5248.0 | 2838.1 |
| 0.25 | 2659.6 | 7646.7 | 2399.6 | 2829.4 | 4000.6 | 3907.2 | 2178.5 |
| 0.5 | 502.1 | 2589.2 | 2111.5 | 967.5 | 2100.7 | 1654.2 | 877.7 |
| 1 | 376.9 | 332.3 | 425.8 | 391.7 | 837.3 | 472.8 | 206.5 |
| 2 | 311.9 | 186.8 | 184.7 | 66.8 | 273.1 | 204.7 | 94.8 |
| 4 | 291.1 | 130.9 | 170.4 | 117.0 | 166.5 | 175.2 | 68.7 |
| 6 | 91.5 | 138.7 | 61.7 | 47.7 | 79.7 | 83.9 | 34.9 |
| 8 | 34.7 | 11.7 | 44.3 | 35.1 | 46.9 | 34.5 | 13.9 |
| 10 | 32.3 | <5.0 | 21.0 | 20.0 | 27.0 | 25.1 | 5.7 |
| 24 | <5.0 | <5.0 | <5.0 | <5.0 | <5.0 | Not applicable | Not applicable |
| Half-life (h) | | | | | 2.08 | | |

TABLE 7

Concentration of nitroxoline in SD rat plasma after intravenous administration of compound 1

| Time (hours) | Concentration of nitroxoline in plasma (ng/ml) | | | | |
|---|---|---|---|---|---|
| | Rat-12 | Rat-13 | Rat-14 | Average value | Standard deviation |
| 0 | <5.0 | <5.0 | <5.0 | Not applicable | Not applicable |
| 0.0833 | 3299.5 | 3672.1 | 4203.7 | 3725.1 | 454.4 |
| 0.25 | 558.5 | 626.9 | 915.1 | 700.2 | 189.2 |
| 0.5 | 54.6 | 77.1 | 191.1 | 107.6 | 73.2 |
| 1 | 10.9 | 15.2 | 27.9 | 18.0 | 8.9 |
| 2 | 10.0 | 11.8 | 7.3 | 9.7 | 2.3 |
| 4 | <5.0 | <5.0 | <5.0 | Not applicable | Not applicable |
| 6 | <5.0 | <5.0 | <5.0 | Not applicable | Not applicable |
| 8 | <5.0 | <5.0 | <5.0 | Not applicable | Not applicable |
| 10 | <5.0 | <5.0 | <5.0 | Not applicable | Not applicable |
| 24 | <5.0 | <5.0 | <5.0 | Not applicable | Not applicable |
| Half-life (h) | | | 0.325 | | |

TABLE 8

Concentration of nitroxoline in SD rat plasma after intravenous administration of compound 3

| Time (hours) | Concentration of nitroxoline in plasma (ng/mL) | | | | |
|---|---|---|---|---|---|
| | Rat-15 | Rat-16 | Rat-17 | Average value | Standard deviation |
| 0 | <5.0 | <5.0 | <5.0 | Not applicable | Not applicable |
| 0.083 | 4729.3 | 7326.0 | 8085.4 | 6713.6 | 1759.9 |
| 0.25 | 6987.4 | 13129.6 | 14278.7 | 11465.2 | 3920.3 |
| 0.5 | 2727.4 | 3567.5 | 8094.8 | 4796.6 | 2887.1 |
| 1 | 1000.4 | 882.8 | 2422.1 | 1435.1 | 856.8 |
| 2 | 1140.9 | 513.8 | 2094.0 | 1249.5 | 795.7 |
| 4 | 421.6 | 123.6 | 285.7 | 276.9 | 149.2 |
| 6 | 50.5 | 34.7 | 79.1 | 54.8 | 22.5 |
| 8 | 46.7 | 5.2 | 37.4 | 29.8 | 21.8 |
| 10 | 47.0 | <5.0 | <5.0 | 47.0 | Not applicable |
| 24 | <5.0 | <5.0 | <5.0 | Not applicable | Not applicable |
| Half-life (h) | | | 1.44 | | |

TABLE 9

Concentration of nitroxoline in SD rat plasma after intravenous administration of compound 4

| Time (hours) | Concentration of nitroxoline in plasma (ng/ml) | | | | |
|---|---|---|---|---|---|
| | Rat-18 | Rat-19 | Rat-20 | Average value | Standard deviation |
| 0 | <5.0 | <5.0 | <5.0 | Not applicable | Not applicable |
| 0.25 | 1657.1 | 4011.0 | 4242.7 | 3303.6 | 1430.6 |
| 0.5 | 1002.6 | 1661.7 | 2300.4 | 1654.9 | 648.9 |
| 1 | 397.8 | 503.9 | 567.7 | 489.8 | 85.8 |
| 2 | 329.9 | 444.6 | 426.8 | 400.4 | 61.7 |
| 4 | 285.1 | 329.9 | 415.5 | 343.5 | 66.3 |
| 6 | 207.2 | 284.3 | 164.4 | 218.6 | 60.7 |
| 8 | 90.3 | 286.0 | 38.9 | 138.4 | 130.4 |
| 24 | <5.0 | <5.0 | 20.3 | 20.3 | Not applicable |
| Half-life (h) | | | 3.92 | | |

TABLE 10

Concentration of nitroxoline in SD rat plasma after oral administration of compound 5

Concentration of nitroxoline in plasma (ng/ml)

| Time (hours) | Rat-21 | Rat-22 | Rat-23 | Average value | Standard deviation |
|---|---|---|---|---|---|
| 0.00 | <5.0 | <5.0 | <5.0 | Not applicable | Not applicable |
| 0.25 | 9159 | 6274 | 7346 | 7593 | 1458 |
| 0.50 | 3130 | 3784 | 7488 | 4800 | 2350 |
| 1.0 | 1337 | 5670 | 2865 | 3291 | 2198 |
| 2.0 | 722 | 1989 | 2004 | 1572 | 736 |
| 4.0 | 411 | 653 | 1160 | 741 | 382 |
| 6.0 | 26.4 | 375 | 376 | 259 | 201 |
| 8.0 | 16.8 | 56.7 | 158 | 77.1 | 72.7 |
| 24 | 5.00 | 5.92 | <5.0 | 5.46 | Not applicable |
| Half-life (h) | | | | 2.79 | |

TABLE 11

Concentration of nitroxoline in SD rat plasma after intravenous administration of compound 6

Concentration of nitroxoline in plasma (ng/mL)

| Time (hours) | Rat-24 | Rat-25 | Rat-26 | Average value | Standard deviation |
|---|---|---|---|---|---|
| 0.00 | <5.0 | <5.0 | <5.0 | Not applicable | Not applicable |
| 0.08 | 253.0 | 99.6 | 134.0 | 162.0 | 80.7 |
| 0.25 | 115.0 | 69.1 | 65.2 | 82.9 | 27.4 |
| 0.50 | 80.1 | 39.6 | 24.7 | 48.2 | 28.7 |
| 1.0 | 38.3 | 17.9 | 15.5 | 23.9 | 12.6 |
| 2.0 | 21.0 | 8.5 | 11.0 | 13.5 | 6.6 |
| 4.0 | 11.6 | <5.0 | 5.3 | 8.4 | Not applicable |
| 6.0 | <5.0 | <5.0 | <5.0 | Not applicable | Not applicable |
| 8.0 | <5.0 | <5.0 | <5.0 | Not applicable | Not applicable |
| 10 | <5.0 | <5.0 | <5.0 | Not applicable | Not applicable |
| 24 | <5.0 | <5.0 | <5.0 | Not applicable | Not applicable |
| 28 | <5.0 | <5.0 | <5.0 | Not applicable | Not applicable |
| 36 | <5.0 | <5.0 | <5.0 | Not applicable | Not applicable |
| 48 | <5.0 | <5.0 | <5.0 | Not applicable | Not applicable |
| Half-life (h) | | | | 1.02 | |

TABLE 12

Concentration of nitroxoline in SD rat plasma after oral administration of compound 6

Concentration of nitroxoline in plasma (ng/ml)

| Time (hours) | Rat-27 | Rat-28 | Rat-29 | Average value | Standard deviation |
|---|---|---|---|---|---|
| 0.00 | <5.0 | <5.0 | <5.0 | Not applicable | Not applicable |
| 0.08 | 101.0 | 84.2 | 98.5 | 94.5 | 9.0 |
| 0.25 | 193.0 | 106.0 | 169.0 | 156.0 | 45.1 |
| 0.50 | 191.0 | 77.0 | 129.0 | 132.0 | 57.3 |
| 1.0 | 120.0 | 69.2 | 146.0 | 112.0 | 39.0 |
| 2.0 | 63.2 | 52.3 | 99.4 | 71.6 | 24.7 |
| 4.0 | 54.2 | 43.6 | 29.7 | 42.5 | 12.3 |
| 6.0 | 27.3 | 32.6 | 14.3 | 24.7 | 9.4 |
| 8.0 | 17.0 | 26.6 | 19.1 | 20.9 | 5.0 |
| 10 | 15.2 | 23.8 | 20.7 | 19.9 | 4.4 |
| 24 | 37.2 | 24.2 | 24.4 | 28.6 | 7.5 |
| 28 | 27.5 | 17.3 | 13.8 | 19.5 | 7.1 |
| 36 | 16.3 | 11.9 | 10.1 | 12.8 | 3.2 |
| 48 | 5.6 | 5.5 | 7.2 | 6.1 | 1.0 |
| Half-life (h) | | | 19.1 | | |

TABLE 13

Concentration of nitroxoline in SD rat plasma after intravenous administration of compound 7

Concentration of nitroxoline in plasma (ng/ml)

| Time (hours) | Rat-30 | Rat-31 | Rat-32 | Average value | Standard deviation |
|---|---|---|---|---|---|
| 0.00 | <5.0 | <5.0 | <5.0 | Not applicable | Not applicable |
| 0.08 | 215.0 | 217.0 | 270.0 | 234.0 | 31.0 |
| 0.25 | 128.0 | 140.0 | 134.0 | 134.0 | 6.1 |
| 0.50 | 49.4 | 60.8 | 69.5 | 59.9 | 10.1 |
| 1.0 | 41.9 | 35.4 | 32.4 | 36.6 | 4.9 |
| 2.0 | 12.5 | 13.5 | 18.5 | 14.8 | 3.2 |
| 4.0 | 7.0 | 8.4 | 6.2 | 7.2 | 1.1 |
| 6.0 | <5.0 | <5.0 | <5.0 | Not applicable | Not applicable |
| 8.0 | <5.0 | <5.0 | <5.0 | Not applicable | Not applicable |
| 10 | <5.0 | <5.0 | <5.0 | Not applicable | Not applicable |
| 24 | <5.0 | <5.0 | <5.0 | Not applicable | Not applicable |
| 28 | <5.0 | <5.0 | <5.0 | Not applicable | Not applicable |
| 36 | <5.0 | <5.0 | <5.0 | Not applicable | Not applicable |
| 48 | <5.0 | <5.0 | <5.0 | Not applicable | Not applicable |
| Half-life (h) | | | 0.98 | | |

TABLE 14

Concentration of nitroxoline in SD rat plasma after oral administration of compound 7

Concentration of nitroxoline in plasma (ng/ml)

| Time (hours) | Rat-33 | Rat-34 | Rat-35 | Average value | Standard deviation |
|---|---|---|---|---|---|
| 0.00 | <5.0 | <5.0 | <5.0 | Not applicable | Not applicable |
| 0.08 | 36.8 | 50.1 | 44.5 | 43.8 | 6.7 |
| 0.25 | 86.8 | 148.0 | 63.3 | 99.3 | 43.6 |
| 0.50 | 124.0 | 158.0 | 100.0 | 127.0 | 29.3 |
| 1.0 | 144.0 | 171.0 | 100.0 | 139.0 | 35.6 |
| 2.0 | 102.0 | 80.1 | 84.7 | 89.1 | 11.7 |
| 4.0 | 59.1 | 56.5 | 52.6 | 56.1 | 3.3 |
| 6.0 | 41.2 | 33.7 | 31.6 | 35.5 | 5.1 |
| 8.0 | 45.5 | 18.5 | 25.1 | 29.7 | 14.1 |
| 10 | 23.3 | 13.6 | 16.1 | 17.7 | 5.1 |
| 24 | 6.8 | 6.8 | 6.1 | 6.6 | 0.4 |
| 28 | <5.0 | <5.0 | <5.0 | Not applicable | Not applicable |

TABLE 14-continued

Concentration of nitroxoline in SD rat plasma after oral administration of compound 7

| | Concentration of nitroxoline in plasma (ng/ml) | | | | |
|---|---|---|---|---|---|
| Time (hours) | Rat-33 | Rat-34 | Rat-35 | Average value | Standard deviation |
| 36 | <5.0 | <5.0 | <5.0 | Not applicable | Not applicable |
| 48 | <5.0 | <5.0 | <5.0 | Not applicable | Not applicable |
| Half-life (h) | | | 6.25 | | |

TABLE 15

Concentration of nitroxoline in SD rat plasma after intravenous administration of compound 20

| | Concentration of nitroxoline in plasma (ng/ml) | | | | |
|---|---|---|---|---|---|
| Time (hours) | Rat-36 | Rat-37 | Rat-38 | Average value | Standard deviation |
| 0 | <5.0 | <5.0 | <5.0 | Not applicable | Not applicable |
| 0.083 | 7900 | 5400 | 4350 | 5880 | 1820 |
| 0.25 | 2880 | 1570 | 984 | 1810 | 971 |
| 0.5 | 767 | 288 | 260 | 438 | 285 |
| 1 | 130 | 29.0 | 31.8 | 63.6 | 57.5 |
| 2 | 59.1 | 15.7 | 12.9 | 29.2 | 25.9 |
| 4 | 6.49 | <5.0 | <5.0 | 6.49 | Not applicable |
| 6 | <5.0 | <5.0 | <5.0 | <5.0 | Not applicable |
| 8 | <5.0 | <5.0 | <5.0 | <5.0 | Not applicable |
| 10 | <5.0 | <5.0 | <5.0 | <5.0 | Not applicable |
| 12 | <5.0 | <5.0 | <5.0 | <5.0 | Not applicable |
| Half-life (h) | | | 0.420 | | |

TABLE 16

Concentration of nitroxoline in SD rat plasma after oral administration of compound 20

| | Concentration of nitroxoline in plasma (ng/ml) | | | | |
|---|---|---|---|---|---|
| Time (hours) | Rat-39 | Rat-40 | Rat-41 | Average value | Standard deviation |
| 0 | <5.0 | <5.0 | <5.0 | Not applicable | Not applicable |
| 0.083 | 1210 | 545 | 846 | 867 | 333 |
| 0.25 | 9380 | 1300 | 4470 | 5050 | 4071 |
| 0.5 | 8240 | 1330 | 1640 | 3740 | 3903 |
| 1 | 2540 | 798 | 490 | 1280 | 1105 |
| 2 | 1670 | 1020 | 329 | 1010 | 671 |
| 4 | 958 | 274 | 174 | 469 | 427 |
| 6 | 349 | 4.53 | 30.6 | 128 | 192 |
| 8 | 518 | <5.0 | 20.6 | 269 | Not applicable |
| 10 | 319 | <5.0 | 26.6 | 173 | Not applicable |
| 12 | 93.2 | <5.0 | 17.6 | 55.4 | Not applicable |
| Half-life (h) | | | 1.68 | | |

TABLE 17

Concentration of nitroxoline in SD rat plasma after oral administration of compound 21

| | Concentration of nitroxoline in plasma (ng/mL) | | | | |
|---|---|---|---|---|---|
| Time (hours) | Rat-42 | Rat-43 | Rat-44 | Average value | Standard deviation |
| 0 | <5.0 | <5.0 | <5.0 | Not applicable | Not applicable |
| 0.083 | 2535.6 | 12956.0 | 5926.3 | 7139.3 | 5315.0 |
| 0.25 | 3899.2 | 16391.4 | 4591.9 | 8294.2 | 7021.0 |
| 0.5 | 5384.1 | 2563.8 | 1877.3 | 3275.1 | 1858.4 |
| 1 | 1692.2 | 705.9 | 669.1 | 1022.4 | 580.4 |
| 2 | 802.8 | 212.4 | 195.3 | 403.5 | 345.9 |
| 4 | 126.8 | 161.7 | 134.9 | 141.1 | 18.3 |
| 6 | 68.7 | 20.4 | 98.5 | 62.6 | 39.4 |
| 8 | 27.6 | 6.0 | 54.3 | 29.3 | 24.2 |
| 10 | 10.2 | 13.6 | 33.1 | 19.0 | 12.4 |
| 24 | <5.0 | <5.0 | <5.0 | Not applicable | Not applicable |
| Half-life (h) | | | 1.61 | | |

TABLE 18

Concentration of nitroxoline in SD rat plasma after oral administration of compound 23

| | Concentration of nitroxoline in plasma (ng/ml) | | | | |
|---|---|---|---|---|---|
| Time (hours) | Rat-45 | Rat-46 | Rat-47 | Average value | Standard deviation |
| 0 | <5.0 | <5.0 | <5.0 | Not applicable | Not applicable |
| 0.083 | 7110.5 | 1158.7 | 6724.4 | 4997.9 | 3330.4 |
| 0.25 | 5783.9 | 4415.4 | 5456.1 | 5218.5 | 714.6 |
| 0.5 | 955.4 | 813.9 | 1271.5 | 1013.6 | 234.3 |
| 1 | 385.4 | 297.0 | 238.9 | 307.1 | 73.8 |
| 2 | 187.4 | 216.5 | 195.4 | 199.8 | 15.0 |
| 4 | 98.3 | 106.6 | 91.7 | 98.9 | 7.5 |
| 6 | 21.3 | 61.7 | 38.0 | 40.3 | 20.3 |
| 8 | 19.2 | 68.2 | 21.2 | 36.2 | 27.7 |
| 10 | 23.6 | 59.3 | <5.0 | 41.5 | Not applicable |
| 24 | <5.0 | <5.0 | <5.0 | Not applicable | Not applicable |
| Half-life (h) | | | 2.71 | | |

TABLE 19

Concentration of nitroxoline in SD rat plasma after oral administration of compound 24

| | Concentration of nitroxoline in plasma (ng/ml) | | | | |
|---|---|---|---|---|---|
| Time (hours) | Rat-48 | Rat-49 | Rat-50 | Average value | Standard deviation |
| 0 | <5.0 | <5.0 | <5.0 | Not applicable | Not applicable |
| 0.083 | 4082.9 | 4560.0 | 3657.7 | 4100.2 | 451.4 |
| 0.25 | 2447.2 | 10339.5 | 4758.0 | 5848.2 | 4057.5 |
| 0.5 | 980.3 | 4086.3 | 1836.4 | 2301.0 | 1604.3 |
| 1 | 241.9 | 1400.9 | 319.6 | 654.1 | 647.9 |
| 2 | 171.3 | 492.2 | 84.4 | 249.3 | 214.8 |
| 4 | 159.7 | 590.5 | 140.3 | 296.9 | 254.5 |
| 6 | 50.2 | 447.3 | 24.4 | 174.0 | 237.0 |
| 8 | 73.8 | 567.4 | 9.3 | 216.8 | 305.3 |
| 10 | 33.8 | 246.6 | 14.1 | 98.2 | 128.9 |
| 24 | 6.6 | 15.9 | <5.0 | 11.3 | Not applicable |
| Half-life (h) | | | 3.34 | | |

TABLE 20

Concentration of nitroxoline in SD rat plasma after oral administration of compound 34

Concentration of nitroxoline in plasma (ng/mL)

| Time (hours) | Rat-51 | Rat-52 | Rat-53 | Average value | Standard deviation |
|---|---|---|---|---|---|
| 0 | <5.0 | <5.0 | <5.0 | Not applicable | Not applicable |
| 0.083 | 4300.7 | 4027.6 | 1913.1 | 3413.8 | 1306.8 |
| 0.25 | 4195.6 | 4233.0 | 3797.0 | 4075.2 | 241.6 |
| 0.5 | 710.5 | 2129.3 | 1839.6 | 1559.8 | 749.6 |
| 1 | 402.6 | 835.6 | 205.4 | 481.2 | 322.4 |
| 2 | 281.8 | 481.0 | 114.6 | 292.5 | 183.4 |
| 4 | 98.8 | 323.0 | 79.5 | 167.1 | 135.3 |
| 6 | 64.3 | 93.2 | 97.3 | 84.9 | 18.0 |
| 8 | 5.9 | 232.875* | 151.160* | 130.0 | 114.9 |
| 10 | <5.0 | 66.8 | 40.8 | 53.8 | 18.4 |
| 24 | <5.0 | 54.3 | <5.0 | 54.3 | Not applicable |
| Half-life (h) | | | 3.01 | | |

TABLE 21

Concentration of nitroxoline in SD rat plasma after intravenous administration of compound 34

Concentration of nitroxoline in plasma (ng/ml)

| Time (hours) | Rat-54 | Rat-55 | Rat-56 | Average value | Standard deviation |
|---|---|---|---|---|---|
| 0 | <5.0 | <5.0 | <5.0 | Not applicable | Not applicable |
| 0.083 | 2718.3 | 2869.1 | 3605.5 | 3064.3 | 474.7 |
| 0.25 | 738.4 | 970.6 | 1771.1 | 1160.0 | 541.8 |
| 0.5 | 177.6 | 255.8 | 460.8 | 298.1 | 146.3 |
| 1 | 29.5 | 36.2 | 91.5 | 52.4 | 34.0 |
| 2 | 17.1 | 11.9 | 67.0 | 32.0 | 30.4 |
| 4 | <5.0 | 6.0 | 19.7 | 12.8 | Not applicable |
| 6 | <5.0 | <5.0 | <5.0 | Not applicable | Not applicable |
| 8 | <5.0 | <5.0 | <5.0 | Not applicable | Not applicable |
| 10 | <5.0 | <5.0 | <5.0 | Not applicable | Not applicable |
| 24 | <5.0 | <5.0 | <5.0 | Not applicable | Not applicable |
| Half-life (h) | | | 0.53 | | |

TABLE 22

Concentration of nitroxoline in SD rat plasma after oral administration of compound 47

Concentration of nitroxoline in plasma (ng/mL)

| Time (hours) | Rat-57 | Rat-58 | Rat-59 | Average value | Standard deviation |
|---|---|---|---|---|---|
| 0 | <5.0 | <5.0 | <5.0 | Not applicable | Not applicable |
| 0.083 | 3788.5 | 5768.9 | 9059.3 | 6205.6 | 2662.4 |
| 0.25 | 5610.3 | 4642.5 | 9537.7 | 6596.8 | 2592.4 |
| 0.5 | 2407.9 | 746.1 | 1991.3 | 1715.1 | 864.7 |
| 1 | 747.4 | 240.7 | 572.9 | 520.3 | 257.2 |
| 2 | 129.3 | 52.0 | 431.1 | 204.2 | 200.3 |
| 4 | 91.4 | 40.3 | 209.9 | 113.9 | 87.0 |
| 6 | 9.3 | 12.6 | 35.0 | 18.9 | 14.0 |
| 8 | <5.0 | <5.0 | 17.3 | Not applicable | Not applicable |

TABLE 22-continued

Concentration of nitroxoline in SD rat plasma after oral administration of compound 47

Concentration of nitroxoline in plasma (ng/mL)

| Time (hours) | Rat-57 | Rat-58 | Rat-59 | Average value | Standard deviation |
|---|---|---|---|---|---|
| 10 | <5.0 | <5.0 | 11.7 | Not applicable | Not applicable |
| 24 | <5.0 | <5.0 | <5.0 | Not applicable | Not applicable |
| Half-life (h) | | | 1.30 | | |

TABLE 23

Concentration of nitroxoline in SD rat plasma after oral administration of compound 49

Concentration of nitroxoline in plasma (ng/ml)

| Time (hours) | Rat-60 | Rat-61 | Rat-62 | Average value | Standard deviation |
|---|---|---|---|---|---|
| 0 | <5.0 | <5.0 | <5.0 | Not applicable | Not applicable |
| 0.083 | 6203.1 | 3006.0 | 4223.5 | 4477.5 | 1613.6 |
| 0.25 | 16626.2 | 5608.9 | 4629.6 | 8954.9 | 6661.6 |
| 0.5 | 7277.6 | 1088.7 | 1643.3 | 3336.5 | 3424.3 |
| 1 | 922.6 | 140.5 | 185.6 | 416.2 | 439.1 |
| 2 | 737.7 | 125.0 | 41.8 | 301.5 | 380.0 |
| 4 | 495.4 | 43.2 | 35.3 | 191.3 | 263.4 |
| 6 | 51.4 | 6.0 | 7.0 | 21.5 | 26.0 |
| 8 | 17.0 | 5.6 | 7.5 | 10.0 | 6.1 |
| 10 | <5.0 | <5.0 | 5.4 | 5.4 | Not applicable |
| 24 | <5.0 | <5.0 | <5.0 | Not applicable | Not applicable |
| Half-life (h) | | | 1.59 | | |

TABLE 24

Concentration of nitroxoline in SD rat plasma after oral administration of compound 51

Concentration of nitroxoline in plasma (ng/ml)

| Time (hours) | Rat-63 | Rat-64 | Rat-65 | Average value | Standard deviation |
|---|---|---|---|---|---|
| 0 | <5.0 | <5.0 | <5.0 | Not applicable | Not applicable |
| 0.083 | 4278.0 | 2124.1 | 7791.7 | 4731.3 | 2860.8 |
| 0.25 | 7271.9 | 2305.3 | 7541.7 | 5706.3 | 2948.5 |
| 0.5 | 5618.9 | 2736.9 | 4892.2 | 4416.0 | 1498.8 |
| 1 | 3457.1 | 887.0 | 1027.2 | 1790.4 | 1445.0 |
| 2 | 831.0 | 165.9 | 224.0 | 407.0 | 368.4 |
| 4 | 1092.5 | 576.9 | 178.4 | 615.9 | 458.3 |
| 6 | 278.9 | 235.1 | 37.6 | 183.9 | 128.6 |
| 8 | 330.4 | 99.5 | 19.0 | 149.6 | 161.7 |
| 10 | 218.1 | 43.8 | 23.7 | 95.2 | 106.9 |
| 24 | 127.2 | 32.9 | <5.0 | 80.1 | Not applicable |
| Half-life (h) | | | 5.59 | | |

TABLE 25

Concentration of nitroxoline in SD rat plasma after intravenous administration of compound 52

Concentration of nitroxoline in plasma (ng/ml)

| Time (hours) | Rat-66 | Rat-67 | Rat-68 | Average value | Standard deviation |
|---|---|---|---|---|---|
| 0.00 | <5.0 | <5.0 | <5.0 | Not applicable | Not applicable |
| 0.08 | 4278.0 | 2124.1 | 7791.7 | 4731.3 | 2860.8 |
| 0.25 | 7271.9 | 2305.3 | 7541.7 | 5706.3 | 2948.5 |
| 0.50 | 5618.9 | 2736.9 | 4892.2 | 4416.0 | 1498.8 |
| 1.0 | 3457.1 | 887.0 | 1027.2 | 1790.4 | 1445.0 |
| 2.0 | 831.0 | 165.9 | 224.0 | 407.0 | 368.4 |
| 4.0 | 1092.5 | 576.9 | 178.4 | 615.9 | 458.3 |
| 6.0 | 278.9 | 235.1 | 37.6 | 183.9 | 128.6 |
| 8.0 | 330.4 | 99.5 | 19.0 | 149.6 | 161.7 |
| 10 | 218.1 | 43.8 | 23.7 | 95.2 | 106.9 |
| 24 | 127.2 | 32.9 | <5.0 | 80.1 | Not applicable |
| Half-life (h) | | | 1.45 | | |

TABLE 26

Concentration of nitroxoline in SD rat plasma after oral administration of compound 52

Concentration of nitroxoline in plasma (ng/ml)

| Time (hours) | Rat-69 | Rat-70 | Rat-71 | Average value | Standard deviation |
|---|---|---|---|---|---|
| 0.00 | <5.0 | <5.0 | <5.0 | Not applicable | Not applicable |
| 0.08 | 14.7 | 9.1 | 13.3 | 12.4 | 2.9 |
| 0.25 | 144.0 | 68.5 | 103.0 | 105.0 | 38.0 |
| 0.50 | 78.2 | 81.4 | 144.0 | 101.0 | 37.0 |
| 1.0 | 89.2 | 111.0 | 126.0 | 109.0 | 18.7 |
| 2.0 | 73.4 | 50.8 | 104.0 | 76.1 | 26.7 |
| 4.0 | 54.8 | 65.9 | 128.0 | 82.9 | 39.4 |
| 6.0 | 16.2 | 21.2 | 44.7 | 27.3 | 15.3 |
| 8.0 | <5.0 | 11.0 | 18.6 | 14.8 | Not applicable |
| 10 | <5.0 | <5.0 | 8.1 | 8.1 | Not applicable |
| 24 | <5.0 | <5.0 | <5.0 | Not applicable | Not applicable |
| Half-life (h) | | | 2.17 | | |

TABLE 27

Concentration of nitroxoline in SD rat plasma after oral administration of compound 53

Concentration of nitroxoline in plasma (ng/ml)

| Time (hours) | Rat-72 | Rat-73 | Rat-74 | Average value | Standard deviation |
|---|---|---|---|---|---|
| 0 | <5.0 | <5.0 | <5.0 | Not applicable | Not applicable |
| 0.083 | 94.5 | 93.9 | 94.2 | 94.2 | 0.3 |
| 0.25 | 213.6 | 542.3 | 378.0 | 378.0 | 164.3 |
| 0.5 | 153.2 | 261.0 | 207.1 | 207.1 | 53.9 |
| 1 | 63.0 | 141.6 | 102.3 | 102.3 | 39.3 |
| 2 | 43.1 | 43.2 | 43.1 | 43.1 | 0.0 |
| 4 | 19.6 | 18.6 | 19.1 | 19.1 | 0.5 |
| 6 | <5.0 | <5.0 | <5.0 | Not applicable | Not applicable |
| 8 | <5.0 | <5.0 | <5.0 | Not applicable | Not applicable |
| 10 | <5.0 | <5.0 | <5.0 | Not applicable | Not applicable |

TABLE 27-continued

Concentration of nitroxoline in SD rat plasma after oral administration of compound 53

Concentration of nitroxoline in plasma (ng/ml)

| Time (hours) | Rat-72 | Rat-73 | Rat-74 | Average value | Standard deviation |
|---|---|---|---|---|---|
| 24 | <5.0 | <5.0 | <5.0 | Not applicable | Not applicable |
| Half-life (h) | | | 1.13 | | |

TABLE 28

Concentration of nitroxoline in SD rat plasma after oral administration of compound 54

Concentration of nitroxoline in plasma (ng/ml)

| Time (hours) | Rat-75 | Rat-76 | Rat-77 | Average value | Standard deviation |
|---|---|---|---|---|---|
| 0 | <5.0 | <5.0 | <5.0 | Not applicable | Not applicable |
| 0.083 | 94.49 | 93.87 | 94.18 | 94.18 | 0.31 |
| 0.25 | 213.64 | 542.28 | 377.96 | 377.96 | 164.32 |
| 0.5 | 153.20 | 261.02 | 207.11 | 207.11 | 53.91 |
| 1 | 62.99 | 141.59 | 102.29 | 102.29 | 39.30 |
| 2 | 43.08 | 43.18 | 43.13 | 43.13 | 0.05 |
| 4 | 19.63 | 18.63 | 19.13 | 19.13 | 0.50 |
| 6 | <5.0 | <5.0 | <5.0 | Not applicable | Not applicable |
| 8 | <5.0 | <5.0 | <5.0 | Not applicable | Not applicable |
| 10 | <5.0 | <5.0 | <5.0 | Not applicable | Not applicable |
| 24 | <5.0 | <5.0 | <5.0 | Not applicable | Not applicable |
| Half-life (h) | | | 1.63 | | |

TABLE 29

Concentration of nitroxoline in SD rat plasma after oral administration of compound 55

Concentration of nitroxoline in plasma (ng/ml)

| Time (hours) | Rat-78 | Rat-79 | Rat-80 | Average value | Standard deviation |
|---|---|---|---|---|---|
| 0 | <5.0 | <5.0 | <5.0 | Not applicable | Not applicable |
| 0.083 | 375.9 | 466.6 | 413.9 | 418.8 | 45.6 |
| 0.25 | 717.7 | 666.0 | 671.2 | 684.9 | 28.5 |
| 0.5 | 834.8 | 788.5 | 634.7 | 752.7 | 104.8 |
| 1 | 185.3 | 212.3 | 186.2 | 194.6 | 15.3 |
| 2 | 79.1 | 95.0 | 100.1 | 91.4 | 11.0 |
| 4 | 68.2 | 57.2 | 85.9 | 70.4 | 14.5 |
| 6 | 33.9 | 14.2 | 36.6 | 28.2 | 12.2 |
| 8 | 31.3 | <5.0 | 26.5 | 28.9 | 3.4 |
| 10 | 15.6 | <5.0 | <5.0 | 15.6 | Not applicable |
| 24 | <5.0 | <5.0 | <5.0 | Not applicable | Not applicable |
| Half-life (h) | | | 2.28 | | |

TABLE 30

Concentration of nitroxoline in SD rat plasma after oral administration of compound 56

| Time (hours) | Rat-81 | Rat-82 | Rat-83 | Average value | Standard deviation |
|---|---|---|---|---|---|
| 0 | <5.0 | <5.0 | <5.0 | Not applicable | Not applicable |
| 0.083 | 526.0 | 300.4 | 413.0 | 413.1 | 112.8 |
| 0.25 | 687.8 | 483.0 | 794.8 | 655.2 | 158.4 |
| 0.5 | 363.6 | 348.3 | 537.7 | 416.5 | 105.2 |
| 1 | 197.7 | 286.7 | 265.5 | 249.9 | 46.5 |
| 2 | 57.3 | 38.1 | 168.7 | 88.0 | 70.5 |
| 4 | 40.6 | 24.6 | 79.9 | 48.4 | 28.5 |
| 6 | <5.0 | <5.0 | 25.5 | 25.5 | Not applicable |
| 8 | <5.0 | <5.0 | 14.8 | 14.8 | Not applicable |
| 10 | <5.0 | <5.0 | <5.0 | Not applicable | Not applicable |
| 24 | <5.0 | <5.0 | <5.0 | Not applicable | Not applicable |
| Half-life (h) | | | 1.22 | | |

TABLE 31

Concentration of nitroxoline in SD rat plasma after oral administration of compound 59

| Time (hours) | Rat-84 | Rat-85 | Rat-86 | Average value | Standard deviation |
|---|---|---|---|---|---|
| 0 | <5.0 | <5.0 | <5.0 | Not applicable | Not applicable |
| 0.083 | 70.6 | 28.6 | 21.5 | 40.3 | 26.6 |
| 0.25 | 188.6 | 41.6 | 70.4 | 100.2 | 77.9 |
| 0.5 | 171.5 | 42.7 | 89.1 | 101.1 | 65.3 |
| 1 | 165.9 | 57.2 | 74.3 | 99.1 | 58.4 |
| 2 | 96.8 | 58.0 | 66.6 | 73.8 | 20.4 |
| 4 | 67.8 | 32.4 | 29.8 | 43.3 | 21.2 |
| 6 | 61.0 | 30.4 | 15.0 | 35.5 | 23.4 |
| 8 | 35.4 | 10.8 | <5.0 | 23.1 | Not applicable |
| 10 | 36.8 | <5.0 | <5.0 | 36.8 | Not applicable |
| 24 | 11.7 | <5.0 | <5.0 | 11.7 | Not applicable |
| Half-life (h) | | | 4.05 | | |

TABLE 32

Concentration of nitroxoline in SD rat plasma after oral administration of compound 60

| Time (hours) | Rat-87 | Rat-88 | Rat-89 | Average value | Standard deviation |
|---|---|---|---|---|---|
| 0 | <5.0 | <5.0 | <5.0 | Not applicable | Not applicable |
| 0.083 | 302.6 | 428.1 | 300.2 | 343.6 | 73.2 |
| 0.25 | 507.9 | 267.9 | 411.8 | 395.9 | 120.8 |
| 0.5 | 284.9 | 319.3 | 405.2 | 336.5 | 62.0 |
| 1 | 300.2 | 257.8 | 308.8 | 289.0 | 27.3 |
| 2 | 144.2 | 196.6 | 283.6 | 208.2 | 70.4 |
| 4 | 111.0 | 64.3 | 165.4 | 113.5 | 50.6 |
| 6 | 74.5 | 39.3 | 176.1 | 96.7 | 71.1 |
| 8 | 23.4 | 9.4 | 60.6 | 31.1 | 26.5 |

TABLE 32-continued

Concentration of nitroxoline in SD rat plasma after oral administration of compound 60

| Time (hours) | Rat-87 | Rat-88 | Rat-89 | Average value | Standard deviation |
|---|---|---|---|---|---|
| 10 | 11.9 | <5.0 | 31.9 | 21.9 | Not applicable |
| 24 | 24.357* | <5.0 | <5.0 | 24.3570* | Not applicable |
| Half-life (h) | | | 2.03 | | |

TABLE 33

Concentration of nitroxoline in SD rat plasma after oral administration of compound 61

| Time (hours) | Rat-90 | Rat-91 | Rat-92 | Average value | Standard deviation |
|---|---|---|---|---|---|
| 0 | <5.0 | <5.0 | <5.0 | Not applicable | Not applicable |
| 0.083 | 137.4 | 615.4 | 251.5 | 334.7 | 249.7 |
| 0.25 | 1174.5 | 646.5 | 851.8 | 890.9 | 266.1 |
| 0.5 | 969.5 | 745.8 | 107.8 | 607.7 | 447.2 |
| 1 | 139.0 | 90.2 | 191.0 | 140.0 | 50.4 |
| 2 | 184.1 | 85.7 | 117.2 | 129.0 | 50.3 |
| 4 | 84.5 | 15.4 | 63.8 | 54.6 | 35.5 |
| 6 | 6.7 | 12.5 | <5.0 | 9.6 | Not applicable |
| 8 | <5.0 | 6.6 | <5.0 | 6.6 | Not applicable |
| 10 | <5.0 | <5.0 | <5.0 | Not applicable | Not applicable |
| 24 | <5.0 | <5.0 | <5.0 | Not applicable | Not applicable |
| Half-life (h) | | | 1.55 | | |

TABLE 34

Concentration of nitroxoline in SD rat plasma after oral administration of compound 62

| Time (hours) | Rat-93 | Rat-94 | Rat-95 | Average value | Standard deviation |
|---|---|---|---|---|---|
| 0 | <5.0 | <5.0 | <5.0 | Not applicable | Not applicable |
| 0.083 | 19.5 | 22.4 | 85.6 | 42.5 | 37.3 |
| 0.25 | 53.6 | 98.6 | 130.6 | 94.3 | 38.7 |
| 0.5 | 81.2 | 145.3 | 155.3 | 127.3 | 40.2 |
| 1 | 69.5 | 147.6 | 169.2 | 128.8 | 52.4 |
| 2 | 121.6 | 40.9 | 84.6 | 82.4 | 40.4 |
| 4 | 21.9 | 65.3 | 32.5 | 39.9 | 22.6 |
| 6 | 18.5 | 42.5 | 14.9 | 25.3 | 15.1 |
| 8 | 28.9 | 9.8 | <5.0 | 19.4 | Not applicable |
| 10 | 17.5 | <5.0 | <5.0 | 17.5 | Not applicable |
| 24 | <5.0 | <5.0 | <5.0 | Not applicable | Not applicable |
| Half-life (h) | | | 2.80 | | |

TABLE 35

Concentration of nitroxoline in SD rat plasma after oral administration of compound 67

| | Concentration of nitroxoline in plasma (ng/ml) | | | | |
|---|---|---|---|---|---|
| Time (hours) | Rat-96 | Rat-97 | Rat-98 | Average value | Standard deviation |
| 0 | <5.0 | <5.0 | <5.0 | Not applicable | Not applicable |
| 0.083 | 21.3 | 6.2 | 19.8 | 15.8 | 8.3 |
| 0.25 | 50.3 | 28.6 | 98.5 | 59.1 | 35.8 |
| 0.5 | 54.7 | 48.4 | 123.0 | 75.4 | 41.4 |
| 1 | 23.2 | 47.5 | 39.4 | 36.7 | 12.3 |
| 2 | 18.1 | 20.1 | 29.5 | 22.6 | 6.1 |
| 4 | 20.1 | 14.4 | 14.2 | 16.2 | 3.4 |
| 6 | 17.6 | 14.2 | 17.8 | 16.5 | 2.0 |
| 8 | 33.1 | 16.0 | 8.6 | 19.2 | 12.5 |
| 10 | 21.3 | 11.8 | 10.5 | 14.5 | 5.9 |
| 24 | 7.4 | 12.3 | 7.2 | 9.0 | 2.9 |
| Half-life (h) | | | | 15.28 | |

TABLE 36

Concentration of nitroxoline in SD rat plasma after oral administration of compound 70

| | Concentration of nitroxoline in plasma (ng/ml) | | | | |
|---|---|---|---|---|---|
| Time (hours) | Rat-99 | Rat-100 | Rat-101 | Average value | Standard deviation |
| 0.00 | <5.0 | <5.0 | <5.0 | Not applicable | Not applicable |
| 0.25 | 6416 | 8063 | 2228 | 5569 | 3009 |
| 0.50 | 1931 | 4141 | 1735 | 2602 | 1336 |
| 1.0 | 281 | 580 | 463 | 441 | 151 |
| 2.0 | 353 | 200 | 437 | 330 | 120 |
| 4.0 | 206 | 181 | 259 | 215 | 39.6 |
| 6.0 | 74.8 | 95.9 | 155 | 108 | 41.4 |
| 8.0 | 117 | 39.4 | 124.704 | 93.7 | 47.1 |
| 24 | 30.5 | 7.82 | <5.0 | 19.2 | Not applicable |
| Half-life (h) | | | | 4.51 | |

TABLE 37

Concentration of nitroxoline in SD rat plasma after oral administration of compound 71

| | Concentration of nitroxoline in plasma (ng/mL) | | | | |
|---|---|---|---|---|---|
| Time (hours) | Rat-102 | Rat-103 | Rat-104 | Average value | Standard deviation |
| 0 | <5.0 | <5.0 | <5.0 | Not applicable | Not applicable |
| 0.25 | 4000.6 | 2954.2 | 3790.8 | 3581.9 | 553.6 |
| 0.5 | 2501.6 | 3636.6 | 5144.7 | 3761.0 | 1325.9 |
| 1 | 680.3 | 465.1 | 1041.9 | 729.1 | 291.5 |
| 2 | 415.9 | 809.2 | 321.7 | 515.6 | 258.6 |
| 4 | 207.3 | 239.8 | 516.1 | 321.1 | 169.7 |
| 6 | 149.6 | 123.1 | 197.3 | 156.7 | 37.6 |
| 8 | 30.3 | 21.3 | 68.6 | 40.1 | 25.1 |
| 24 | <5.0 | <5.0 | <5.0 | Not applicable | Not applicable |
| Half-life (h) | | | | 1.68 | |

TABLE 38

Concentration of nitroxoline in SD rat plasma after oral administration of compound 72

| | Concentration of nitroxoline in plasma (ng/ml) | | | | |
|---|---|---|---|---|---|
| Time (hours) | Rat-105 | Rat-106 | Rat-107 | Average value | Standard deviation |
| 0 | <5.0 | <5.0 | <5.0 | Not applicable | Not applicable |
| 0.083 | 610.0 | 491.0 | 468.0 | 523.0 | 76.2 |
| 0.25 | 2520.0 | 2810.0 | 2550.0 | 2630.0 | 159.0 |
| 0.5 | 3140.0 | 858.0 | 1110.0 | 1700.0 | 1251.0 |
| 1 | 491.0 | 59.1 | 213.0 | 254.0 | 219.0 |
| 2 | 318.0 | 168.0 | 108.0 | 198.0 | 108.0 |
| 4 | 69.3 | 235.0 | 65.7 | 123.0 | 96.7 |
| 6 | 47.5 | 23.1 | 29.3 | 33.3 | 12.7 |
| 8 | 21.4 | 34.3 | 15.6 | 23.8 | 9.6 |
| 10 | <5.0 | 17.7 | <5.0 | 17.7 | Not applicable |
| 12 | <5.0 | 10.7 | 15.8 | 13.3 | Not applicable |
| Half-life (h) | | | | 2.26 | |

TABLE 39

Concentration of nitroxoline in SD rat plasma after oral administration of compound 78

| | Concentration of nitroxoline in plasma (ng/ml) | | | | |
|---|---|---|---|---|---|
| Time (hours) | Rat-108 | Rat-109 | Rat-110 | Average value | Standard deviation |
| 0.00 | <5.0 | <5.0 | <5.0 | Not applicable | Not applicable |
| 0.08 | 2117.0 | 2257.0 | 3268.0 | 2547.0 | 628.0 |
| 0.25 | 4837.0 | 3834.0 | 5693.0 | 4788.0 | 930.0 |
| 0.50 | 3887.0 | 5155.0 | 6359.0 | 5134.0 | 1236.0 |
| 1.0 | 2010.0 | 2139.0 | 3489.0 | 2546.0 | 820.0 |
| 2.0 | 231.0 | 319.0 | 360.0 | 303.0 | 66.0 |
| 4.0 | 217.0 | 110.0 | 309.0 | 212.0 | 99.9 |
| 6.0 | 102.0 | 193.0 | 291.0 | 196.0 | 94.6 |
| 8.0 | 55.1 | 60.7 | 207.0 | 107.0 | 85.9 |
| 10 | 47.8 | 22.4 | 49.9 | 40.0 | 15.3 |
| 24 | <5.0 | <5.0 | <5.0 | Not applicable | Not applicable |
| Half-life (h) | | | | 2.47 | |

TABLE 40

Concentration of nitroxoline in SD rat plasma after oral administration of compound 53

| | Concentration of nitroxoline in plasma (ng/ml) | | | | |
|---|---|---|---|---|---|
| Time (hours) | Rat-111 | Rat-112 | | Average value | Standard deviation |
| 0.00 | <5.0 | <5.0 | | <5.0 | Not applicable |
| 0.08 | 94.5 | 93.9 | | 94.2 | Not applicable |
| 0.25 | 214 | 542 | | 378 | Not applicable |
| 0.50 | 153 | 261 | | 207 | Not applicable |
| 1.0 | 63.0 | 142 | | 102 | Not applicable |
| 2.0 | 43.1 | 43.2 | | 43.1 | Not applicable |
| 4.0 | 19.6 | 18.6 | | 19.1 | Not applicable |
| 6.0 | <5.0 | <5.0 | | Not applicable | Not applicable |
| 8.0 | <5.0 | <5.0 | | Not applicable | Not applicable |
| 10 | <5.0 | <5.0 | | Not applicable | Not applicable |
| 24 | <5.0 | <5.0 | | Not applicable | Not applicable |
| Half-life (h) | | | | 1.13 | |

TABLE 41

Concentration of nitroxoline in SD rat plasma after oral administration of compound 54

| Time (hours) | Concentration of nitroxoline in plasma (ng/ml) | | | | |
|---|---|---|---|---|---|
| | Rat-113 | Rat-114 | Rat-115 | Average value | Standard deviation |
| 0.00 | <5.0 | <5.0 | <5.0 | Not applicable | Not applicable |
| 0.08 | 442 | 713 | 150 | 435 | 282 |
| 0.25 | 802 | 1073 | 531 | 802 | 271 |
| 0.50 | 513 | 650 | 575 | 579 | 68.8 |
| 1.0 | 136 | 202 | 179 | 172 | 33.3 |
| 2.0 | 73.9 | 70.3 | 70.5 | 71.6 | 2.07 |
| 4.0 | 19.7 | 21.2 | 69.2 | 36.7 | 28.2 |
| 6.0 | 5.74 | 12.0 | <5.0 | 8.85 | 4.40 |
| 8.0 | <5.0 | <5.0 | <5.0 | Not applicable | Not applicable |
| 10 | <5.0 | <5.0 | <5.0 | Not applicable | Not applicable |
| 24 | <5.0 | <5.0 | <5.0 | Not applicable | Not applicable |
| Half-life (h) | | | 1.63 | | |

TABLE 42

Concentration of nitroxoline in SD rat plasma after oral administration of compound 55

| Time (hours) | Concentration of nitroxoline in plasma (ng/ml) | | | | |
|---|---|---|---|---|---|
| | Rat-116 | Rat-117 | Rat-118 | Average value | Standard deviation |
| 0.00 | <5.0 | <5.0 | <5.0 | Not applicable | Not applicable |
| 0.08 | 376 | 467 | 414 | 419 | 45.6 |
| 0.25 | 718 | 666 | 671 | 685 | 28.4 |
| 0.50 | 835 | 789 | 635 | 753 | 105 |
| 1.0 | 185 | 212 | 186 | 195 | 15.3 |
| 2.0 | 79.1 | 95.0 | 100 | 91.4 | 11.0 |
| 4.0 | 68.2 | 57.2 | 85.9 | 70.4 | 14.5 |
| 6.0 | 33.9 | 14.2 | 36.6 | 28.2 | 12.2 |
| 8.0 | 31.3 | <5.0 | 26.5 | 28.9 | 3.41 |
| 10 | 15.6 | <5.0 | <5.0 | 15.6 | Not applicable |
| 24 | <5.0 | <5.0 | <5.0 | Not applicable | Not applicable |
| Half-life (h) | | | 2.28 | | |

TABLE 43

Concentration of nitroxoline in SD rat plasma after oral administration of compound 56

| Time (hours) | Concentration of nitroxoline in plasma (ng/ml) | | | | |
|---|---|---|---|---|---|
| | Rat-119 | Rat-120 | Rat-121 | Average value | Standard deviation |
| 0.00 | <5.0 | <5.0 | <5.0 | Not applicable | Not applicable |
| 0.08 | 526 | 300 | 413 | 413 | 113 |
| 0.25 | 688 | 483 | 795 | 655 | 158 |
| 0.50 | 364 | 348 | 538 | 417 | 105 |
| 1.0 | 198 | 287 | 265 | 250 | 46.5 |
| 2.0 | 57.3 | 38.1 | 169 | 88.0 | 70.5 |
| 4.0 | 40.6 | 24.6 | 79.9 | 48.4 | 28.5 |
| 6.0 | <5.0 | <5.0 | 25.5 | 25.5 | Not applicable |
| 8.0 | <5.0 | <5.0 | 14.8 | 14.8 | Not applicable |
| 10 | <5.0 | <5.0 | <5.0 | Not applicable | Not applicable |
| 24 | <5.0 | <5.0 | <5.0 | Not applicable | Not applicable |
| Half-life (h) | | | 1.22 | | |

TABLE 44

Concentration of nitroxoline in SD rat plasma after oral administration of compound 57

| Time (hours) | Concentration of nitroxoline in plasma (ng/ml) | | | | |
|---|---|---|---|---|---|
| | Rat-122 | Rat-123 | Rat-124 | Average value | Standard deviation |
| 0.00 | <5.0 | <5.0 | <5.0 | Not applicable | Not applicable |
| 0.08 | 24145 | 44294 | 47003 | 38480 | 12489 |
| 0.25 | 51112 | 57675 | 65809 | 58198 | 7363 |
| 0.50 | 46177 | 46371 | 60050 | 50866 | 7954 |
| 1.0 | 23917 | 27404 | 31396 | 27572 | 3742 |
| 2.0 | 8562 | 16525 | 18167 | 14418 | 5137 |
| 4.0 | 5879 | 11697 | 7964 | 8513 | 2947 |
| 6.0 | 5993 | 8009 | 5214 | 6405 | 1442 |
| 8.0 | 1378 | 4029 | 5056 | 3487 | 1898 |
| 10 | 3295 | 5411 | 3186 | 3964 | 1254 |
| 24 | <5.0 | <5.0 | <5.0 | Not applicable | Not applicable |
| Half-life (h) | | | 18.0 | | |

TABLE 45

Concentration of nitroxoline in SD rat plasma after oral administration of compound 51

| Time (hours) | Concentration of nitroxoline in plasma (ng/ml) | | | | |
|---|---|---|---|---|---|
| | Rat-125 | Rat-126 | Rat-127 | Average value | Standard deviation |
| 0.00 | <5.0 | <5.0 | <5.0 | Not applicable | Not applicable |
| 0.08 | 4278 | 2124 | 7792 | 4731 | 2861 |
| 0.25 | 7272 | 2305 | 7542 | 5706 | 2948 |
| 0.50 | 5619 | 2737 | 4892 | 4416 | 1499 |
| 1.0 | 3457 | 887 | 1027 | 1790 | 1445 |
| 2.0 | 831 | 166 | 224 | 407 | 368 |
| 4.0 | 1092 | 577 | 178 | 616 | 458 |
| 6.0 | 279 | 235 | 37.6 | 184 | 129 |
| 8.0 | 330 | 99.5 | 19.0 | 150 | 162 |
| 10 | 218 | 43.8 | 23.7 | 95.2 | 107 |
| 24 | 127 | 32.9 | <5.0 | 80.1 | Not applicable |
| Half-life (h) | | | 5.59 | | |

Conclusion

The prodrug molecules have a significant increase in absorption or half-life in rat compared with nitroxoline due to the structure optimization. The compliance of drug will thus be improved since the administration dose or frequency is reduced.

Test Example 4: Pharmacokinetics Assay of the Compounds of the Present Invention in Dog Nitroxoline is mainly metabolized by the phase II metabolism in liver with a fast metabolism rate, so it has a short half-life in the body. The present invention modified its structure and 13 compounds of formula (I) were obtained through chemical synthesis. The change of nitroxoline concentration in dog plasma after a single intravenous or oral administration of nitroxoline and the compound of formula (I) was studied to evaluate the pharmacokinetic behavior of nitroxoline and the compound of formula (I) in dog body.

1. Experimental Instruments

Tandem quadrupole mass spectrometer (API4000, Applied Biosystems, USA); liquid chromatography (1200, Agilent); auto sample injector (CTC Analytics HTC PAL); Applied Biosystems Analyst v 1.6.2.

2. Pharmacokinetics Experiment

Male beagle dog (Beijing Marshall Biotechnology Co., Ltd., Certificate No.: SCXK (BJ) 2016-0001, Qualified number: 11400600001728), 3 dogs per group, weight 10 to 13 kg, 20 to 22 months old. The dogs were fasted overnight before the administration with free access to water, and fed 4 hours after the administration. The test compound was added to an EP tube, and then added with DMSO, solutol and sterilized water for injection (the volume ratio of the three was 1:2:17, v:v:v). The EP tube was subjected to ultrasound for 20 minutes to make the test compound dissolve well (compound concentration: 0.005 mmol/mL). The dose for intravenous administration was 0.01 mmol/kg, and the dose for oral administration was 0.1 mmol/kg. 0.3 ml of whole blood was collected from jugular vein before the administration (0 hour) and 0.0833, 0.25, 0.5, 1, 2, 4, 6, 8, 10 and 12 hours after the administration (sampling points can be adjusted according to the specific situation) respectively. The blood sample was placed in a centrifuge tube containing EDTA-K2 anticoagulant (Aldrich), and the centrifuge tube was left to stand in ice. The blood sample was centrifuged for 10 minutes at 1530 g within 0.5 hour to obtain all clean plasma. The plasma was placed in another clean centrifuge tube, and stored in a refrigerator at −20° C. for later use.

3. Determination of Sample Concentration

Solution for standard curve was formulated. 1000 µL of internal standard working solution (containing a solution of verapamil (5 ng/mL, Aldrich), glibenclamide (50 ng/mL, Aldrich) and diclofenac (50 ng/mL, Aldrich) in acetonitrile) was added to 10 µL of the solution for standard curve and sample, and the mixture was shaked by vortex for 5 minutes. The mixture was centrifuged for 10 minutes at 4° C., 3700 rpm. 60 µL of the supernatant were placed in an injection tube, and mixed with 120 µL of water. 10 µL of the solution were injected into the liquid chromatography-mass spectrometry system for determination. The pharmacokinetic parameters were calculated by the WinNonlin V 6.2 non-compartmental model.

The results are shown in Table 46 to Table 52 below.

TABLE 46

Concentration of nitroxoline in beagle dog plasma after intravenous administration of nitroxoline

| Time (hours) | Concentration of nitroxoline in plasma (ng/ml) | | | | |
|---|---|---|---|---|---|
| | Dog-01 | Dog-02 | Dog-03 | Average value | Standard deviation |
| 0 | <5.0 | <5.0 | <5.0 | Not applicable | Not applicable |
| 0.083 | 8360 | 11500 | 10400 | 10100 | 1590 |
| 0.25 | 4420 | 5140 | 3320 | 4290 | 917 |
| 0.5 | 1220 | 1250 | 670 | 1050 | 327 |
| 0.75 | 406 | 393 | 299 | 366 | 58.4 |
| 1 | 187 | 164 | 178 | 176 | 11.6 |
| 2 | 37.1 | 34.8 | 20.1 | 30.7 | 9.22 |
| 4 | <5.0 | <5.0 | <5.0 | <5.0 | Not applicable |
| 6 | <5.0 | <5.0 | <5.0 | <5.0 | Not applicable |
| 8 | <5.0 | <5.0 | <5.0 | <5.0 | Not applicable |
| 10 | <5.0 | <5.0 | <5.0 | <5.0 | Not applicable |
| 12 | <5.0 | <5.0 | <5.0 | <5.0 | Not applicable |
| Half-life (h) | | | 0.36 | | |
| $AUC_{0-inf}$ (ng*hmL$^{-1}$) | | | 3300 | | |

TABLE 47

Concentration of nitroxoline in beagle dog plasma after oral administration of nitroxoline

| Time (hours) | Concentration of nitroxoline in plasma (ng/ml) | | | | |
|---|---|---|---|---|---|
| | Dog-04 | Dog-05 | Dog-06 | Average value | Standard deviation |
| 0 | <5.0 | <5.0 | <5.0 | Not applicable | Not applicable |
| 0.083 | 4710 | 4930 | 914 | 3520 | 2258 |
| 0.25 | 6590 | 5960 | 4320 | 5620 | 1172 |
| 0.5 | 3990 | 3260 | 3300 | 3520 | 410 |
| 0.75 | 1860 | 2370 | 2250 | 2160 | 267 |
| 1 | 1030 | 1490 | 1360 | 1290 | 237 |
| 2 | 120 | 257 | 457 | 278 | 169 |
| 4 | 72.3 | 49.4 | 71.6 | 64.4 | 13.0 |
| 6 | 58.9 | 54.6 | 42.1 | 51.9 | 8.73 |
| 8 | 45.2 | 34.9 | 30.9 | 37.0 | 7.38 |
| 10 | 29.2 | 32.2 | <5.0 | 30.7 | Not applicable |
| 12 | <5.0 | 22.3 | 35.6 | 29.0 | Not applicable |
| Half-life (h) | | | 3.62 | | |
| $AUC_{0-inf}$ (ng*hmL$^{-1}$) | | | 4780 | | |

TABLE 48

Concentration of nitroxoline in beagle dog plasma after oral administration of compound 5

| Time (hours) | Concentration of nitroxoline in plasma (ng/ml) | | | | |
|---|---|---|---|---|---|
| | Dog-07 | Dog-08 | Dog-09 | Average value | Standard deviation |
| 0 | <5.0 | <5.0 | <5.0 | Not applicable | Not applicable |
| 0.083 | 106.3 | 972.3 | 358.3 | 479.0 | 445.4 |
| 0.25 | 935.2 | 2551.5 | 2580.1 | 2022.2 | 941.6 |
| 0.5 | 518.7 | 794.9 | 1184.1 | 832.6 | 334.3 |
| 1 | 292.7 | 369.4 | 538.3 | 400.1 | 125.7 |

TABLE 48-continued

Concentration of nitroxoline in beagle dog plasma after oral administration of compound 5

Concentration of nitroxoline in plasma (ng/ml)

| Time (hours) | Dog-07 | Dog-08 | Dog-09 | Average value | Standard deviation |
|---|---|---|---|---|---|
| 2 | 307.5 | 132.6 | 191.0 | 210.4 | 89.0 |
| 4 | 146.5 | 28.0 | 68.8 | 81.1 | 60.2 |
| 6 | 79.6 | 27.8 | 20.9 | 42.8 | 32.1 |
| 8 | 44.1 | 11.5 | 9.1 | 21.6 | 19.6 |
| 10 | 33.7 | 5.2 | <5.0 | 19.5 | Not applicable |
| 24 | <5.0 | <5.0 | <5.0 | Not applicable | Not applicable |
| Half-life (h) | | | 1.80 | | |
| $AUC_{0-inf}$ $(ng*hmL^{-1})$ | | | 1760 | | |

TABLE 49

Concentration of nitroxoline in beagle dog plasma after intravenous administration of compound 20

Concentration of nitroxoline in plasma (ng/ml)

| Time (hours) | Dog-10 | Dog-11 | Dog-12 | Average value | Standard deviation |
|---|---|---|---|---|---|
| 0 | <5.0 | <5.0 | <5.0 | Not applicable | Not applicable |
| 0.083 | 6280 | 4660 | 5630 | 5520 | 815 |
| 0.25 | 2170 | 1130 | 1620 | 1640 | 520 |
| 0.5 | 593 | 232 | 391 | 405 | 181 |
| 0.75 | 185 | 75.6 | 151 | 137 | 56.0 |
| 1 | 88.2 | 37.5 | 76.7 | 67.5 | 26.6 |
| 2 | 16.9 | 16.7 | 22.5 | 18.7 | 3.29 |
| 4 | 6.30 | 5.21 | 12.5 | 8.00 | 3.93 |
| 6 | 7.52 | 3.93 | 12.2 | 7.88 | 4.15 |
| 8 | 3.59 | <5.0 | 7.71 | 5.65 | Not applicable |
| 10 | <5.0 | <5.0 | <5.0 | <5.0 | Not applicable |
| 12 | <5.0 | <5.0 | <5.0 | <5.0 | Not applicable |
| Half-life (h) | | | 2.42 | | |
| $AUC_{0-inf}$ $(ng*hmL^{-1})$ | | | 1290 | | |

TABLE 50

Concentration of nitroxoline in beagle dog plasma after oral administration of compound 20

Concentration of nitroxoline in plasma (ng/ml)

| Time (hours) | Dog-13 | Dog-14 | Dog-15 | Average value | Standard deviation |
|---|---|---|---|---|---|
| 0 | <5.0 | <5.0 | <5.0 | Not applicable | Not applicable |
| 0.083 | 13000 | 2940 | 13000 | 9650 | 5808 |
| 0.25 | 10000 | 6580 | 8580 | 8390 | 1718 |
| 0.5 | 3500 | 4220 | 8900 | 5540 | 2932 |
| 0.75 | 1430 | 2190 | 7610 | 3740 | 3370 |
| 1 | 795 | 895 | 4770 | 2150 | 2267 |
| 2 | 123 | 76.5 | 224 | 141 | 75.4 |
| 4 | 33.9 | 26.3 | 179 | 79.7 | 86.1 |
| 6 | 31.1 | 30.4 | 100 | 53.8 | 40.0 |
| 8 | 20.1 | 22.6 | 67.4 | 36.7 | 26.6 |

TABLE 50-continued

Concentration of nitroxoline in beagle dog plasma after oral administration of compound 20

Concentration of nitroxoline in plasma (ng/ml)

| Time (hours) | Dog-13 | Dog-14 | Dog-15 | Average value | Standard deviation |
|---|---|---|---|---|---|
| 10 | 18.4 | 34.8 | 23.7 | 25.6 | 8.37 |
| 12 | 9.60 | 27.1 | 11.8 | 16.2 | 9.53 |
| Half-life (h) | | | 3.07 | | |
| $AUC_{0-inf}$ $(ng*hmL^{-1})$ | | | 8750 | | |

TABLE 51

Concentration of nitroxoline in beagle dog plasma after intravenous administration of compound 51

Concentration of nitroxoline in plasma (ng/ml)

| Time (hours) | Dog-16 | Dog-17 | Dog-18 | Average value | Standard deviation |
|---|---|---|---|---|---|
| 0 | <5.0 | <5.0 | <5.0 | Not applicable | Not applicable |
| 0.083 | 3708.1 | 3193.7 | 3092.4 | 3331.4 | 330.2 |
| 0.25 | 1198.2 | 1392.8 | 1006.1 | 1199.0 | 193.4 |
| 0.5 | 453.7 | 363.2 | 230.1 | 349.0 | 112.5 |
| 1 | 135.5 | 97.6 | 60.4 | 97.8 | 37.5 |
| 2 | 31.8 | 17.9 | 8.1 | 19.3 | 11.9 |
| 4 | 19.9 | 6.4 | <5.0 | 13.1 | Not applicable |
| 6 | 6.6 | <5.0 | <5.0 | 6.6 | Not applicable |
| 8 | <5.0 | <5.0 | <5.0 | Not applicable | Not applicable |
| 10 | <5.0 | <5.0 | <5.0 | Not applicable | Not applicable |
| 24 | <5.0 | <5.0 | <5.0 | Not applicable | Not applicable |
| Half-life (h) | | | 0.73 | | |
| $AUC_{0-inf}$ $(ng*hmL^{-1})$ | | | 1153 | | |

TABLE 52

Concentration of nitroxoline in beagle dog plasma after oral administration of compound 51

Concentration of nitroxoline in plasma (ng/ml)

| Time (hours) | Dog-19 | Dog-20 | Dog-21 | Average value | Standard deviation |
|---|---|---|---|---|---|
| 0 | <5.0 | <5.0 | <5.0 | Not applicable | Not applicable |
| 0.083 | 53.2 | 16.0 | 111.4 | 60.2 | 48.1 |
| 0.25 | 1368.8 | 1493.5 | 2022.5 | 1628.3 | 347.1 |
| 0.5 | 2929.8 | 2267.6 | 2266.8 | 2488.0 | 382.6 |
| 1 | 1263.6 | 836.0 | 567.3 | 889.0 | 351.2 |
| 2 | 238.4 | 174.2 | 64.0 | 158.9 | 88.2 |
| 4 | 30.0 | 35.7 | 18.2 | 28.0 | 8.9 |
| 6 | 13.4 | 29.5 | 20.6 | 21.2 | 8.0 |
| 8 | 15.6 | 53.6 | 39.5 | 36.2 | 19.2 |
| 10 | 10.6 | 34.3 | 30.5 | 25.1 | 12.7 |
| 24 | <5.0 | <5.0 | <5.0 | Not applicable | Not applicable |
| Half-life (h) | | | 2.32 | | |
| $AUC_{0-inf}$ $(ng*hmL^{-1})$ | | | 2474 | | |

Conclusion

It can be seen from the data that the prodrug compounds 5, 20 and 51 are well absorbed in beagle dogs compared with nitroxoline, indicating that the administration dose can be effectively reduced by using the prodrug molecules.

What is claimed is:
1. A compound of formula (II),

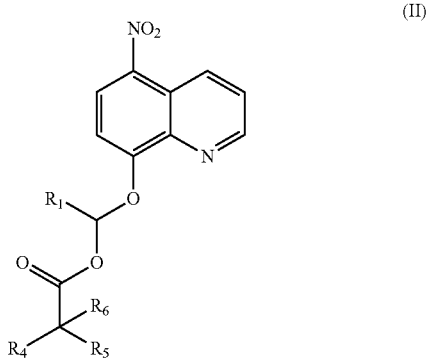

or a mesomer, racemate, enantiomer, or diastereomer thereof, or a mixture thereof, or a pharmaceutically acceptable salt thereof,
wherein,
$R_1$ is selected from the group consisting of hydrogen and $C_{1-6}$ alkyl;
$R_4$, $R_5$ and $R_6$ are each independently selected from the group consisting of hydrogen, halogen, alkyl, cycloalkyl, heterocyclyl, aryl, heteroaryl, $-OR_{12}$, $-SR_{12}$, $-C(O)R_1$, $-C(O)OR_{12}$, $-C(O)-(CH)_m-C(O)R_{11}$, $-OC(O)R_{11}$, $-NR^aR^b$, $-N(R^c)C(O)R^d$, $-C(O)N(R^a)(R^b)$, $-N(R^c)S(O)_pR^d$, $-S(O)_pN(R^a)(R^b)$, $-O(CH_2)_mO(CH_2)_qR_{12}$ and $-N(R^c)C(O)-(CH)_m-N(R^c)C(O)R^d$, wherein the alkyl, cycloalkyl, heterocyclyl, aryl and heteroaryl are optionally further substituted by one or more substituents selected from the group consisting of halogen, amino, nitro, cyano, hydroxy, thiol, alkyl, alkoxy, alkenyl, alkynyl, $OR_{12}$, $SR_{12}$, $NR^aR^b$, $-COR_{11}$, $-C(O)OR_{12}$, $-OC(O)R_{11}$, $-N(R^c)C(O)R^d$, $-O(CH_2)_mO(CH_2)_qR_{12}$, cycloalkyl, heterocyclyl, aryl, arylalkyl, heteroaryl and heteroarylalkyl, wherein the aryl, arylalkyl, heteroaryl and heteroarylalkyl are optionally further substituted by one or more substituents selected from the group consisting of halogen, amino, nitro, cyano, hydroxy, thiol, carboxy, alkoxycarbonyl, oxo, alkyl and alkoxy; or
any one of $R_4$, $R_5$ and $R_6$ is hydrogen, and the remaining two together with the carbon atom to which they are attached form a cycloalkyl or heterocyclyl, wherein the cycloalkyl or heterocyclyl is optionally further substituted by one or more substituents selected from the group consisting of halogen, amino, nitro, cyano, hydroxy, thiol, alkyl, alkoxy, alkenyl, alkynyl, $-C(O)R_{11}$, $-C(O)OR_{12}$, $-OC(O)R_{11}$, cycloalkyl, heterocyclyl, aryl and heteroaryl;
$R_{11}$ and $R_{12}$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the alkyl, alkoxy, alkenyl, alkynyl, cycloalkyl, heterocyclyl, aryl and heteroaryl are optionally further substituted by one or more substituents selected from the group consisting of halogen, amino, nitro, cyano, hydroxy, thiol, carboxy, alkoxycarbonyl, oxo, alkyl, alkoxy, $-NR^aR^b$, $-OR^d$, $-N(R^c)C(O)R^d$, $-C(O)N(R^a)(R^b)$, $-N(R^c)S(O)_pR^d$, $-S(O)_pN(R^a)(R^b)$, alkenyl, alkynyl, cycloalkyl, heterocyclyl, aryl and heteroaryl;
$R^a$ and $R^b$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituents selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;
or, $R^a$ and $R^b$ together with the atoms to which they are attached form a heterocyclyl, wherein the heterocyclyl is optionally further substituted by one or more substituents selected from the group consisting of halogen, amino, nitro, cyano, oxo, hydroxy, thiol, carboxy, alkoxycarbonyl, alkyl, alkoxy, alkenyl, alkynyl, cycloalkyl, heterocyclyl, aryl and heteroaryl;
$R^c$ and $R^d$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituents selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;
m is selected from an integer from 0 to 6;
p is selected from the group consisting of 0, 1 and 2; and
q is selected from an integer from 0 to 6.
2. The compound of formula (II) according to claim 1, wherein,
$R_4$, $R_5$ and $R_6$ are each independently selected from the group consisting of hydrogen, alkyl, aryl, heteroaryl, $-OR_{12}$, $-SR_{12}$, $-C(O)R_{11}$, $-C(O)OR_{12}$, $-C(O)-(CH)_m-C(O)R_{11}$, $-OC(O)R_1$, $-(CH)_m-N(R^c)C(O)R_1$, $-NR^aR^b$, $-N(R^c)C(O)R^d$, $-C(O)N(R^a)(R^b)$, $-N(R^c)S(O)_pR^d$, $-S(O)_pN(R^a)(R^b)$, $-O(CH_2)_mO(CH_2)_qR_{12}$ and $-N(R^c)C(O)-(CH)_m-N(R^c)C(O)R^d$, wherein the alkyl, aryl and heteroaryl are optionally further substituted by one or more substituents selected from the group consisting of halogen, hydroxy, alkyl, $OR_{12}$, $SR_{12}$, $NR^aR^b$, $-COR_{11}$, $-C(O)OR_{12}$, $-O(O)CR_{11}$, $-N(R^c)C(O)R^d$, $-O(CH_2)_mO(CH_2)_qR_{12}$, cycloalkyl, heterocyclyl, aryl, arylalkyl, heteroaryl and heteroarylalkyl, wherein the aryl, arylalkyl, heteroaryl and heteroarylalkyl are optionally further substituted by one or more substituents selected from the group consisting of halogen, hydroxy, thiol, alkyl and alkoxy;
$R_{11}$ and $R_{12}$ are each independently selected from the group consisting of hydrogen, halogen, hydroxy, alkyl, alkoxy, cycloalkyl, heterocyclyl, aryl and heteroaryl, wherein the alkyl, alkoxy, cycloalkyl, heterocyclyl, aryl and heteroaryl are optionally further substituted by one or more substituents selected from the group consisting of halogen, amino, hydroxy, alkyl, alkoxy, $-NR^aR^b$, —OR$^d$, —N(R$^c$)C(O)R$^d$, —C(O)N(R$^a$)(R$^b$), —N(R$^c$)S(O)$_p$R$^d$, —S(O)$_p$N(R$^a$)(R$^b$), cycloalkyl, heterocyclyl, aryl and heteroaryl;

R$^a$ and R$^b$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituents selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

or, R$^a$ and R$^b$ together with the atoms to which they are attached form a heterocyclyl, wherein the heterocyclyl is optionally further substituted by one or more substituents selected from the group consisting of halogen, amino, nitro, cyano, oxo, hydroxy, thiol, carboxy, alkoxycarbonyl, alkyl, alkoxy, alkenyl, alkynyl, cycloalkyl, heterocyclyl, aryl and heteroaryl;

R$^c$ and R$^d$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituents selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

m is selected from an integer from 0 to 6;

p is selected from the group consisting of 0, 1 and 2; and q is selected from an integer from 0 to 6.

3. The compound of formula (II) according to claim 2, wherein,

R$_4$, R$_5$ and R$_6$ are each independently selected from the group consisting of hydrogen, alkyl, aryl, heteroaryl, —OR$_{12}$, —SR$_{12}$, —C(O)R$_{11}$, —C(O)OR$_{12}$, —C(O)—(CH)$_m$—C(O)R$_{11}$, —OC(O)R$_{11}$ and —(CH)$_m$—N(R$^c$)C(O)R$_{11}$, wherein the alkyl, aryl and heteroaryl are optionally further substituted by one or more substituents selected from the group consisting of halogen, hydroxy, alkyl, OR$_{12}$, SR$_{12}$, NR$^a$R$^b$, —COR$_{11}$, —C(O)OR$_{12}$, —O(O)CR$_{11}$, —N(R$^c$)C(O)R$^d$, —O(CH$_2$)$_m$O(CH$_2$)$_q$R$_{12}$, cycloalkyl, heterocyclyl, aryl and heteroaryl, wherein the aryl, arylalkyl, heteroaryl and heteroarylalkyl are optionally further substituted by one or more substituents selected from the group consisting of halogen and hydroxy;

R$_{11}$ and R$_{12}$ are each independently selected from the group consisting of hydrogen, halogen, hydroxy, alkyl, alkoxy, cycloalkyl, heterocyclyl, aryl and heteroaryl, wherein the alkyl, alkoxy, cycloalkyl, heterocyclyl, aryl and heteroaryl are optionally further substituted by one or more substituents selected from the group consisting of halogen, amino, hydroxy, alkyl, —OR$^d$, —N(R$^c$)C(O)R$^d$, cycloalkyl, heterocyclyl, aryl and heteroaryl;

R$^a$ and R$^b$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituents selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

or, R$^a$ and R$^b$ together with the atoms to which they are attached form a heterocyclyl, wherein the heterocyclyl is optionally further substituted by one or more substituents selected from the group consisting of halogen, amino, nitro, cyano, oxo, hydroxy, thiol, carboxy, alkoxycarbonyl, alkyl, alkoxy, alkenyl, alkynyl, cycloalkyl, heterocyclyl, aryl and heteroaryl;

R$^c$ and R$^d$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituents selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

m is selected from an integer from 0 to 6; and q is selected from an integer from 0 to 6.

4. The compound of formula (II) according to claim 1, wherein, any one of R$_4$, R$_5$ and R$_6$ is hydrogen, and the remaining two together with the carbon atom to which they are attached form a cycloalkyl or heterocyclyl, wherein the cycloalkyl or heterocyclyl is optionally further substituted by one or more substituents selected from the group consisting of halogen, amino, nitro, cyano, hydroxy, thiol, alkyl, alkoxy, alkenyl, alkynyl, —C(O)R$_{11}$, —C(O)OR$_{12}$, —OC(O)R$_{11}$, cycloalkyl, heterocyclyl, aryl and heteroaryl;

R$_{11}$ and R$_{12}$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the alkyl, alkoxy, alkenyl, alkynyl, cycloalkyl, heterocyclyl, aryl and heteroaryl are optionally further substituted by one or more substituents selected from the group consisting of halogen, amino, nitro, cyano, hydroxy, thiol, carboxy, alkoxycarbonyl, oxo, alkyl, alkoxy, —NR$^a$R$^b$, —OR$^d$, —N(R$^c$)C(O)R$^d$, —C(O)N(R$^a$)(R$^b$), —N(R$^c$)S(O)$_p$R$^d$, —S(O)$_p$N(R$^a$)(R$^b$), alkenyl, alkynyl, cycloalkyl, heterocyclyl, aryl, hydroxyaryl and heteroaryl;

R$^a$ and R$^b$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituents selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

or, R$^a$ and R$^b$ together with the atoms to which they are attached form a heterocyclyl, wherein the heterocyclyl is optionally further substituted by one or more substituents selected from the group consisting of halogen, amino, nitro, cyano, oxo, hydroxy, thiol, carboxy, alkoxycarbonyl, alkyl, alkoxy, alkenyl, alkynyl, cycloalkyl, heterocyclyl, aryl and heteroaryl;

R$^c$ and R$^d$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituents selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl; and p is selected from the group consisting of 0, 1 and 2.

5. The compound of formula (II) according to claim 4, wherein, any one of $R_4$, $R_5$ and $R_6$ is hydrogen, and the remaining two together with the carbon atom to which they are attached form a cycloalkyl or heterocyclyl, wherein the cycloalkyl or heterocyclyl is optionally further substituted by one or more substituents selected from the group consisting of —C(O)$R_{11}$ and —C(O)O$R_{12}$;

$R_{11}$ and $R_{12}$ are each independently selected from the group consisting of hydrogen, halogen, hydroxy, alkyl, alkoxy, cycloalkyl, heterocyclyl, aryl and heteroaryl, wherein the alkyl, alkoxy, cycloalkyl, heterocyclyl, aryl and heteroaryl are optionally further substituted by one or more substituents selected from the group consisting of halogen, hydroxy, alkyl, —OR$^d$, —N(R$^c$)C(O)R$^d$, aryl, hydroxyaryl and heteroaryl; and R$^c$ and R$^d$ are each independently selected from the group consisting of hydrogen, alkyl, alkoxy, aryl and heteroaryl, wherein the alkyl, alkoxy, aryl and heteroaryl are optionally further substituted by one or more substituents selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl.

6. A compound of formula (III),

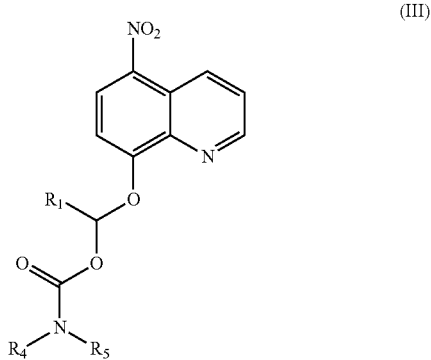

(III)

or a mesomer, racemate, enantiomer, or diastereomer thereof, or a mixture thereof, or a pharmaceutically acceptable salt thereof, wherein, $R_1$ is selected from the group consisting of hydrogen and $C_{1-6}$ alkyl;

$R_4$ and $R_5$ are each independently selected from the group consisting of hydrogen, halogen, alkyl, cycloalkyl, heterocyclyl, aryl, heteroaryl, —O$R_{12}$, —S$R_{12}$, —C(O)$R_{11}$, —C(O)O$R_{12}$, —OC(O)$R_{11}$, —NR$^a$R$^b$, —N(R$^c$)C(O)R$^d$, —C(O)N(R$^a$)(R$^b$), —N(R$^c$)S(O)$_p$R$^d$, —S(O)$_p$N(R$^a$)(R$^b$), —O(CH$_2$)$_m$O(CH$_2$)$_q$R$_{12}$ and —N(R$^c$)C(O)—(CH)$_m$—N(R$^c$)C(O)R$^d$, wherein the alkyl, cycloalkyl, heterocyclyl, aryl and heteroaryl are optionally further substituted by one or more substituents selected from the group consisting of halogen, amino, nitro, cyano, hydroxy, thiol, alkyl, alkoxy, alkenyl, alkynyl, O$R_{12}$, S$R_{12}$, NR$^a$R$^b$, —C(O)$R_{11}$, —C(O)O$R_{12}$, —O(O)C$R_{11}$, —(CH)$_m$—OC(O)$R_{11}$, cycloalkyl, heterocyclyl, aryl, arylalkyl, heteroaryl and heteroarylalkyl; or $R_4$, $R_5$ and N atom together form a heterocyclyl, wherein the heterocyclyl is optionally further substituted by one or more substituents selected from the group consisting of halogen, amino, nitro, cyano, hydroxy, thiol, alkyl, alkoxy, alkenyl, alkynyl, —C(O)$R_{11}$, —C(O)O$R_{12}$, —O(O)C$R_{11}$, cycloalkyl, heterocyclyl, aryl and heteroaryl;

$R_{11}$ and $R_{12}$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the alkyl, alkoxy, alkenyl, alkynyl, cycloalkyl, heterocyclyl, aryl and heteroaryl are optionally further substituted by one or more substituents selected from the group consisting of halogen, amino, nitro, cyano, hydroxy, thiol, carboxy, alkoxycarbonyl, oxo, alkyl, alkoxy, —NR$^a$R$^b$, —OR$^d$, —N(R$^c$)C(O)R$^d$, —C(O)N(R$^a$)(R$^b$), —N(R$^c$)S(O)$_p$R$^d$, —S(O)$_p$N(R$^a$)(R$^b$), alkenyl, alkynyl, cycloalkyl, heterocyclyl, aryl and heteroaryl;

R$^a$ and R$^b$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituents selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

or, R$^a$ and R$^b$ together with the atoms to which they are attached form a heterocyclyl, wherein the heterocyclyl is optionally further substituted by one or more substituents selected from the group consisting of halogen, amino, nitro, cyano, oxo, hydroxy, thiol, carboxy, alkoxycarbonyl, alkyl, alkoxy, alkenyl, alkynyl, cycloalkyl, heterocyclyl, aryl and heteroaryl;

R$^c$ and R$^d$ are each independently selected from the group consisting of hydrogen, halogen, hydroxy, cyano, amino, carboxy, alkoxycarbonyl, alkyl, alkoxy, alkenyl, alkynyl, cycloalkyl, heterocyclyl, aryl and heteroaryl, wherein the amino, alkyl, alkoxy, alkenyl, alkynyl, cycloalkyl, heterocyclyl, aryl and heteroaryl are optionally further substituted by one or more substituents selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

m is selected from an integer from 0 to 6;

p is selected from the group consisting of 0, 1 and 2; and q is selected from an integer from 0 to 6.

7. The compound of formula (III) according to claim 6, wherein, $R_4$ and $R_5$ are each independently selected from the group consisting of hydrogen, alkyl, aryl and heteroaryl, wherein the alkyl, aryl and heteroaryl are optionally further substituted by one or more substituents selected from the group consisting of halogen, hydroxy, thiol, alkyl, —C(O)$R_{11}$, —C(O)O$R_{12}$, —O(O)C$R_{11}$, —(CH)$_m$—OC(O)$R_{11}$, aryl and heteroaryl;

R₁₁ and R₁₂ are each independently selected from the group consisting of hydrogen and alkyl, wherein the alkyl is optionally further substituted by one or more substituents selected from the group consisting of halogen, —OR$^d$ and —N(R$^c$)C(O)R$^d$;

R$^c$ and R$^d$ are each independently selected from the group consisting of hydrogen, alkyl, aryl and heteroaryl, wherein the alkyl, aryl and heteroaryl are optionally further substituted by one or more substituents selected from the group consisting of halogen, amino, nitro, cyano, hydroxy, thiol, carboxy, alkoxycarbonyl, oxo, alkyl, alkoxy, alkenyl, alkynyl, cycloalkyl, heterocyclyl, aryl and heteroaryl;

m is selected from an integer from 0 to 6; and p is selected from the group consisting of 0, 1 and 2.

8. A compound selecting from the group consisting of:

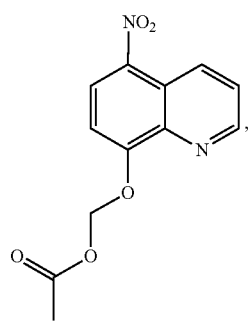

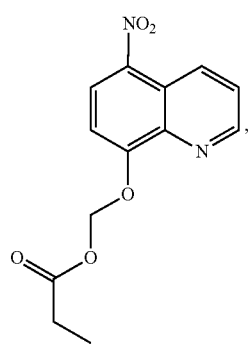

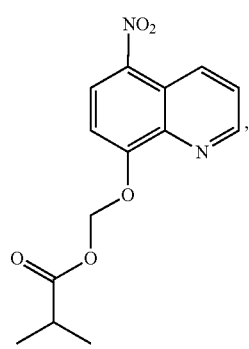

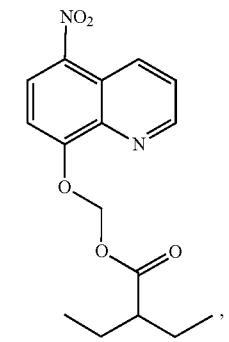

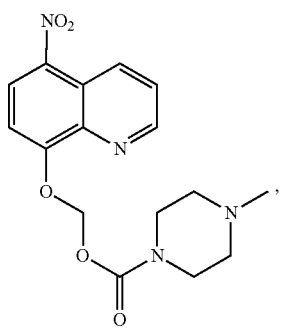

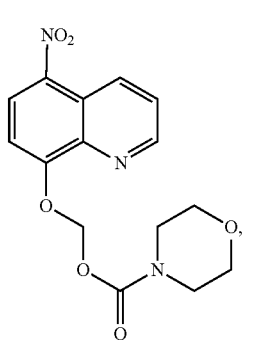

195
-continued
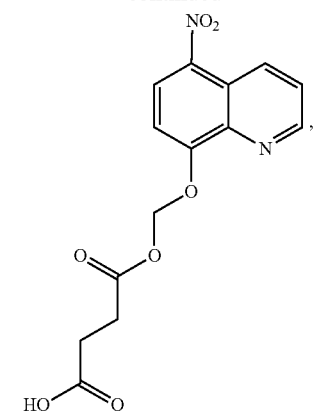
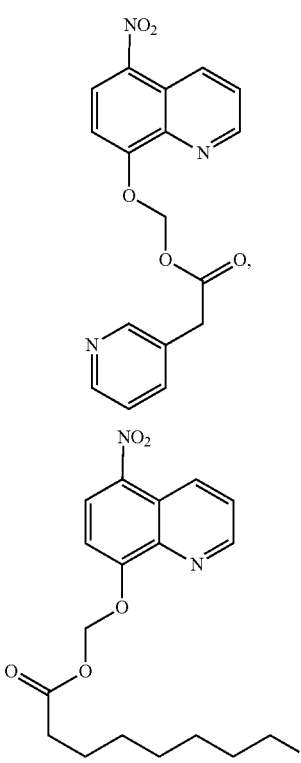
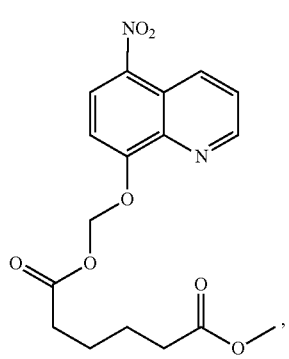
196
-continued
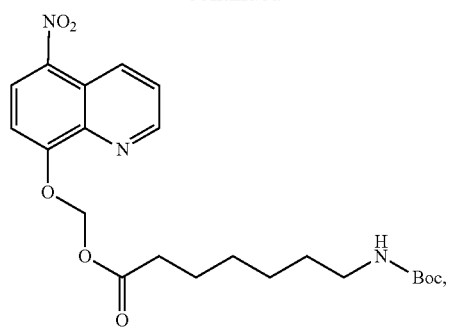
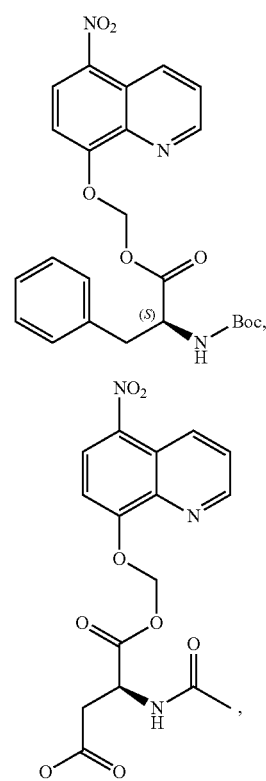
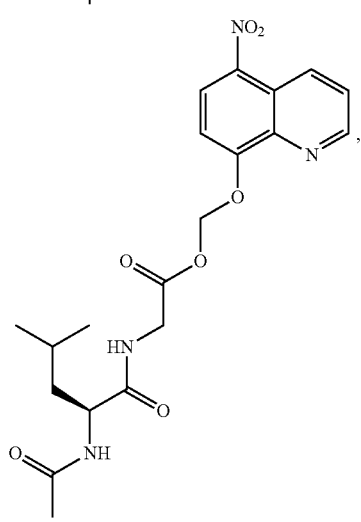

197
-continued

198
-continued

199
-continued
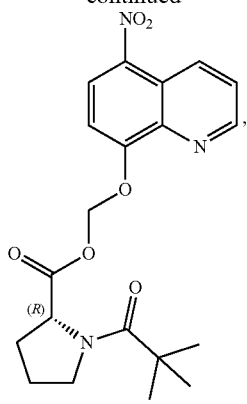
200
-continued
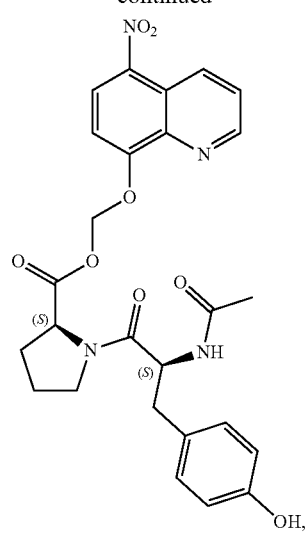
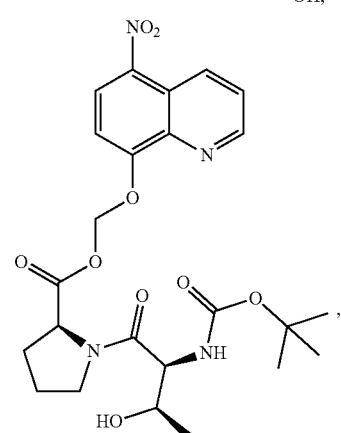
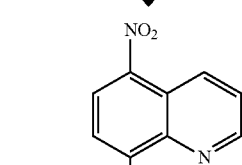
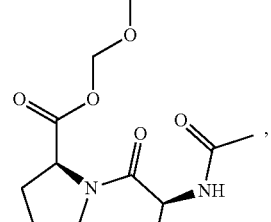
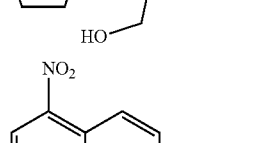
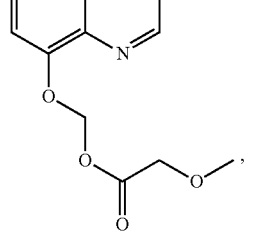

201
-continued
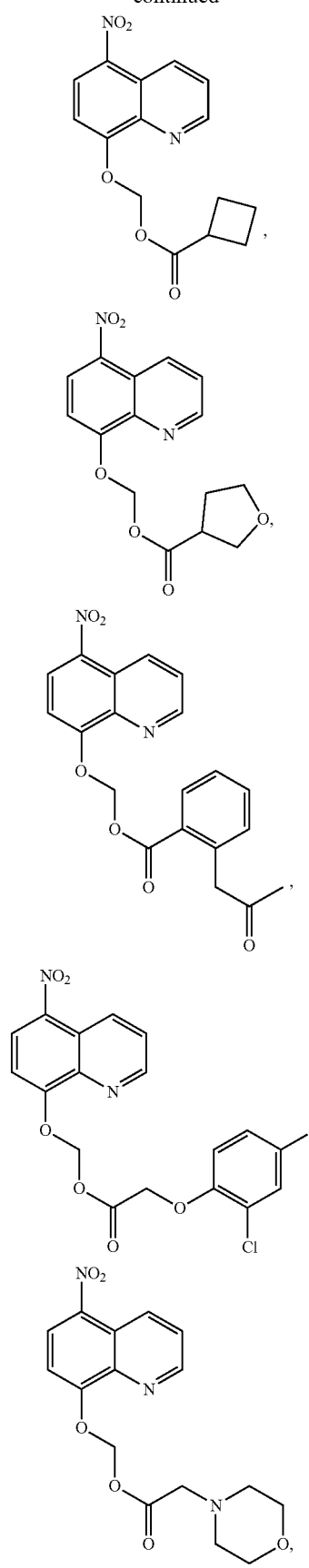
202
-continued
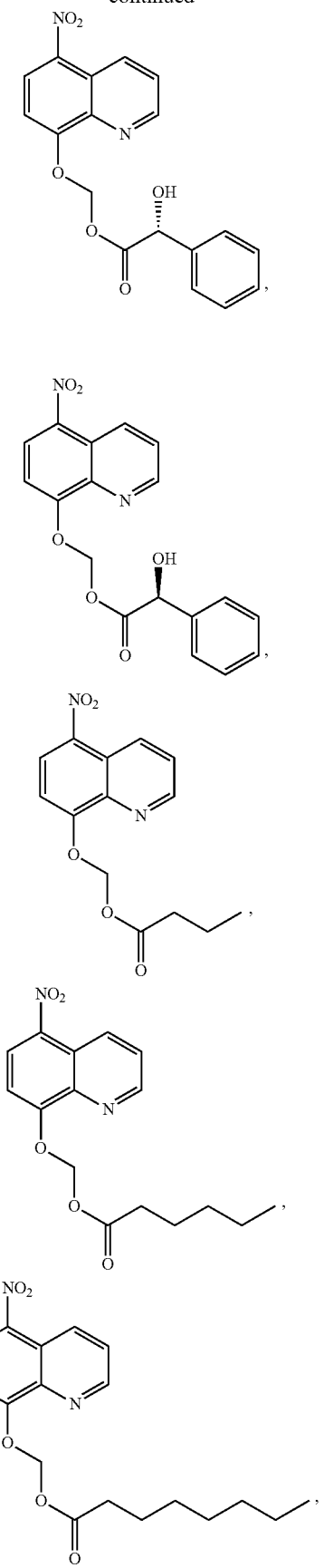

203
-continued
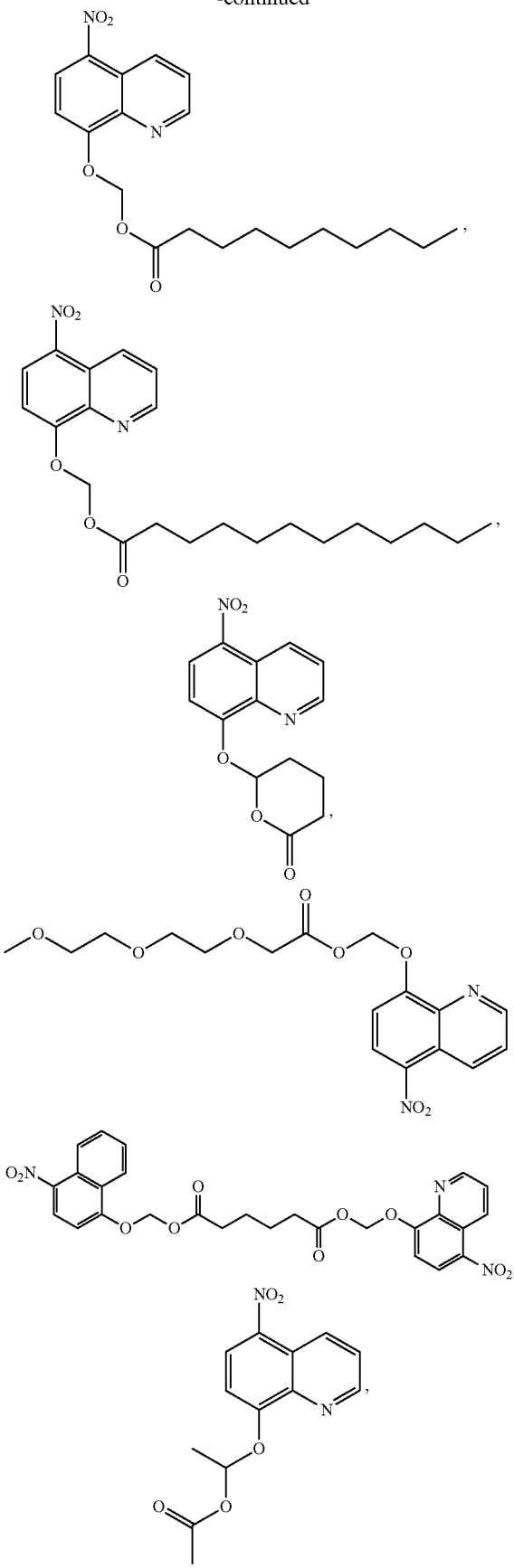
204
-continued
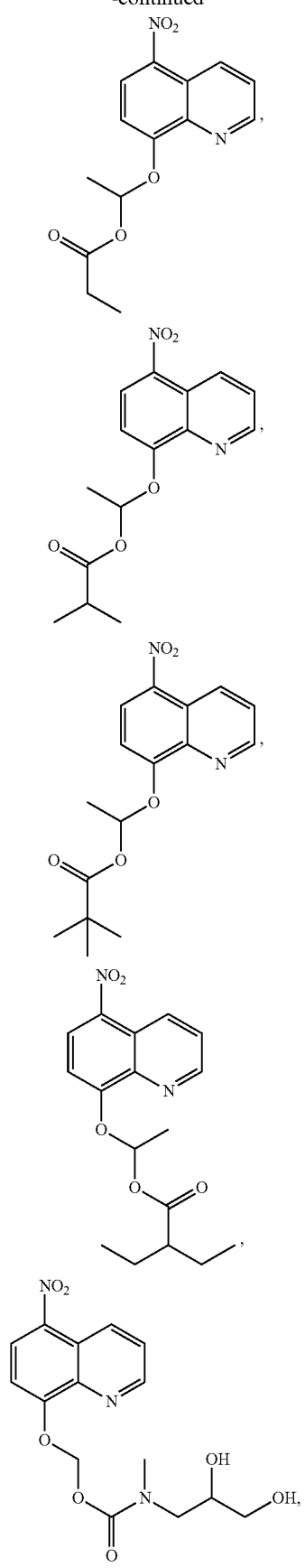

205
-continued
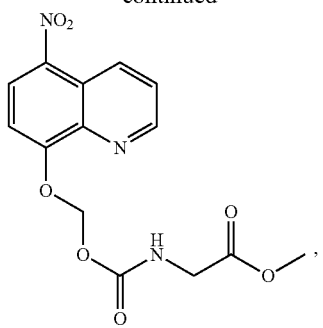
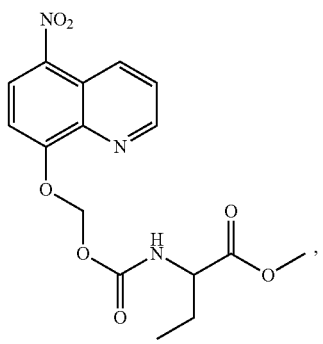
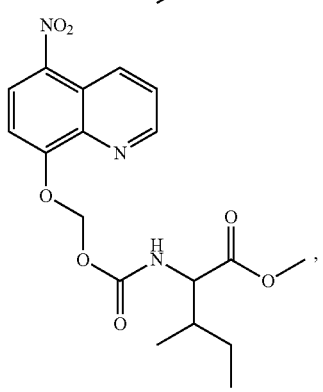
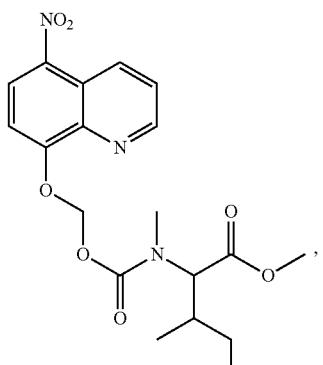
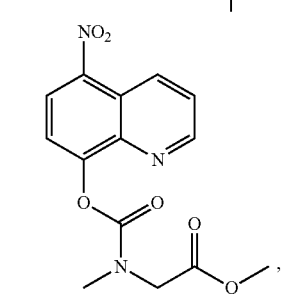
206
-continued
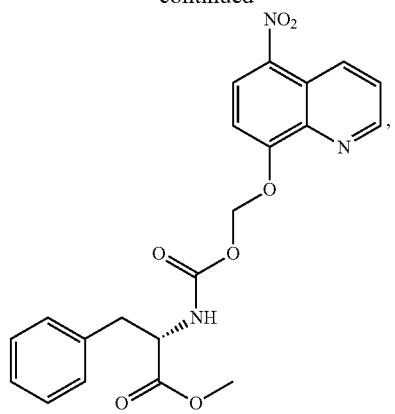
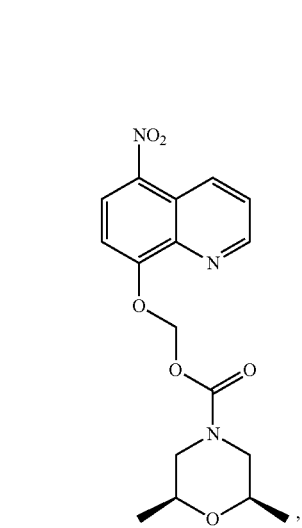
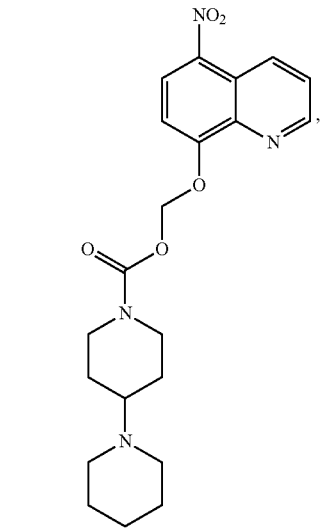

207
-continued
208
-continued
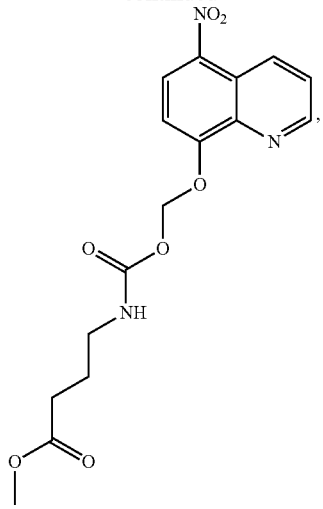
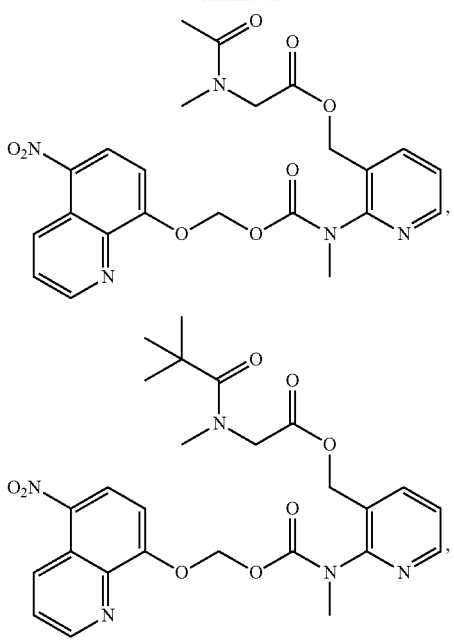
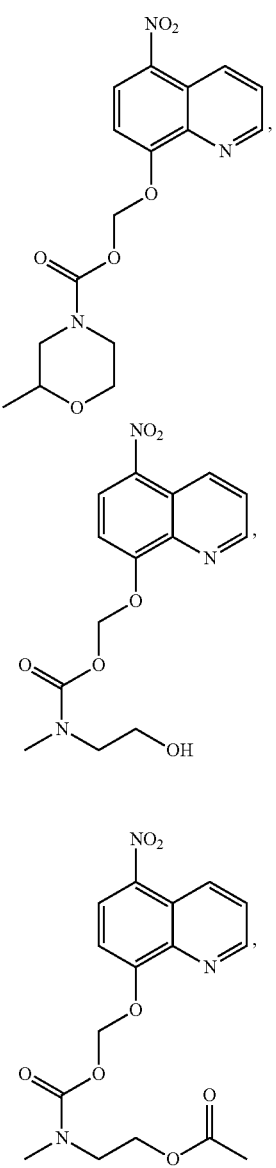

-continued

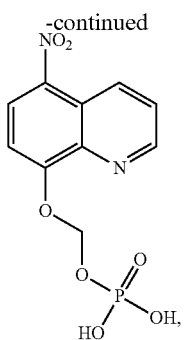

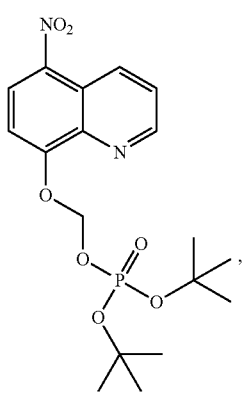

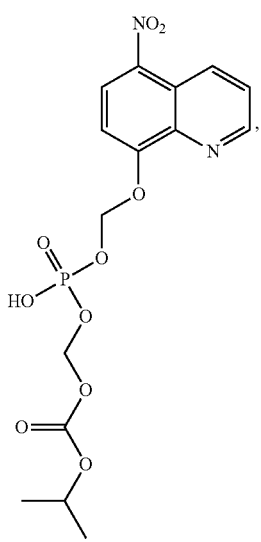

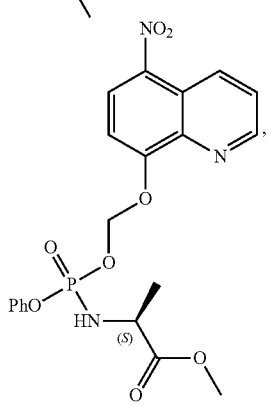

-continued

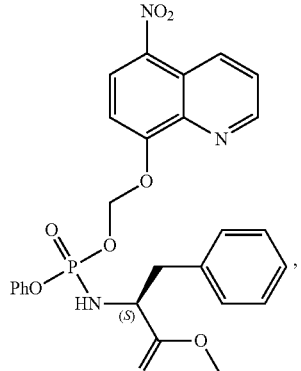

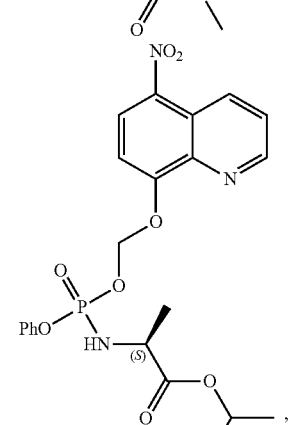

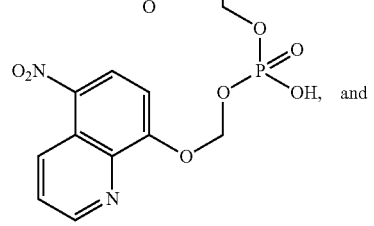

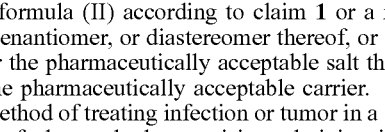

or a mesomer, racemate, enantiomer, or diastereomer thereof, or a mixture thereof, or a pharmaceutically acceptable salt thereof.

9. A pharmaceutical composition, comprising the compound of formula (II) according to claim 1 or a mesomer, racemate, enantiomer, or diastereomer thereof, or a mixture thereof, or the pharmaceutically acceptable salt thereof and at least one pharmaceutically acceptable carrier.

10. A method of treating infection or tumor in a subject in need thereof, the method comprising administering to the subject a therapeutically amount of the compound of formula (II) according to claim 1 or the pharmaceutically acceptable salt thereof, wherein the tumor is selected from the group consisting of bladder cancer, prostate cancer and kidney cancer, and the infection is urinary tract infection.

11. A pharmaceutical composition, comprising the compound of formula (III) according to claim 6 or a mesomer, racemate, enantiomer, or diastereomer thereof, or a mixture thereof, or the pharmaceutically acceptable salt thereof and at least one pharmaceutically acceptable carrier.

12. A method of treating infection or tumor in a subject in need thereof, the method comprising administering to the subject a therapeutically amount of the compound of formula (III) according to claim 6 or the pharmaceutically acceptable salt thereof, wherein the tumor is selected from the group consisting of bladder cancer, prostate cancer and kidney cancer, and the infection is urinary tract infection.

\* \* \* \* \*